US012805185B2

(12) United States Patent
Park et al.

(10) Patent No.: US 12,805,185 B2
(45) Date of Patent: Nov. 17, 2026

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Sang Yong Park, Cheonan-si (KR); Moon Sung Kang, Cheonan-si (KR); Jung Geun Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 19/243,577

(22) Filed: Jun. 19, 2025

(65) Prior Publication Data

US 2026/0173750 A1 Jun. 18, 2026

Related U.S. Application Data

(63) Continuation of application No. PCT/KR2024/096166, filed on Sep. 19, 2024.

(30) Foreign Application Priority Data

Oct. 5, 2023 (KR) ........................ 10-2023-0132445

(51) Int. Cl.
*H10K 85/60* (2023.01)
*C07B 59/00* (2006.01)
(Continued)

(52) U.S. Cl.
CPC ......... *H10K 85/633* (2023.02); *C07B 59/002* (2013.01); *C07C 211/61* (2013.01); *C07D 307/91* (2013.01); *C07D 333/76* (2013.01); *C07D 409/12* (2013.01); *C07F 7/0816* (2013.01); *H10K 85/636* (2023.02); *C07B 2200/05* (2013.01); *H10K 50/11* (2023.02);
(Continued)

(58) Field of Classification Search
CPC ... C07C 211/61; H10K 85/633; H10K 85/636
See application file for complete search history.

(56) References Cited

FOREIGN PATENT DOCUMENTS

| | | | |
|---|---|---|---|
| KR | 10-2017-0017701 | A | 2/2017 |
| KR | 10-2019-0103773 | A | 9/2019 |

(Continued)

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound of Formula 1 that can improve the luminescence efficiency, stability, and lifespan of an element employing the compound, an organic electric element employing the same, and an electronic device having the same, Formula 1

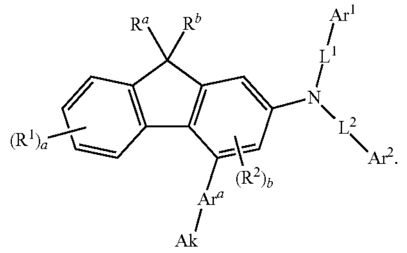

17 Claims, 2 Drawing Sheets

(51) Int. Cl.

| | |
|---|---|
| ***C07C 211/61*** | (2006.01) |
| ***C07D 307/91*** | (2006.01) |
| ***C07D 333/76*** | (2006.01) |
| ***C07D 409/12*** | (2006.01) |
| ***C07F 7/08*** | (2006.01) |
| ***H10K 50/11*** | (2023.01) |
| ***H10K 85/40*** | (2023.01) |

(52) U.S. Cl.
CPC ........... *H10K 85/40* (2023.02); *H10K 85/623* (2023.02); *H10K 85/626* (2023.02); *H10K 85/6574* (2023.02)

(56) References Cited

FOREIGN PATENT DOCUMENTS

| | | | | | |
|---|---|---|---|---|---|
| KR | 20190103773 | A | * | 9/2019 | ............. C09K 11/06 |
| KR | 20210046208 | A | * | 4/2021 | ........... C07C 211/57 |
| KR | 10-2021-0128205 | A | | 10/2021 | |
| KR | 20210120526 | A | * | 10/2021 | ........... C07C 211/54 |
| KR | 10-2023-0014596 | A | | 1/2023 | |
| KR | 10-2023-0069585 | A | | 5/2023 | |

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

The present invention relates to compounds for organic electronic elements, organic electronic elements using the same, and an electronic device thereof. This application is a continuation of PCT International Application No.: PCT/KR2024/096166, filed on Sep. 19, 2024, which claims the benefit of priority from Korean Patent Application No. 10-2023-0132445, filed on Oct. 5, 2023, the contents of each of which are incorporated herein by reference in their entirety.

TECHNICAL FIELD

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer etc.

A material used as an organic material layer in an organic electronic element may be classified into a light emitting material and a charge transport material, such as a hole injection material, a hole transport material, an electron transport material, an electron injection material etc. depending on its function.

The biggest issues with organic light emitting devices are their lifetime and efficiency, and as displays become larger in size, the problem of efficiency and lifetime must also be solved.

Efficiency, lifetime and driving voltage are related to each other, and when the efficiency is increased, the driving voltage is relatively decreased, and as the driving voltage is decreased, crystallization of organic materials due to Joule heating generated during driving decreases, and consequently, the lifetime tends to increase.

However, the efficiency cannot be maximized simply by improving the organic material layer. This is because, when the energy level and T1 value between each organic material layer, and the intrinsic properties (mobility, interfacial properties, etc.) of materials are optimally combined, long lifetime and high efficiency can be achieved at the same time.

Further, recently, in organic electroluminescent devices, in order to solve the emission problem in the hole transport layer, an emitting-auxiliary layer must be present between the hole transport layer and an emitting layer, and it is necessary to develop different emitting-auxiliary layers according to each of the emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value, therefore the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic element are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against Joule heating generated when the device is driven, while delaying penetration of the metal oxide from the anode electrode (ITO), which is one of the causes of shortening the lifetime of the organic electronic element, into the organic layer. The low glass transition temperature of the hole transport layer material has a characteristic that when the device is driven, the uniformity of the surface of the thin film is lowered, which has been reported to have a great influence on the lifetime of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, the development of new materials continues to be required, and in particular, the development of materials for the emitting-auxiliary layer is urgently required.

BRIEF DESCRIPTION OF THE INVENTION

Summary

In order to solve the problems of the background art described above, the present invention has revealed a compound having a novel structure, and that when the compound is applied to an organic electronic element, the luminous efficiency, stability and lifetime of the element are greatly improved.

Accordingly, it is an object of the present invention to provide a novel compound, an organic electronic element using the same, and an electronic device thereof.

Technical Solution

The present invention provides a compound represented by Formula 1.

<Formula 1>

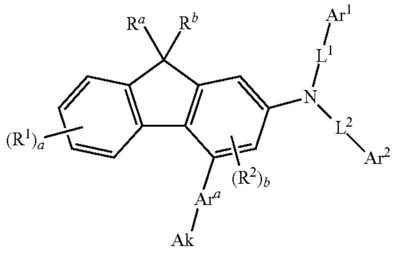

In another aspect, the present invention provides an organic electronic element comprising a compound represented by Formula 1 and an electronic device thereof.

Effects of the Invention

By using the compound according to the present invention, it is possible to achieve a high luminous efficiency, a low driving voltage, and a high heat resistance of the element, and can greatly improve the color purity and lifetime of the element.

Figure 1:
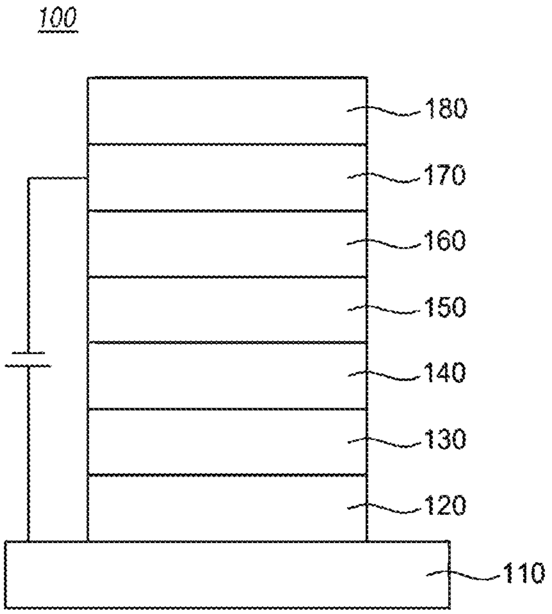
FIG. 1 to FIG. 3 illustrate an example of an organic light emitting device according to the present invention.

100, 200, 300: organic electronic element
110: the first electrode
120: hole injection layer
130: hole transport layer
140: emitting layer
150: electron transport layer
160: electron injection layer
170: second electrode
180: light efficiency enhancing Layer
210: buffer layer
220: emitting-auxiliary layer
320: first hole injection layer
330: first hole transport layer
340: first emitting layer
350: first electron transport layer
360: first charge generation layer
361: second charge generation layer
420: second hole injection layer
430: second hole transport layer
440: second emitting layer
450: second electron transport layer
CGL: charge generation layer
ST1: first stack
ST2: second stack

DETAILED DESCRIPTION OF THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine(F), bromine(Br), chlorine(Cl), or iodine(I).

Unless otherwise stated, the term "alkyl" or "alkyl group", as used herein, has a single bond of 1 to 60 carbon atoms, 1 to 30 carbon atoms, 1 to 25 carbon atoms, 1 to 18 carbon atoms, or 1 to 12 carbon atoms, and means saturated aliphatic functional radicals including a linear alkyl group, a branched chain alkyl group, a cycloalkyl group (alicyclic), a Cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, 2 to 30 carbon atoms, 2 to 25 carbon atoms, 2 to 18 carbon atoms, 2 to 12 carbon atoms, but is not limited thereto, and includes a linear or a branched chain group.

Unless otherwise stated, the term "cycloalkyl", as used herein, means alkyl forming a ring having 3 to 60 carbon atoms, 3 to 30 carbon atoms, 3 to 25 carbon atoms, 3 to 18 carbon atoms, 3 to 12 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms, 1 to 30 carbon atoms, 1 to 25 carbon atoms, 1 to 18 carbon atoms, or 1 to 12 carbon atoms.

Unless otherwise stated, the term "aryloxyl group" or "aryloxy group", as used herein, means an aryl group bonded to oxygen radical, but is not limited thereto, and has 6 to 60 carbon atoms, 6 to 30 carbon atoms, 6 to 25 carbon atoms, 6 to 18 carbon atoms, or 6 to 12 carbon atoms.

Unless otherwise specified, the terms "aryl group" and "arylene group" used in the present invention have 6 to 60 carbon atoms, 6 to 30 carbon atoms, 6 to 25 carbon atoms, 6 to 18 carbon atoms, or 6 to 12 carbon atoms, respectively, but are not limited thereto. In the present invention, an aryl group or arylene group refers to an aromatic group of a single ring or multiple rings, and contain aromatic rings formed by bonding or reacting with adjacent substituents. For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, 2 to 30 carbon atoms, 2 to 25 carbon atoms, 2 to 18 carbon atoms, 2 to 12 carbon atoms, and includes any one of a single ring or multiple ring, and may include heteroaliphatic ring and heteroaromatic ring. Also, the heterocyclic group may also be formed by bonding with an adjacent group.

Unless otherwise stated, the term "heteroatom", as used herein, represents at least one of N, O, S, P, or Si.

Also, "heterocyclic group" refers to a single ring containing heteroatoms, a ring aggregate, multiple fused ring systems, spiro compounds, etc. Additionally, compounds containing heteroatom groups such as $SO_2$, P═O, etc., such as the compounds below, instead of carbon forming a ring, may also be included in the heterocyclic group. For example, "heterocyclic group" includes the following compound.

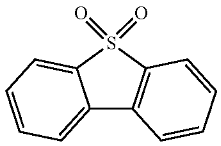 [SMILES: O=S1(=O)c2ccccc2-c2ccccc21]

The term "aliphatic ring group" used in the present invention refers to cyclic hydrocarbons excluding aromatic hydrocarbons, and includes single rings, ring aggregates, fused multiple ring systems, spiro compounds, etc., and means a ring having 3 to 60 carbon atoms, 3 to 30 carbon atoms, 3 to 25 carbon atoms, 3 to 18 carbon atoms, 3 to 12 carbon atoms, but is not limited thereto. For example, even when benzene, an aromatic ring, and cyclohexane, a non-aromatic ring, are fused, it is an aliphatic ring.

Unless otherwise stated, the term "fluorenyl group", "fluorenylene group" or "fluorentriyl group" as used herein, means a monovalent, divalent or trivalent functional group, in which R, R' and R" are all hydrogen in the following structures, and the term "substituted fluorenyl group", "substituted fluorenylene group" or "substituted fluorentriyl group" means that at least one of the substituents R, R' and R" is a substituent other than hydrogen, and include those in which R and R' are bonded to each other to form a spiro compound together with the carbon to which they are bonded. In this specification, fluorenyl group, fluorenylene group, and fluorenetriyl group may all be referred to as fluorene groups, regardless of valence.

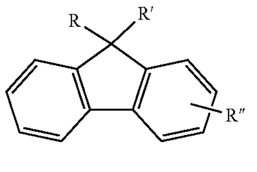

The term "spiro compound", as used herein, has a 'spiro union', and a spiro union means a connection formed by 2 rings sharing only one atom. Wherein, the atoms shared between the 2 rings are called 'spiro atoms', and depending on the number of spiro atoms contained in a compound, they are called 'monospiro-', 'dispiro-', and 'trispiro-' compounds, respectively.

Unless otherwise stated, the term "aliphatic" as used herein means an aliphatic hydrocarbon having 1 to 60 carbon atoms, 1 to 30 carbon atoms, 1 to 25 carbon atoms, 1 to 18 carbon atoms or 1 to 12 carbon atoms, and "aliphatic ring" means an aliphatic hydrocarbon ring having 3 to 60 carbon atoms, 3 to 30 carbon atoms, 3 to 25 carbon atoms, 3 to 18 carbon atoms or 3 to 12 carbon atoms.

Unless otherwise stated, the term "ring", as used herein, means an aliphatic ring having 3 to 60 carbon atoms, 3 to 30 carbon atoms, 3 to 25 carbon atoms, 3 to 18 carbon atoms or 3 to 12 carbon atoms; or an aromatic ring having 6 to 60 carbon atoms, 6 to 30 carbon atoms, 6 to 25 carbon atoms, 6 to 18 carbon atoms, or 6 to 12 carbon atoms; or a heterocyclic having 2 to 60 carbon atoms, 2 to 30 carbon atoms, 2 to 25 carbon atoms, 2 to 18 carbon atoms, 2 to 12 carbon atoms, or a fused ring formed by the combination thereof, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

In this specification, the 'group name' corresponding to the aryl group, arylene group, heterocyclic group, etc., as examples of each symbol and its substituent, may be written as the 'name of the group reflecting the valence', but is written as the 'parent compound name'. For example, in the case of 'phenanthrene', a type of aryl group, the name of the group may be written by distinguishing the valence, such as the monovalent 'group' is 'phenanthryl' and the divalent group is 'phenanthrylene', but may be written as 'phenanthrene', which is the name of the parent compound, regardless of the valence. Similarly, in the case of pyrimidine, it can be written as 'pyrimidine' regardless of the valence, or it can be written as the 'name of the group' of the valence, such as pyrimidineyl group in the case of monovalent group, pyrimidineylene in the case of divalent group, etc. Additionally, in this specification, when describing compound names or substituent names, numbers or alphabets indicating positions may be omitted. For example, pyrido[4,3-d]pyrimidine to pyridopyrimidine, benzofuro[2,3-d]pyrimidine to benzofuropyrimidine, 9,9-dimethyl-9H-fluorene can be described as dimethylfluorene, etc. Therefore, both benzo[g]quinoxaline and benzo[f]quinoxaline can be described as benzoquinoxaline.

Also, unless there is an explicit explanation, the formula used in the present invention is the same as the definition of the substituent by the exponent definition of the following formula.

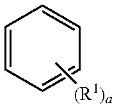

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

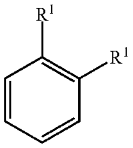

(a = 2)

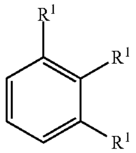

(a = 3)

Unless otherwise expressly stated, the terms "ortho", "meta", and "para" used in the present invention refer to the substitution positions of all substituents, and the ortho position refers to a compound in which the position of the substituent is immediately adjacent, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para-positions are substituted by linear type.

[Example of Ortho-Position]

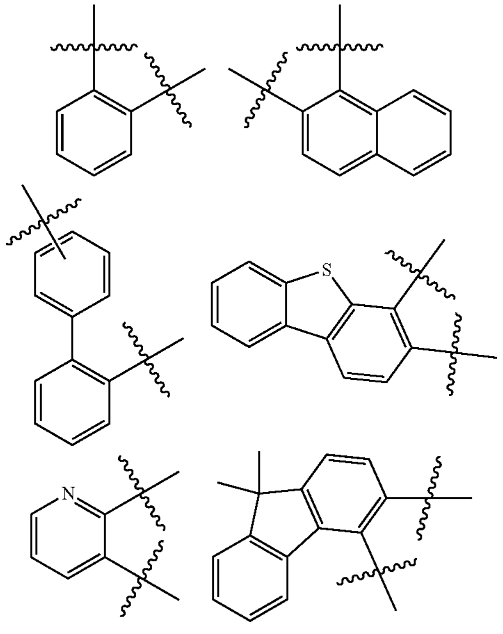

[Example of Meta-Position]

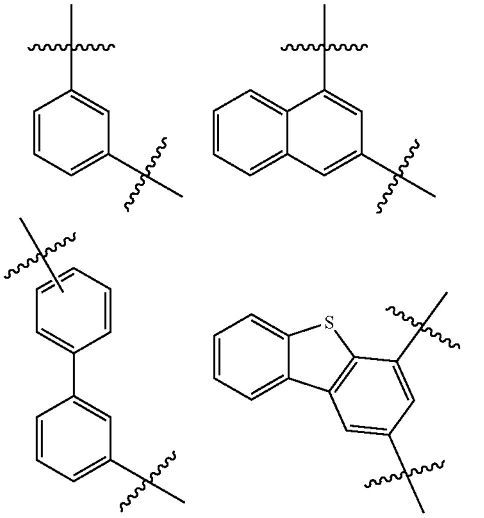

-continued

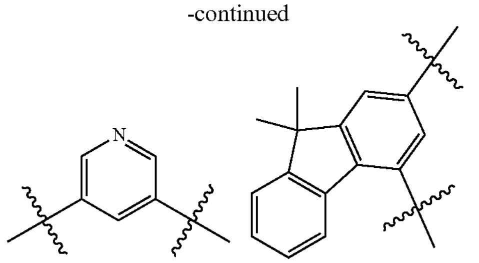

[Example of Para-Position]

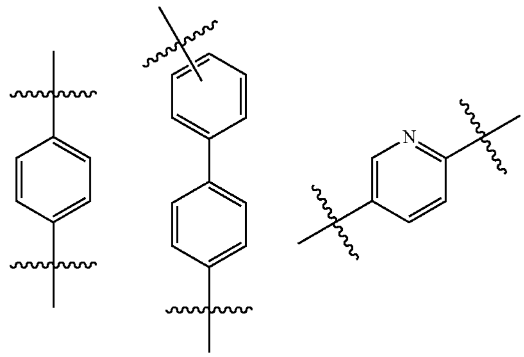

Hereinafter, a compound according to an aspect of the present invention and an organic electronic element comprising the same will be described.

The present invention provides a compound represented by Formula 1.

<Formula 1>

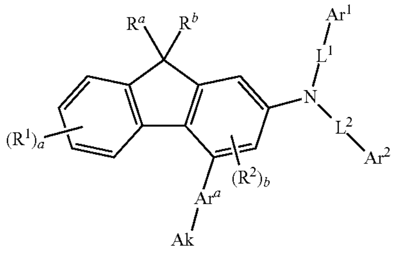

wherein:

$L^1$ and $L^2$ are independently selected from the group consisting of a single bond; a $C_6$-$C_{60}$ arylene group; a fluorenylene group; a $C_2$-$C_{60}$ heterocyclic group including at least one heteroatom of O, N, S, Si or P;

Wherein when $L^1$ and $L^2$ are an arylene group, preferably a $C_6$-$C_{60}$ arylene group, more preferably a $C_6$-$C_{25}$ arylene group, a $C_6$-$C_{18}$ arylene group or a $C_6$-$C_{12}$ arylene group, such as phenylene, biphenylene, naphthylene, terphenylene, anthracenylene, phenanthrenylen, etc.

Wherein when $L^1$ and $L^2$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

$Ar^1$ and $Ar^2$ are independently selected from the group consisting of a $C_6$-$C_{60}$ aryl group; a fluorenyl group; a $C_2$-$C_{60}$ heterocyclic group including at least one heteroatom of O, N, S, Si or P;

Wherein when $Ar^1$ and $Ar^2$ are an aryl group, preferably a $C_6$-$C_{60}$ aryl group, more preferably a $C_6$-$C_{25}$ aryl group, a $C_6$-$C_{18}$ aryl group or a $C_6$-$C_{12}$ aryl group, such as phenyl, biphenyl, terphenyl, naphthalene, phenanthrene, chryshen, etc.

Wherein when $Ar^1$ and $Ar^2$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

$R^a$ and $R^b$ are independently selected from the group consisting of a $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{60}$ aryloxy group; a plurality of adjacent groups thereof may be bonded to each other to form a spirobifluorene group, Wherein when $R^a$ and $R^b$ are an aryl group, preferably a $C_6$-$C_{60}$ aryl group, more preferably a $C_6$-$C_{25}$ aryl group, a $C_6$-$C_{18}$ aryl group or a $C_6$-$C_{12}$ aryl group, such as phenyl, biphenyl, terphenyl, naphthalene, phenanthrene, chryshen, etc.

Wherein when $R^a$ and $R^b$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

Wherein when $R^a$ and $R^b$ are an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when $R^a$ and $R^b$ are an alkoxyl group, preferably a $C_1$-$C_{25}$ alkoxyl group, a $C_1$-$C_{18}$ alkoxyl group or a $C_1$-$C_{12}$ alkoxyl group.

Wherein when $R^a$ and $R^b$ are an aryloxy group, preferably a $C_6$-$C_{25}$ aryloxy group, a $C_6$-$C_{18}$ aryloxy group or a $C_6$-$C_{12}$ aryloxy group.

$R^1$ and $R^2$ are independently the same or different from each other, and are independently selected from the group consisting of a hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; a plurality of adjacent groups thereof may be bonded to each other to form a ring, Wherein when $R^1$ and $R^2$ are an aryl group, preferably a $C_6$-$C_{30}$ aryl group, more preferably a $C_6$-$C_{25}$ aryl group, a $C_6$-$C_{18}$ aryl group or a $C_6$-$C_{12}$ aryl group, such as phenyl, biphenyl, terphenyl, naphthalene, phenanthrene, chryshen, etc.

Wherein when $R^1$ and $R^2$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

Wherein when $R^1$ and $R^2$ are a fused ring group, preferably a fused ring group of a $C_3$-$C_{30}$ aliphatic ring and a $C_6$-$C_{30}$ aromatic ring, more preferably a fused ring group of a $C_3$-$C_{25}$ aliphatic ring and a $C_6$-$C_{25}$ aromatic ring.

Wherein when $R^1$ and $R^2$ are an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when $R^1$ and $R^2$ are an alkoxyl group, preferably a $C_1$-$C_{25}$ alkoxyl group, a $C_1$-$C_{18}$ alkoxyl group or a $C_1$-$C_{12}$ alkoxyl group.

Wherein when $R^1$ and $R^2$ are an aryloxy group, preferably a $C_6$-$C_{25}$ aryloxy group, a $C_6$-$C_{18}$ aryloxy group or a $C_6$-$C_{12}$ aryloxy group.

a is an integer of 0 to 4, b is an integer of 0 to 2, $Ar^a$ is a $C_6$-$C_{60}$ arylene group, preferably a $C_6$-$C_{30}$ arylene group, more preferably a $C_6$-$C_{25}$ arylene group, a $C_6$-$C_{18}$ arylene group or a $C_6$-$C_{12}$ arylene group, such as phenylene, biphenylene, naphthylene, terphenylene, anthracenylene, phenanthrenylen, etc.

Ak is a $C_1$-$C_{50}$ alkyl group; or a $C_3$-$C_{60}$ aliphatic ring;

Wherein when Ak is an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when Ak is an aliphatic ring, preferably a $C_3$-$C_{30}$ aliphatic ring; more preferably a $C_3$-$C_{25}$ aliphatic ring; a $C_3$-$C_{18}$ aliphatic ring; or a $C_3$-$C_{12}$ aliphatic ring; and specifically, cyclobutane, cyclopentane, cyclohexane, bicycloheptane, adamantyl, etc.

wherein the aryl group, arylene group, heterocyclic group, fluorenyl group, fluorenylene group, aliphatic ring group, fused ring group, alkyl group, alkenyl group, alkynyl group, alkoxy group and aryloxy group may be substituted with one or more substituents selected from the group consisting of deuterium; halogen; silane group; siloxane group; boron group; germanium group; a cyano group; a nitro group; a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ aliphatic ring; a $C_7$-$C_{20}$ arylalkyl group; a $C_8$-$C_{20}$ arylalkenyl group; and a $C_7$-$C_{20}$ alkylaryl group; and the hydrogen of these substituents may be further substituted with one or more deuterium, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Additionally, any one of the $Ar^1$ or $Ar^2$ is substituted with at least one $C_1$-$C_{20}$ alkyl group; or a $C_3$-$C_{20}$ aliphatic ring group;

Additionally, Formula 1 is represented by Formula 1-1.

<Formula 1-1>

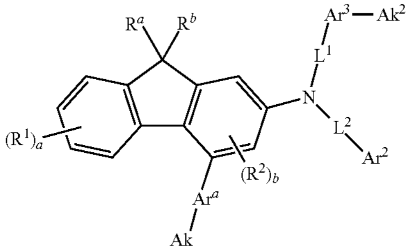

Wherein:

$R^a$, $R^b$, $R^1$, $R^2$, a, b, $Ar^a$, Ak, $L^1$, $L^2$ and $Ar^2$ are the same as defined in Formula 1, $Ar^3$ is a $C_6$-$C_0$ arylene group, or a $C_2$-$C_{60}$ heterocyclic group including at least one heteroatom of O, N, S, Si or P;

Wherein when $Ar^3$ is an arylene group, preferably a $C_6$-$C_{60}$ arylene group, more preferably a $C_6$-$C_{25}$ arylene group, a $C_6$-$C_{18}$ arylene group or a $C_6$-$C_{12}$ arylene group, such as phenylene, biphenylene, naphthylene, terphenylene, anthracenylene, phenanthrenylen, etc.

Wherein when $Ar^3$ is a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

$Ak^2$ is a $C_1$-$C_{20}$ alkyl group; or a $C_3$-$C_{20}$ aliphatic ring; Formula 1 is represented by Formula 1-2.

Formula 1-2

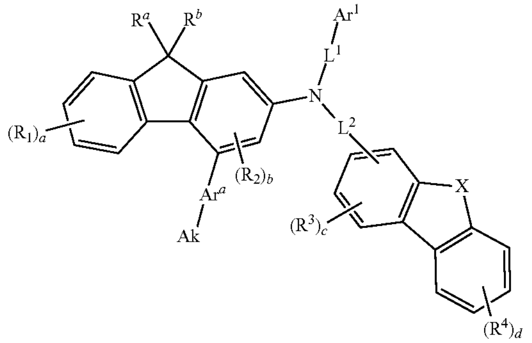

Wherein:

$R^a$, $R^b$, $R^1$, $R^2$, a, b, $Ar^a$, Ak, $L^1$, $L^2$ and $Ar^1$ are the same as defined in Formula 1.

$R^3$ and $R^4$ are independently the same or different from each other, and are independently selected from the group consisting of a hydrogen; deuterium; a $C_1$-$C_{20}$ alkoxyl group; a $C_6$-$C_{20}$ aryloxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{60}$ heterocyclic group including at least one heteroatom of O, N, S, Si or P; a fused ring group of a $C_3$-$C_{20}$ aliphatic ring and a $C_6$-$C_{20}$ aromatic ring; and a $C_3$-$C_{20}$ aliphatic ring;

c is an integer of 0 to 3, d is an integer of 0 to 4,

X is O, S, $CR^5R^6$ or $SiR^5R^6$, $R^5$ and $R^6$ are independently selected from the group consisting of a $C_6$-$C_{20}$ aryl group; a fluorenyl group; a $C_2$-$C_{20}$ heterocyclic group including at least one heteroatom of O, N, S, Si or P; a fused ring group of a $C_3$-$C_{20}$ aliphatic ring and a $C_6$-$C_{20}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{20}$ aryloxy group; or $R^5$ and $R^6$ may be bonded to each other to form a ring.

Additionally, Ak is represented by any one of Formulas Ak-1 to Ak-8:

Formula Ak-1

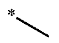

Formula Ak-2

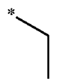

Formula Ak-3

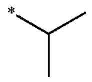

Formula Ak-4

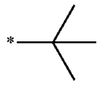

-continued

Formula Ak-5

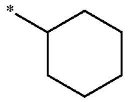

Formula Ak-6

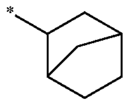

Formula Ak-7

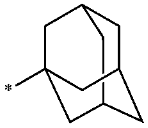

Formula Ak-8

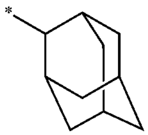

Wherein:

* indicates the position to be bonded,

Formulas Ak-1 to Ak-8 may be further substituted with one or more deuterium.

Also, any one of $Ar^1$ or $Ar^2$ is represented by one of Formulas Ar-1 to Ar-11:

Formula Ar-1

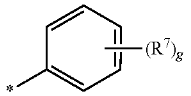

Formula Ar-2

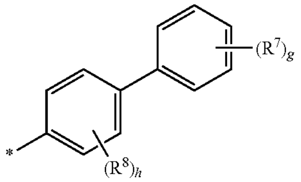

Formula Ar-3

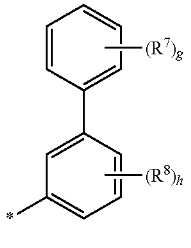

Formula Ar-4

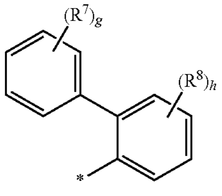

Formula Ar-5

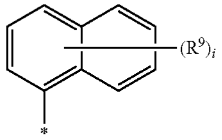

-continued

Formula Ar-6

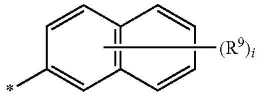

Formula Ar-7

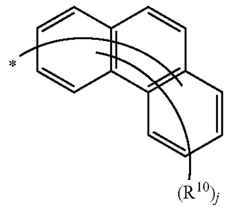

Formula Ar-8

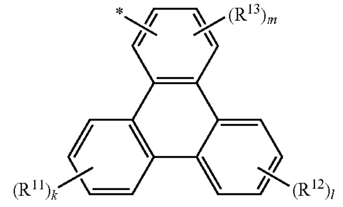

Formula Ar-9

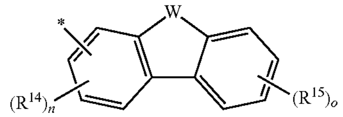

Formula Ar-10

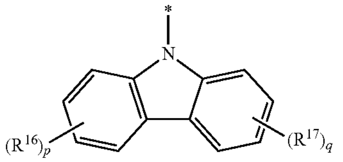

Formula Ar-11

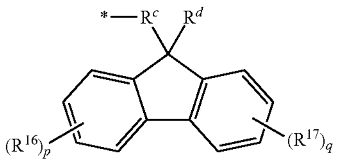

Wherein:

$R^7$, $R^8$, $R^9$, $R^{10}$, $R^{11}$, $R^{12}$, $R^{13}$, $R^{14}$, $R^{15}$, $R^{16}$ and $R^{17}$ are independently the same or different from each other and are independently selected from the group consisting of a hydrogen; deuterium; a $C_6$-$C_{20}$ aryl group; a fluorenyl group; a $C_2$-$C_{20}$ heterocyclic group including at least one heteroatom of O, N, S, Si or P; a $C_3$-$C_{20}$ aliphatic ring; $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{20}$ aryloxy group; and an adjacent plurality of groups may be bonded to each other to form a ring, $R^c$ is selected from the group consisting of a $C_1$-$C_{50}$ alkyl group; a $C_2$-$C_{20}$ alkenyl group; a $C_6$-$C_{60}$ aryl group and a $C_2$-$C_{60}$ heterocyclic group including at least one heteroatom of O, N, S, Si or P;

$R^d$ is selected from the group consisting of a hydrogen; deuterium; a $C_1$-$C_{50}$ alkyl group; a $C_2$-$C_{20}$ alkenyl group; a $C_6$-$C_{60}$ aryl group and a $C_2$-$C_{60}$ heterocyclic group including at least one heteroatom of O, N, S, Si or P;

Wherein when $R^c$ and $R^d$ are an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when $R^C$ and $R^d$ are an aryl group, preferably a $C_6$-$C_{60}$ aryl group, more preferably a $C_6$-$C_{25}$ aryl group, a $C_6$-$C_{18}$ aryl group or a $C_6$-$C_{12}$ aryl group, such as phenyl, biphenyl, terphenyl, naphthalene, phenanthrene, chryshen, etc.

Wherein when $R^C$ and $R^d$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

$R^c$ and $R^d$ may be bonded to each other to form a spiro, g is an integer of 0 to 5, h, k, l, o, p and q are independently an integer of 0 to 4, i is an integer of 0 to 7, j is an integer of 0 to 9, m and n are independently an integer of 0 to 3, W is O, S, $CR^{27}R^{28}$, $SiR^{27}R^{28}$ or $NR^{29}$, $R^{27}$, $R^{28}$ and $R^{29}$ are independently selected from the group consisting of a $C_6$-$C_{20}$ aryl group; a fluorenyl group; a $C_2$-$C_{20}$ heterocyclic group including at least one heteroatom of O, N, S, Si or P; a fused ring group of a $C_3$-$C_{20}$ aliphatic ring and a $C_6$-$C_{20}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{20}$ aryloxy group; or $R^{27}$ and $R^{28}$ may be bonded to each other to form a ring.

* indicates the position to be bonded.

Also, $Ar^a$, $L^1$ and $L^2$ are selected from a single bond or any one of Formulas L-1 to L-27.

[Formula L-1]

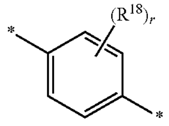

[Formula L-2]

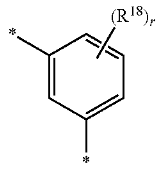

[Formula L-3]

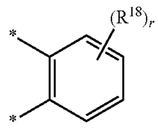

[Formula L-4]

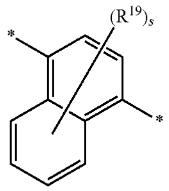

-continued

[Formula L-5]

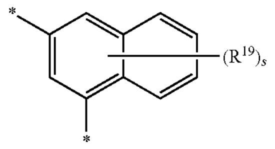

[Formula L-6]

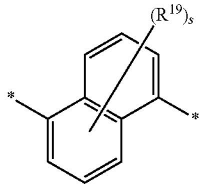

[Formula L-7]

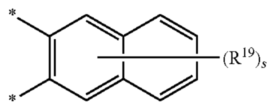

[Formula L-8]

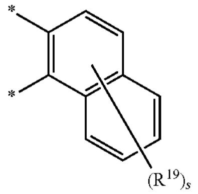

[Formula L-9]

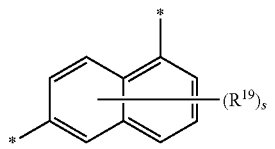

[Formula L-10]

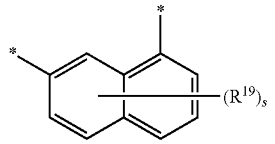

[Formula L-11]

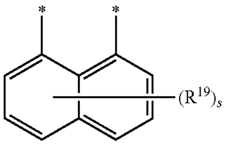

[Formula L-12]

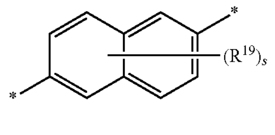

[Formula L-13]

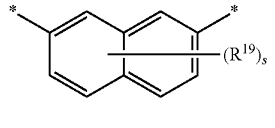

[Formula L-14]

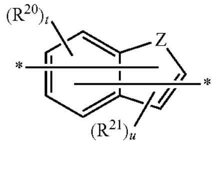

-continued

[Formula L-15]

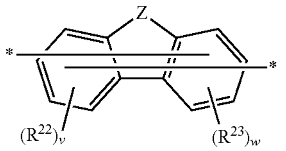

[Formula L-16]

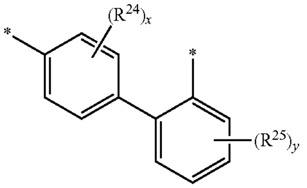

[Formula L-17]

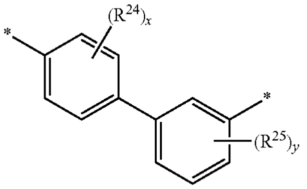

[Formula L-18]

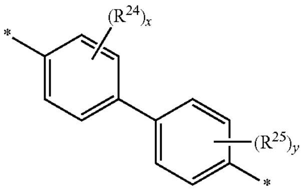

[Formula L-19]

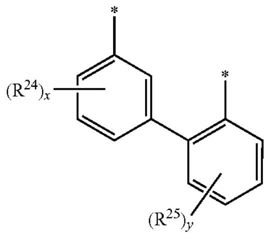

[Formula L-20]

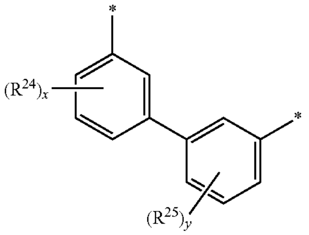

[Formula L-21]

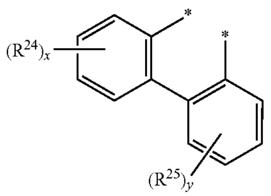

-continued

[Formula L-22]

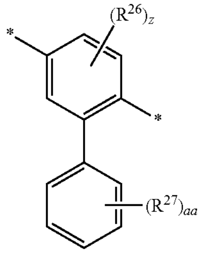

[Formula L-23]

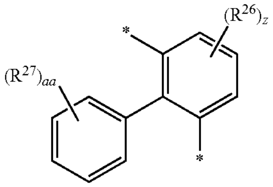

[Formula L-24]

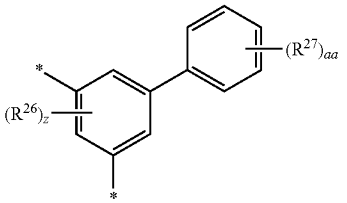

[Formula L-25]

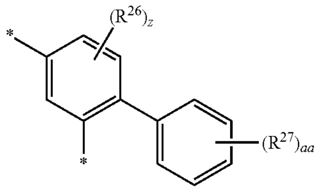

[Formula L-26]

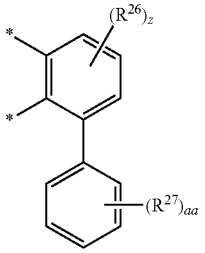

[Formula L-27]

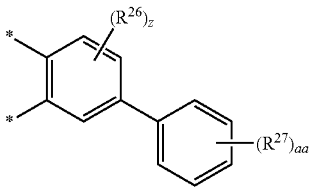

Wherein:

Z is O, S, $CR^{30}R^{31}$ or N—$Ar^5$, $R^{18}$, $R^{19}$, $R^{20}$, $R^{21}$, $R^{22}$, $R^{23}$, $R^{24}$, $R^{25}$, $R^{26}$ and $R^{27}$ are the same as the definition of $R^7$, and an adjacent plurality of groups may be bonded to each other to form a ring, $Ar^5$ is selected from the group consisting of a $C_1$-$C_{20}$ alkyl group; a $C_2$-$C_{20}$ alkenyl group; a $C_6$-$C_{20}$ aryl group; and a $C_2$-$C_{20}$ heterocyclic group including at least one heteroatom of O, N, S, Si or P;

r, t, v, w, x and y are independently an integer of 0 to 4, s is an integer of 0 to 6, u is an integer of 0 to 2, z is an integer 0 to 3, aa is an integer of 0 to 5,

* indicates the position to be bonded.

Also, at least one of $L^1$, $L^2$, $Ar^1$ and $Ar^2$ is a substituent containing deuterium.

Specifically, the compound of Formula 1 may be any one of the following compounds P-1 to P-136, but is not limited thereto.

P-1

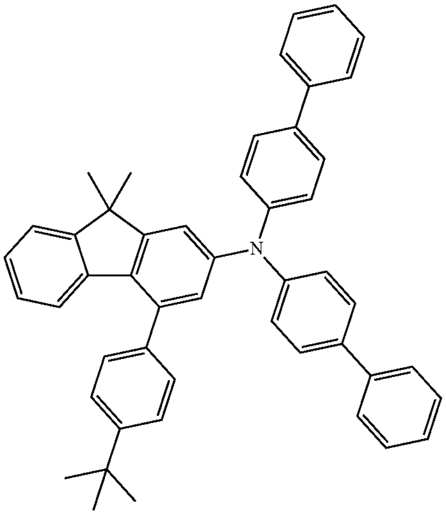

P-2

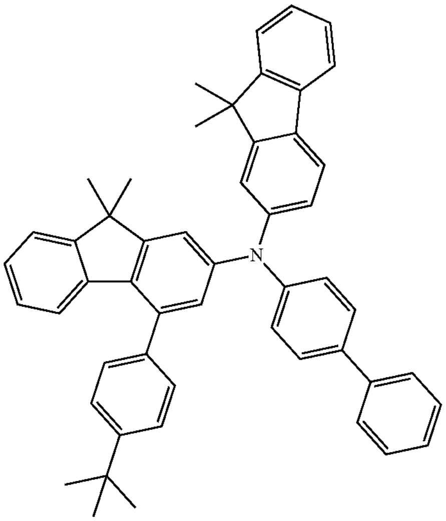

-continued

P-3

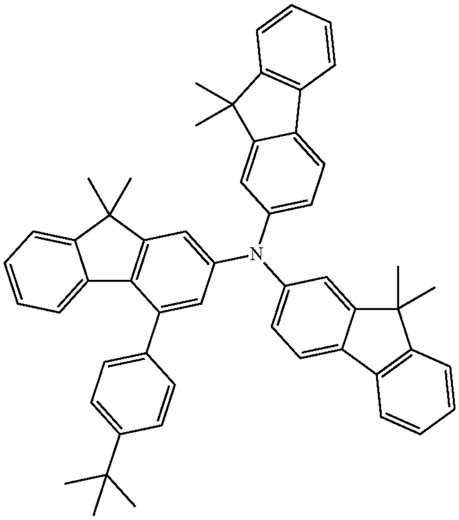

P-4

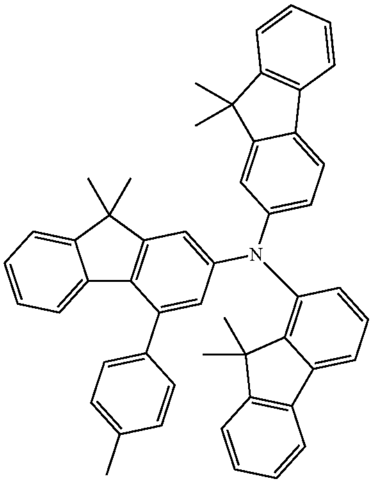

P-5

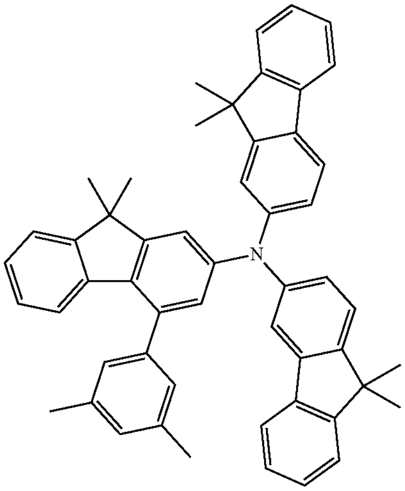

-continued
P-6
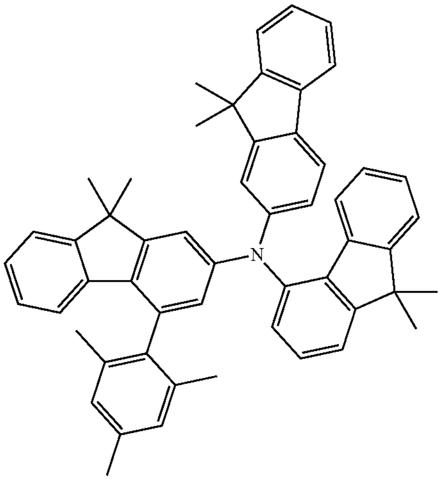
P-7
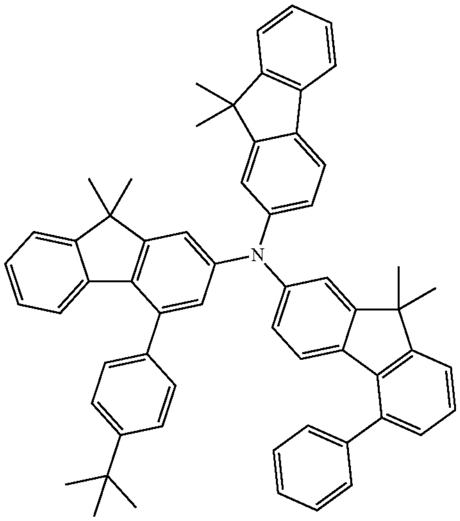
P-8
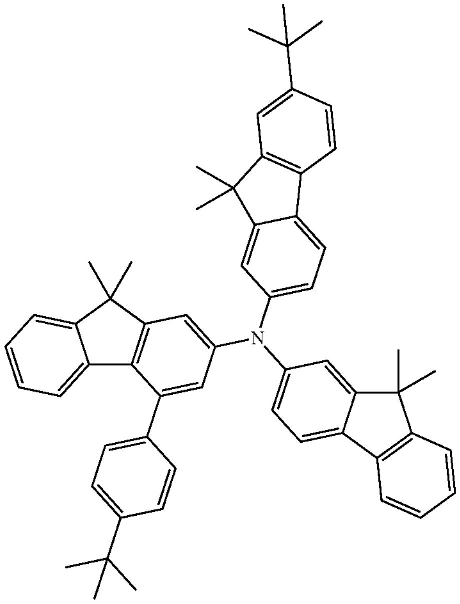
-continued
P-9
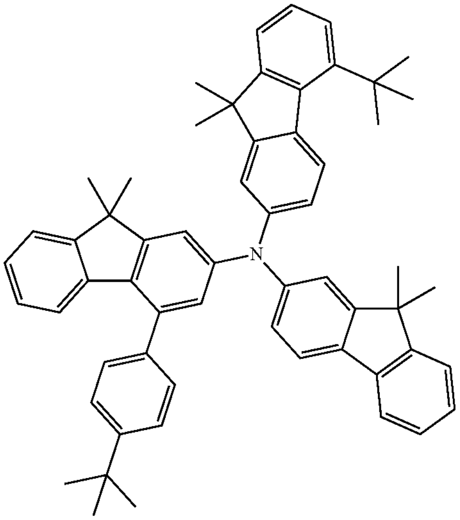
P-10
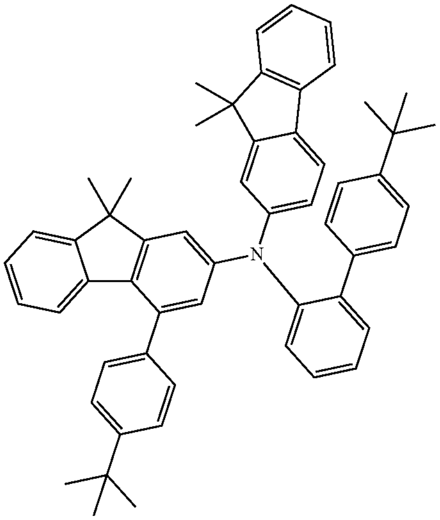
P-11
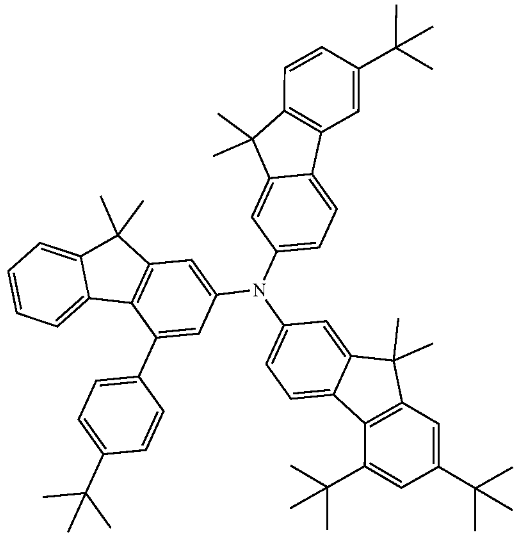

P-12
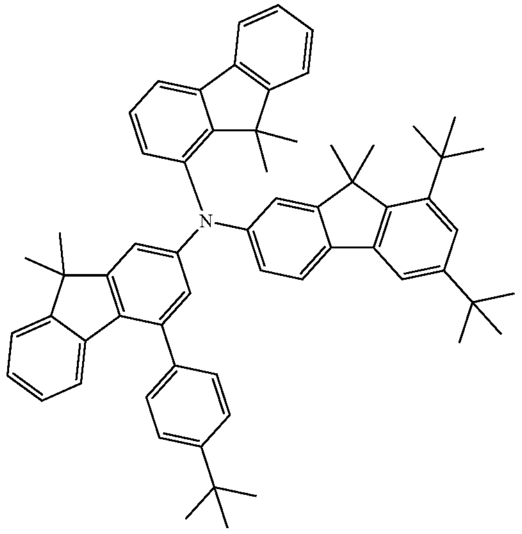
P-13
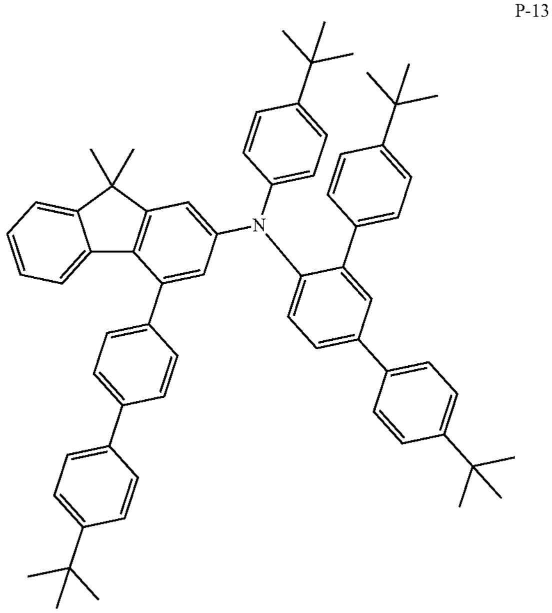
P-14
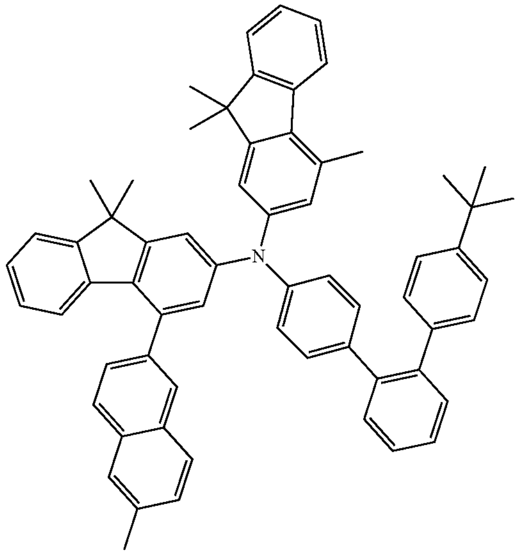
P-15
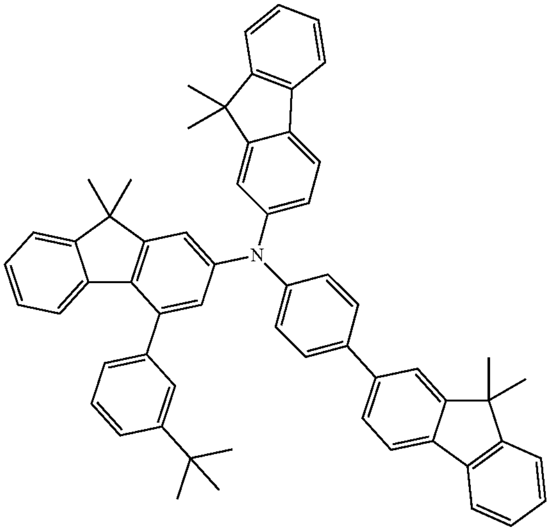

-continued
P-16
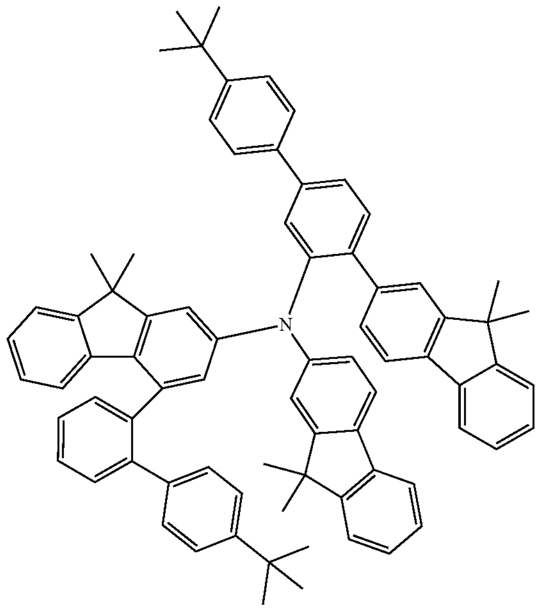
P-17
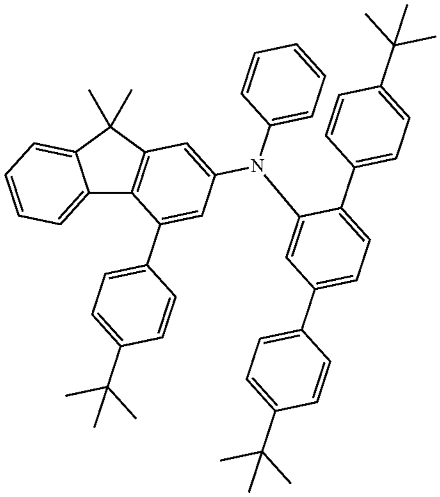
P-18
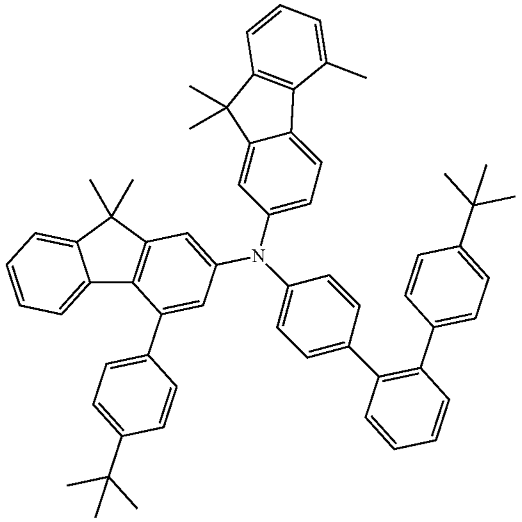
-continued
P-19
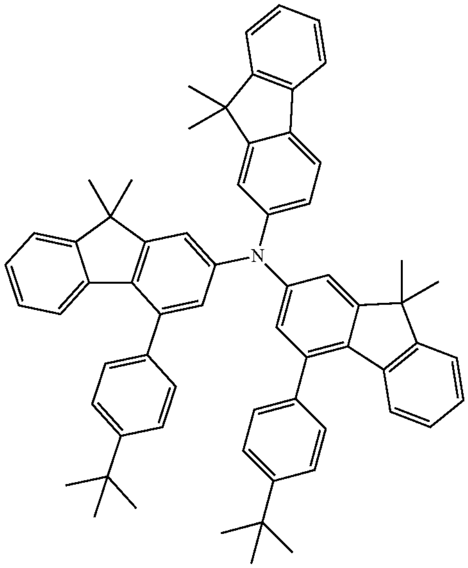
P-20
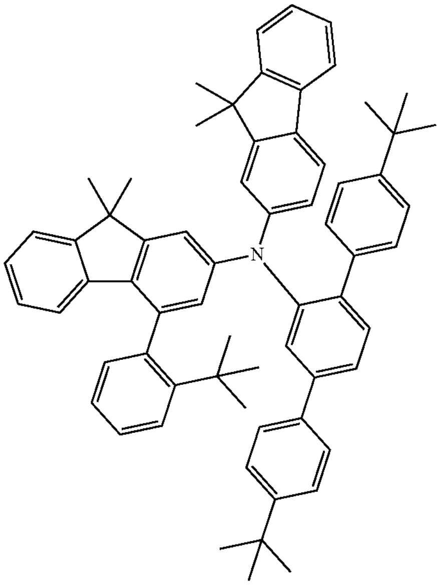

-continued
P-21
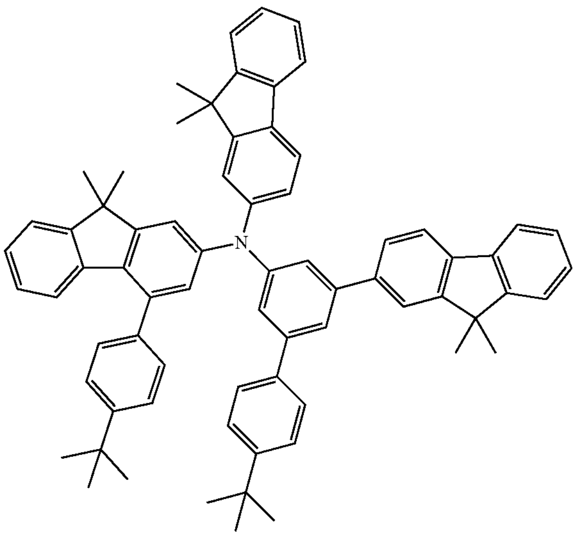
P-22
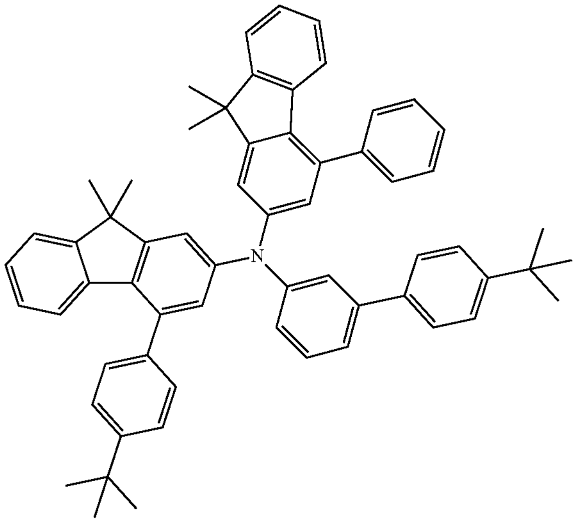
P-23
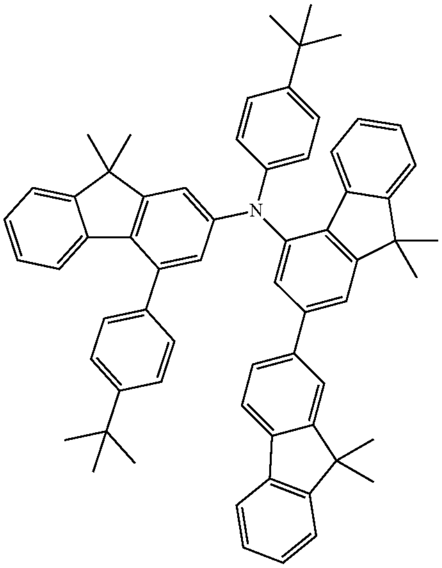
-continued
P-24
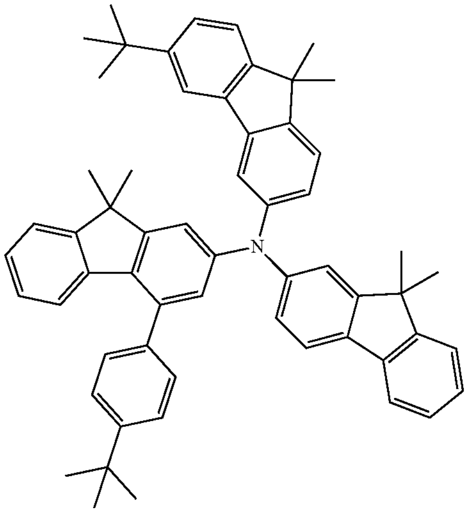
P-25
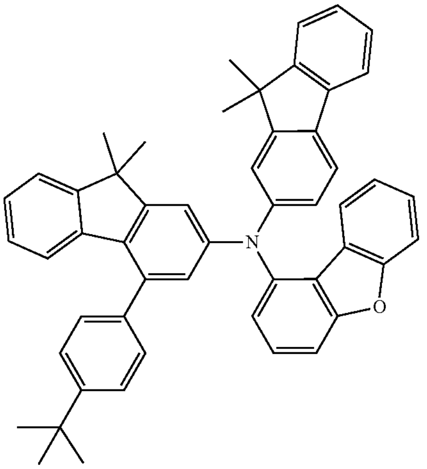
P-26
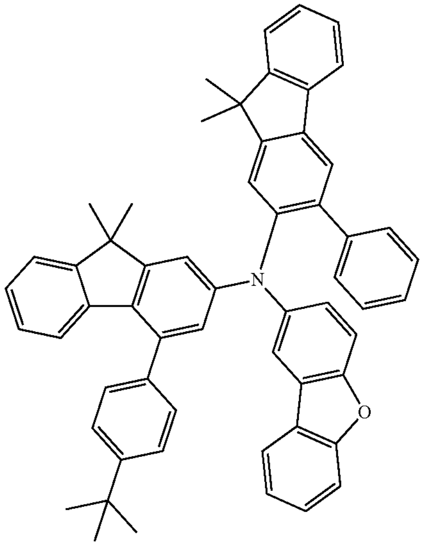

-continued
P-27
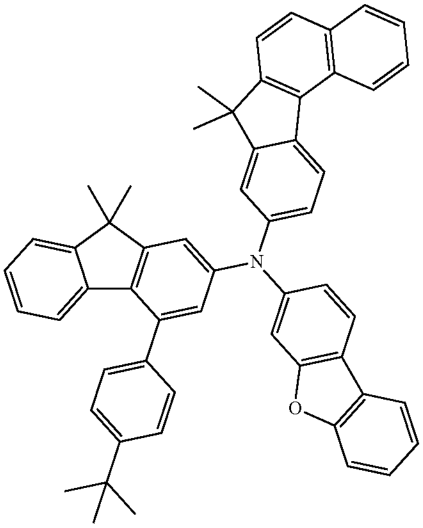
P-28
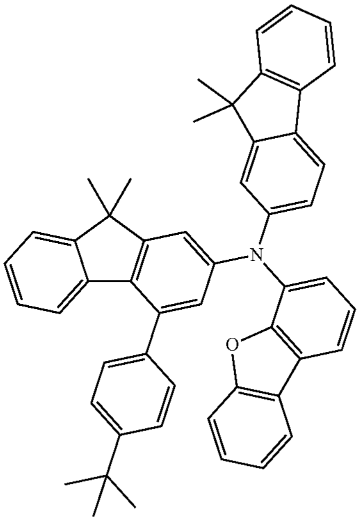
P-29
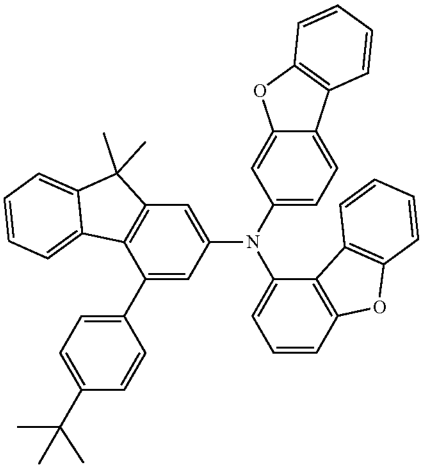
-continued
P-30
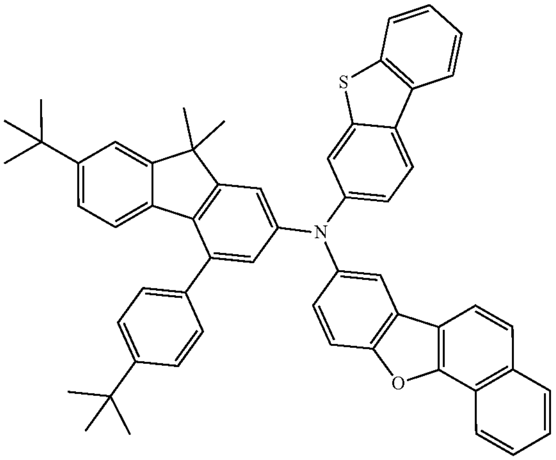
P-31
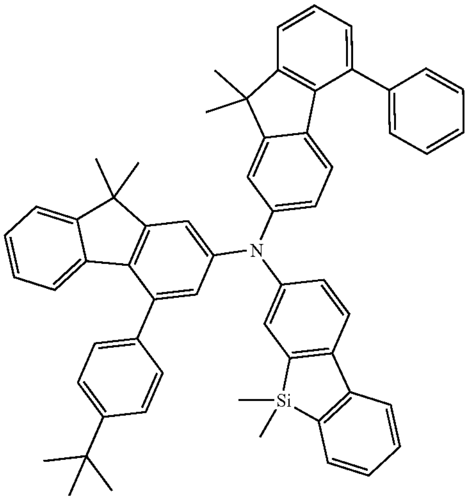
P-32
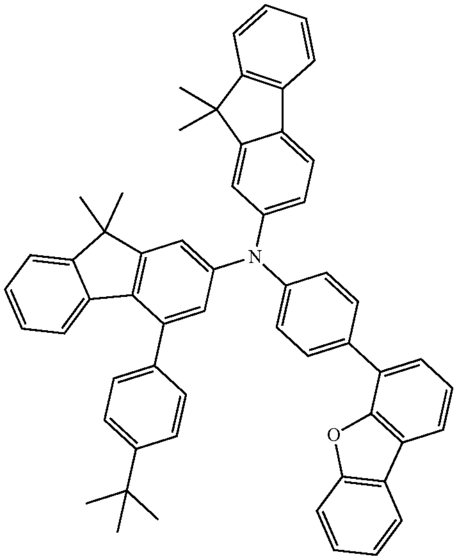

-continued
P-33
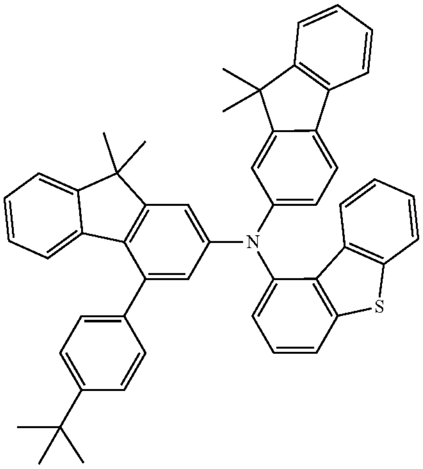
P-34
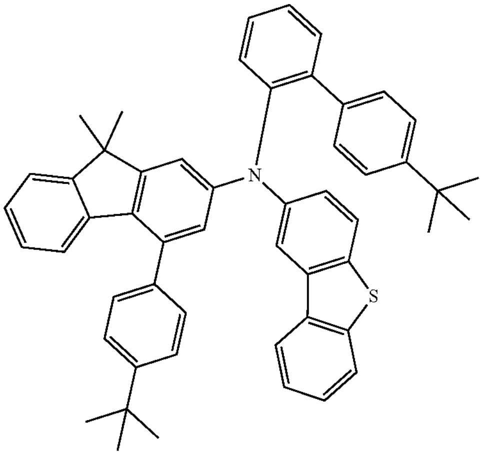
P-35
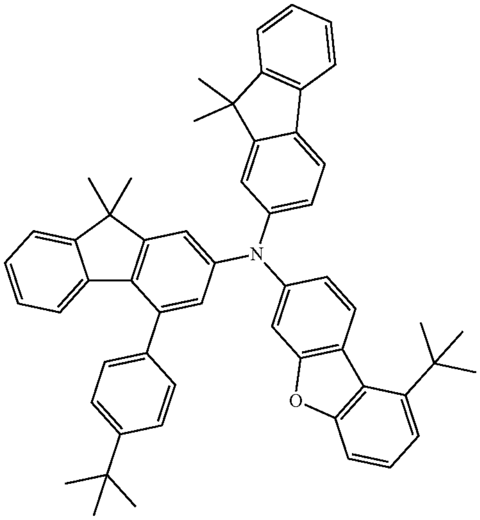
-continued
P-36
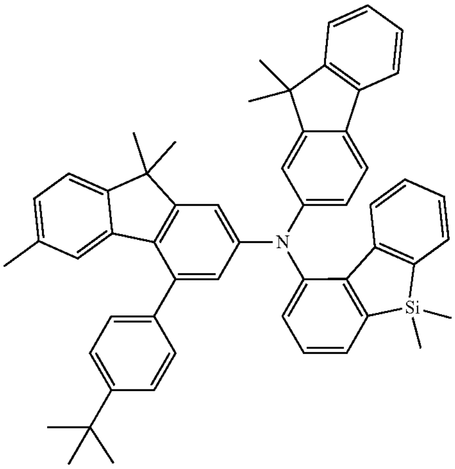
P-37
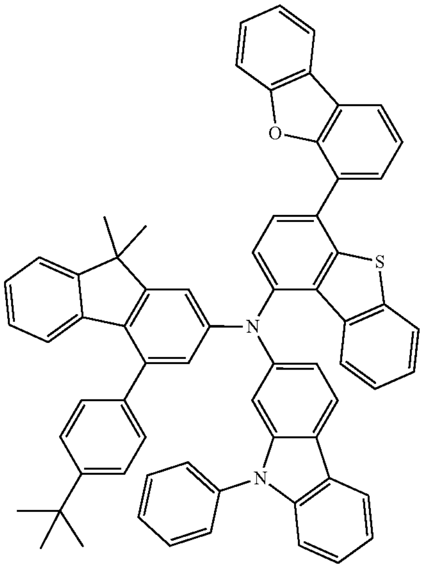
P-38
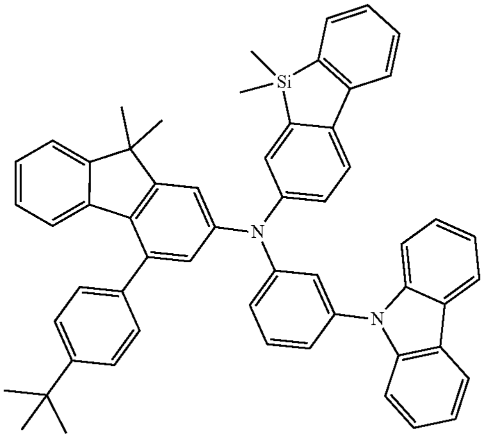

-continued
P-39
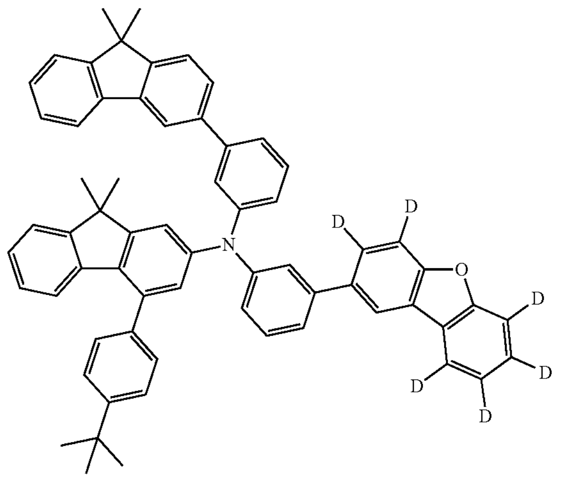
P-40
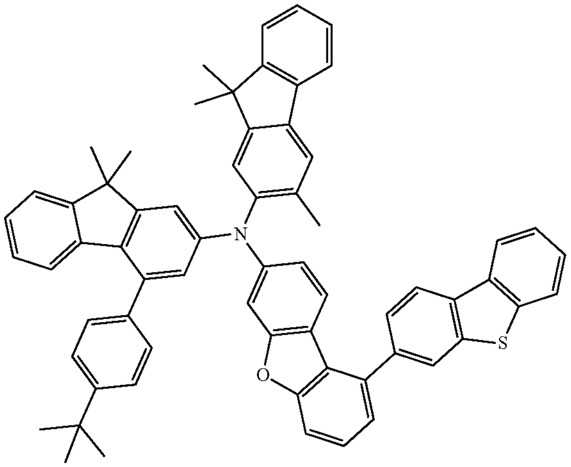
P-41
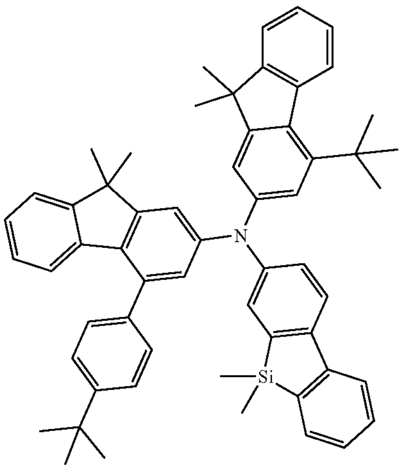
-continued
P-42
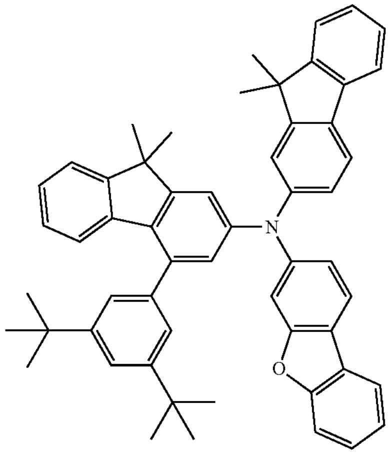
P-43
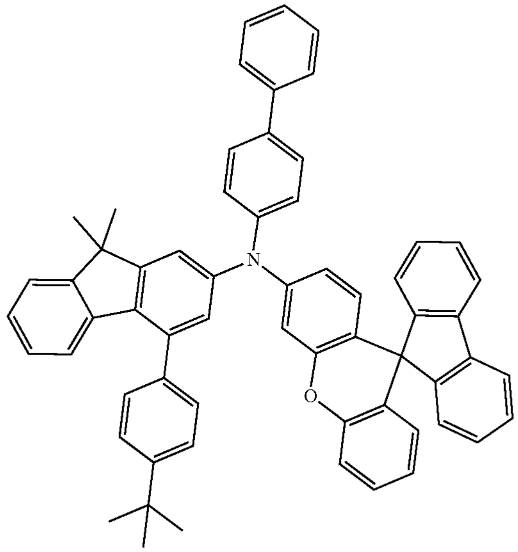
P-44
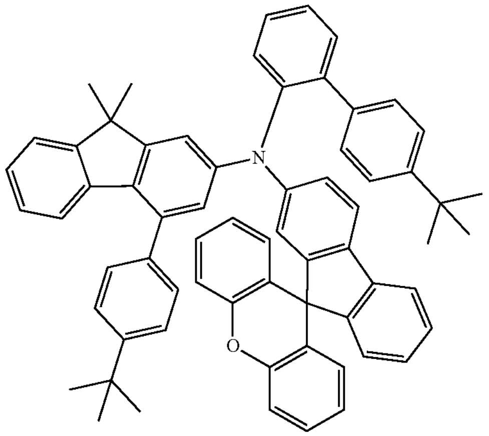

-continued
P-45
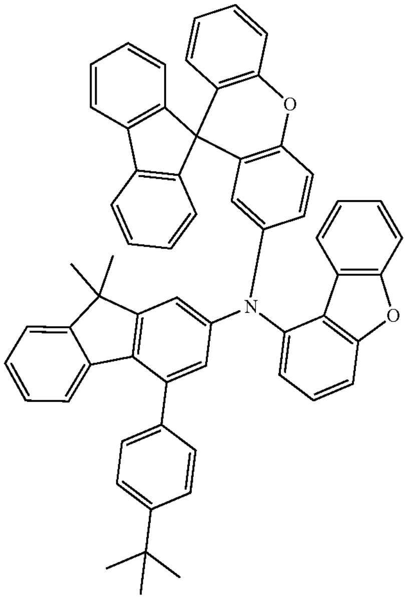
P-46
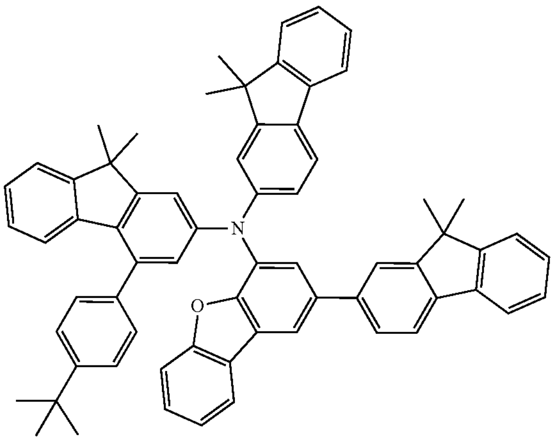
P-47
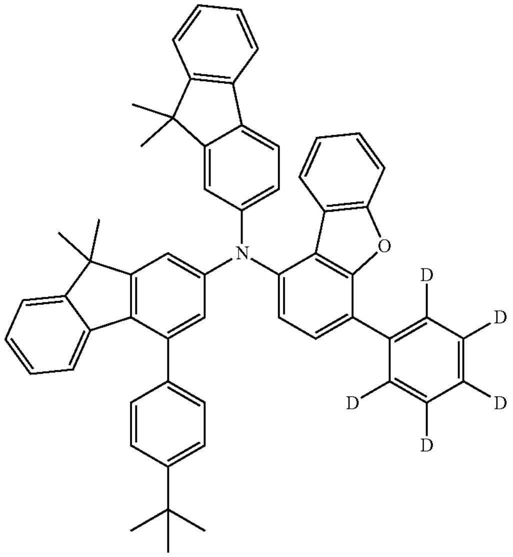
-continued
P-48
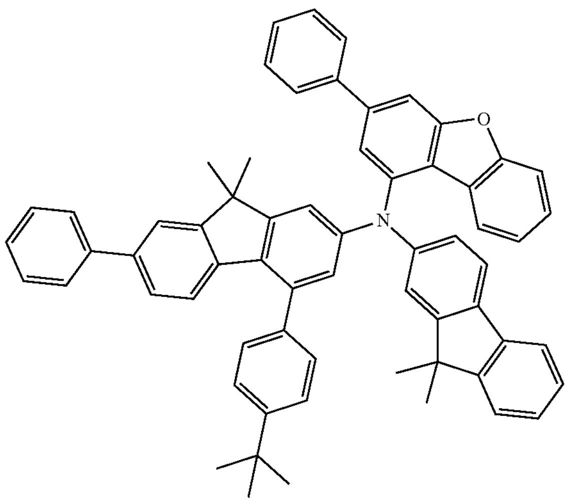
P-49
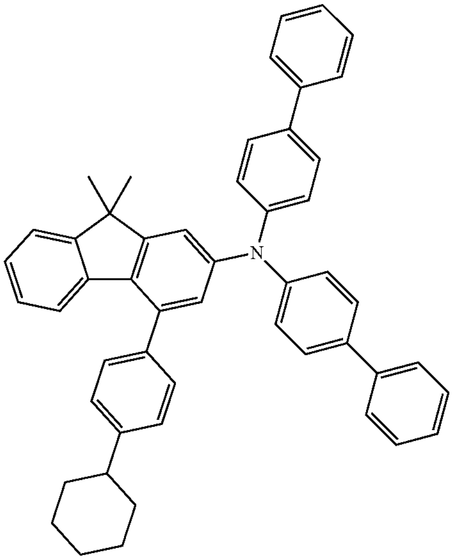
P-50
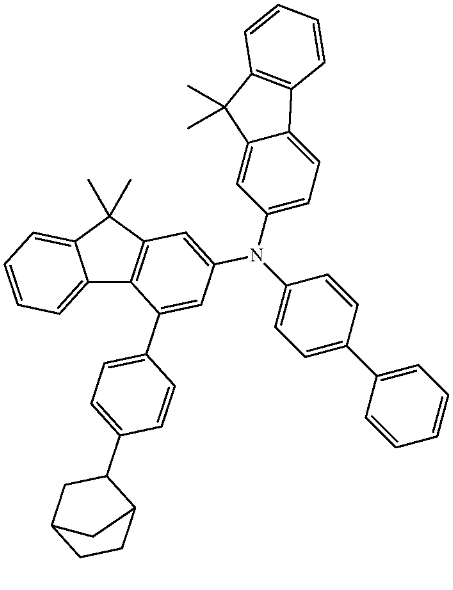

-continued
P-51
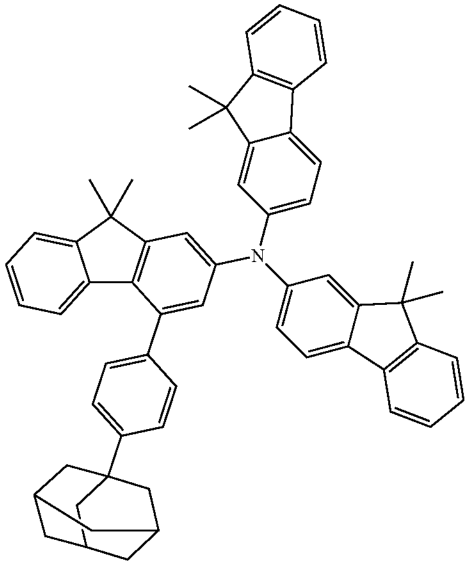
P-52
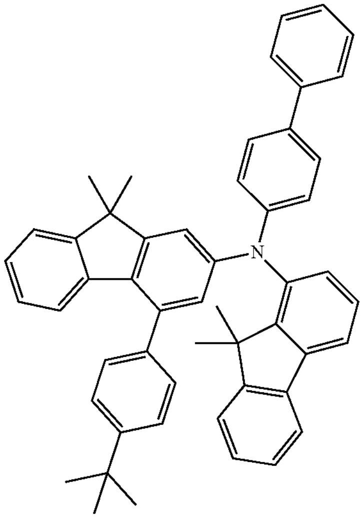
P-53
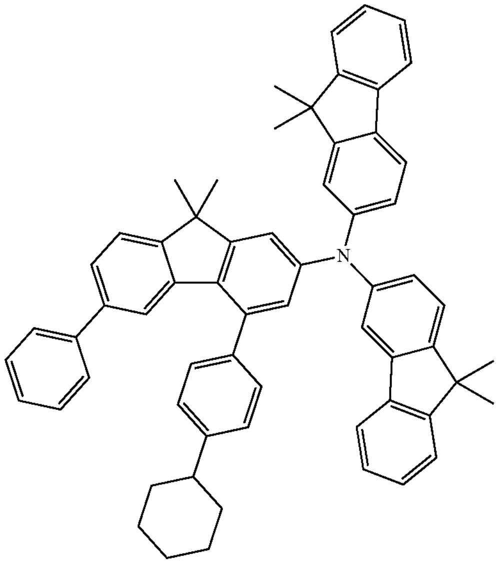
-continued
P-54
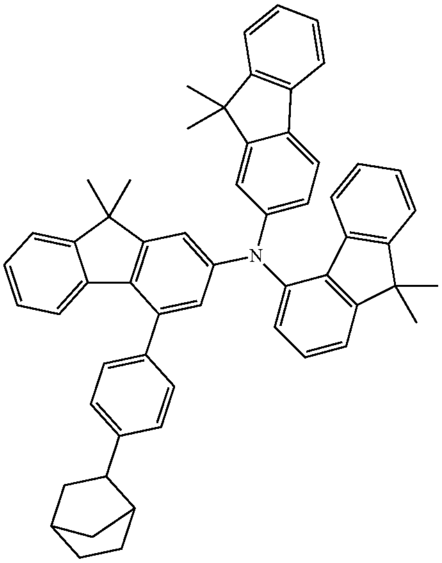
P-55
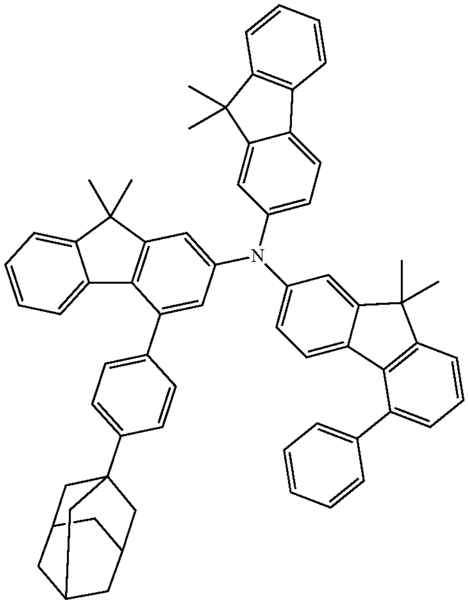

P-56
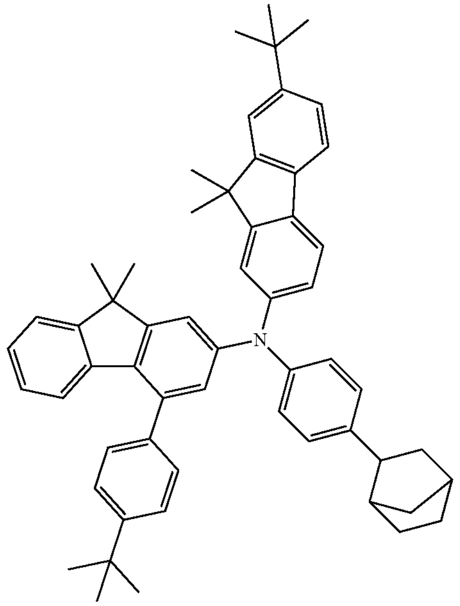
P-57
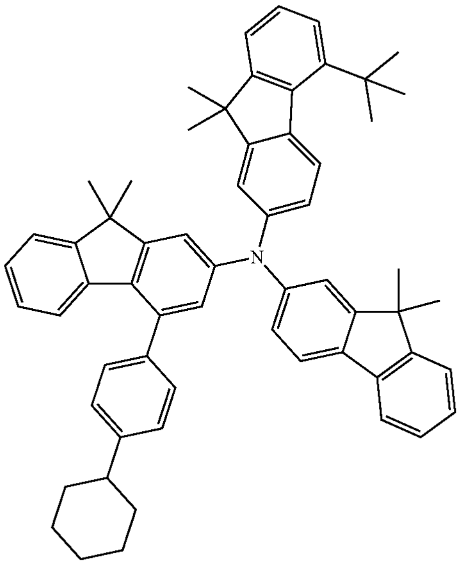
P-58
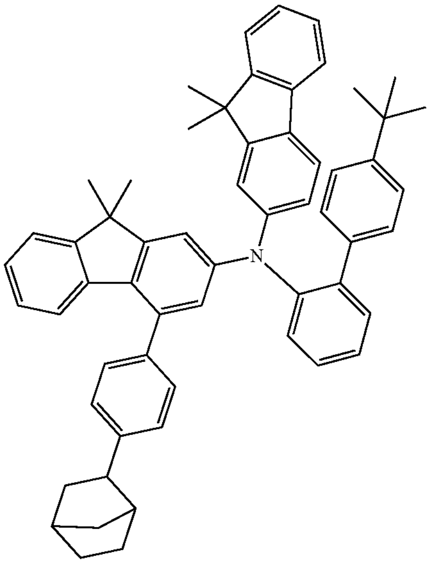
P-59
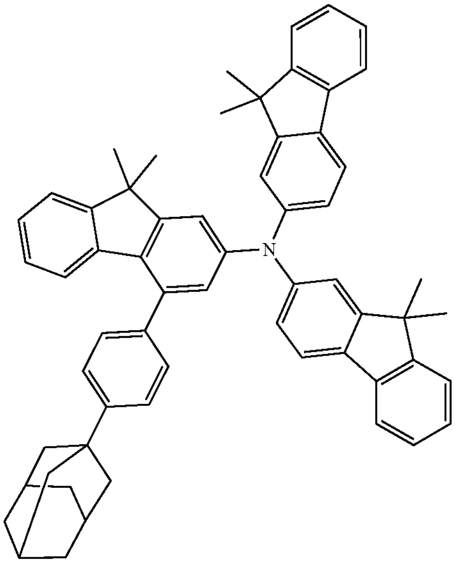

-continued
P-60
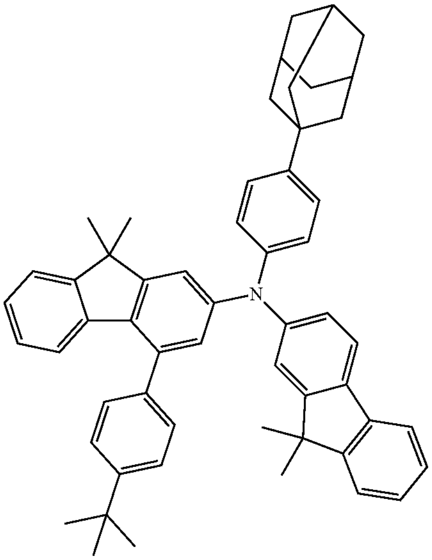
P-61
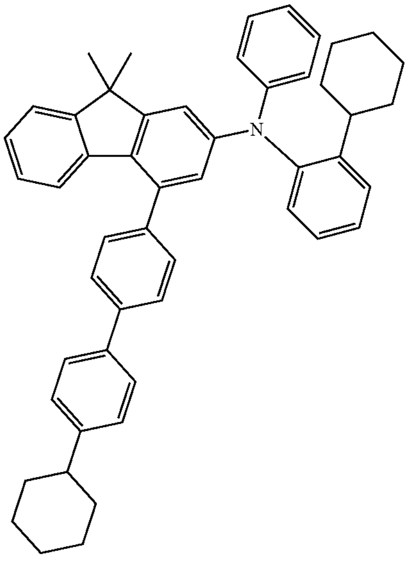
P-62
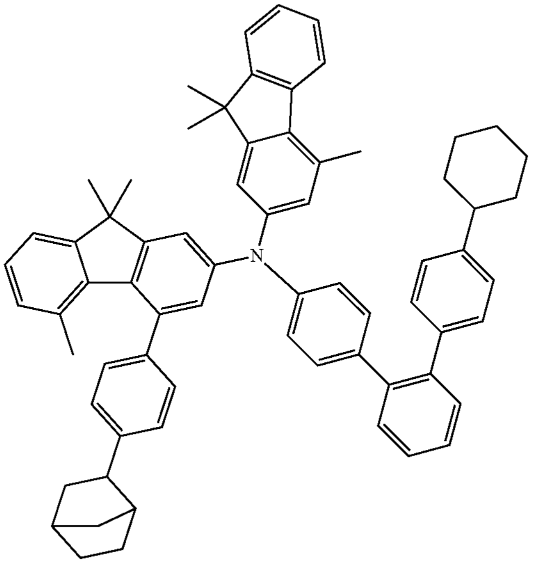
P-63
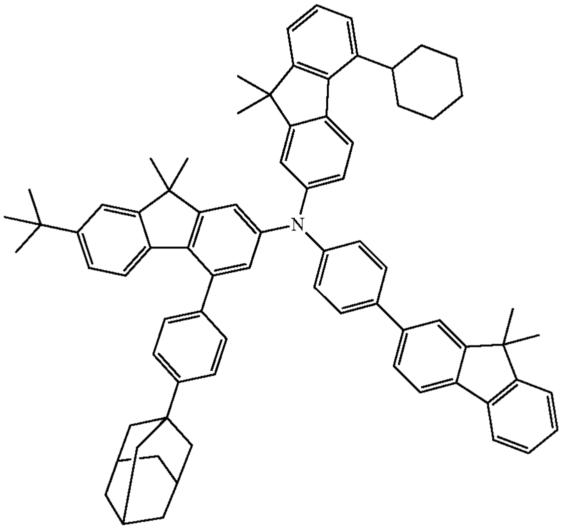
P-64
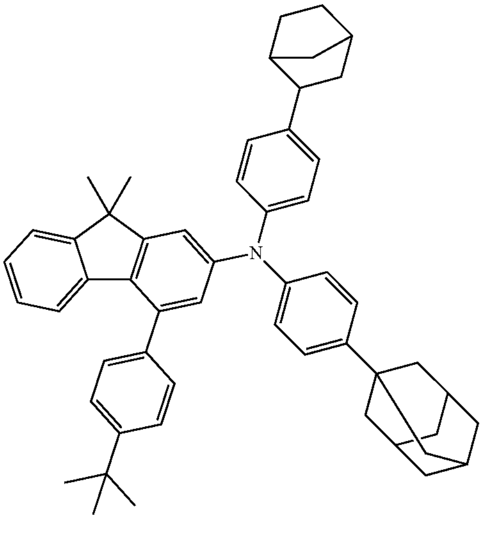

-continued
P-65
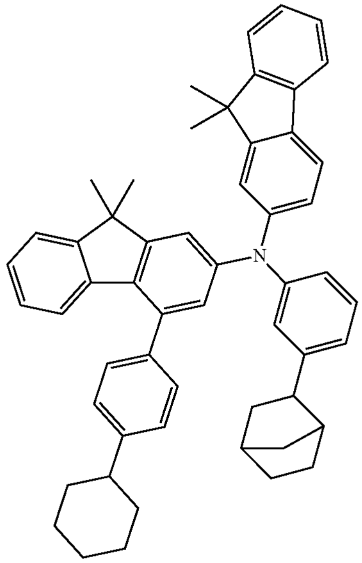
P-66
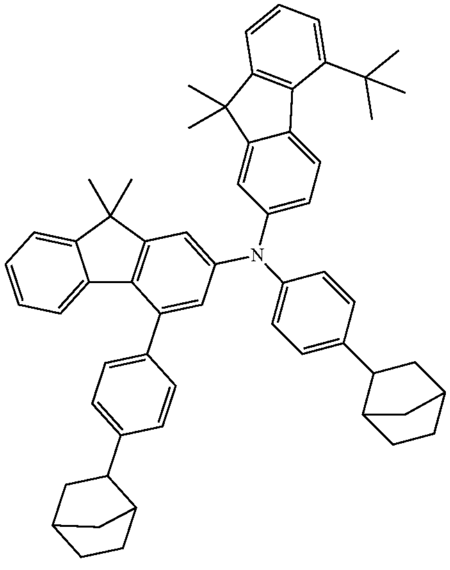
-continued
P-67
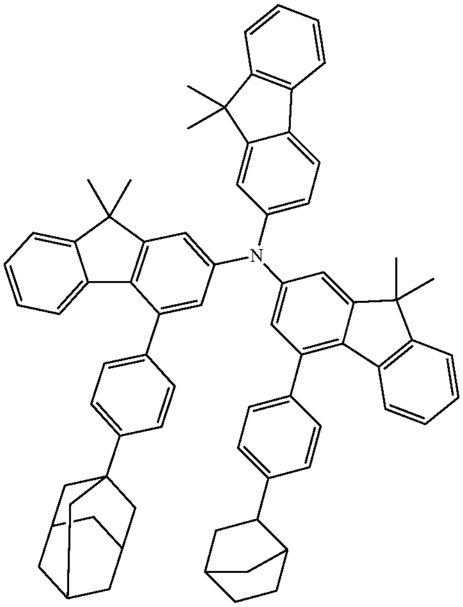
P-68
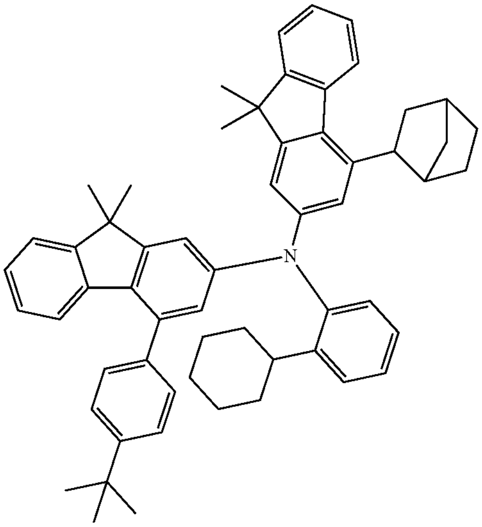

P-69
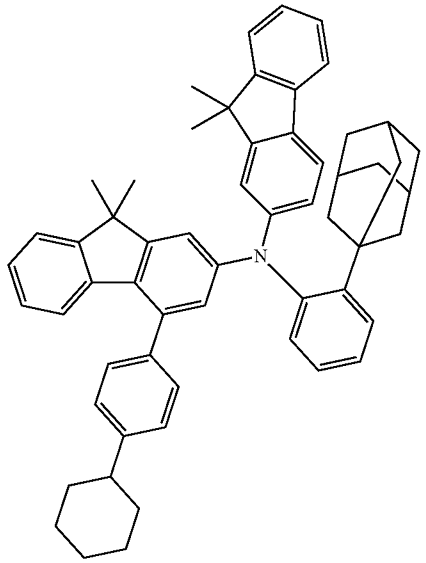
P-70
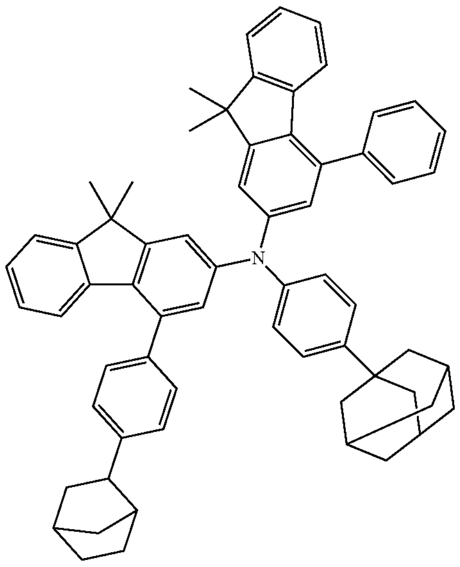
P-71
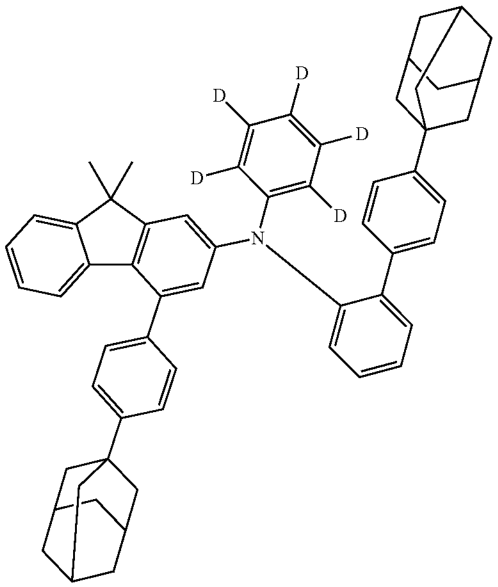
P-72
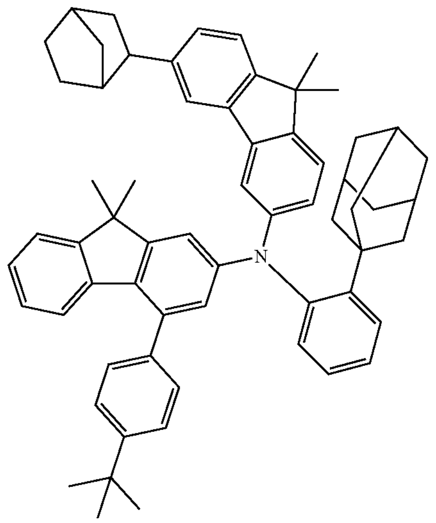
P-73
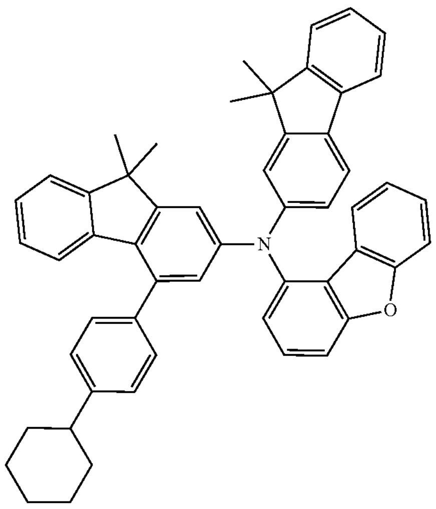

-continued
P-74
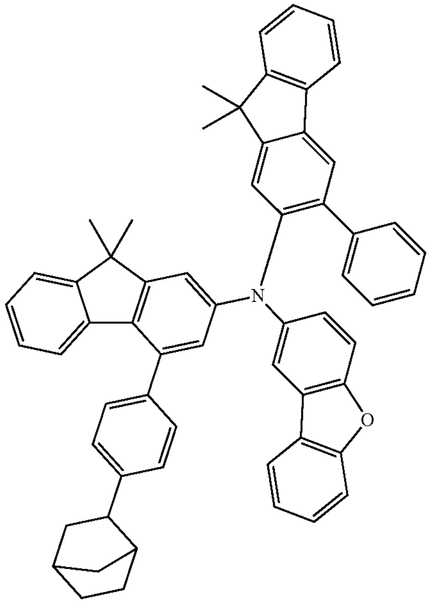
P-75
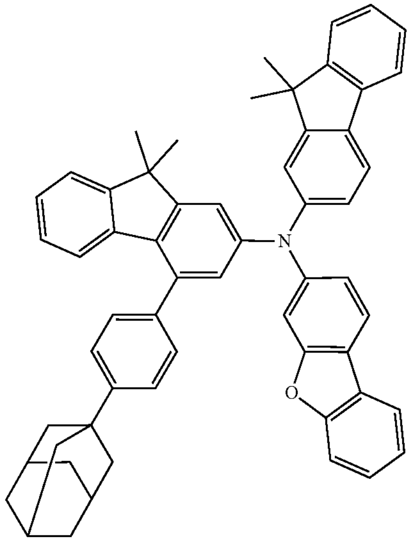
P-76
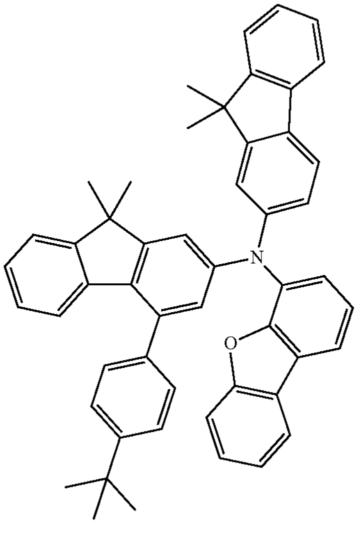
-continued
P-77
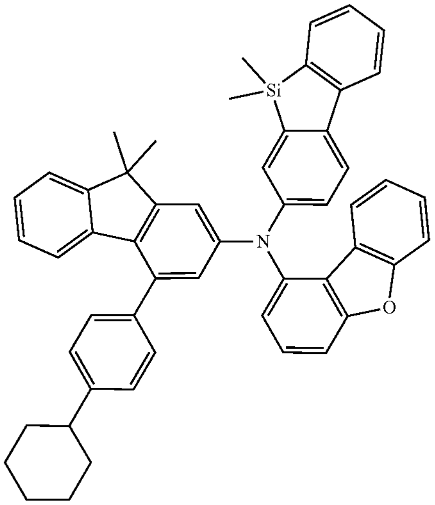
P-78
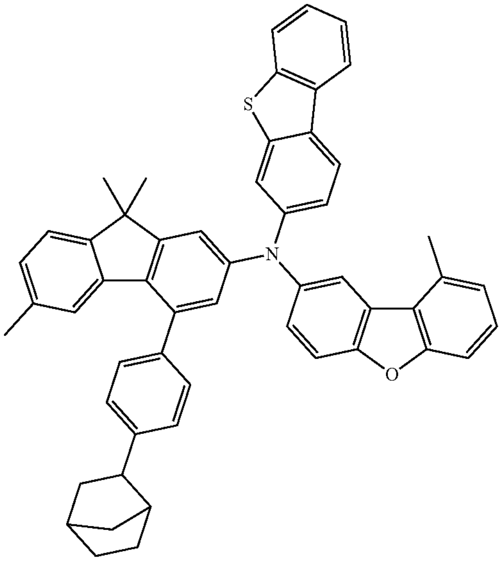
P-79
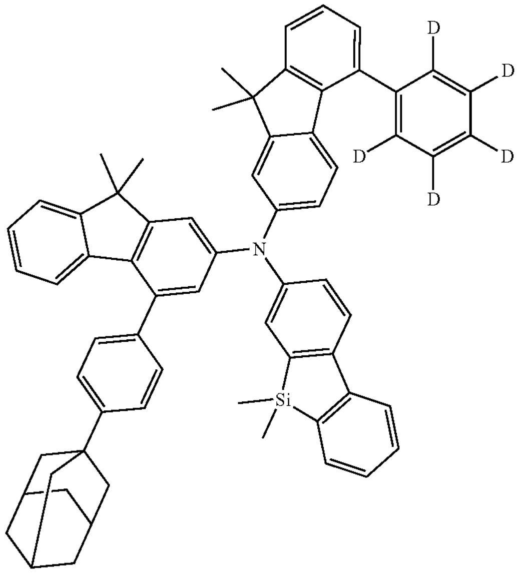

-continued
P-80
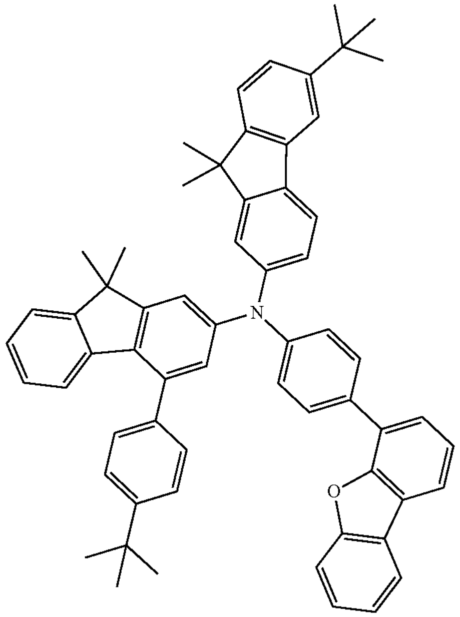
P-81
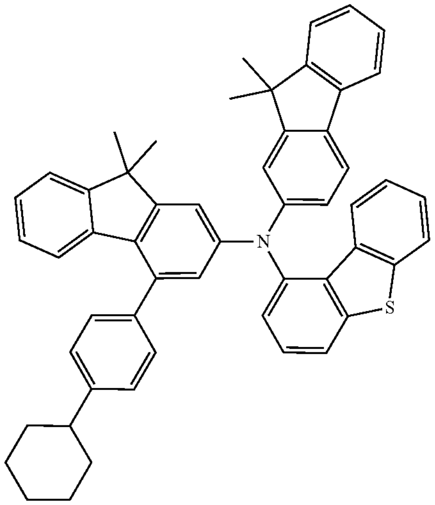
-continued
P-82
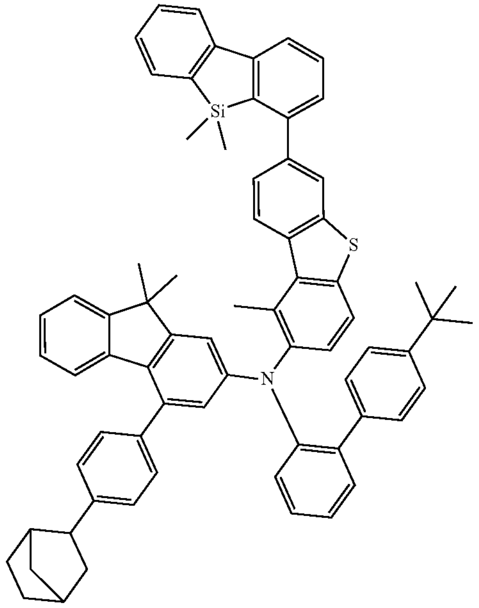
P-83
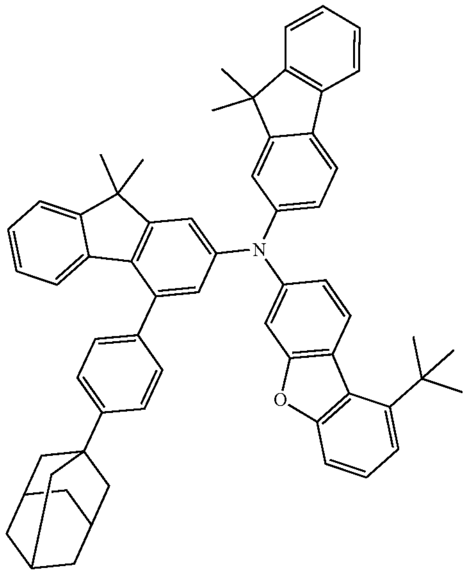
P-84
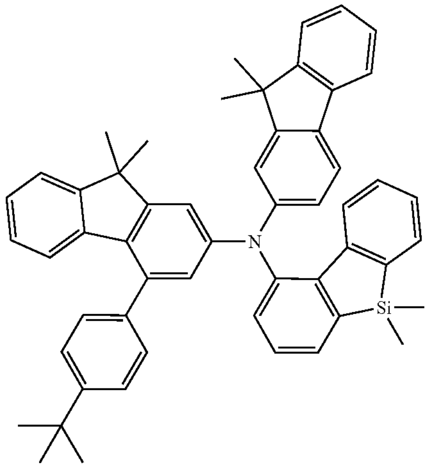

-continued
P-85
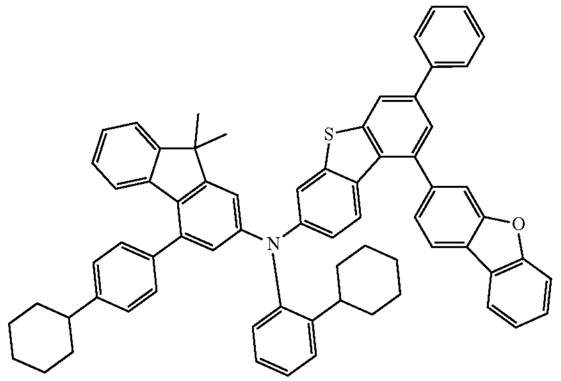
P-86
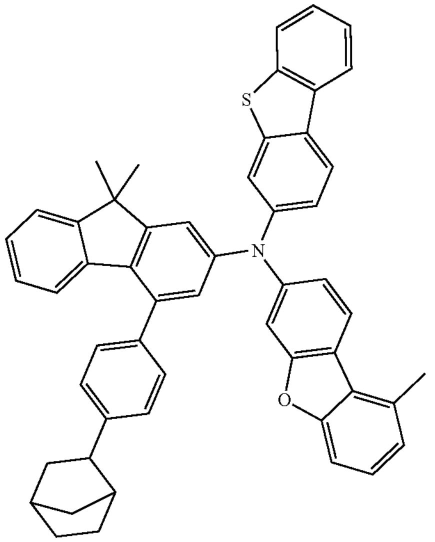
P-87
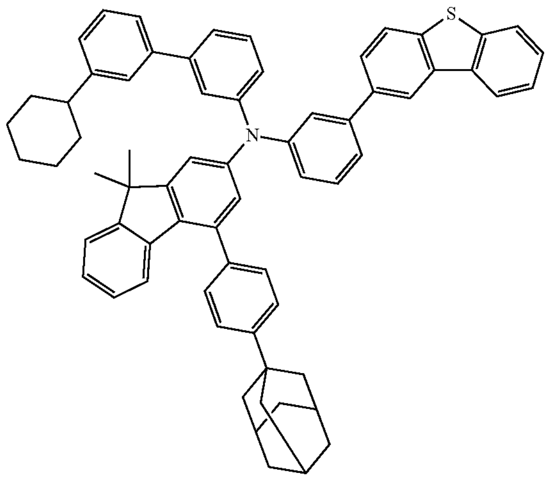
-continued
P-88
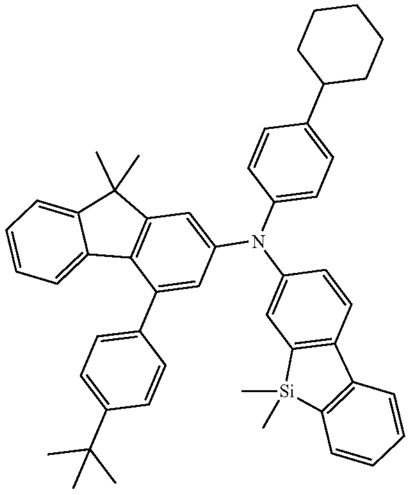
P-89
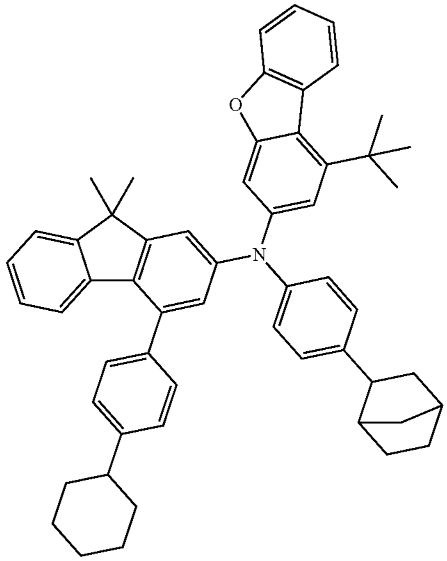
P-90
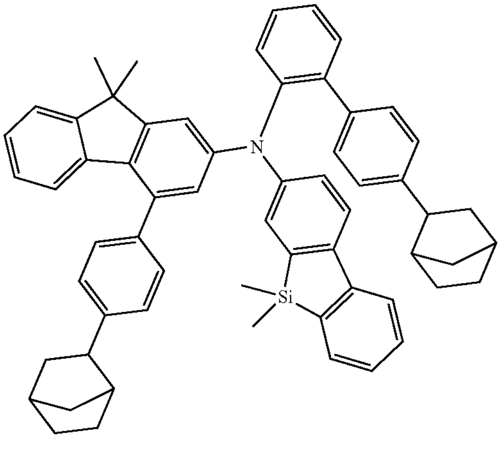

P-91
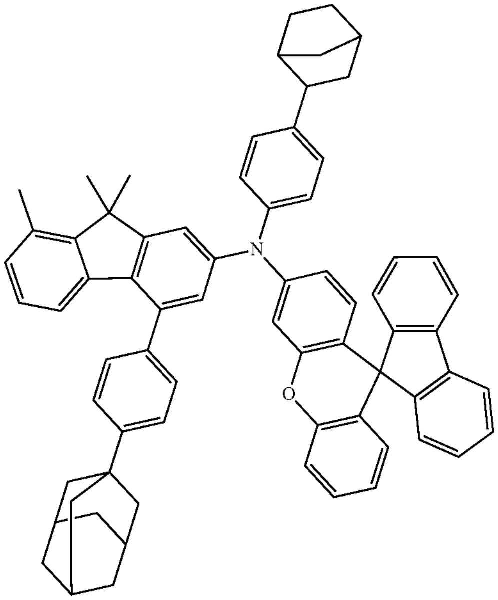
P-92
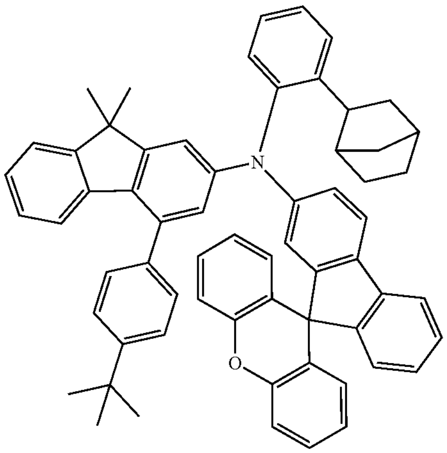
P-93
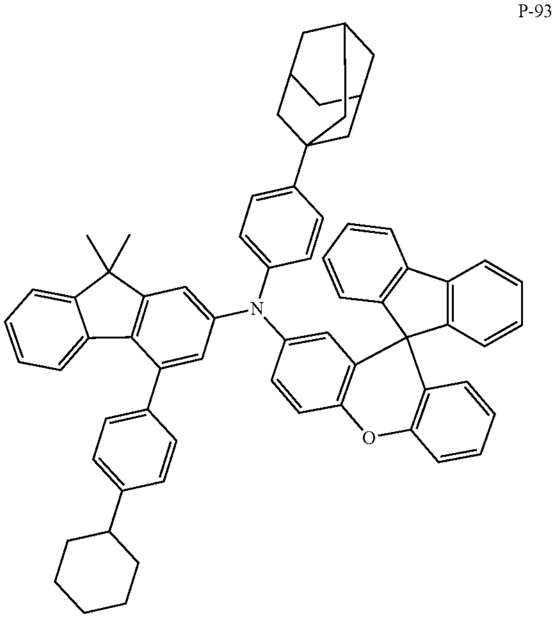
P-94
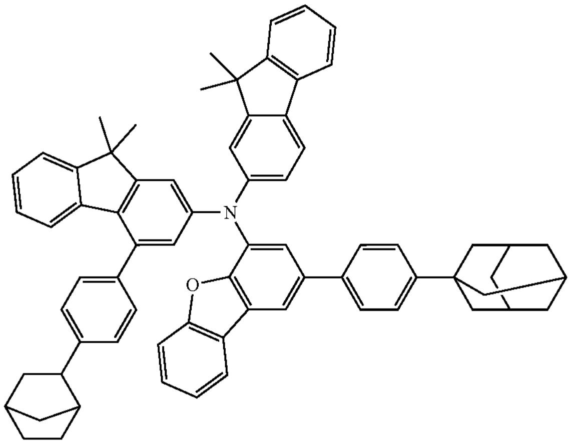
P-95
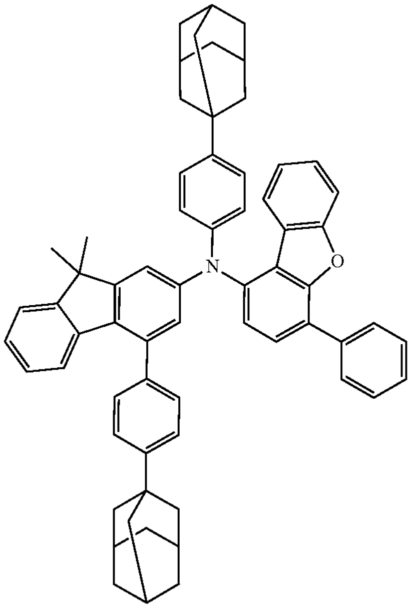
P-96
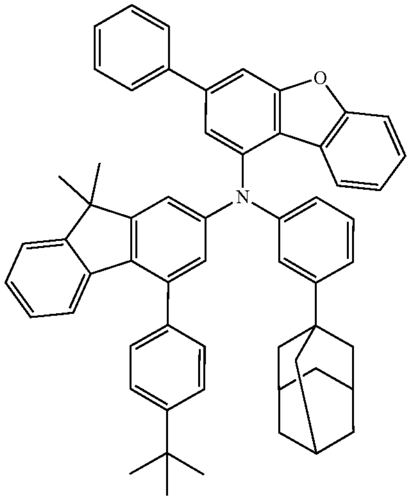

-continued
P-97
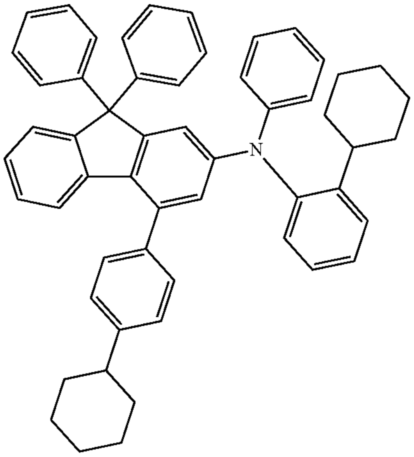
P-98
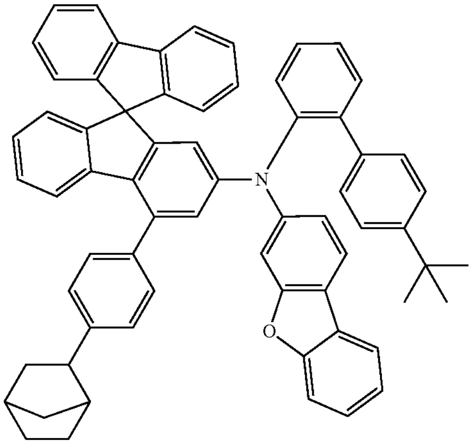
P-99
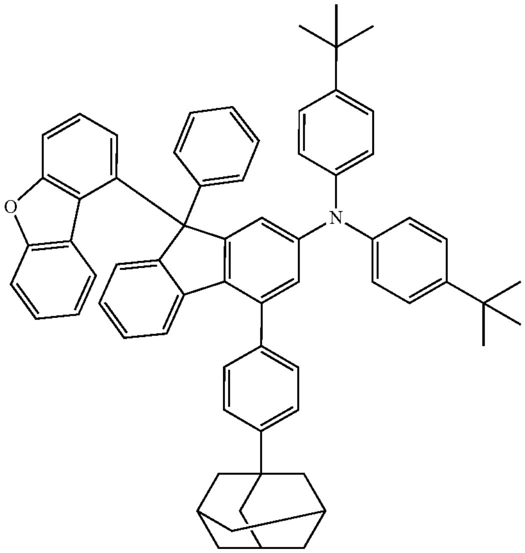
-continued
P-100
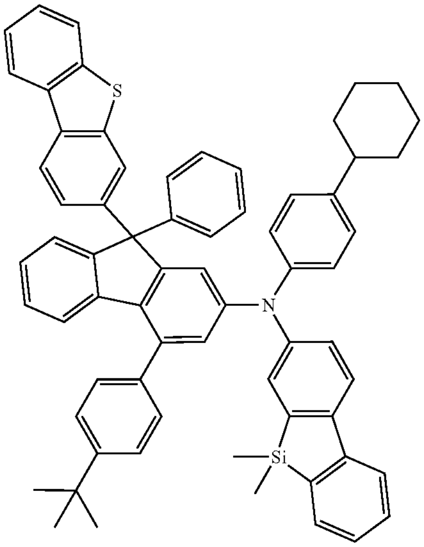
P-101
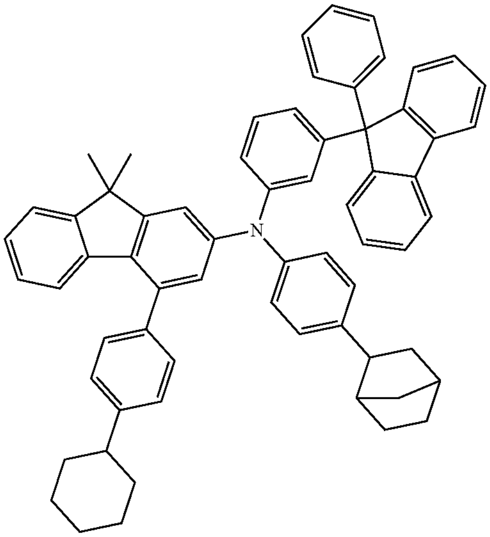

-continued
P-102
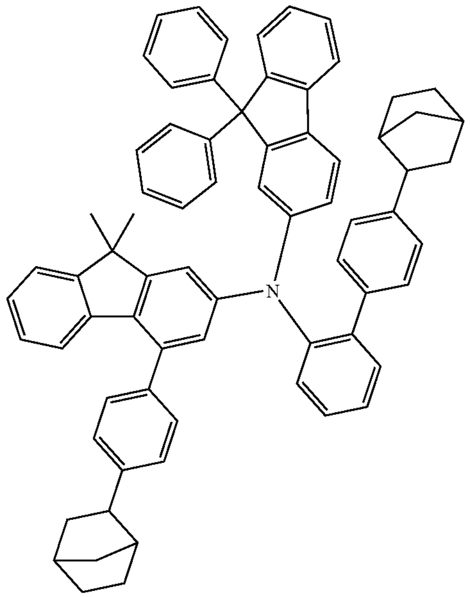
P-103
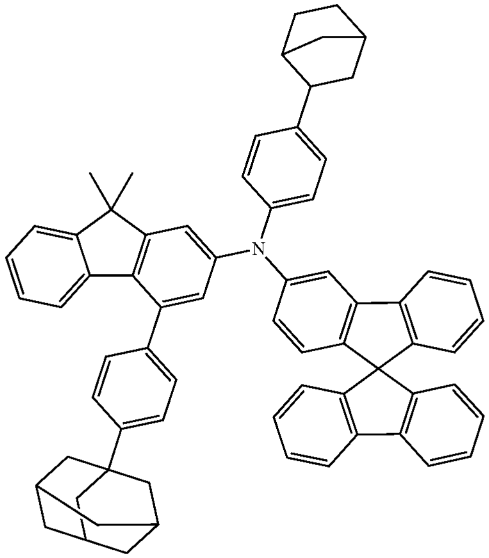
-continued
P-104
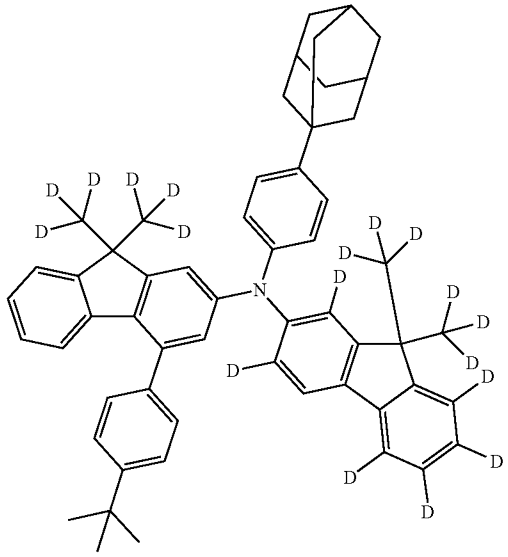
P-105
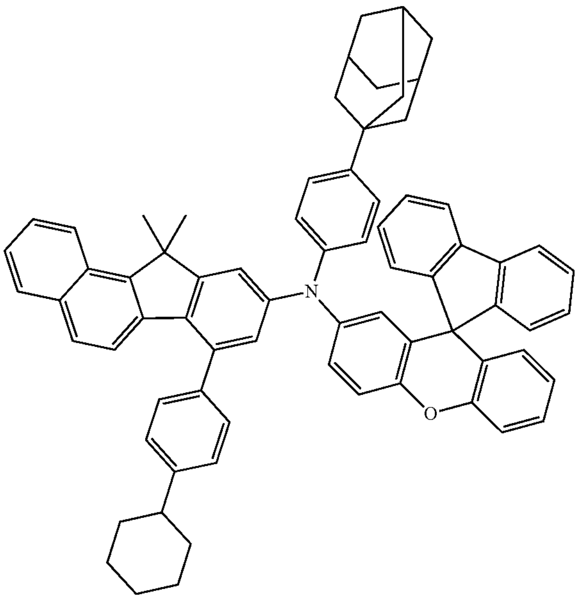
P-106
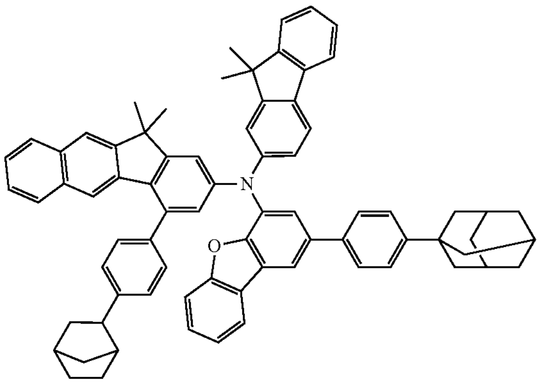

-continued
P-107
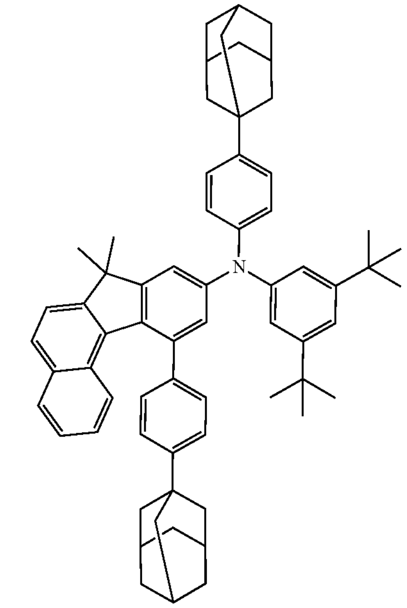
p-108
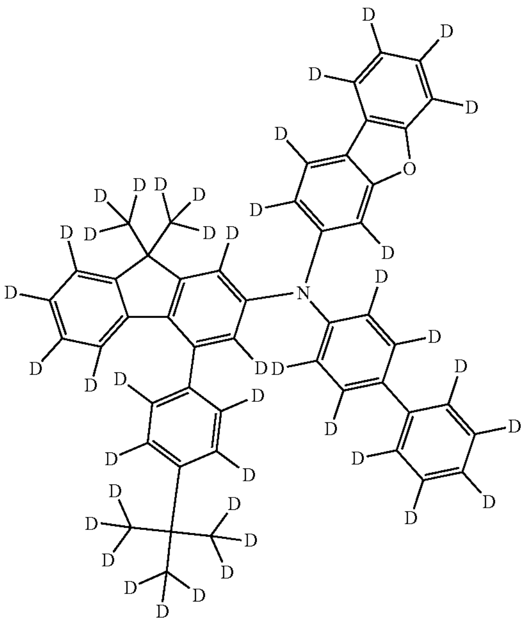
P-109
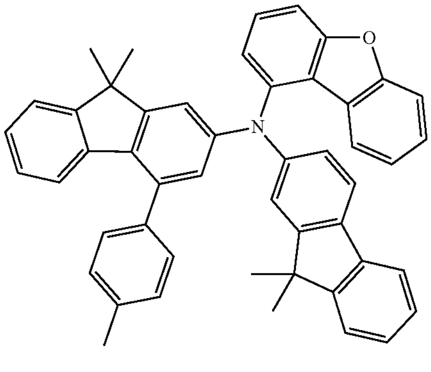
-continued
P-110
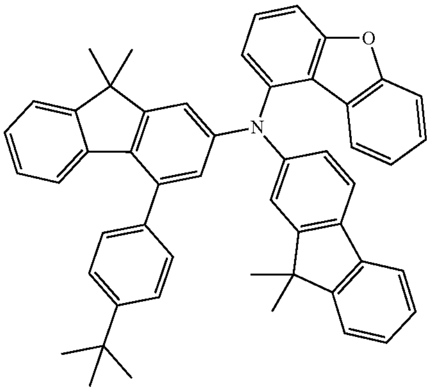
P-111
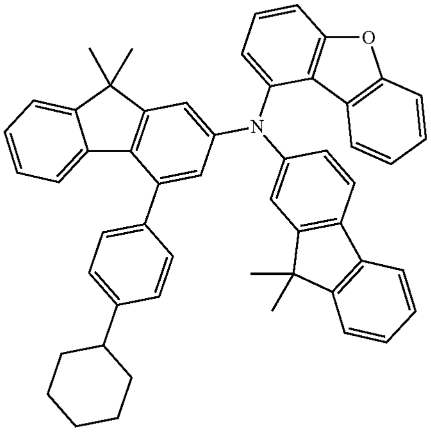
P-112
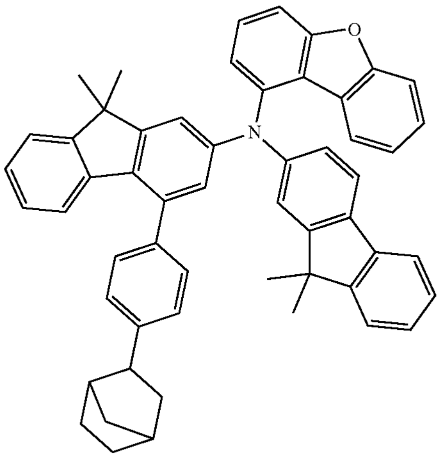

-continued
P-113
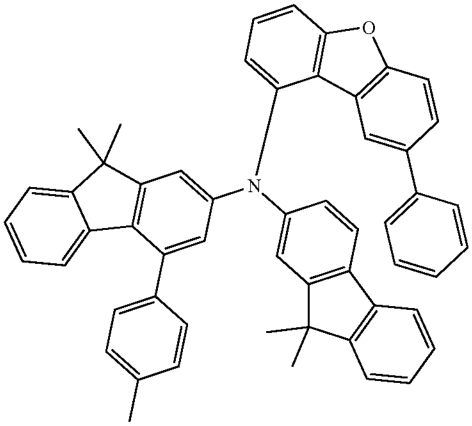
P-114
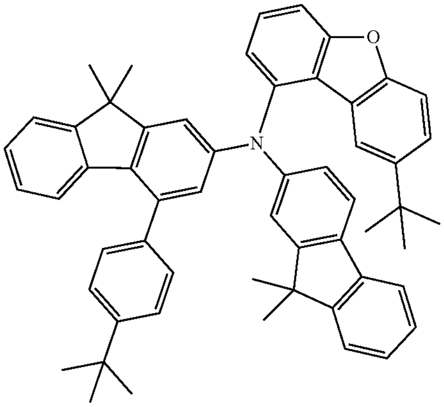
P-115
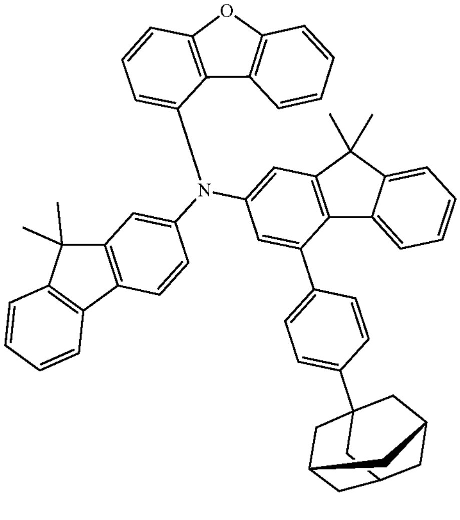
-continued
P-116
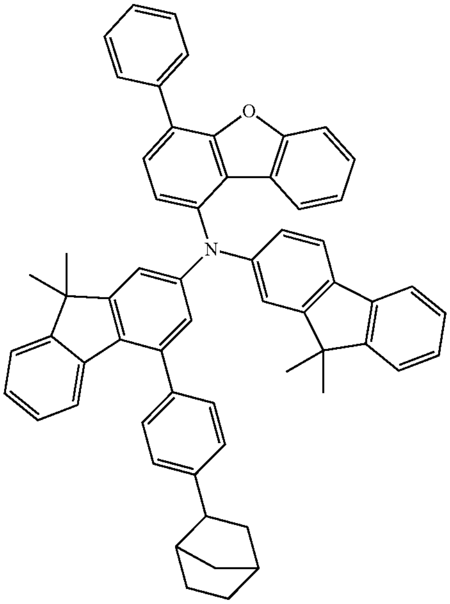
P-117
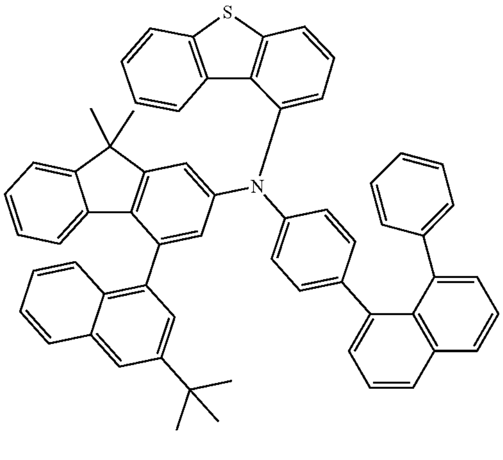

P-118
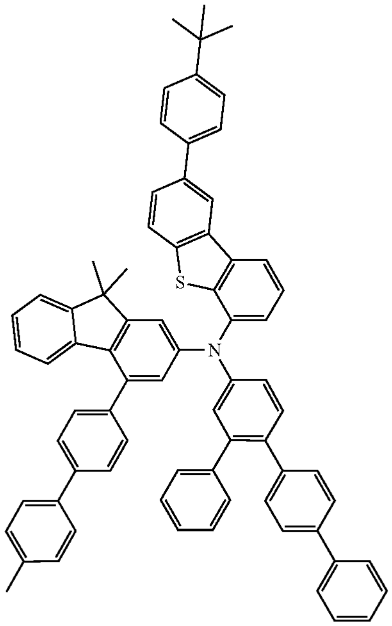
P-119
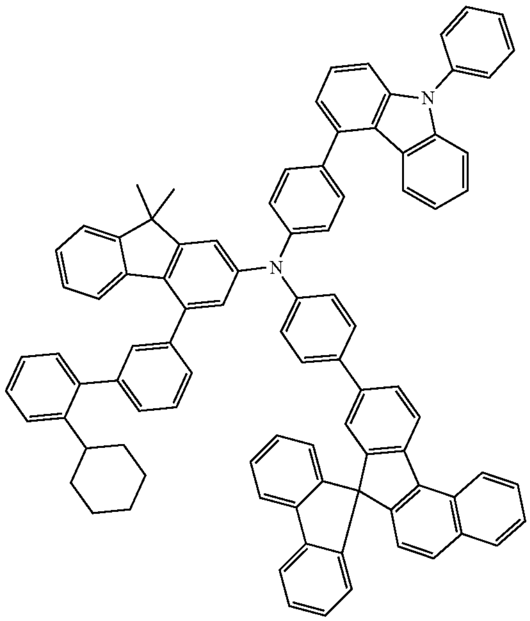
P-120
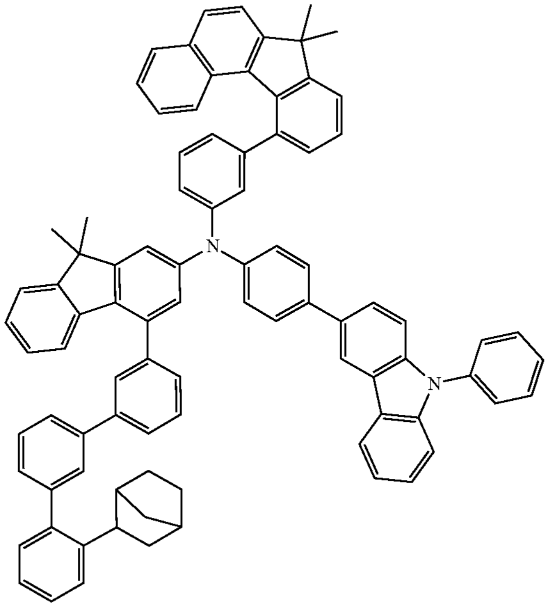
P-121
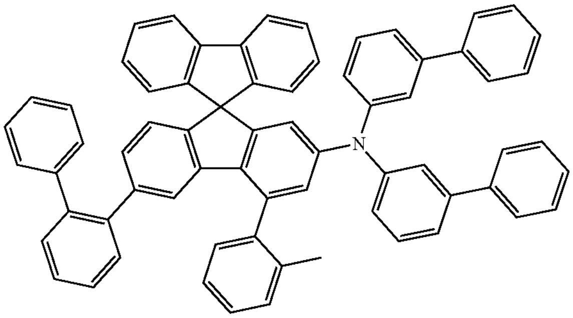
P-122
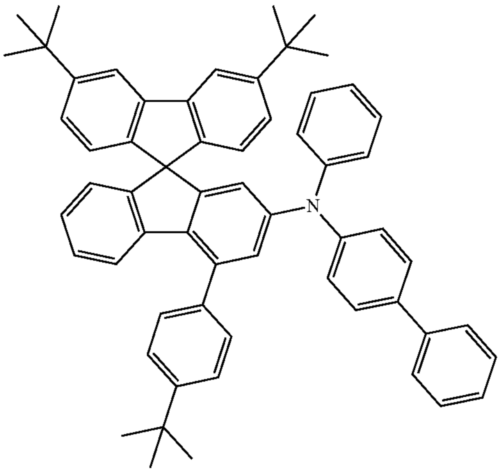

-continued
P-123
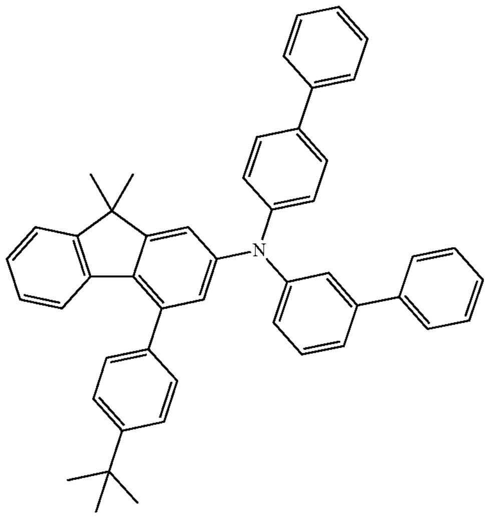
P-124
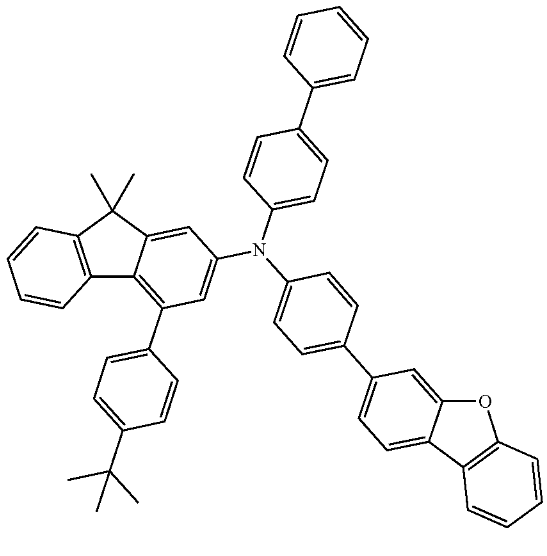
P-125
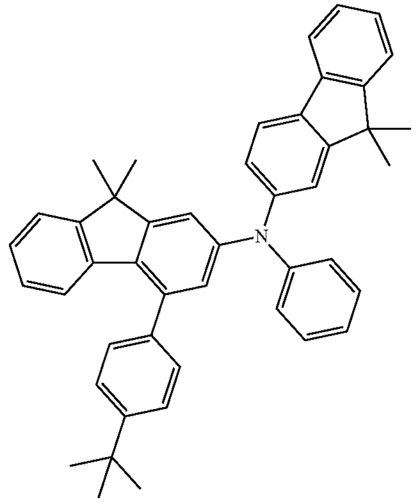
P-126
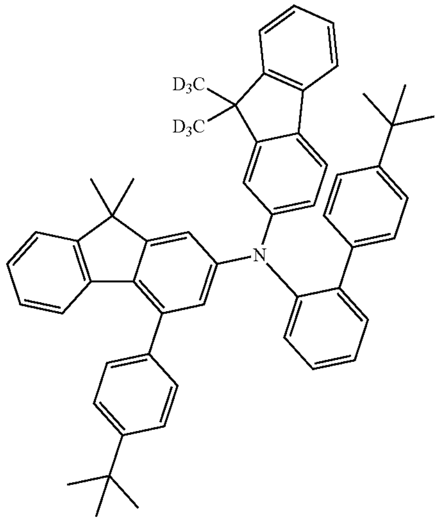
P-127
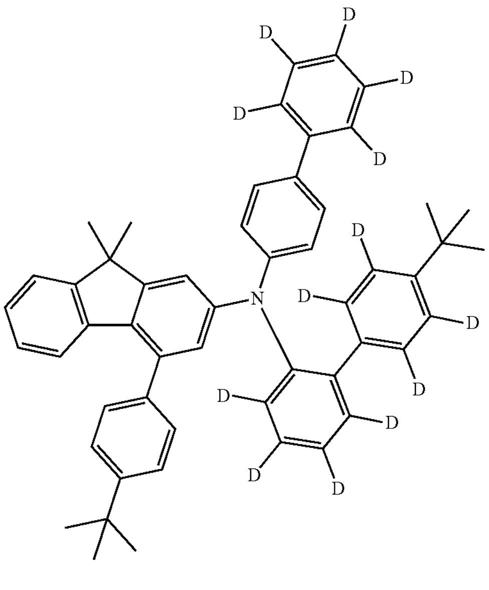

-continued
P-128
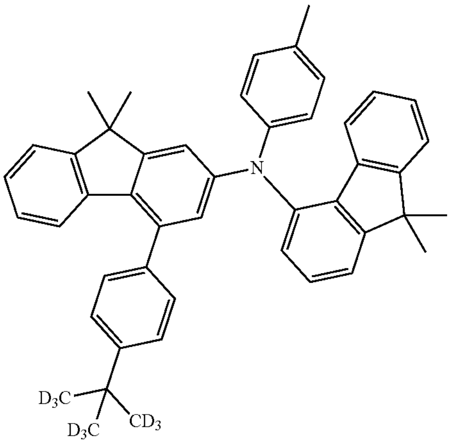
P-129
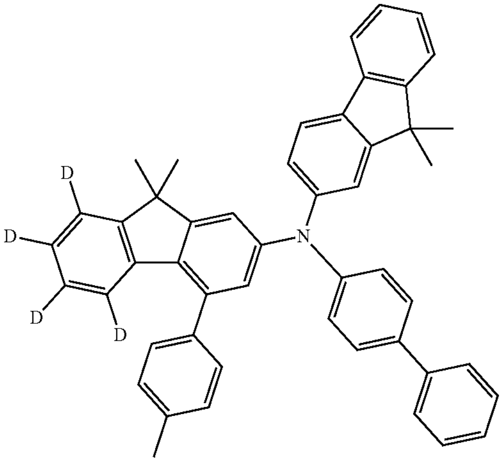
P-130
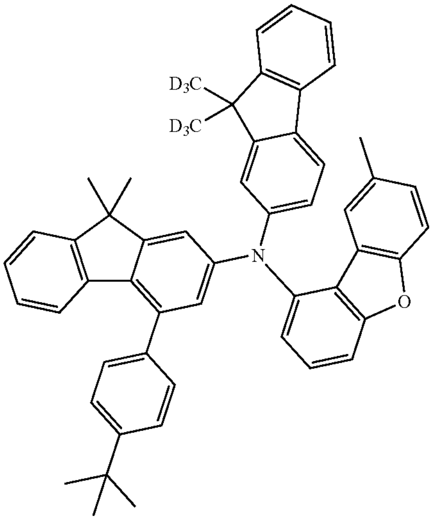
-continued
P-131
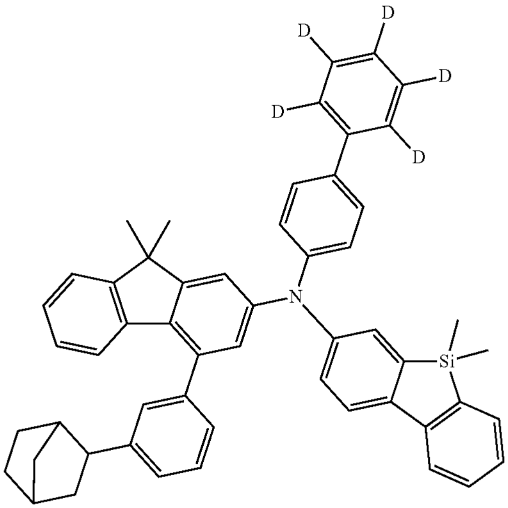
P-132
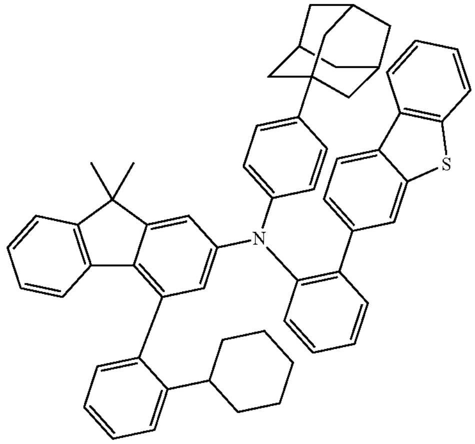
P-133
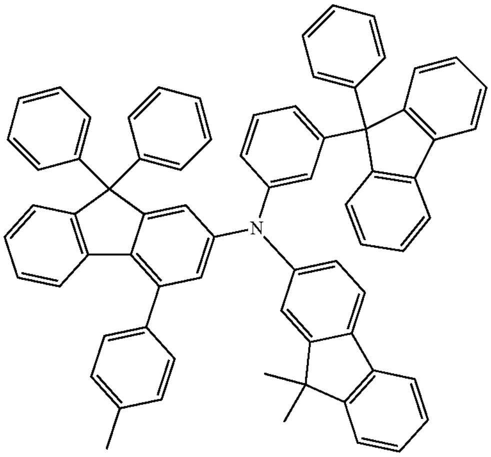

-continued

P-134

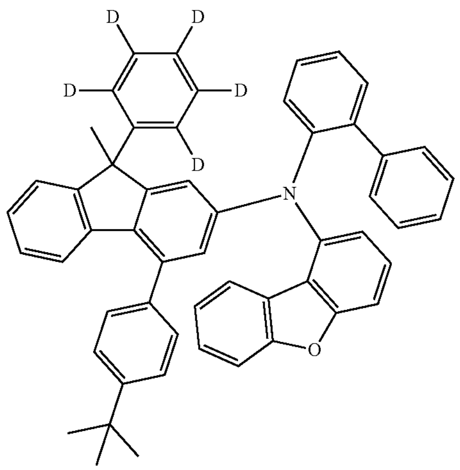

P-135

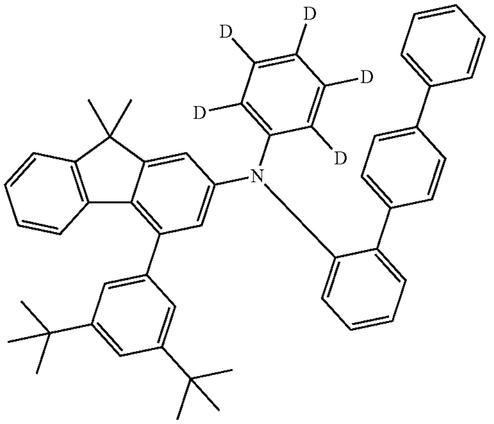

P-136

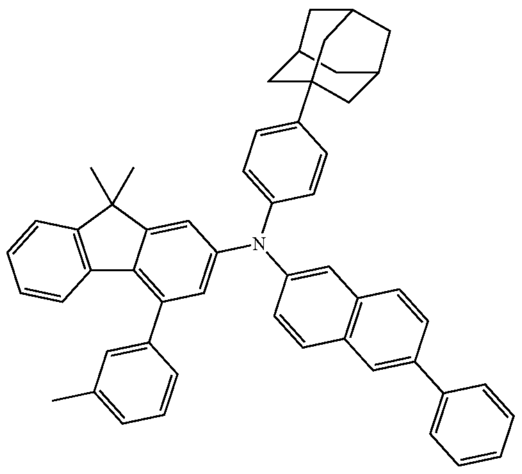

In another aspect, the present invention provides a method for reusing a compound of Formula 1 comprising: recovering a crude organic light emitting material comprising the compound of Formula 1 from a deposition apparatus used in the process for depositing the organic emitting material to prepare an organic light emitting device; removing impurities from the crude organic light emitting material; recovering the removed impurities; and purifying the recovered impurities to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent is preferably a single solvent of N-Methylpyrrolidone (NMP); or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a mixture of a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising single compound or 2 or more compounds represented by Formula 1 between the first electrode (110) and the second electrode (170). Wherein, the first electrode (110) may be an anode or a positive electrode, and the second electrode (170) may be a cathode or a negative electrode. In the case of an inverted organic electronic element, the first electrode may be a cathode, and the second electrode may be an anode.

The organic material layer may sequentially comprise a hole injection layer (120), a hole transport layer (130), an emitting layer (140), an electron transport layer(150), and an electron injection layer (160) on the first electrode(110).

Figure 2:
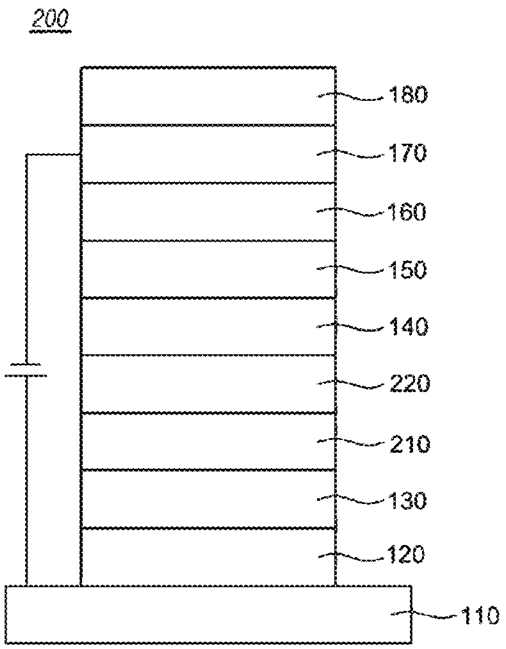

Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150), etc. may serve as a hole blocking layer (see FIG. 2).

Also, the organic electronic element according to an embodiment of the present invention may further include a protective layer or a light efficiency enhancing layer (180). Wherein the light efficiency enhancing layer is formed on one of both surfaces of the first electrode that is not in contact with the organic material layer or on one of both surfaces of the second electrode that is not in contact with the organic material layer. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, a compound according to Formula 1 of the present invention can be used as a material of an emitting auxiliary layer.

Figure 3:
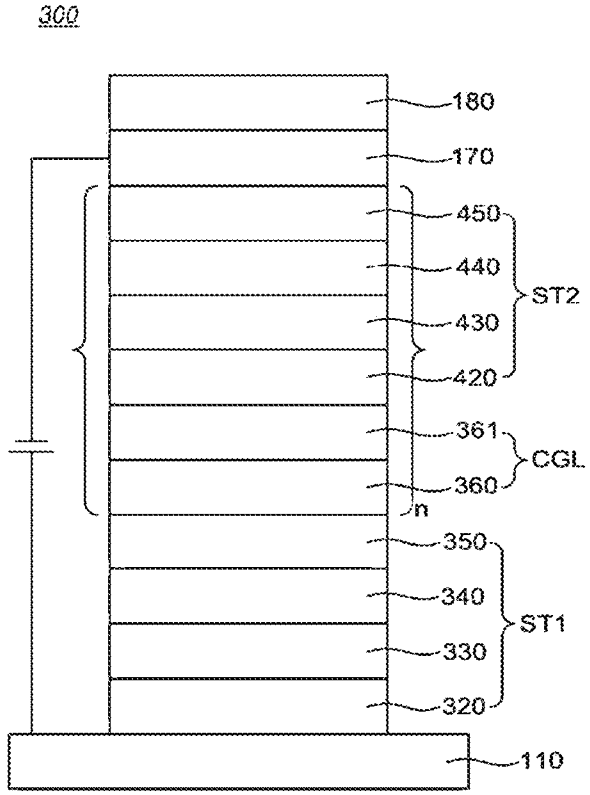
Figure 4:
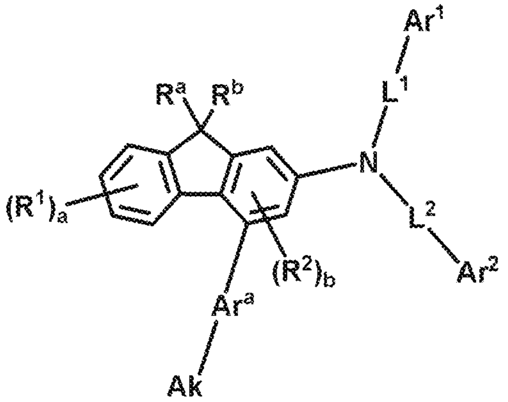
FIG. 4 shows a Formula according to one aspect of the present invention.

The organic material layer may comprise 2 or more stacks comprising a hole transport layer, an emitting layer and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, etc. may vary depending on which substituent is bonded at which position, therefore the choice of core and the combination of sub-substituents associated therewith is also very important, and in particular, when the optimal combination of energy levels and T1 values, and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer(120), the hole transport layer(130), the emitting layer (140), the electron transport layer(150), and the electron injection layer(160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound or a composition for an organic electronic element as an electron transport material.

As another specific example, the present invention provides an organic electronic element used by mixing the same or different compounds of the compound represented by Formula 1 to the organic material layer.

Additionally, the present invention provides an emitting auxiliary layer composition comprising a compound represented by Formula 1, and provides an organic electronic element comprising the emitting auxiliary layer.

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, Synthesis examples of the compound represented by Formula 1 of the present invention and preparation examples of the organic electronic element of the present invention will be described in detail by way of example, but are not limited to the following examples.

Synthesis Example 1

The compound (final products) represented by Formula 1 according to the present invention can be synthesized as shown in Reaction Scheme 1, but is not limited thereto.

<Reaction Scheme 1>

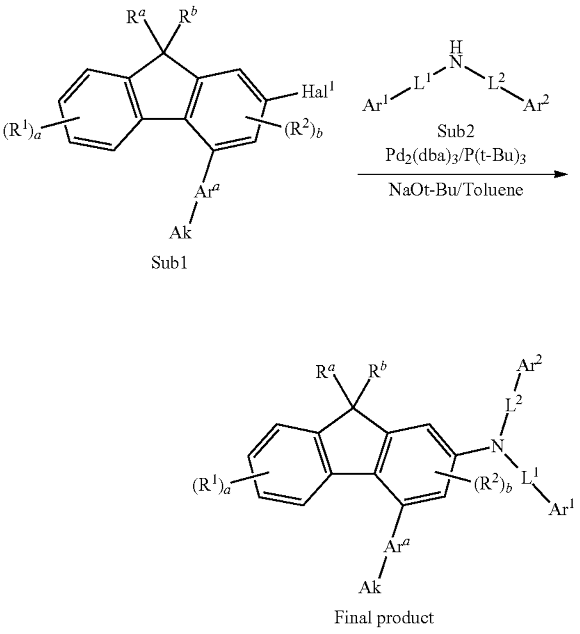

Wherein: $Ar^1$, $Ar^2$, $Ar^a$, Ak, $R^1$, $R^2$, $R^a$, $R^b$, $L^1$, $L^2$, a and b are the same as defined in Formula 1, $Hal^1$ is Br or $C_1$.

I. Synthesis of Sub 1

Sub1 of Reaction scheme 1 can be synthesized by the reaction path of Reaction scheme 2, but is not limited thereto.

<Reaction Scheme 2>

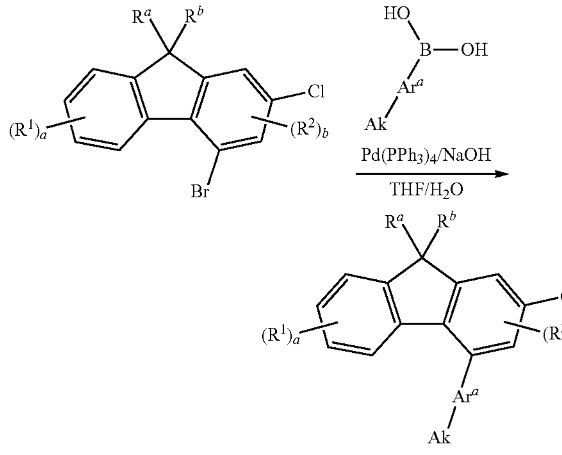

Sub1

1. Synthesis Example of Sub 1-1

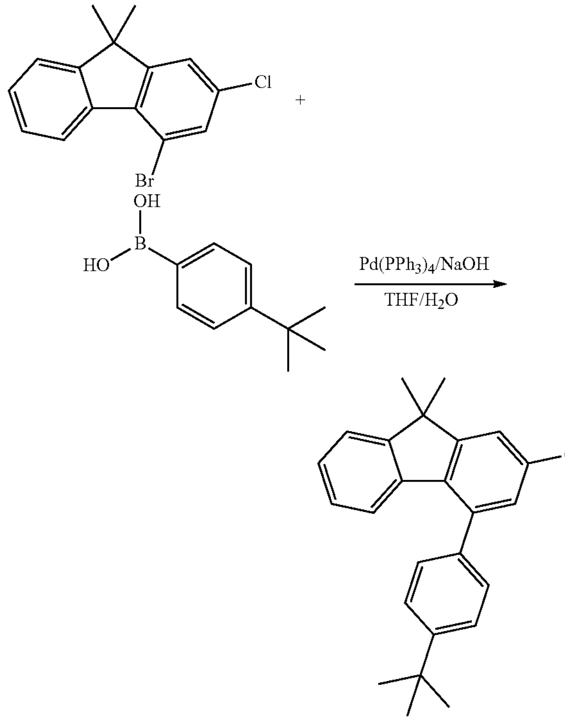

Sub1-1

4-bromo-2-chloro-9,9-dimethyl-9H-fluorene (50.0 g, 162.5 mmol) was dissolved in THF (540 mL), and (4-(tert-butyl)phenyl)boronic acid (31.8 g, 178.8 mmol), NaOH (19.5 g, 487.6 mmol), $Pd(PPh_3)_4$ (9.39 g, 8.31 mmol) and Water (270 mL) were added and stirred under reflux at 80° C. When the reaction was complete, the reaction product was extracted with $CH_2Cl_2$ and water, and then the organic layer was dried over $MgSO_4$, concentrated, and the resulting compound was recrystallized a silica gel column to obtain 52.8 g (90%).

2. Synthesis Example of Sub 1-16

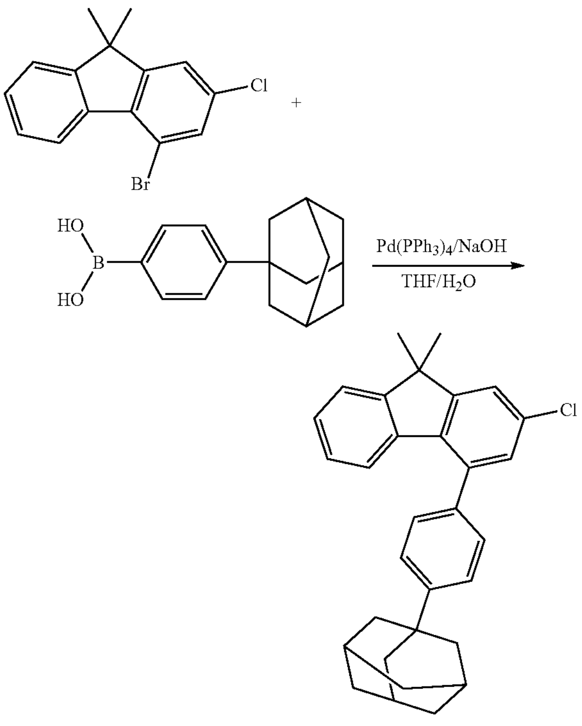

Sub1-16

4-bromo-2-chloro-9,9-dimethyl-9H-fluorene (50.0 g, 162.5 mmol) was dissolved in THF (540 mL), and (4-(adamantan-1-yl)phenyl)boronic acid (45.8 g, 178.8 mmol), NaOH (19.5 g, 487.6 mmol), $Pd(PPh_3)_4$ (9.39 g, 8.31 mmol) and Water (270 mL) were added and stirred under reflux at 80° C. When the reaction was complete, the reaction product was extracted with $CH_2Cl_2$ and water, and then the organic layer was dried over $MgSO_4$, concentrated, and the resulting compound was recrystallized a silica gel column to obtain 63.5 g (89%).

3. Synthesis Example of Sub 1-23

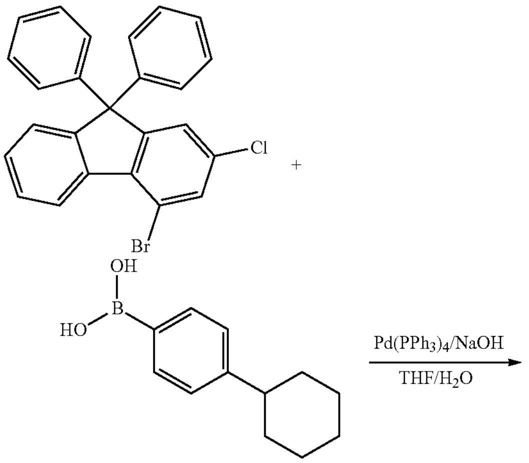

-continued

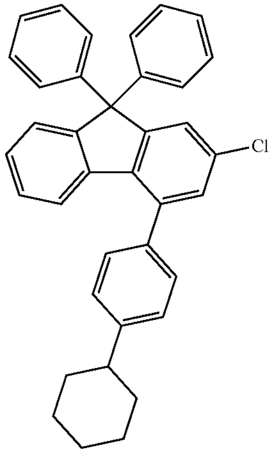

Sub1-23

4-bromo-2-chloro-9,9-diphenyl-9H-fluorene (50.0 g, 115.8 mmol) was dissolved in THF (380 mL), and (4-cyclohexylphenyl)boronic acid (26.0 g, 127.4 mmol), NaOH (13.9 g, 347.4 mmol), $Pd(PPh_3)_4$ (6.69 g, 5.79 mmol) and Water (190 mL) were added and stirred under reflux at 80° C. When the reaction was complete, the reaction product was extracted with $CH_2Cl_2$ and water, and then the organic layer was dried over $MgSO_4$, concentrated, and the resulting compound was recrystallized a silica gel column to obtain 54.4 g (92%).

Compounds belonging to Sub1 may comprise, but are not limited to, the compounds below, and Table 1 shows the FD-MS (Field Desorption-Mass Spectrometry) values of some compounds belonging to Sub1.

Sub1-1

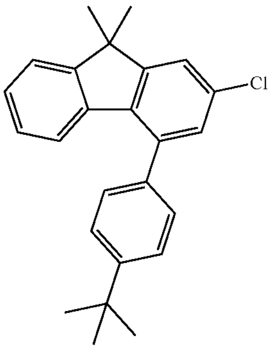

Sub1-2

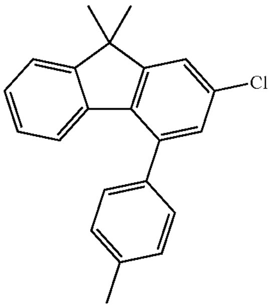

-continued

Sub1-3

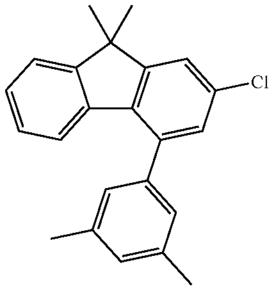

Sub1-4

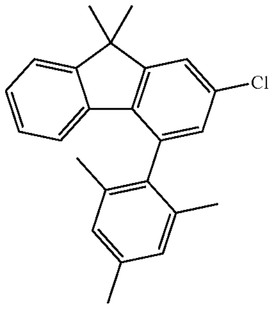

Sub1-5

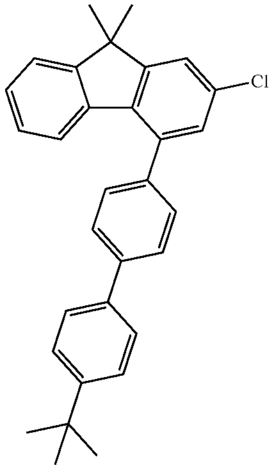

Sub1-6

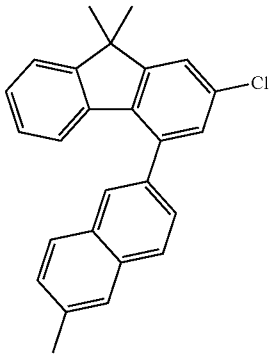

-continued
Sub1-7
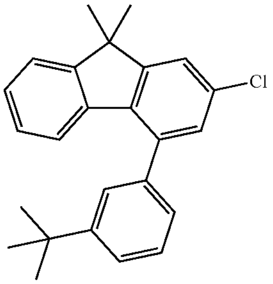
Sub1-8
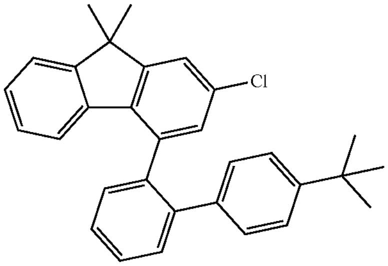
Sub1-9
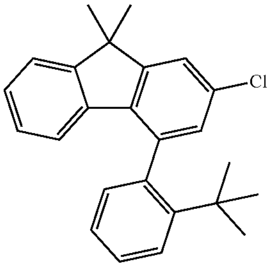
Sub1-10
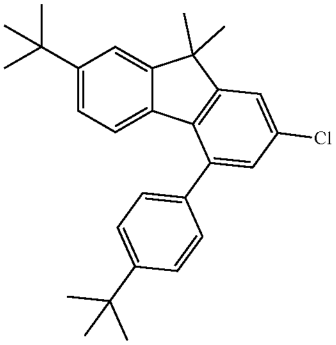
Sub1-11
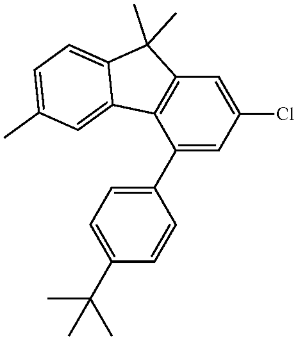
-continued
Sub1-12
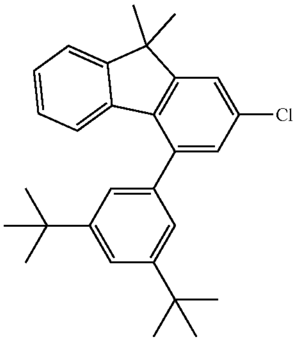
Sub1-13
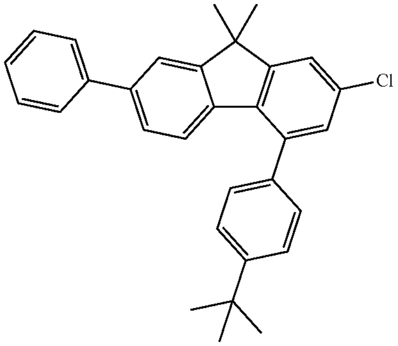
Sub1-14
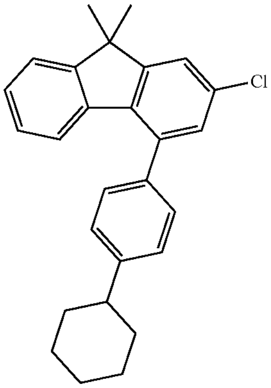
Sub1-15
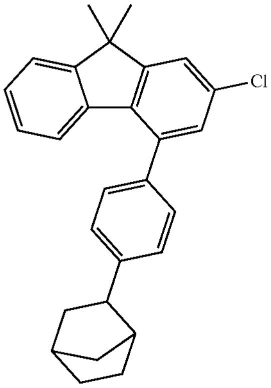

-continued
Sub1-16
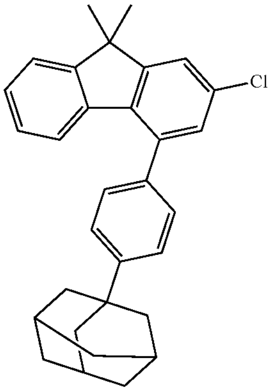
Sub1-17
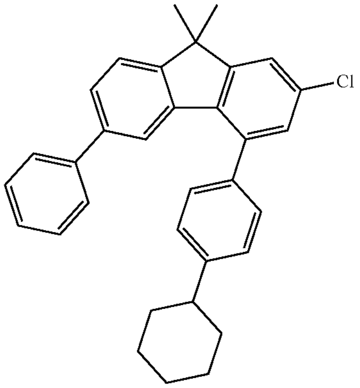
Sub1-18
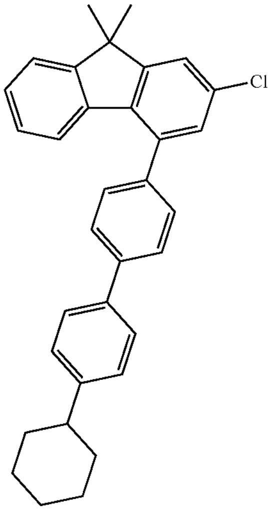
-continued
Sub1-19
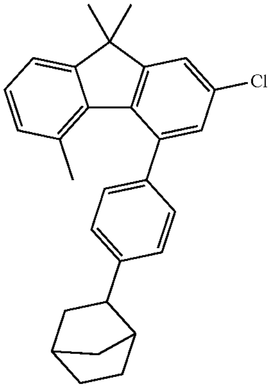
Sub1-20
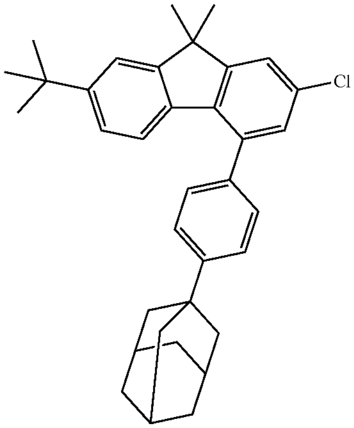
Sub1-21
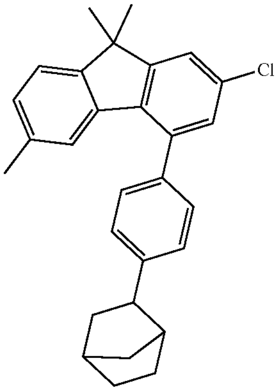

-continued
Sub1-22
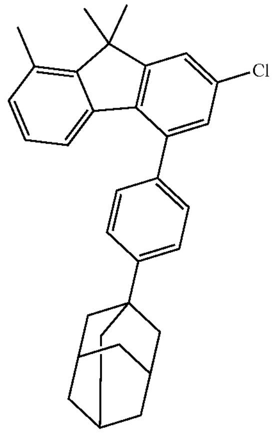
Sub1-23
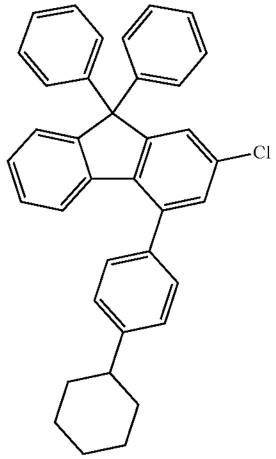
Sub1-24
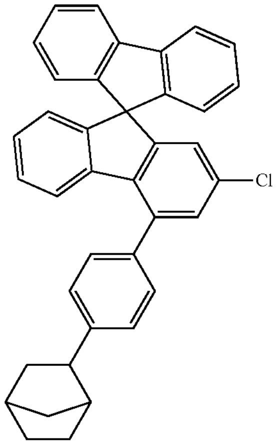
-continued
Sub1-25
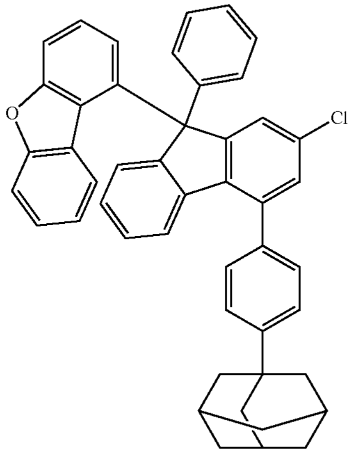
Sub1-26
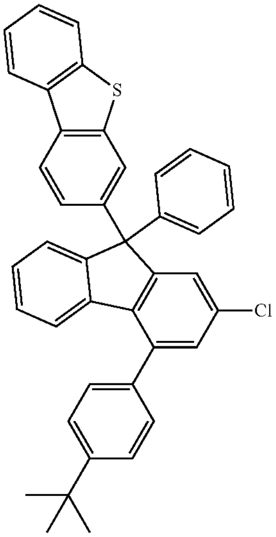
Sub1-27
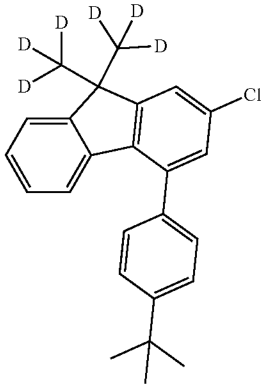

-continued

Sub1-28

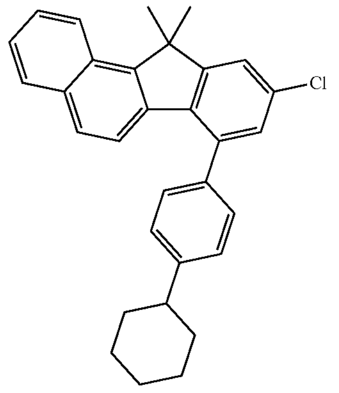

Sub1-29

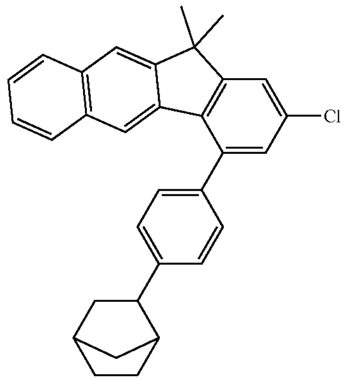

-continued

Sub1-30

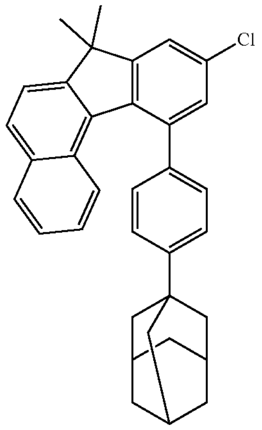

Sub1-31

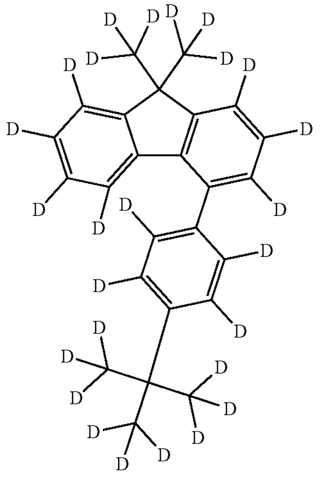

TABLE 1

| Compound | FD-MS | Compound | FD-MS |
|---|---|---|---|
| Sub 1-1 | m/z = 360.2($C_{25}H_{25}Cl$ = 360.9) | Sub 1-2 | m/z = 318.1($C_{22}H_{19}Cl$ = 318.8) |
| Sub 1-3 | m/z = 332.1($C_{23}H_{21}Cl$ = 332.9) | Sub 1-4 | m/z = 346.1($C_{24}H_{23}Cl$ = 346.9) |
| Sub 1-5 | m/z = 436.2($C_{31}H_{29}Cl$ = 437) | Sub 1-6 | m/z = 368.1($C_{26}H_{21}Cl$ = 368.9) |
| Sub 1-7 | m/z = 360.2($C_{25}H_{25}Cl$ = 360.9) | Sub 1-8 | m/z = 436.2($C_{31}H_{29}Cl$ = 437) |
| Sub 1-9 | m/z = 360.2($C_{25}H_{25}Cl$ = 360.9) | Sub 1-10 | m/z = 416.2($C_{29}H_{33}Cl$ = 417) |
| Sub 1-11 | m/z = 374.2($C_{26}H_{27}Cl$ = 375) | Sub 1-12 | m/z = 416.2($C_{29}H_{33}Cl$ = 417) |
| Sub 1-13 | m/z = 436.2($C_{31}H_{29}Cl$ = 437) | Sub 1-14 | m/z = 386.2($C_{27}H_{27}Cl$ = 387) |
| Sub 1-15 | m/z = 398.2($C_{28}H_{27}Cl$ = 399) | Sub 1-16 | m/z = 438.2($C_{31}H_{31}Cl$ = 439) |
| Sub 1-17 | m/z = 462.2($C_{33}H_{31}Cl$ = 463.1) | Sub 1-18 | m/z = 462.2($C_{33}H_{31}Cl$ = 463.1) |
| Sub 1-19 | m/z = 412.2($C_{29}H_{29}Cl$ = 413) | Sub 1-20 | m/z = 494.3($C_{35}H_{39}Cl$ = 495.1) |
| Sub 1-21 | m/z = 412.2($C_{29}H_{29}Cl$ = 413) | Sub 1-22 | m/z = 452.2($C_{32}H_{33}Cl$ = 453.1) |
| Sub 1-23 | m/z = 510.2($C_{37}H_{31}Cl$ = 511.1) | Sub 1-24 | m/z = 520.2($C_{38}H_{29}Cl$ = 521.1) |
| Sub 1-25 | m/z = 652.3($C_{47}H_{37}ClO$ = 653.3) | Sub 1-26 | m/z = 590.2($C_{41}H_{31}ClS$ = 591.2) |
| Sub 1-27 | m/z = 366.2($C_{25}H_{19}D_6Cl$ = 367) | Sub 1-28 | m/z = 436.2($C_{31}H_{29}Cl$ = 437) |
| Sub 1-29 | m/z = 448.2($C_{32}H_{29}Cl$ = 449) | Sub 1-30 | m/z = 488.2($C_{35}H_{33}Cl$ = 489.1) |
| Sub 1-31 | m/z = 385.3($C_{25}D_{25}Cl$ = 386.1) | | |

II. Synthesis of Sub 2

Sub2 of Reaction scheme 1 can be synthesized by the reaction path of Reaction scheme 3, but is not limited thereto. ($Hal^2$ is Br or Cl)

<Reaction Scheme 3>

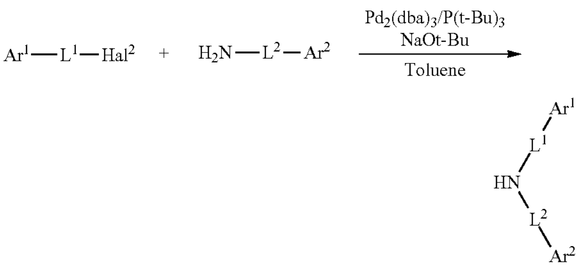

Sub2

1. Synthesis Example of Sub2-3

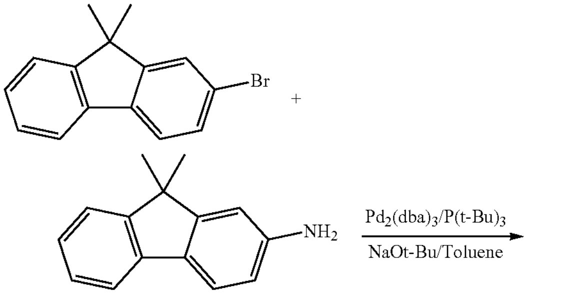

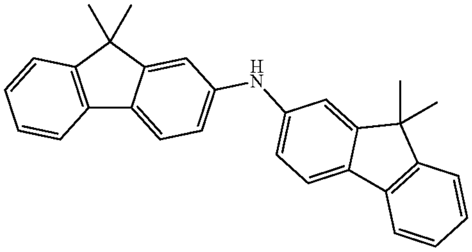

Sub2-3

2-bromo-9,9-dimethyl-9H-fluorene (50.0 g, 183.0 mmol) was dissolved in toluene (915 mL) in a round-bottom flask, and 9,9-dimethyl-9H-fluoren-2-amine (46.0 g, 219.6 mmol), $Pd_2(dba)_3$ (5.03 g, 5.49 mmol), $P(t\text{-}Bu)_3$ (2.22 g, 10.98 mmol), NaOt-Bu (35.2 g, 366.0 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 57.3 g of the product (78%).

2. Synthesis Example of Sub2-10

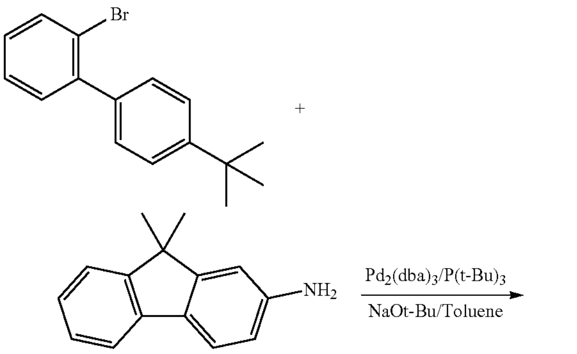

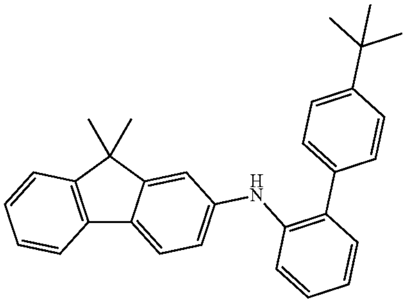

Sub2-10

2-bromo-4'-(tert-butyl)-1,1'-biphenyl (50.0 g, 172.9 mmol) was dissolved in toluene (860 mL) in a round-bottom flask, and 9,9-dimethyl-9H-fluoren-2-amine (43.4 g, 207.5 mmol), $Pd_2(dba)_3$ (4.75 g, 5.19 mmol), $P(t\text{-}Bu)_3$ (2.10 g, 10.37 mmol), NaOt-Bu (33.2 g, 345.8 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 54.1 g of the product (75%).

3. Synthesis Example of Sub2-19

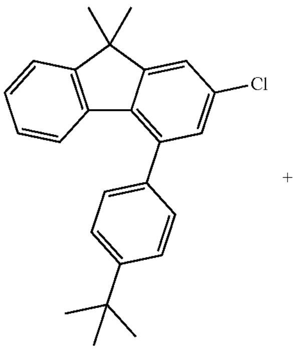

Sub1-1

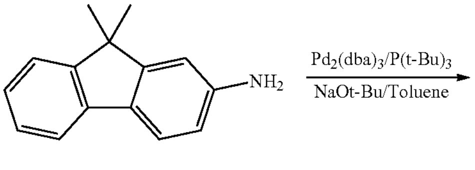

-continued

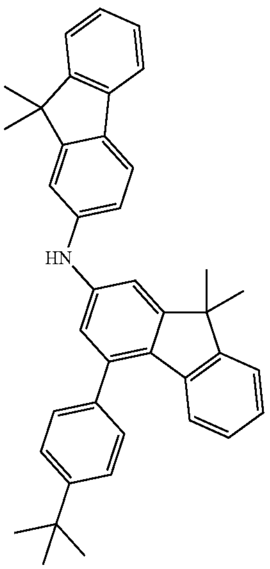

Sub2-19

Sub1-1 (30.0 g, 83.1 mmol) was dissolved in toluene (410 mL) in a round-bottom flask, and 9,9-dimethyl-9H-fluoren-2-amine (20.9 g, 99.8 mmol), $Pd_2(dba)_3$ (2.28 g, 2.49 mmol), $P(t\text{-}Bu)_3$ (1.01 g, 4.99 mmol), NaOt-Bu (16.0 g, 166.3 mmol) were added and stirred at 90° C. When the reaction was complete, the reaction product was extracted with $CH_2Cl_2$ and water, and then the organic layer was dried over $MgSO_4$, concentrated, and the resulting compound was recrystallized using a silica gel column to obtain 34.2 g of the product (77%).

4. Synthesis Example of Sub2-26

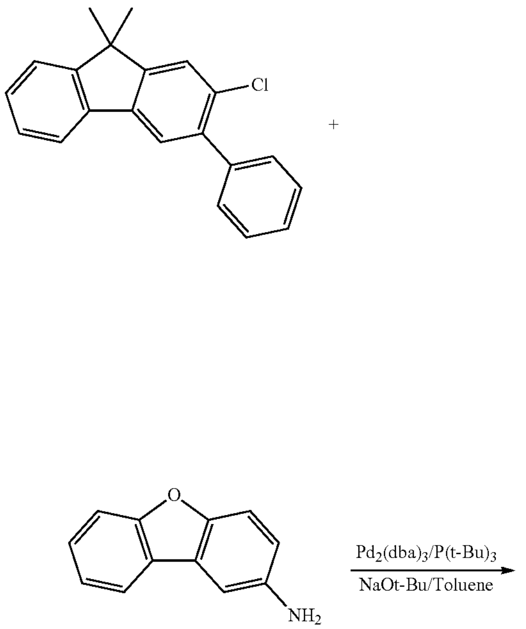

-continued

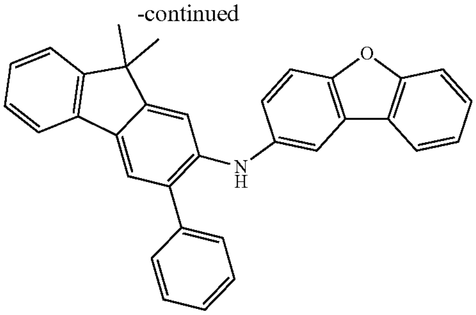

Sub2-26

2-chloro-9,9-dimethyl-3-phenyl-9H-fluorene (50.0 g, 164.0 mmol) was dissolved in toluene (820 mL) in a round-bottom flask, and dibenzo[b,d]furan-2-amine (36.1 g, 196.9 mmol), $Pd_2(dba)_3$ (4.51 g, 4.92 mmol), $P(t\text{-}Bu)_3$ (1.99 g, 9.84 mmol), NaOt-Bu (31.5 g, 328.1 mmol) were added and stirred at 90° C. When the reaction was complete, the reaction product was extracted with $CH_2Cl_2$ and water, and then the organic layer was dried over $MgSO_4$, concentrated, and the resulting compound was recrystallized using a silica gel column to obtain 54.1 g of the product (73%).

5. Synthesis Example of Sub2-31

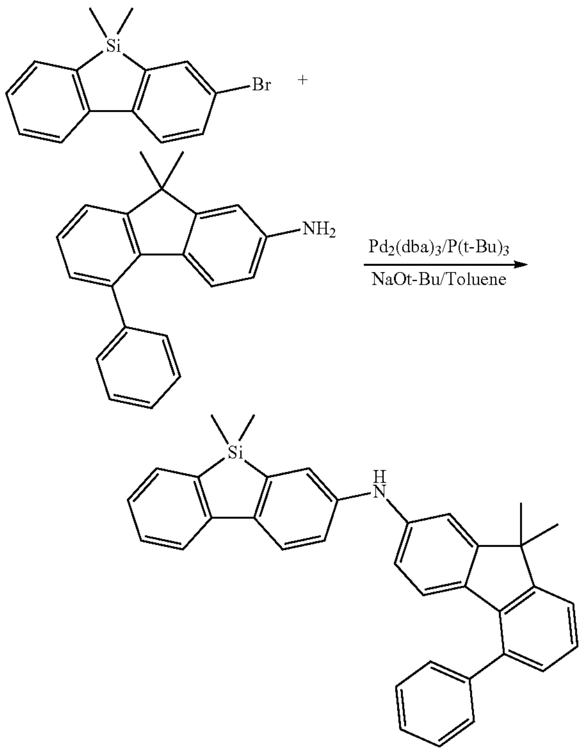

Sub2-31

3-bromo-5,5-dimethyl-5H-dibenzo[b,d]silole (50.0 g, 289.2 mmol) was dissolved in toluene (860 mL) in a round-bottom flask, and 9,9-dimethyl-5-phenyl-9H-fluoren-2-amine (59.2 g, 207.5 mmol), $Pd_2(dba)_3$ (4.75 g, 5.19 mmol), $P(t\text{-}Bu)_3$ (2.10 g, 10.37 mmol), NaOt-Bu (33.2 g, 345.8 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 64 g of the product (75%).

6. Synthesis Example of Sub2-45

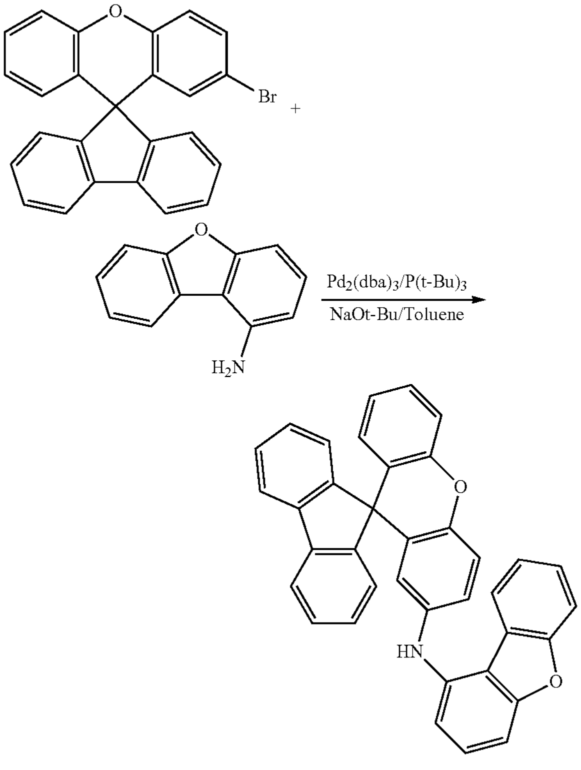

Sub2-45

2'-bromospiro[fluorene-9,9'-xanthene](50.0 g, 121.6 mmol) was dissolved in toluene (600 mL) in a round-bottom flask, and dibenzo[b,d]furan-1-amine (26.7 g, 145.9 mmol), $Pd_2(dba)_3$ (3.34 g, 3.65 mmol), $P(t-Bu)_3$ (1.48 g, 7.29 mmol), NaOt-Bu (23.4 g, 243.1 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 53.7 g of the product (86%).

7. Synthesis Example of Sub2-50

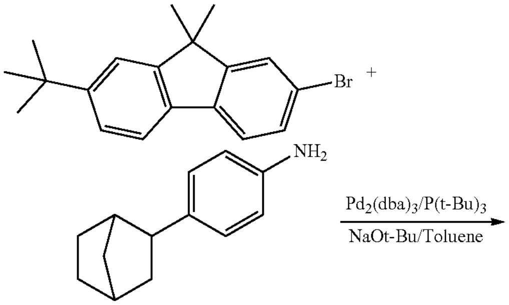

-continued

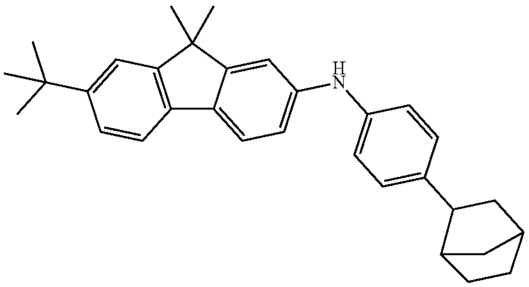

Sub2-50

2-bromo-7-(tert-butyl)-9,9-dimethyl-9H-fluorene (50.0 g, 329.3 mmol) was dissolved in toluene (760 mL) in a round-bottom flask, and 4-(bicyclo[2.2.1]heptan-2-yl)aniline (34.1 g, 182.2 mmol), $Pd_2(dba)_3$ (4.17 g, 4.56 mmol), $P(t-Bu)_3$ (1.84 g, 9.11 mmol), NaOt-Bu (29.2 g, 303.7 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 47.0 g of the product (71%).

8. Synthesis Example of Sub2-63

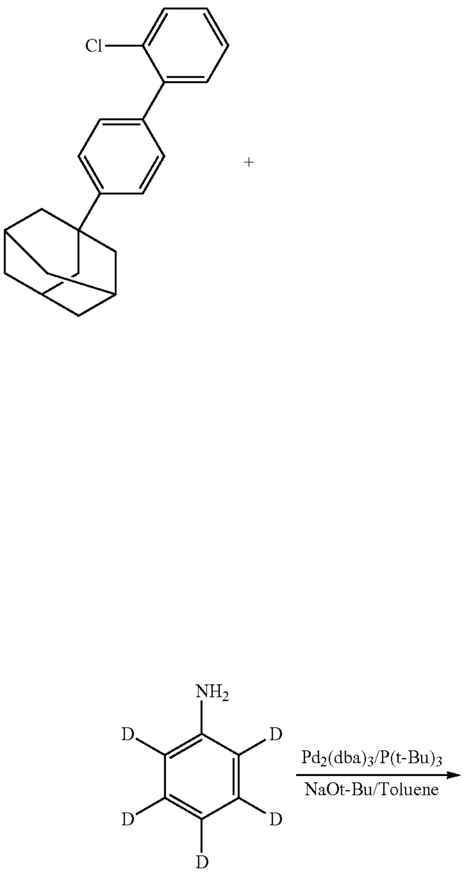

-continued

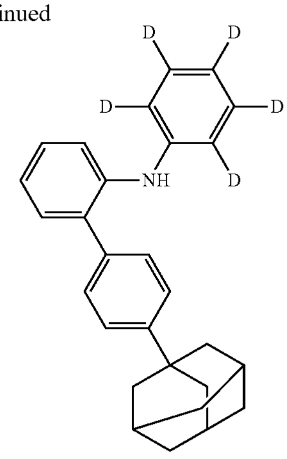

Sub2-63

1-(2'-chloro-[1,1'-biphenyl]-4-yl)adamantane (50.0 g, 154.8 mmol) was dissolved in toluene (770 mL) in a round-bottom flask, and benzen-d5-amine (18.2 g, 185.8 mmol), $Pd_2(dba)_3$ (4.25 g, 4.65 mmol), $P(t\text{-}Bu)_3$ (1.88 g, 9.29 mmol), NaOt-Bu (29.8 g, 309.7 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 46.5 g of the product (78%).

9. Synthesis Example of Sub2-78

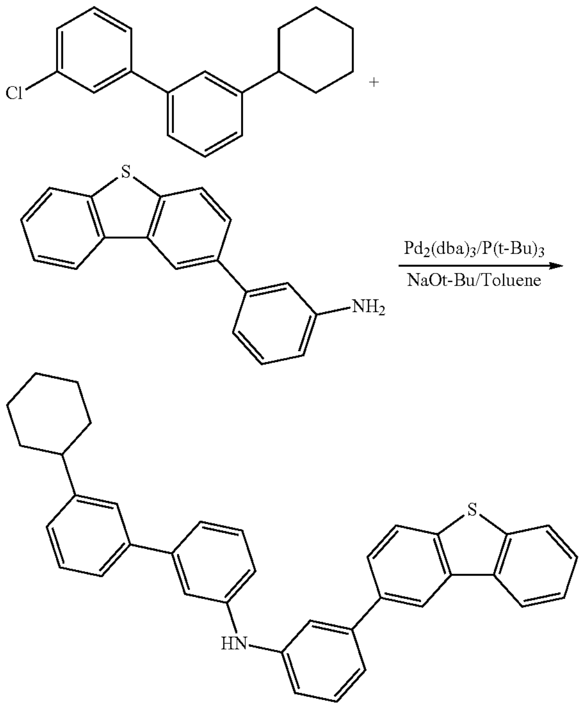

Sub2-78

3-chloro-3'-cyclohexyl-1,1'-biphenyl (50.0 g, 184.6 mmol) was dissolved in toluene (920 mL) in a round-bottom flask, and 3-(dibenzo[b,d]thiophen-2-yl)aniline (61.0 g, 221.6 mmol), $Pd_2(dba)_3$ (5.07 g, 5.54 mmol), $P(t\text{-}Bu)_3$ (2.24 g, 11.08 mmol), NaOt-Bu (35.5 g, 369.3 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 68.7 g of the product (73%).

10. Synthesis Example of Sub2-92

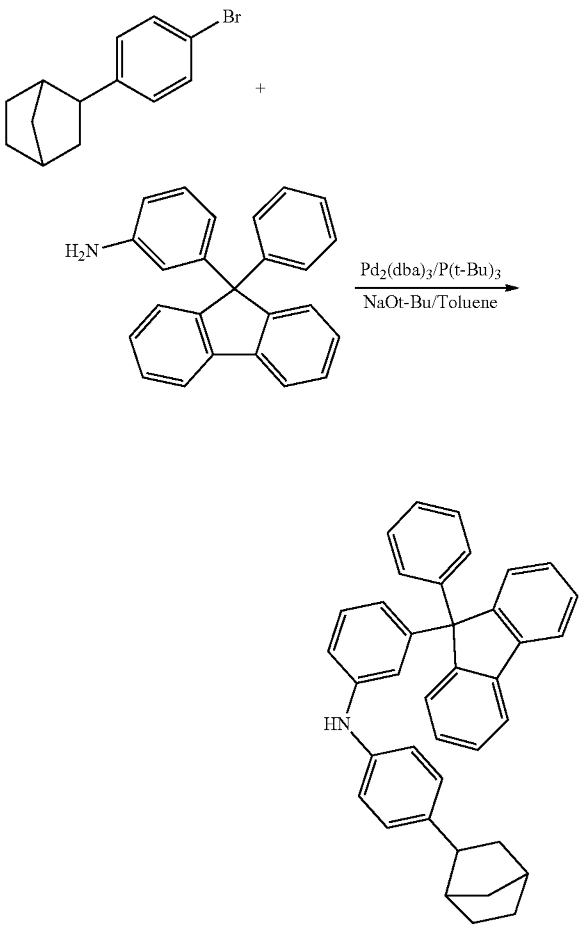

Sub2-92

2-(4-bromophenyl)bicyclo[2.2.1]heptane (50.0 g, 199.0 mmol) were dissolved in toluene (1000 mL) in a round-bottom flask, and 3-(9-phenyl-9H-fluoren-9-yl)aniline (79.6 g, 238.9 mmol), $Pd_2(dba)_3$ (5.47 g, 5.97 mmol), $P(t\text{-}Bu)_3$ (2.42 g, 11.94 mmol), NaOt-Bu (38.3 g, 398.1 mmol) were added and stirred at 60° C. When the reaction was complete, the reaction product was extracted with $CH_2Cl_2$ and water, and then the organic layer was dried over $MgSO_4$, concentrated, and the resulting compound was recrystallized using a silica gel column to obtain 79.2 g of the product (79%).

Compounds belonging to Sub2 may include, but are not limited to, the compounds below, and Table 2 shows the FD-MS (Field Desorption-Mass Spectrometry) values of some compounds belonging to Sub2.

-continued
Sub2-1
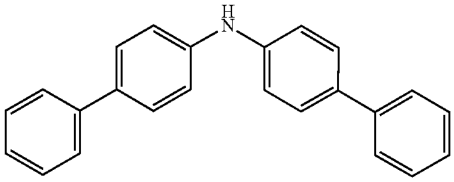
Sub2-2
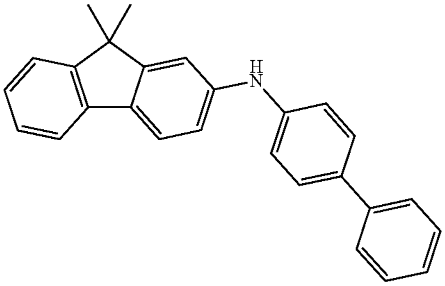
Sub2-3
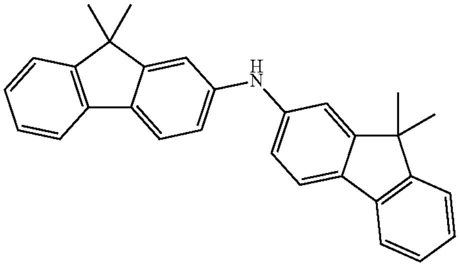
Sub2-4
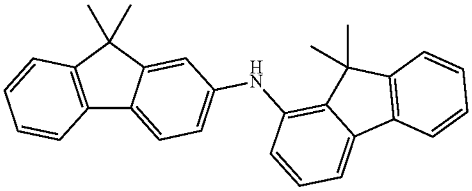
Sub2-5
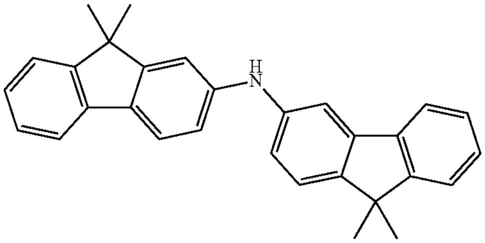
Sub2-6
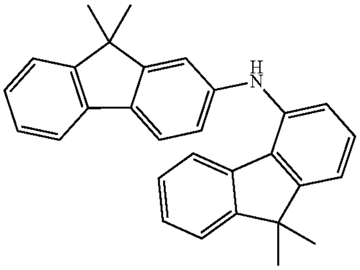
Sub2-7
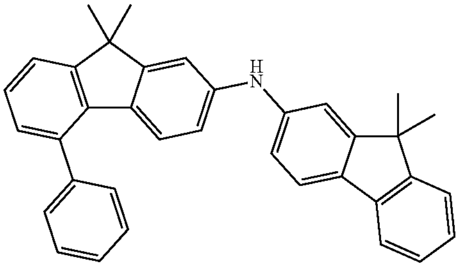
Sub2-8
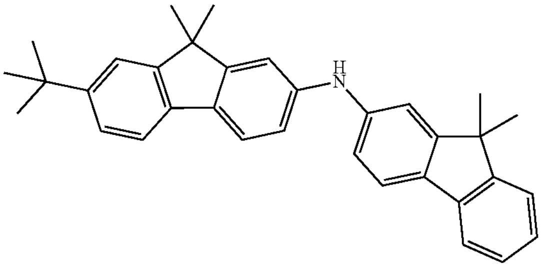
Sub2-9
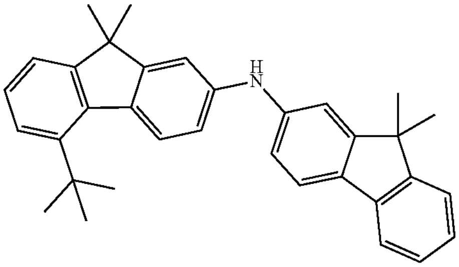
Sub2-10
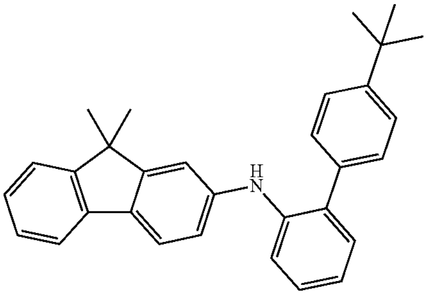
Sub2-11
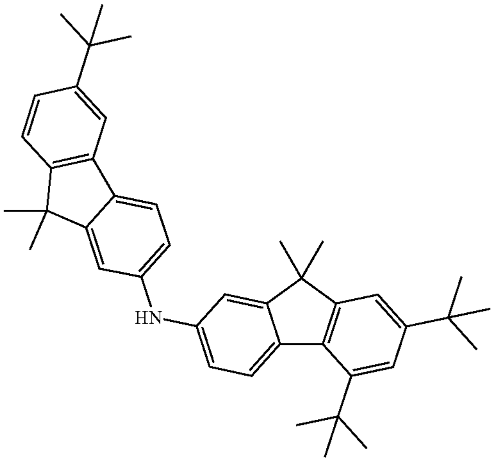

-continued
Sub2-12
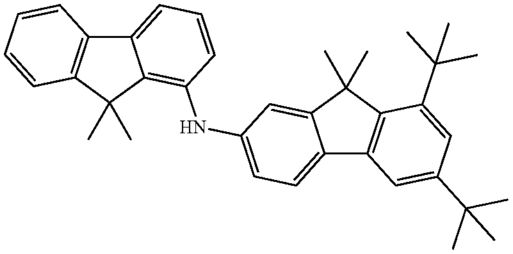
Sub2-13
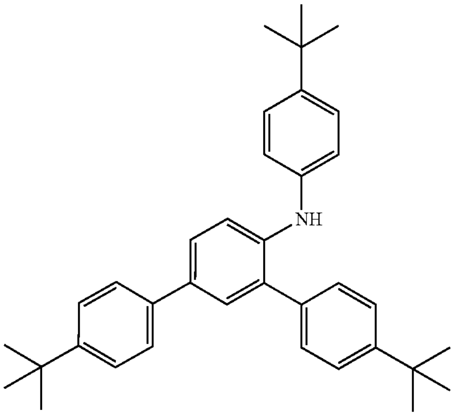
Sub2-14
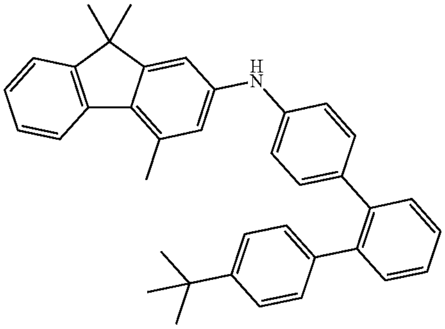
Sub2-15
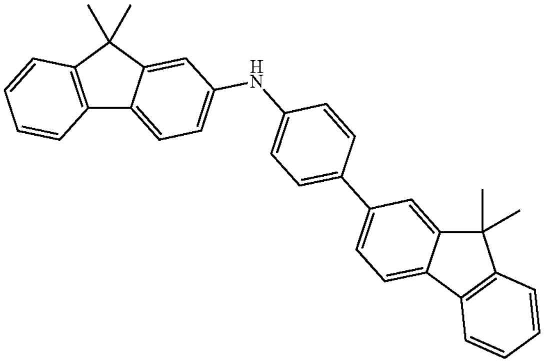
-continued
Sub2-16
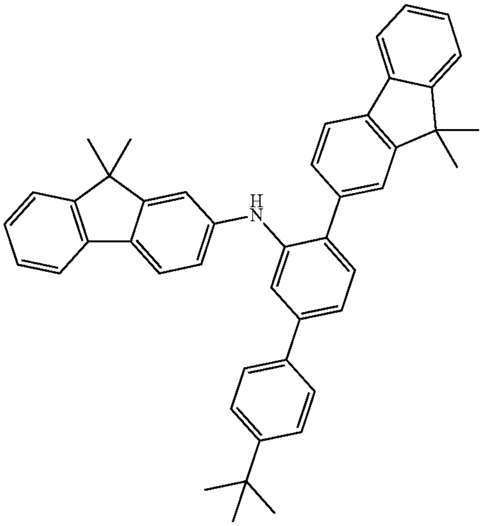
Sub2-17
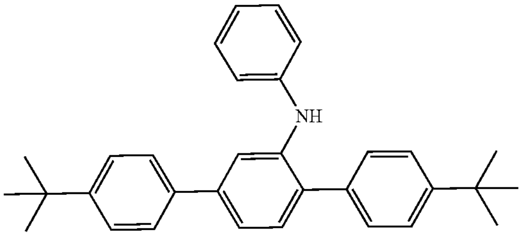
Sub2-18
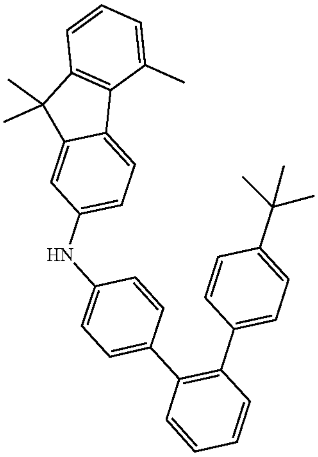

-continued
Sub2-19
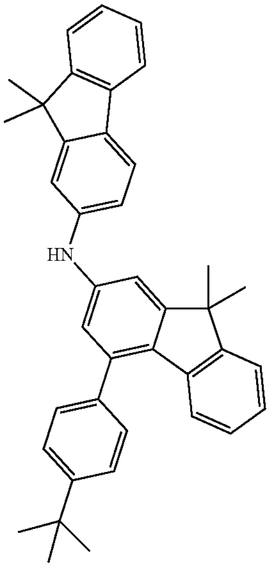
Sub2-20
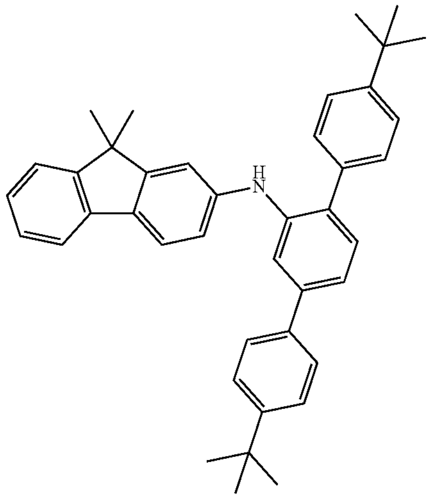
Sub2-21
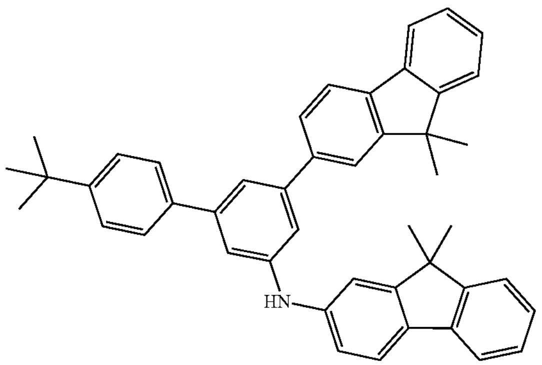
-continued
Sub2-22
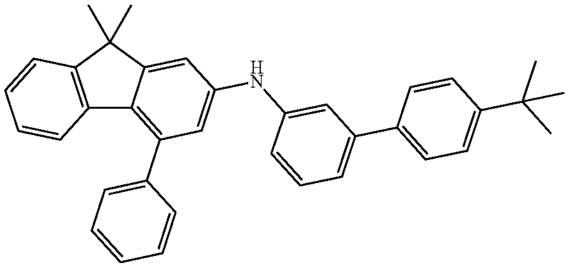
Sub2-23
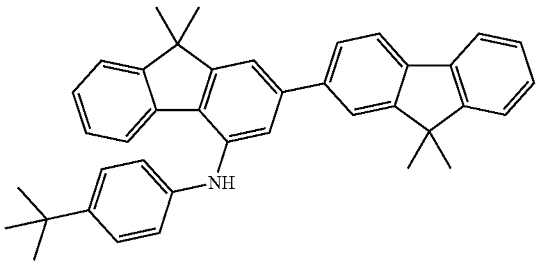
Sub2-24
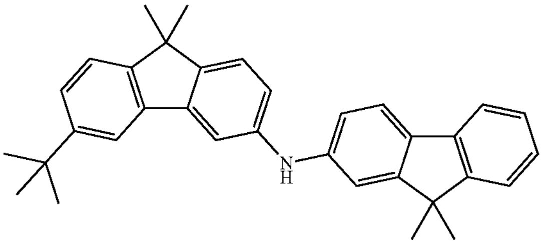
Sub2-25
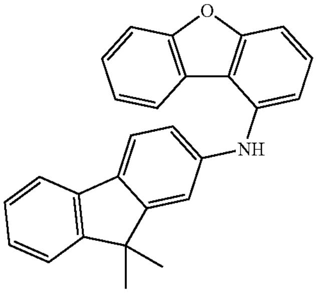
Sub2-26
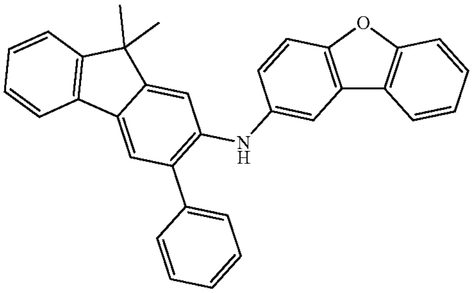

-continued
Sub2-27
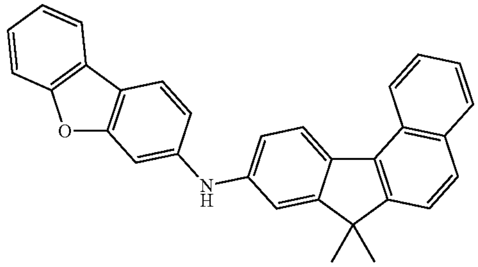
Sub2-28
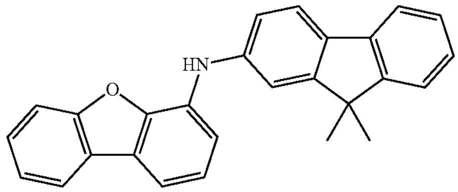
Sub2-29
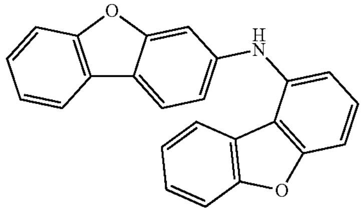
Sub2-30
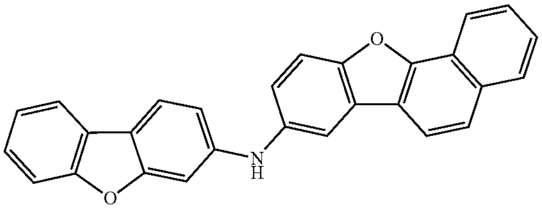
Sub2-31
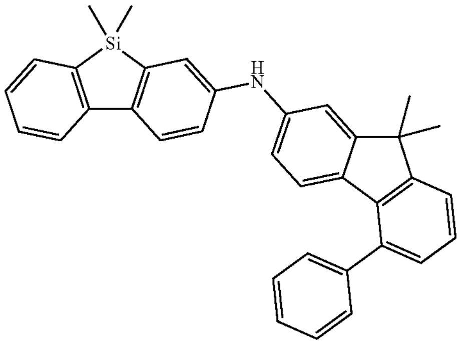
Sub2-32
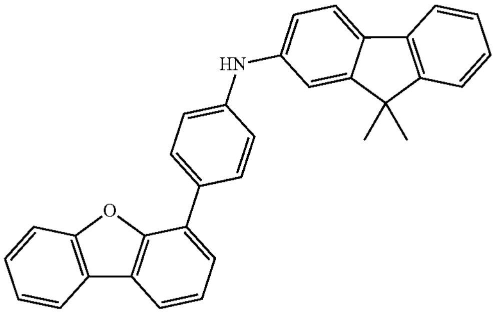
-continued
Sub2-33
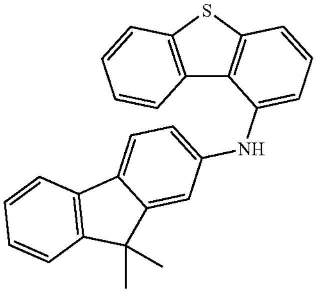
Sub2-34
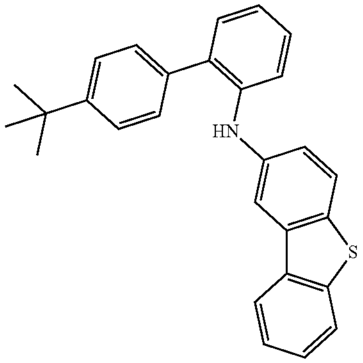
Sub2-35
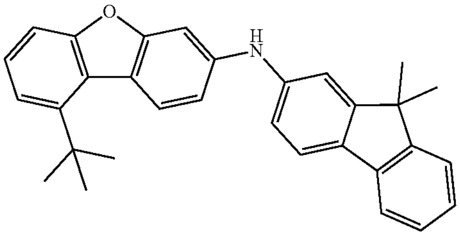
Sub2-36
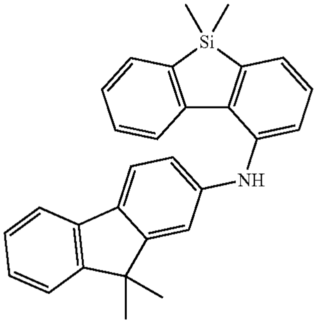

-continued
Sub2-37
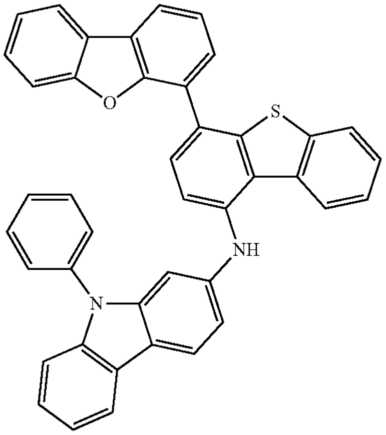
Sub2-38
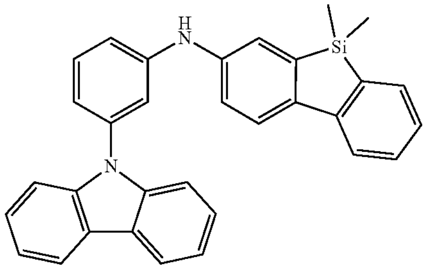
Sub2-39
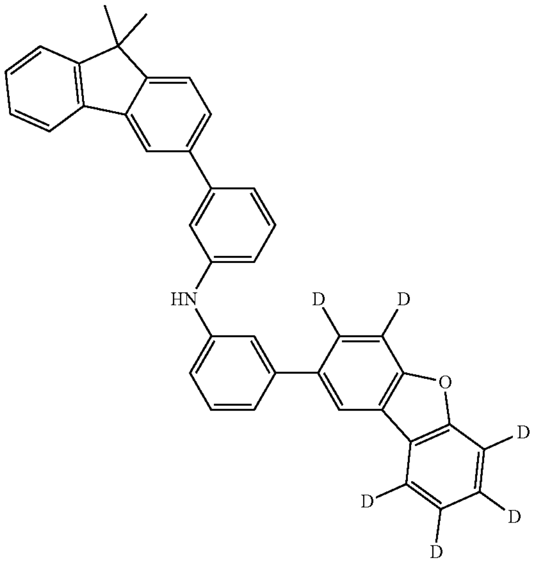
Sub2-40
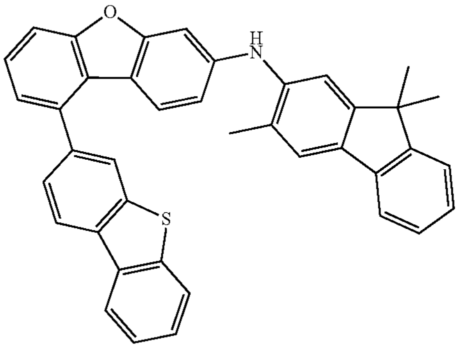
-continued
Sub2-41
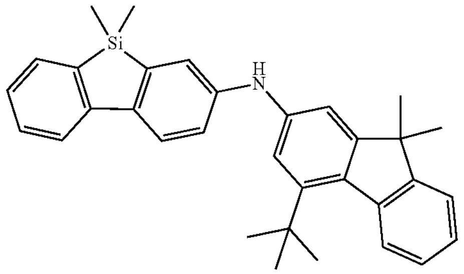
Sub2-42
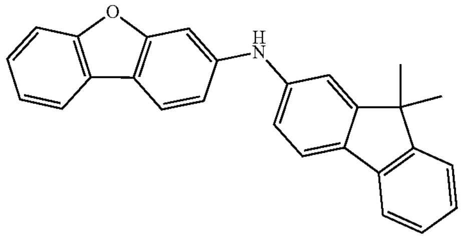
Sub2-43
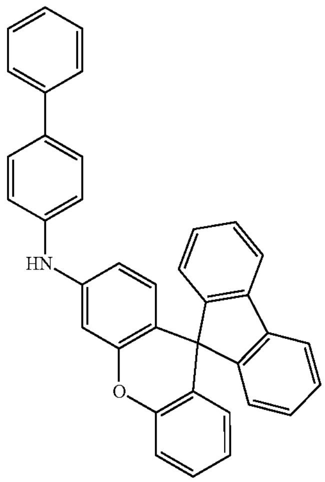
Sub2-44
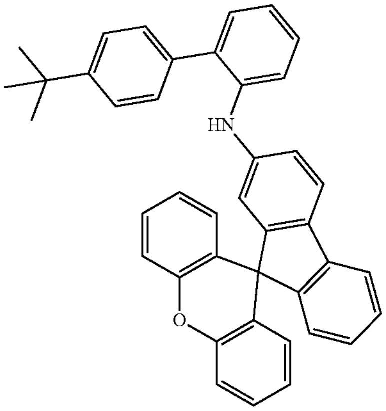

-continued
Sub2-45
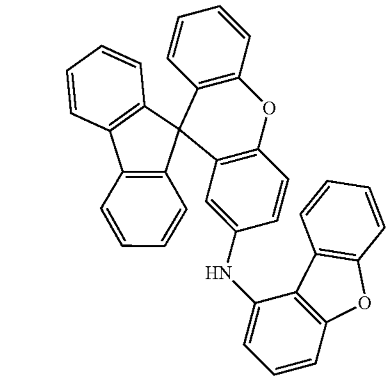
Sub2-46
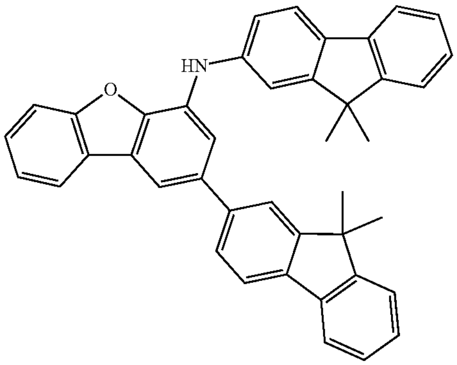
Sub2-47
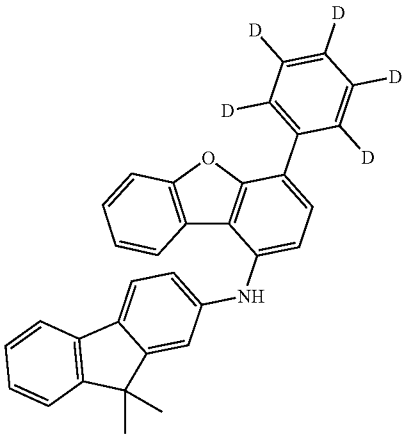
Sub2-48
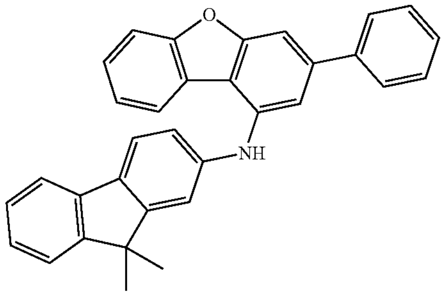
-continued
Sub2-49
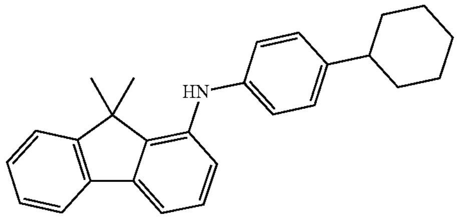
Sub2-50
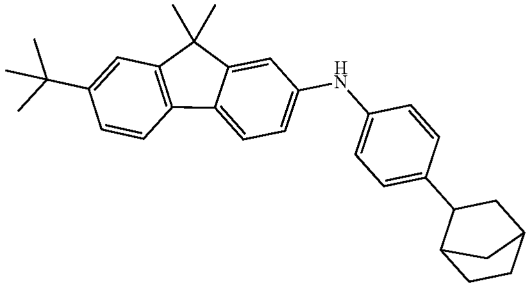
Sub2-51
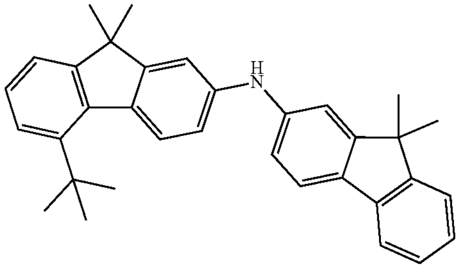
Sub2-52
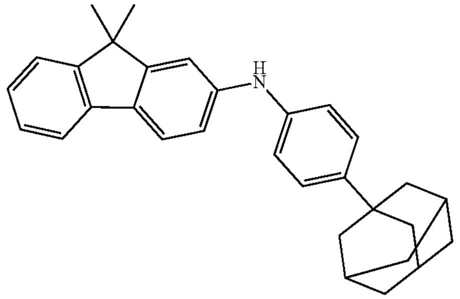
Sub2-53
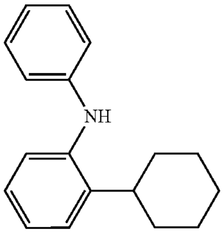

-continued
Sub2-54
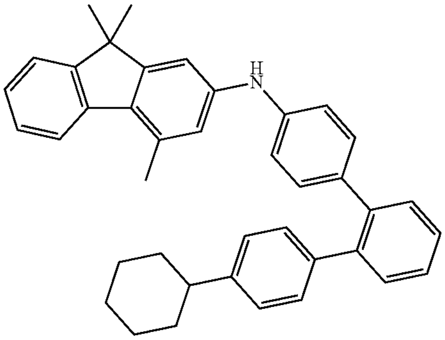
Sub2-55
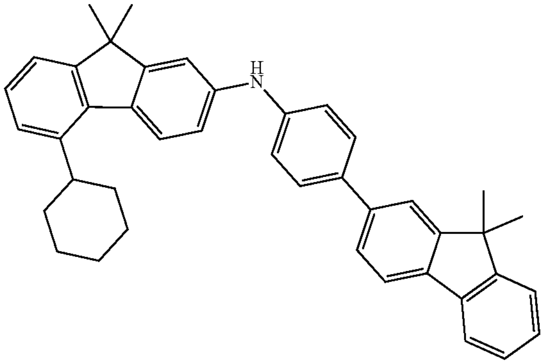
Sub2-56
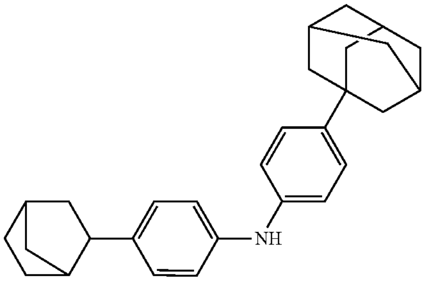
Sub2-57
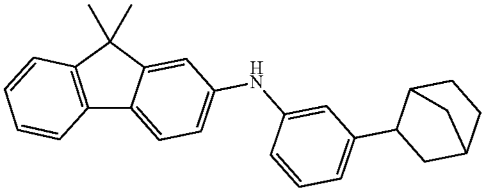
Sub2-58
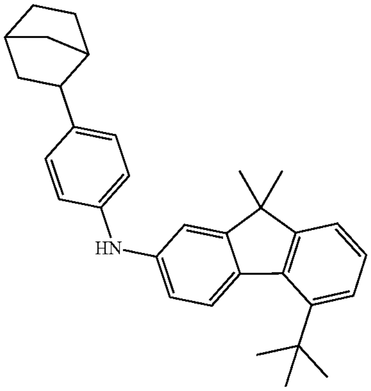
-continued
Sub2-59
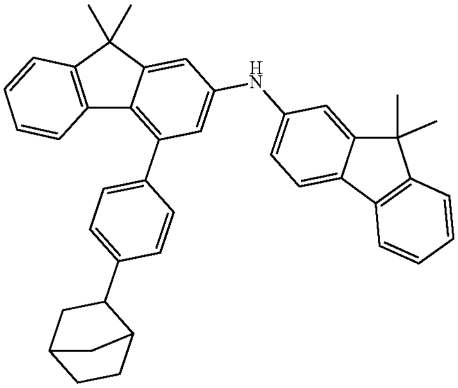
Sub2-60
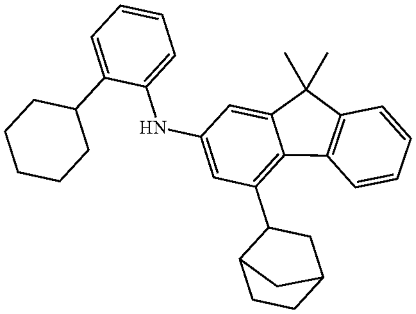
Sub2-61
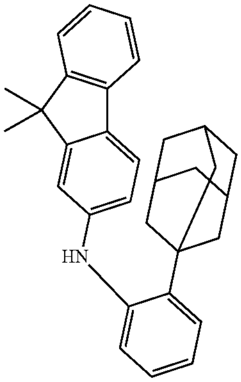
Sub2-62
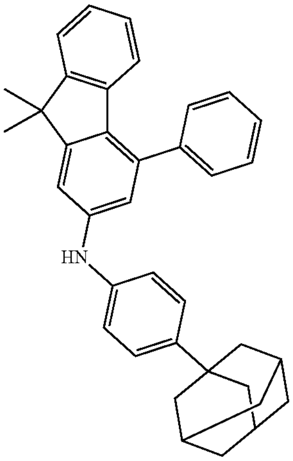

-continued
Sub2-63
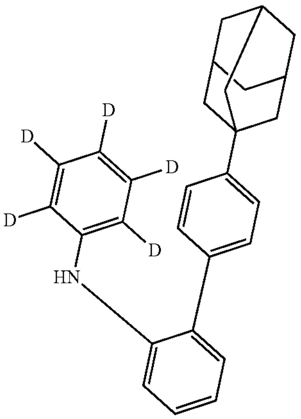
Sub2-64
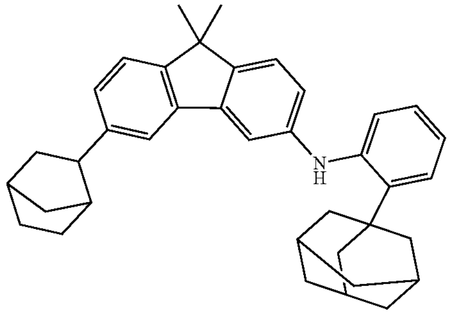
Sub2-65
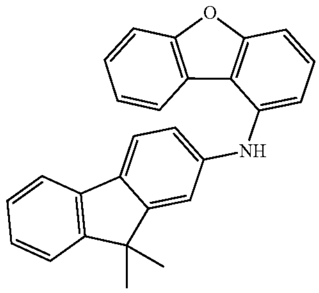
Sub2-66
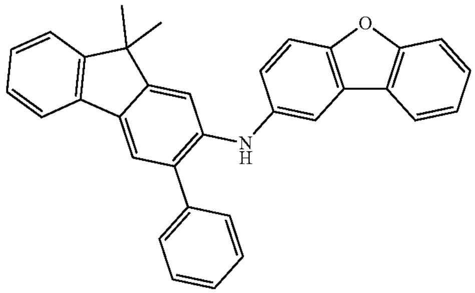
Sub2-67
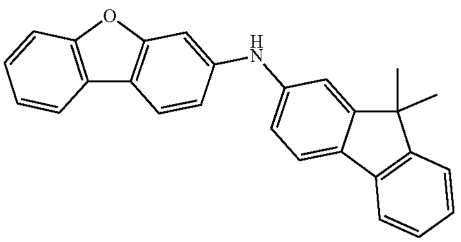
-continued
Sub2-68
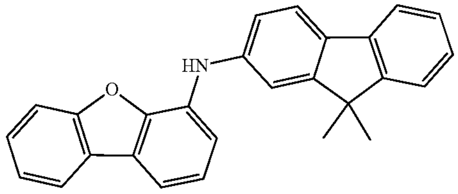
Sub2-69
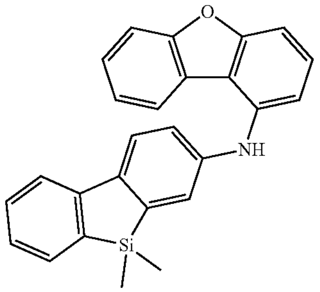
Sub2-70
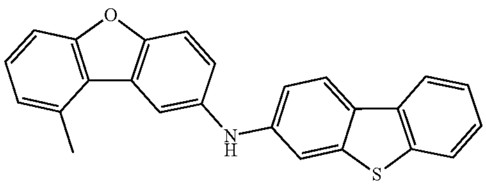
Sub2-71
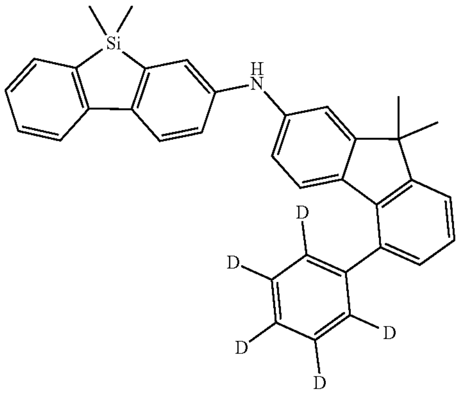
Sub2-72
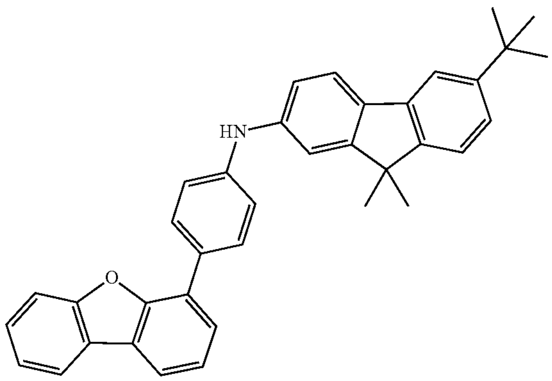

Sub2-73
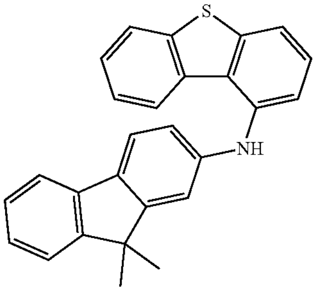
Sub2-74
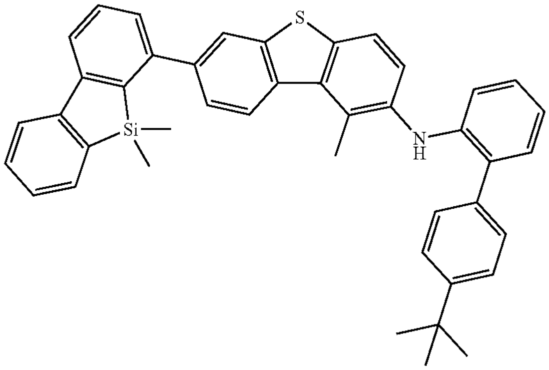
Sub2-75
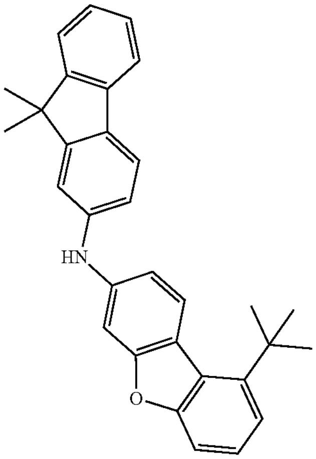
Sub2-76
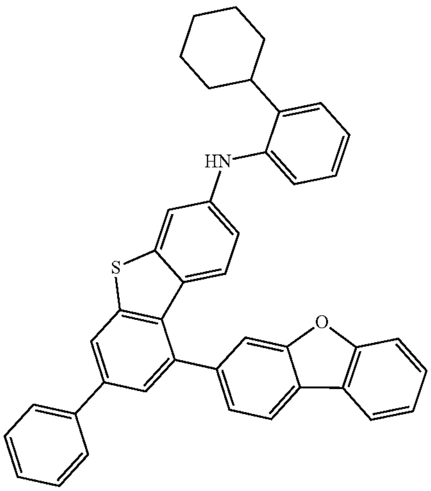
Sub2-77
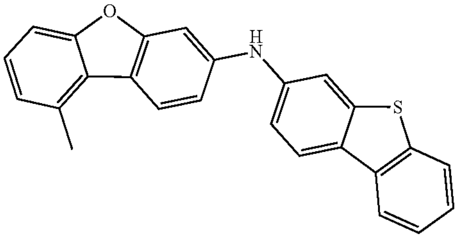
Sub2-78
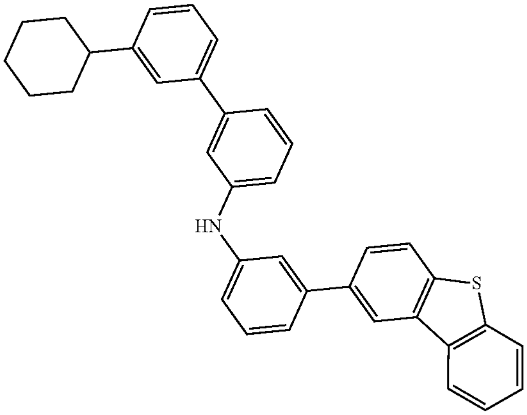
Sub2-79
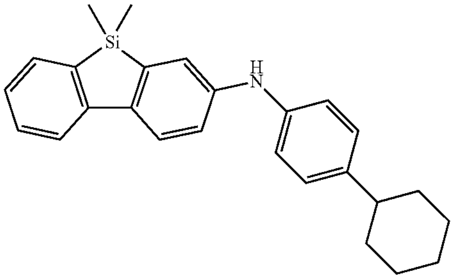
Sub2-80
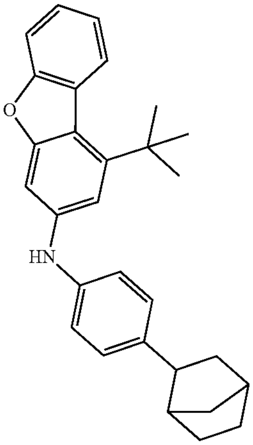

Sub2-81
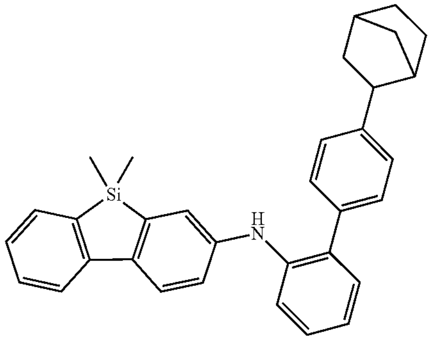
Sub2-82
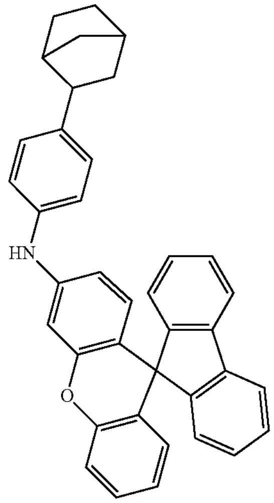
Sub2-83
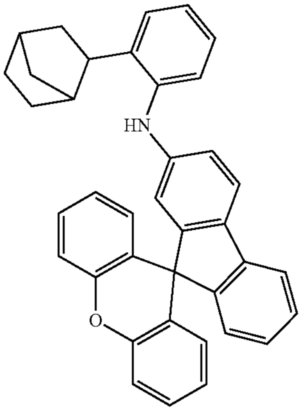
Sub2-84
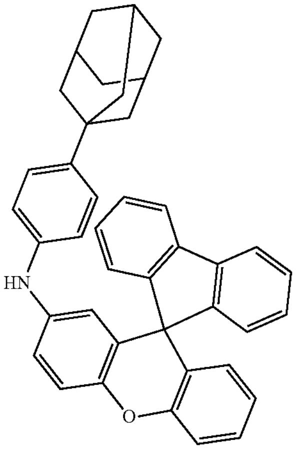
Sub2-85
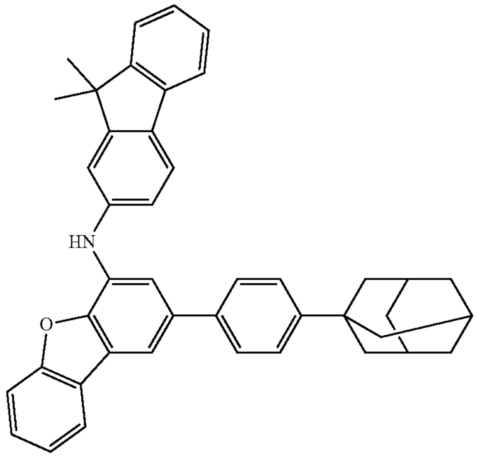
Sub2-86
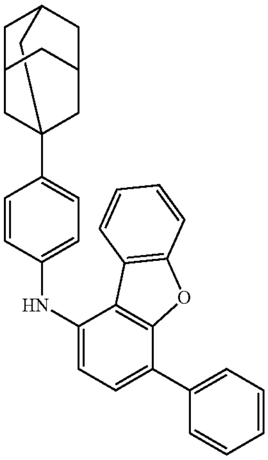

-continued
Sub2-87
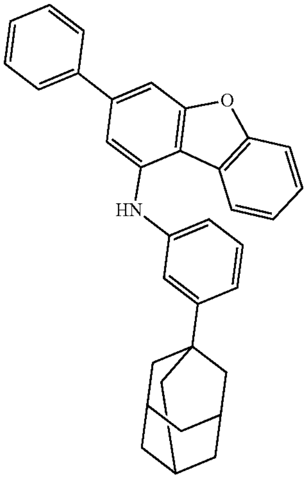
Sub2-88
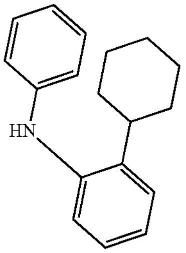
Sub2-89
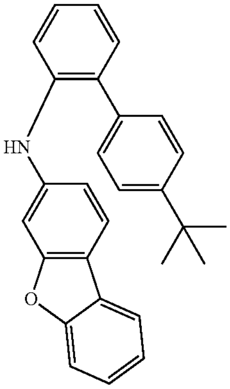
-continued
Sub2-90
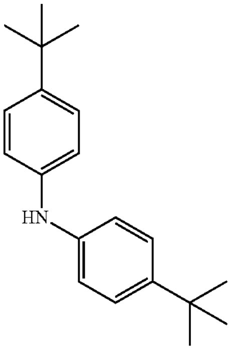
Sub2-91
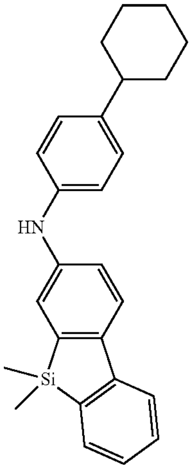
Sub2-92
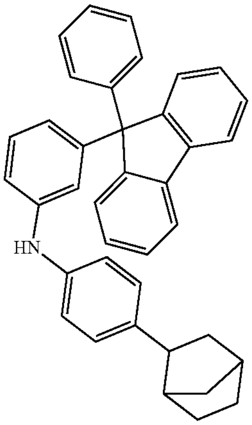

-continued
Sub2-93
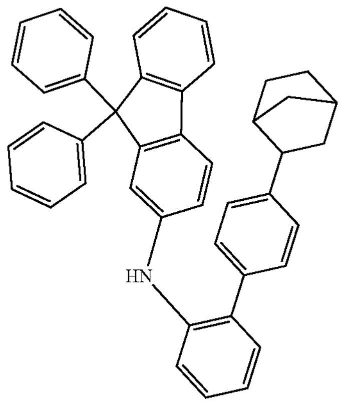
Sub2-94
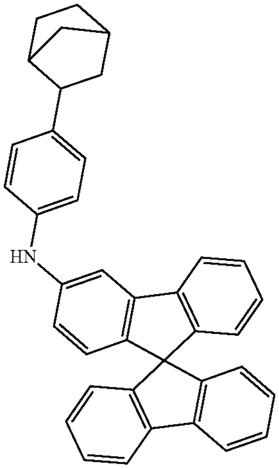
Sub2-95
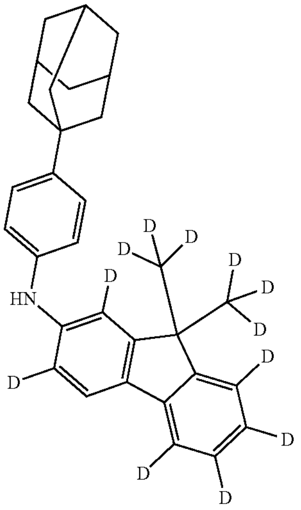
-continued
Sub2-96
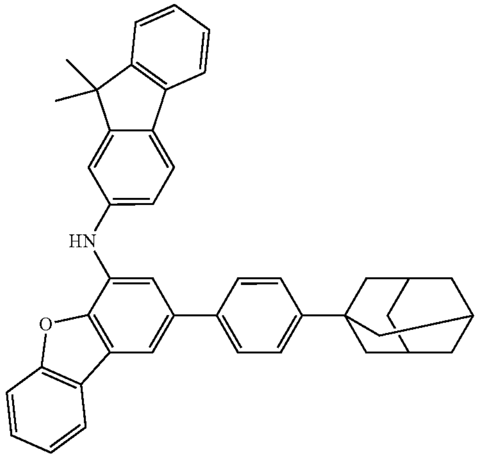
Sub2-97
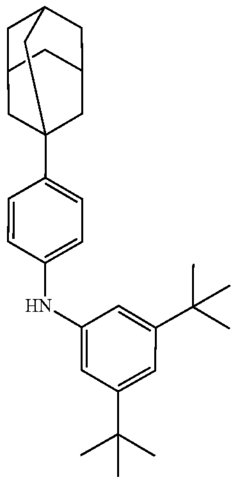
Sub2-98
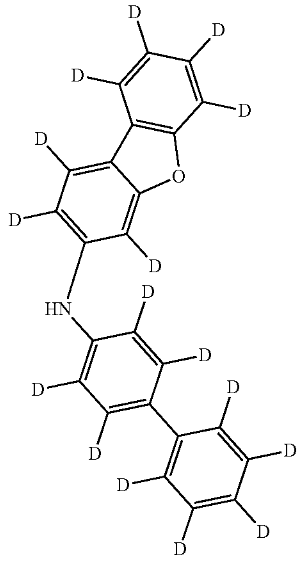

TABLE 2

| Compound | FD-MS | Compound | FD-MS |
|---|---|---|---|
| Sub 2-1 | m/z = 321.2($C_{24}H_{19}N$ = 321.4) | Sub 2-2 | m/z = 361.2($C_{27}H_{23}N$ = 361.5) |
| Sub 2-3 | m/z = 401.2($C_{30}H_{27}N$ = 401.6) | Sub 2-4 | m/z = 401.2($C_{30}H_{27}N$ = 401.6) |
| Sub 2-5 | m/z = 401.2($C_{30}H_{27}N$ = 401.6) | Sub 2-6 | m/z = 401.2($C_{30}H_{27}N$ = 401.6) |
| Sub 2-7 | m/z = 477.2($C_{36}H_{31}N$ = 477.7) | Sub 2-8 | m/z = 457.3($C_{34}H_{35}N$ = 457.7) |
| Sub 2-9 | m/z = 457.3($C_{34}H_{35}N$ = 457.7) | Sub 2-10 | m/z = 417.2($C_{31}H_{31}N$ = 417.6) |
| Sub 2-11 | m/z = 569.4($C_{42}H_{51}N$ = 569.9) | Sub 2-12 | m/z = 513.3($C_{38}H_{43}N$ = 513.8) |
| Sub 2-13 | m/z = 489.3($C_{36}H_{43}N$ = 489.7) | Sub 2-14 | m/z = 507.3($C_{38}H_{37}N$ = 507.7) |
| Sub 2-15 | m/z = 477.2($C_{36}H_{31}N$ = 477.7) | Sub 2-16 | m/z = 609.3($C_{46}H_{43}N$ = 609.9) |
| Sub 2-17 | m/z = 433.3($C_{32}H_{35}N$ = 433.6) | Sub 2-18 | m/z = 507.3($C_{38}H_{37}N$ = 507.7) |
| Sub 2-19 | Mass: 533.3C40H39N533.8) | Sub 2-20 | m/z = 549.3($C_{41}H_{43}N$ = 549.8) |
| Sub 2-21 | m/z = 609.3($C_{46}H_{43}N$ = 609.9) | Sub 2-22 | m/z = 493.3($C_{37}H_{35}N$ = 493.7) |
| Sub 2-23 | m/z = 533.3($C_{40}H_{39}N$ = 533.8) | Sub 2-24 | m/z = 457.3($C_{34}H_{35}N$ = 457.7) |
| Sub 2-25 | m/z = 375.2($C_{27}H_{21}NO$ = 375.5) | Sub 2-26 | m/z = 451.2($C_{33}H_{25}NO$ = 451.6) |
| Sub 2-27 | m/z = 425.2($C_{31}H_{23}NO$ = 425.5) | Sub 2-28 | m/z = 375.2($C_{27}H_{21}NO$ = 375.5) |
| Sub 2-29 | m/z = 349.1($C_{24}H_{15}NO_2$ = 349.4) | Sub 2-30 | m/z = 415.1($C_{28}H_{17}NOS$ = 415.5) |
| Sub 2-31 | m/z = 493.2($C_{35}H_{31}NSi$ = 493.7) | Sub 2-32 | m/z = 451.2($C_{33}H_{25}NO$ = 451.6) |
| Sub 2-33 | m/z = 391.1($C_{27}H_{21}NS$ = 391.5) | Sub 2-34 | m/z = 407.2($C_{28}H_{25}NS$ = 407.6) |
| Sub 2-35 | m/z = 431.2($C_{31}H_{29}NO$ = 431.6) | Sub 2-36 | m/z = 417.2($C_{29}H_{27}NSi$ = 417.6) |
| Sub 2-37 | m/z = 606.2($C_{42}H_{26}N_2OS$ = 606.7) | Sub 2-38 | m/z = 466.2($C_{32}H_{26}N_2Si$ = 466.7) |
| Sub 2-39 | m/z = 533.3($C_{39}H_{23}D_6NO$ = 533.7) | Sub 2-40 | m/z = 571.2($C_{40}H_{29}NOS$ = 571.7) |
| Sub 2-41 | m/z = 473.3($C_{33}H_{35}NSi$ = 473.7) | Sub 2-42 | m/z = 375.2($C_{27}H_{21}NO$ = 375.5) |
| Sub 2-43 | m/z = 499.2($C_{37}H_{25}NO$ = 499.6) | Sub 2-44 | m/z = 555.3($C_{41}H_{33}NO$ = 555.7) |
| Sub 2-45 | m/z = 513.2($C_{37}H_{23}NO_2$ = 513.6) | Sub 2-46 | m/z = 567.3($C_{42}H_{33}NO$ = 567.7) |
| Sub 2-47 | m/z = 456.2($C_{33}H_{20}D_5NO$ = 456.6) | Sub 2-48 | m/z = 451.2($C_{33}H_{25}NO$ = 451.6) |
| Sub 2-49 | m/z = 367.2($C_{27}H_{29}N$ = 367.5) | Sub 2-50 | m/z = 435.3($C_{32}H_{37}N$ = 435.7) |
| Sub 2-51 | m/z = 457.3($C_{34}H_{35}N$ = 457.7) | Sub 2-52 | m/z = 419.3($C_{31}H_{33}N$ = 419.6) |
| Sub 2-53 | m/z = 251.2($C_{18}H_{21}N$ = 251.4) | Sub 2-54 | m/z = 533.3($C_{40}H_{39}N$ = 533.8) |
| Sub 2-55 | m/z = 559.3($C_{42}H_{41}N$ = 559.8) | Sub 2-56 | m/z = 397.3($C_{29}H_{35}N$ = 397.6) |
| Sub 2-57 | m/z = 379.2($C_{28}H_{29}N$ = 379.5) | Sub 2-58 | m/z = 435.3($C_{32}H_{37}N$ = 435.7) |
| Sub 2-59 | m/z = 571.3($C_{43}H_{41}N$ = 571.8) | Sub 2-60 | m/z = 461.3($C_{34}H_{39}N$ = 461.7) |
| Sub 2-61 | m/z = 419.3($C_{31}H_{33}N$ = 419.6) | Sub 2-62 | m/z = 495.3($C_{37}H_{37}N$ = 495.7) |
| Sub 2-63 | m/z = 384.3($C_{28}H_{24}D_5N$ = 384.6) | Sub 2-64 | m/z = 513.3($C_{38}H_{43}N$ = 513.8) |
| Sub 2-65 | m/z = 375.2($C_{27}H_{21}NO$ = 375.5) | Sub 2-66 | m/z = 451.2($C_{33}H_{25}NO$ = 451.6) |
| Sub 2-67 | m/z = 375.2($C_{27}H_{21}NO$ = 375.5) | Sub 2-68 | m/z = 375.2($C_{27}H_{21}NO$ = 375.5) |
| Sub 2-69 | m/z = 391.1($C_{26}H_{21}NOSi$ = 391.5) | Sub 2-70 | m/z = 379.1($C_{25}H_{17}NOS$ = 379.5) |
| Sub 2-71 | m/z = 498.3($C_{35}H_{26}D_5NSi$ = 498.8) | Sub 2-72 | m/z = 507.3($C_{37}H_{33}NO$ = 507.7) |
| Sub 2-73 | m/z = 391.1($C_{27}H_{21}NS$ = 391.5) | Sub 2-74 | m/z = 629.3($C_{43}H_{39}NSSi$ = 629.9) |
| Sub 2-75 | m/z = 431.2($C_{31}H_{29}NO$ = 431.6) | Sub 2-76 | m/z = 599.2($C_{42}H_{33}NOS$ = 599.8) |
| Sub 2-77 | m/z = 379.1($C_{25}H_{17}NOS$ = 379.5) | Sub 2-78 | m/z = 509.2($C_{36}H_{31}NS$ = 509.7) |
| Sub 2-79 | m/z = 383.2($C_{26}H_{29}NSi$ = 383.6) | Sub 2-80 | m/z = 409.2($C_{29}H_{31}NO$ = 409.6) |
| Sub 2-81 | m/z = 471.2($C_{33}H_{33}NSi$ = 471.7) | Sub 2-82 | m/z = 517.2($C_{38}H_{31}NO$ = 517.7) |
| Sub 2-83 | m/z = 517.2($C_{38}H_{31}NO$ = 517.7) | Sub 2-84 | m/z = 557.3($C_{41}H_{35}NO$ = 557.7) |
| Sub 2-85 | m/z = 585.3($C_{43}H_{39}NO$ = 585.8) | Sub 2-86 | m/z = 469.2($C_{34}H_{31}NO$ = 469.6) |
| Sub 2-87 | m/z = 469.2($C_{34}H_{31}NO$ = 469.6) | Sub 2-88 | m/z = 251.2($C_{18}H_{21}N$ = 251.4) |
| Sub 2-89 | m/z = 391.2($C_{28}H_{25}NO$ = 391.5) | Sub 2-90 | m/z = 281.2($C_{20}H_{27}N$ = 281.4) |
| Sub 2-91 | m/z = 383.2($C_{26}H_{29}NSi$ = 383.6) | Sub 2-92 | m/z = 503.3($C_{38}H_{33}N$ = 503.7) |
| Sub 2-93 | m/z = 579.3($C_{44}H_{37}N$ = 579.8) | Sub 2-94 | m/z = 501.2($C_{38}H_{31}N$ = 501.7) |
| Sub 2-95 | m/z = 431.3($C_{31}H_{21}D_{12}N$ = 431.7) | Sub 2-96 | m/z = 585.3($C_{43}H_{39}NO$ = 585.8) |
| Sub 2-97 | m/z = 415.3($C_{30}H_{41}N$ = 415.7) | Sub 2-98 | m/z = 351.2($C_{24}HD_{16}NO$ = 351.5) |

III. Synthesis of Final Product

1. Synthesis Example of P-3

-continued

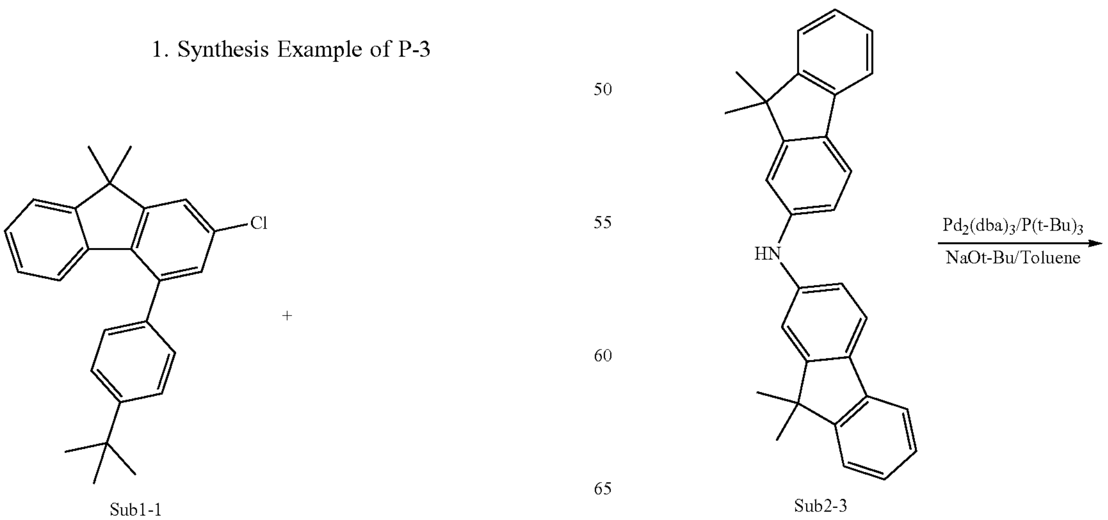

Sub1-1 Sub2-3

-continued

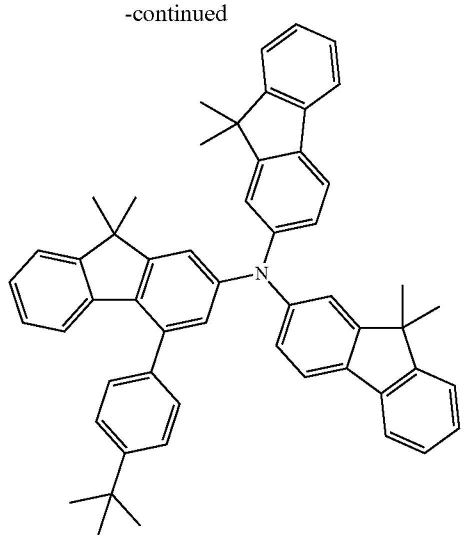

P-3

Sub1-1 (20.0 g, 55.4 mmol) was dissolved in toluene (280 mL) in a round-bottom flask, and Sub2-3 (22.3 g, 55.4 mmol), $Pd_2(dba)_3$ (1.52 g, 1.66 mmol), $P(t\text{-}Bu)_3$ (0.67 g, 3.33 mmol), NaOt-Bu (16.0 g, 166.3 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 35.0 g of the product (87%).

2. Synthesis Example of P-10

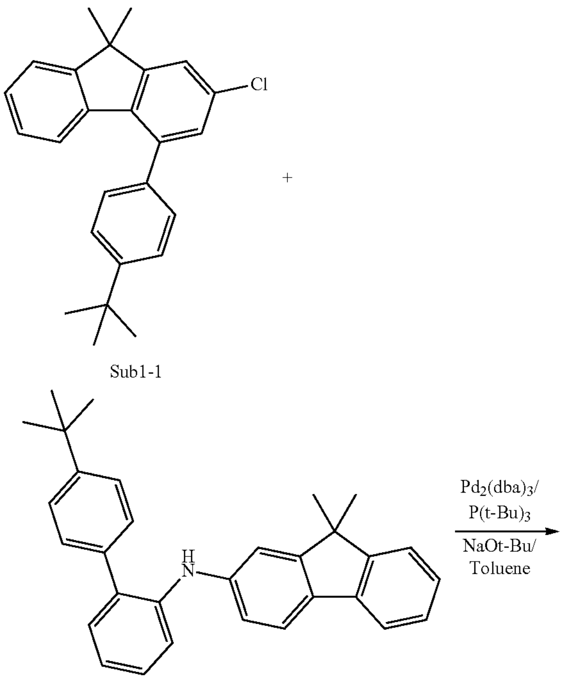

Sub1-1

Sub2-10

-continued

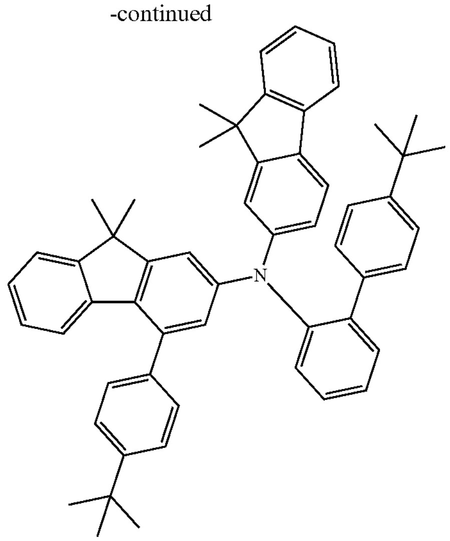

P-10

Sub1-1 (20.0 g, 55.4 mmol) was dissolved in toluene (280 mL) in a round-bottom flask, and Sub2-10 (23.1 g, 55.4 mmol), $Pd_2(dba)_3$ (1.52 g, 1.66 mmol), $P(t\text{-}Bu)_3$ (0.67 g, 3.33 mmol), NaOt-Bu (16.0 g, 166.3 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 33.3 g of the product (81%).

3. Synthesis Example of P-25

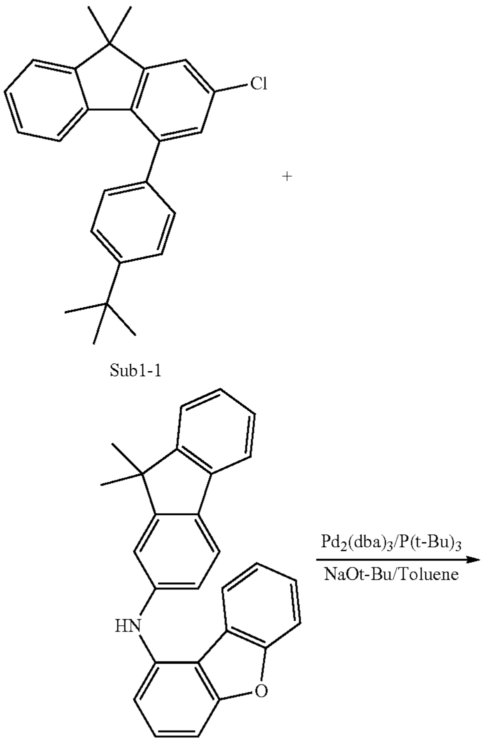

Sub1-1

Sub2-25

-continued

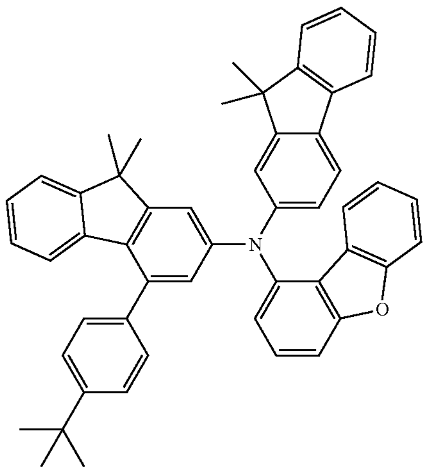

P-25

Sub1-1 (20.0 g, 55.4 mmol) was dissolved in toluene (280 mL) in a round-bottom flask, and Sub2-25 (20.8 g, 55.4 mmol), $Pd_2(dba)_3$ (1.52 g, 1.66 mmol), $P(t\text{-}Bu)_3$ (0.67 g, 3.33 mmol), NaOt-Bu (16.0 g, 166.3 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 31.0 g of the product (80%).

4. Synthesis Example of P-36

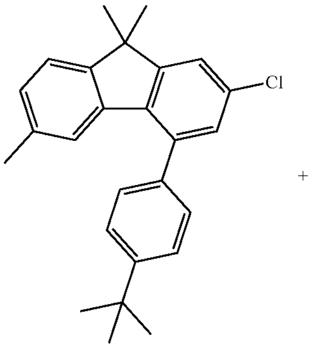

Sub1-11

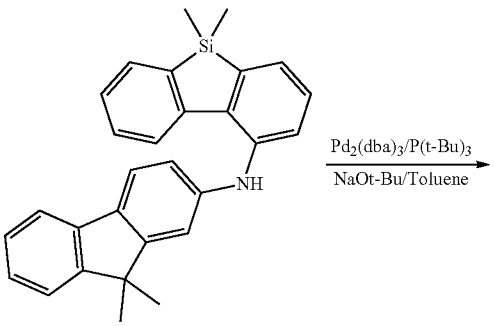

Sub2-36

-continued

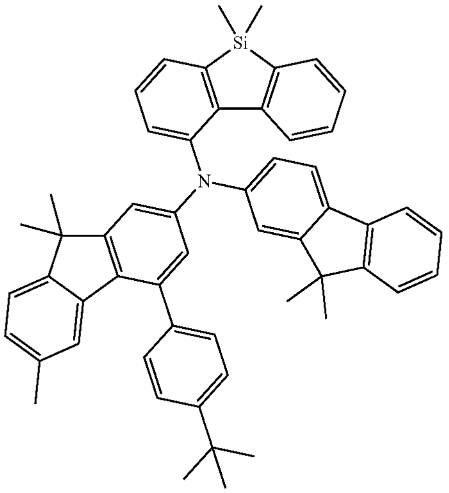

P-36

Sub1-11 (20.0 g, 53.3 mmol) was dissolved in toluene (270 mL) in a round-bottom flask, and Sub2-36 (22.3 g, 53.3 mmol), $Pd_2(dba)_3$ (1.47 g, 1.60 mmol), $P(t\text{-}Bu)_3$ (0.65 g, 3.20 mmol), NaOt-Bu (15.4 g, 160.0 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 31.5 g of the product (78%).

5. Synthesis Example of P-47

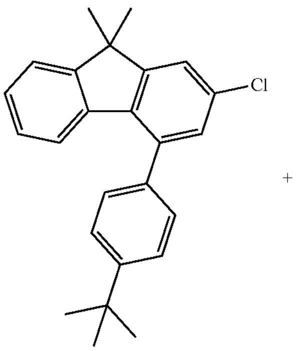

Sub1-1

-continued

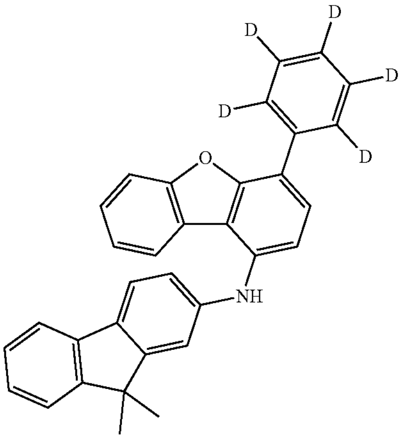

Sub2-47

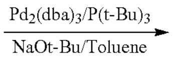

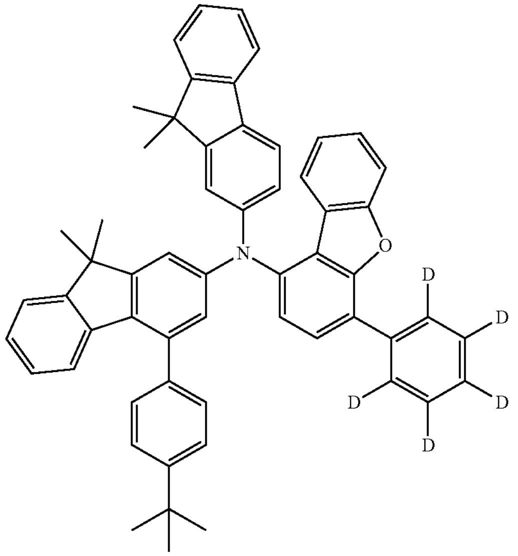

P-47

Sub1-1 (20.0 g, 55.4 mmol) was dissolved in toluene (280 mL) in a round-bottom flask, and Sub2-47 (25.3 g, 55.4 mmol), $Pd_2(dba)_3$ (1.52 g, 1.66 mmol), $P(t-Bu)_3$ (0.67 g, 3.33 mmol), NaOt-Bu (16.0 g, 166.3 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 33.3 g of the product (77%).

6. Synthesis Example of P-70

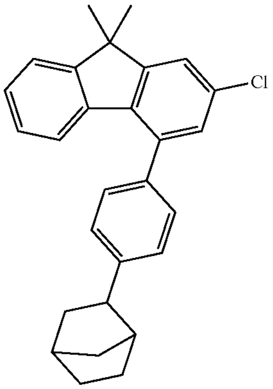

Sub1-15

+

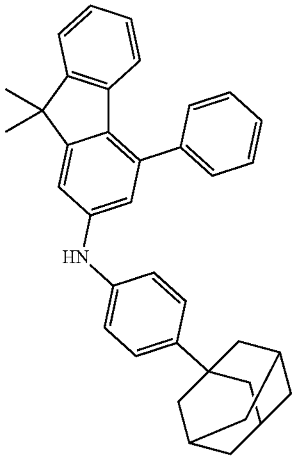

Sub2-62

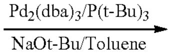

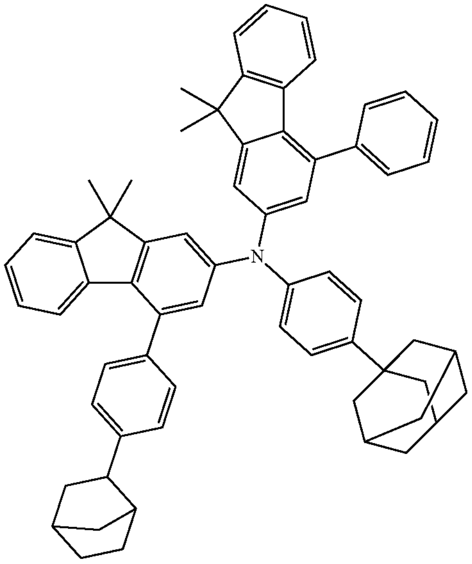

P-70

Sub1-15 (20.0 g, 50.1 mmol) was dissolved in toluene (250 mL) in a round-bottom flask, and Sub2-62 (24.8 g, 50.1 mmol), $Pd_2(dba)_3$ (1.38 g, 1.50 mmol), $P(t-Bu)_3$ (0.61 g, 3.01 mmol), NaOt-Bu (14.5 g, 150.4 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 32.7 g of the product (76%).

7. Synthesis Example of P-79

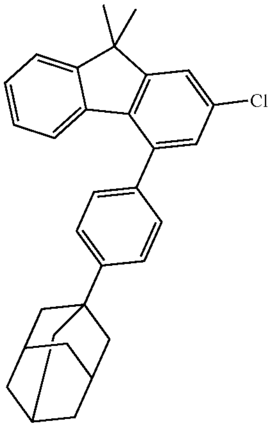

Sub1-16

+

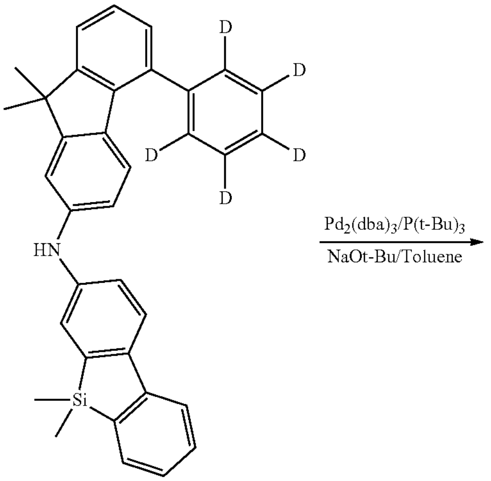

Sub2-71

-continued

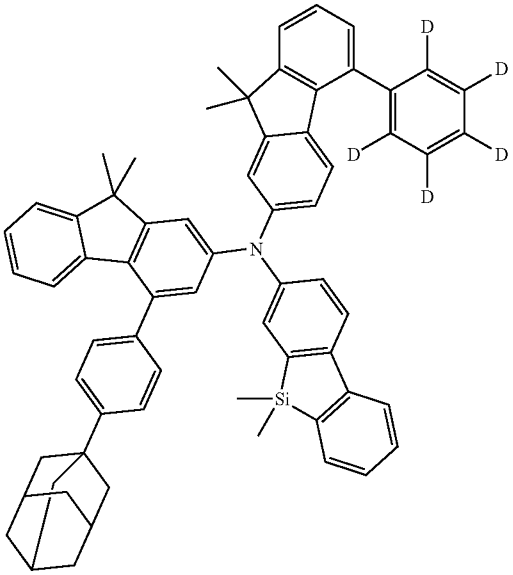

P-79

Sub1-16 (20.0 g, 45.6 mmol) was dissolved in toluene (250 mL) in a round-bottom flask, and Sub2-71 (22.7 g, 45.6 mmol), $Pd_2(dba)_3$ (1.25 g, 1.37 mmol), $P(t-Bu)_3$ (0.55 g, 2.73 mmol), NaOt-Bu (13.1 g, 136.7 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 32.0 g of the product (78%).

8. Synthesis Example of P-93

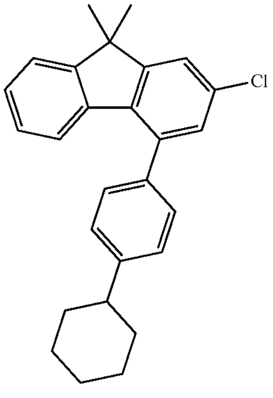

Sub1-14

+

-continued

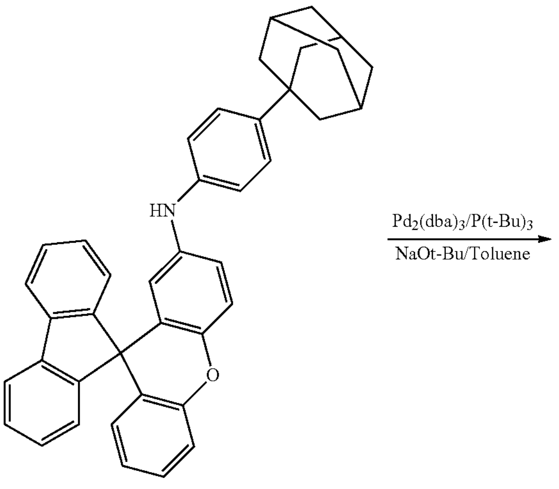

Sub2-84

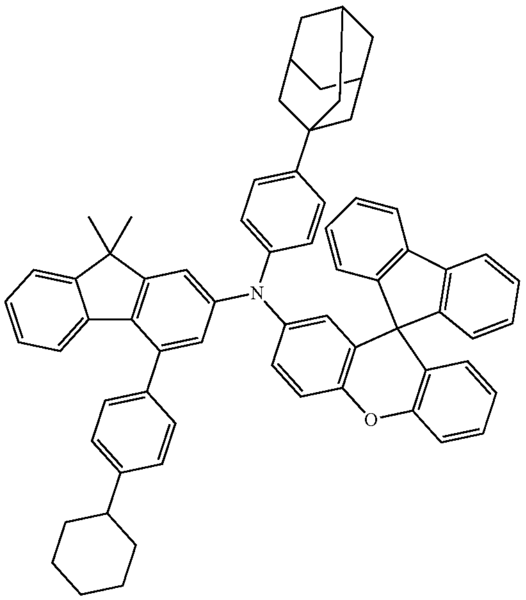

P-93

Sub1-14 (20.0 g, 51.7 mmol) was dissolved in toluene (260 mL) in a round-bottom flask, and Sub2-84 (28.8 g, 51.7 mmol), $Pd_2(dba)_3$ (1.42 g, 1.55 mmol), $P(t\text{-}Bu)_3$ (0.63 g, 3.10 mmol), NaOt-Bu (14.9 g, 155.0 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 38.0 g of the product (81%).

9. Synthesis Example of P-99

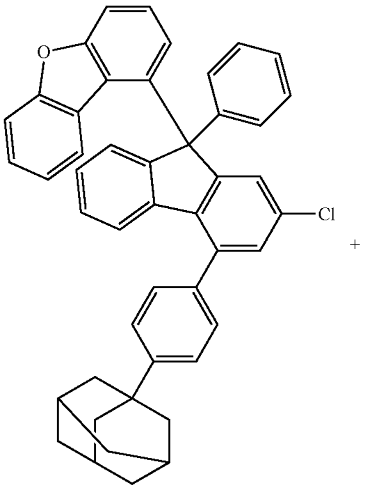

Sub1-25

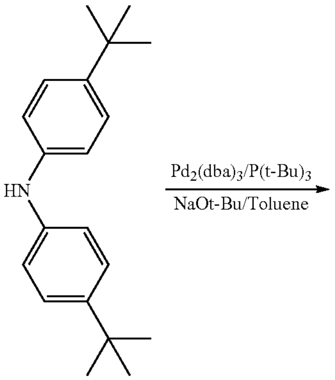

Sub2-90

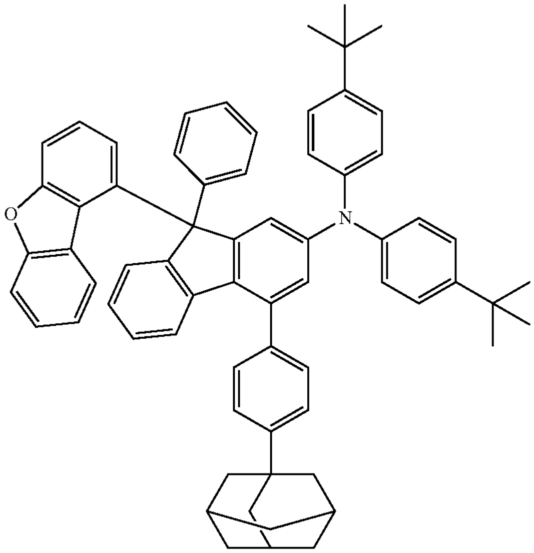

P-99

Sub1-25 (20.0 g, 30.6 mmol) was dissolved in toluene (150 mL) in a round-bottom flask, and Sub2-90 (8.6 g, 30.6 mmol), $Pd_2(dba)_3$ (0.84 g, 0.92 mmol), $P(t\text{-}Bu)_3$ (0.37 g, 1.84 mmol), NaOt-Bu (8.8 g, 91.8 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 19 g of the product (69%).

10. Synthesis Example of P-106

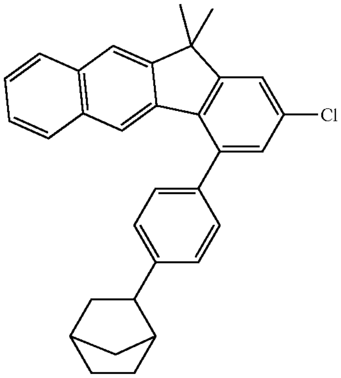

Sub1-29

+

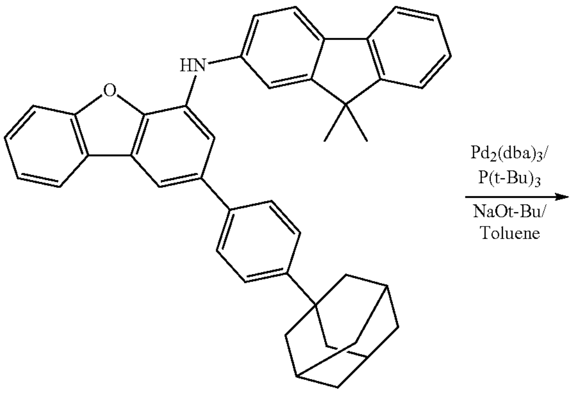

Sub2-96

-continued

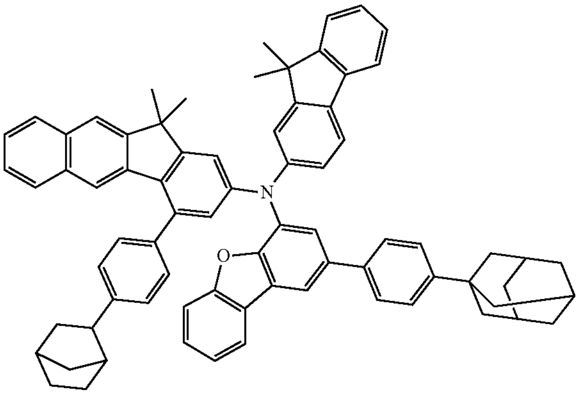

P-106

Sub1-29 (20.0 g, 44.5 mmol) was dissolved in toluene (220 mL) in a round-bottom flask, and Sub2-96 (26.1 g, 44.5 mmol), $Pd_2(dba)_3$ (1.22 g, 1.34 mmol), $P(t-Bu)_3$ (0.54 g, 2.67 mmol), NaOt-Bu (12.8 g, 133.6 mmol) were added and stirred under reflux at 125° C. When the reaction was complete, the reaction product was extracted with $CH_2Cl_2$ and water, and then the organic layer was dried over $MgSO_4$, concentrated, and the resulting compound was recrystallized using a silica gel column to obtain 32.0 g of the product (72%).

Meanwhile, the FD-MS values of compounds P-1 to P-136 of the present invention manufactured according to the above-described synthetic examples are as shown in Table 3.

TABLE 3

| Compound | FD-MS | Compound | FD-MS |
|---|---|---|---|
| P-1 | m/z = 645.3($C_{49}H_{43}N$ = 645.9) | P-2 | m/z = 685.4($C_{52}H_{47}N$ = 686.0) |
| P-3 | m/z = 725.4($C_{55}H_{51}N$ = 726.0) | P-4 | m/z = 683.4($C_{52}H_{45}N$ = 683.9) |
| P-5 | m/z = 697.4($C_{53}H_{47}N$ = 698.0) | P-6 | m/z = 711.4($C_{54}H_{49}N$ = 712.0) |
| P-7 | m/z = 801.4($C_{61}H_{55}N$ = 802.1) | P-8 | m/z = 781.5($C_{59}H_{59}N$ = 782.1) |
| P-9 | m/z = 781.5($C_{59}H_{59}N$ = 782.1) | P-10 | m/z = 741.4($C_{56}H_{55}N$ = 742.1) |
| P-11 | m/z = 893.6($C_{67}H_{75}N$ = 894.3) | P-12 | m/z = 837.5($C_{63}H_{67}N$ = 838.2) |
| P-13 | m/z = 889.6($C_{67}H_{71}N$ = 890.3) | P-14 | m/z = 839.4($C_{64}H_{57}N$ = 840.2) |
| P-15 | m/z = 801.4($C_{61}H_{55}N$ = 802.1) | P-16 | m/z = 1009.6($C_{77}H_{71}N$ = 1010.4) |
| P-17 | m/z = 757.5($C_{57}H_{59}N$ = 758.1) | P-18 | m/z = 831.5($C_{63}H_{61}N$ = 832.2) |
| P-19 | m/z = 857.5($C_{65}H_{63}N$ = 858.2) | P-20 | m/z = 873.5($C_{66}H_{67}N$ = 874.3) |
| P-21 | m/z = 933.5($C_{71}H_{67}N$ = 934.3) | P-22 | m/z = 817.5($C_{62}H_{59}N$ = 818.2) |
| P-23 | m/z = 857.5($C_{65}H_{63}N$ = 858.2) | P-24 | m/z = 781.5($C_{59}H_{59}N$ = 782.1) |
| P-25 | m/z = 699.4($C_{52}H_{45}NO$ = 699.9) | P-26 | m/z = 775.4($C_{58}H_{49}NO$ = 776.0) |
| P-27 | m/z = 749.4($C_{56}H_{47}NO$ = 750.0) | P-28 | m/z = 699.4($C_{52}H_{45}NO$ = 699.9) |
| P-29 | m/z = 673.3($C_{49}H_{39}NO_2$ = 673.9) | P-30 | m/z = 795.4($C_{57}H_{49}NOS$ = 796.1) |
| P-31 | m/z = 817.4($C_{60}H_{55}NSi$ = 818.2) | P-32 | m/z = 775.4($C_{58}H_{49}NO$ = 776.0) |
| P-33 | m/z = 715.3($C_{52}H_{45}NS$ = 716.0) | P-34 | m/z = 731.4($C_{53}H_{49}NS$ = 732.0) |
| P-35 | m/z = 755.4($C_{56}H_{53}NO$ = 756.0) | P-36 | m/z = 755.4($C_{55}H_{53}NSi$ = 756.1) |
| P-37 | m/z = 930.4($C_{67}H_{50}N_2OS$ = 931.2) | P-38 | m/z = 790.4($C_{57}H_{50}N_2Si$ = 791.1) |
| P-39 | m/z = 857.5($C_{64}H_{47}D_6NO$ = 858.2) | P-40 | m/z = 895.4($C_{65}H_{53}NOS$ = 896.2) |
| P-41 | m/z = 797.4($C_{58}H_{59}NSi$ = 798.2) | P-42 | m/z = 755.4($C_{56}H_{53}NO$ = 756.0) |
| P-43 | m/z = 823.4($C_{62}H_{49}NO$ = 824.1) | P-44 | m/z = 879.4($C_{66}H_{57}NO$ = 880.2) |
| P-45 | m/z = 837.4($C_{62}H_{47}NO_2$ = 838.1) | P-46 | m/z = 891.4($C_{67}H_{57}NO$ = 892.2) |
| P-47 | m/z = 780.4($C_{58}H_{44}D_5NO$ = 781.1) | P-48 | m/z = 851.4($C_{64}H_{53}NO$ = 852.1) |

TABLE 3-continued

| Compound | FD-MS | Compound | FD-MS |
|---|---|---|---|
| P-49 | m/z = 671.4($C_{51}H_{45}N$ = 671.9) | P-50 | m/z = 723.4($C_{55}H_{49}N$ = 724.0) |
| P-51 | m/z = 803.4($C_{61}H_{57}N$ = 804.1) | P-52 | m/z = 691.4($C_{52}H_{53}N$ = 692.0) |
| P-53 | m/z = 827.4($C_{63}H_{57}N$ = 828.2) | P-54 | m/z = 763.4($C_{58}H_{53}N$ = 764.1) |
| P-55 | m/z = 879.5($C_{67}H_{61}N$ = 880.2) | P-56 | m/z = 759.5($C_{57}H_{61}N$ = 760.1) |
| P-57 | m/z = 807.5($C_{61}H_{61}N$ = 808.2) | P-58 | m/z = 779.4($C_{59}H_{57}N$ = 780.1) |
| P-59 | m/z = 803.4($C_{61}H_{57}N$ = 804.1) | P-60 | m/z = 743.4($C_{56}H_{57}N$ = 744.1) |
| P-61 | m/z = 677.4($C_{51}H_{51}N$ = 678.0) | P-62 | m/z = 909.5($C_{69}H_{67}N$ = 910.3) |
| P-63 | m/z = 1017.6($C_{77}H_{79}N$ = 1018.5) | P-64 | m/z = 721.5($C_{54}H_{59}N$ = 722.1) |
| P-65 | m/z = 729.4($C_{55}H_{55}N$ = 730.1) | P-66 | m/z = 797.5($C_{60}H_{63}N$ = 798.2) |
| P-67 | m/z = 973.6($C_{74}H_{71}N$ = 974.4) | P-68 | m/z = 785.5($C_{59}H_{63}N$ = 786.2) |
| P-69 | m/z = 769.5($C_{58}H_{59}N$ = 770.1) | P-70 | m/z = 857.5($C_{65}H_{63}N$ = 858.2) |
| P-71 | m/z = 786.5($C_{59}H_{54}D_5N$ = 787.2) | P-72 | m/z = 837.5($C_{63}H_{67}N$ = 838.2) |
| P-73 | m/z = 725.4($C_{54}H_{47}NO$ = 726.0) | P-74 | m/z = 813.4($C_{61}H_{51}NO$ = 814.1) |
| P-75 | m/z = 777.4($C_{58}H_{51}NO$ = 778.1) | P-76 | m/z = 699.4($C_{52}H_{45}NO$ = 699.9) |
| P-77 | m/z = 741.3($C_{53}H_{47}NOSi$ = 742.0) | P-78 | m/z = 755.3($C_{54}H_{45}NOS$ = 756.0) |
| P-79 | m/z = 900.5($C_{66}H_{56}D_5NSi$ = 901.3) | P-80 | m/z = 831.4($C_{62}H_{57}NO$ = 832.1) |
| P-81 | m/z = 741.3($C_{54}H_{47}NS$ = 742.0) | P-82 | m/z = 991.5($C_{71}H_{65}NSSi$ = 992.5) |
| P-83 | m/z = 833.5($C_{62}H_{59}NO$ = 834.2) | P-84 | m/z = 741.4($C_{54}H_{51}NSi$ = 742.1) |
| P-85 | m/z = 949.4($C_{69}H_{59}NOS$ = 950.3) | P-86 | m/z = 741.3($C_{53}H_{43}NOS$ = 742.0) |
| P-87 | m/z = 911.5($C_{67}H_{61}NS$ = 912.3) | P-88 | m/z = 707.4($C_{51}H_{53}NSi$ = 708.1) |
| P-89 | m/z = 759.4($C_{56}H_{57}NO$ = 760.1) | P-90 | m/z = 833.4($C_{61}H_{59}NSi$ = 834.2) |
| P-91 | m/z = 933.5($C_{70}H_{63}NO$ = 934.3) | P-92 | m/z = 841.4($C_{63}H_{55}NO$ = 842.1) |
| P-93 | m/z = 907.5($C_{68}H_{61}NO$ = 908.2) | P-94 | m/z = 947.5($C_{71}H_{65}NO$ = 948.3) |
| P-95 | m/z = 871.5($C_{65}H_{61}NO$ = 872.2) | P-96 | m/z = 793.4($C_{59}H_{55}NO$ = 794.1) |
| P-97 | m/z = 725.4($C_{55}H_{51}N$ = 726.0) | P-98 | m/z = 875.4($C_{66}H_{53}NO$ = 876.2) |
| P-99 | m/z = 897.5($C_{67}H_{63}NO$ = 898.2) | P-100 | m/z = 937.4($C_{67}H_{59}NSSi$ = 938.4) |
| P-101 | m/z = 853.5($C_{65}H_{59}N$ = 854.2) | P-102 | m/z = 941.5($C_{72}H_{63}N$ = 942.3) |
| P-103 | m/z = 903.5($C_{69}H_{61}N$ = 904.3) | P-104 | m/z = 761.6($C_{56}H_{39}D_{18}N$ = 762.2) |
| P-105 | m/z = 957.5($C_{72}H_{63}NO$ = 958.3) | P-106 | m/z = 997.5($C_{75}H_{67}NO$ = 998.4) |
| P-107 | m/z = 867.6($C_{65}H_{73}N$ = 868.3) | P-108 | m/z = 700.6($C_{49}D_{41}NO$ = 701.1) |
| P-109 | m/z = 657.3($C_{49}H_{39}NO$ = 657.8) | P-110 | m/z = 699.3($C_{52}H_{45}NO$ = 699.9) |
| P-111 | m/z = 725.3($C_{54}H_{47}NO$ = 725.9) | P-112 | m/z = 737.3($C_{55}H_{47}NO$ = 737.9) |
| P-113 | m/z = 733.3($C_{55}H_{43}NO$ = 733.9) | P-114 | m/z = 755.4($C_{56}H_{53}NO$ = 756.0) |
| P-115 | m/z = 777.4($C_{58}H_{51}NO$ = 778.0) | P-116 | m/z = 813.4($C_{61}H_{51}NO$ = 814.0) |
| P-117 | m/z = 851.3($C_{63}H_{49}NS$ = 852.1) | P-118 | m/z = 993.4($C_{74}H_{59}NS$ = 994.3) |
| P-119 | m/z = 1200.54($C_{92}H_{68}N_2$ = 1201.5) | P-120 | m/z = 1166.5($C_{89}H_{70}N_2$ = 1167.5) |
| P-121 | m/z = 877.3($C_{68}H_{47}N$ = 878.1) | P-122 | m/z = 803.4($C_{61}H_{57}N$ = 804.1) |
| P-123 | m/z = 645.3($C_{49}H_{43}N$ = 645.8) | P-124 | m/z = 735.3($C_{55}H_{45}NO$ = 735.9) |
| P-125 | m/z = 609.3($C_{46}H_{43}N$ = 609.8) | P-126 | m/z = 747.4($C_{56}H_{49}D_6N$ = 748.1) |
| P-127 | m/z = 714.4($C_{53}H_{38}D_{13}N$ = 715.0) | P-128 | m/z = 632.4($C_{47}H_{36}D_9N$ = 632.9) |
| P-129 | m/z = 647.3($C_{49}H_{37}D_4N$ = 647.9) | P-130 | m/z = 719.4($C_{53}H_{41}D_6NO$ = 720.0) |
| P-131 | m/z = 744.3($C_{54}H_{44}D_5NSi$ = 745.1) | P-132 | m/z = 835.4($C_{61}H_{57}NS$ = 836.1) |
| P-133 | m/z = 931.4($C_{72}H_{53}N$ = 932.2) | P-134 | m/z = 726.3($C_{54}H_{35}D_5NO$ = 726.9) |
| P-135 | m/z = 706.4($C_{53}H_{46}D_5N$ = 707.03) | P-136 | m/z = 711.3($C_{54}H_{49}N$ = 711.9) |

Meanwhile, exemplary synthesis examples of the present invention represented by Formula 1 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and $PPh_3$-mediated reductive cyclization reaction (*J. Org. Chem.* 2005, 70, 5014.), and it will be easily understood by those skilled in the art that the reaction proceeds even when other substituents defined in Formula 1 are bonded in addition to the substituents specified in the specific synthesis examples.

Manufacturing and Evaluation of Organic Electronic Element

[Example 1] Red Organic Light Emitting Device (Emitting Auxiliary Layer)

First, $N^1$-(naphthalen-2-yl)-$N^4$,$N^4$-bis(4-(naphthalen-2-yl (phenyl)amino)phenyl)-$N^1$-phenylbenzene-1,4-diamine (hereinafter abbreviated as 2-TNATA) was vacuum-deposited to a thickness of 60 nm on an ITO layer (anode) formed on a glass substrate to form a hole injection layer, and then N,N'-bis(1-naphthalenyl)-N,N'-bis-phenyl-(1,1' biphenyl)-4,4'-diamine (hereinafter abbreviated as NPB) was vacuum-deposited to a thickness of 60 nm on the hole injection layer to form a hole transport layer.

Next, the compound P-3 of the present invention was vacuum-deposited on the hole transport layer to a thickness of 20 nm to form an emitting auxiliary layer. Thereafter, on the emitting auxiliary layer, 4,4'-N,N'-dicarbazole-biphenyl (hereinafter abbreviated as CBP) was used as a host material and bis-(1-phenylisoquinolyl)iridium(III)acetylacetonate (hereinafter abbreviated as $(piq)_2Ir(acac)$) was used as a dopant, and the dopant was doped such that the weight ratio of the host and dopant was 95:5, thereby forming an emitting layer with a thickness of 30 nm.

Next, (1,1'-biphenyl-4-olato)bis(2-methyl-8-quinolinolato)aluminum (hereinafter abbreviated as BAlq) was vacuum-deposited on the light-emitting layer to form a hole-blocking layer with a thickness of 10 nm, and Tris(8-hydroxyquinolinato)aluminium (hereinafter abbreviated as Alq3) was vacuum-deposited on the hole-blocking layer to a thickness of 40 nm to form an electron transport layer. Afterwards, 8-quinolinolato lithium (hereinafter abbreviated as Liq) was deposited on the electron transport layer to form an electron injection layer with a thickness of 0.2 nm, and then Al was deposited to form a cathode with a thickness of 150 nm.

[Example 2] to [Example 20]

An organic light emitting device was manufactured in the same manner as in Example 1, except that the compound of the present invention described in Table 4 was used instead of the compound P-3 of the present invention as the emitting auxiliary layer material.

[Comparative Example 1] to [Comparative Example 5]

An organic light emitting device was manufactured in the same manner as in Example 1, except that the following comparative compounds A to E were used instead of the compound P-3 of the present invention as an emitting auxiliary layer material.

<comparative compound A>

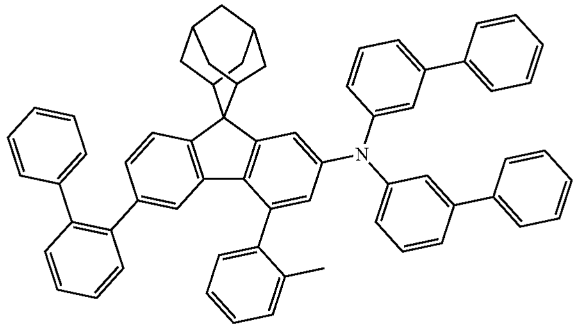

<comparative compound B>

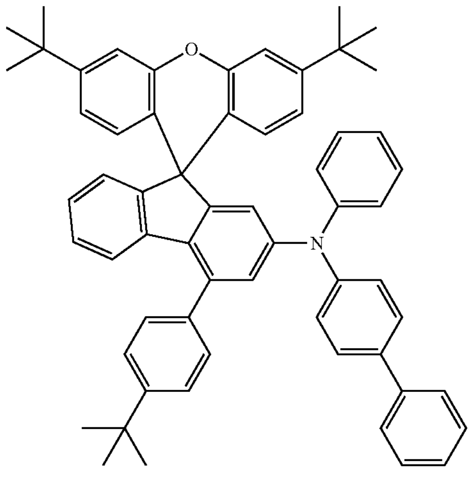

-continued

<comparative compound C>

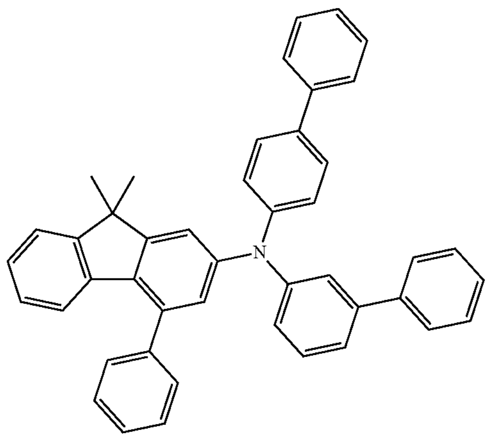

<comparative compound D>

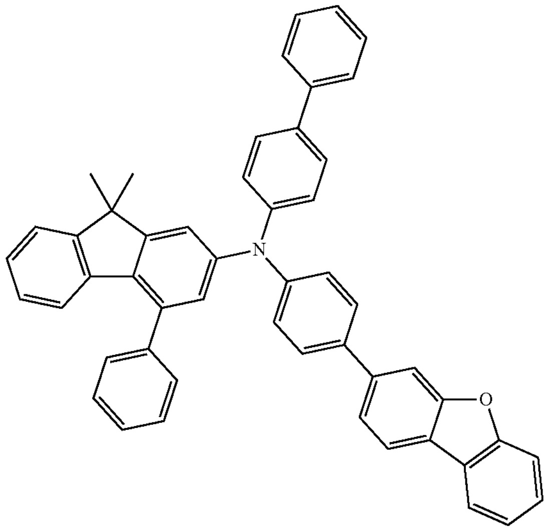

<comparative compound E>

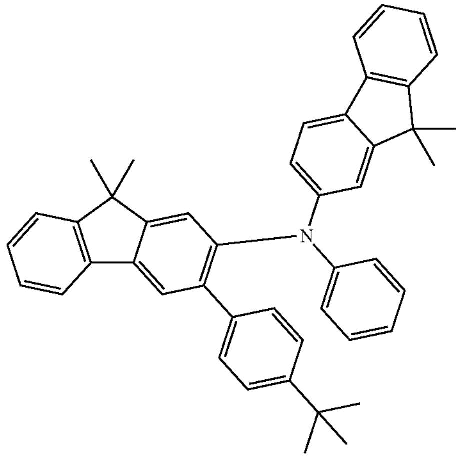

The electroluminescence (EL) characteristics were measured using PR-650 from Photoresearch by applying a forward bias DC voltage to the organic electroluminescence devices manufactured by the examples and comparative examples manufactured by Examples 1 to 20 and Comparative Examples 1 to 5 of the present invention. As a result of the measurement, the T95 lifetime was measured using a lifetime measuring device manufactured by Max Science at a standard brightness of 2,500 cd/$m^2$. Table 4 shows the results of the device fabrication and evaluation.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 4

| | compound | Driving voltage (V) | Current Density (mA/$cm^2$) | Brightness (cd/$m^2$) | Efficiency (cd/A) | T(95) |
|---|---|---|---|---|---|---|
| Comparative example (1) | Comparative compound A | 5.5 | 15.6 | 2500.0 | 16.0 | 81.8 |
| Comparative example (2) | Comparative compound B | 5.6 | 15.9 | 2500.0 | 15.7 | 82.6 |
| Comparative example (3) | Comparative compound C | 5.2 | 13.7 | 2500.0 | 18.2 | 92.4 |
| Comparative example (4) | Comparative compound D | 5.3 | 14.3 | 2500.0 | 17.5 | 91.3 |
| Comparative example (5) | Comparative compound E | 5.4 | 13.3 | 2500.0 | 18.8 | 90.9 |
| Example (1) | P-3 | 4.9 | 10.4 | 2500.0 | 24.0 | 116.5 |
| Example (2) | P-10 | 4.8 | 10.0 | 2500.0 | 25.0 | 119.6 |
| Example (3) | P-25 | 5.0 | 11.3 | 2500.0 | 22.1 | 107.8 |
| Example (4) | P-31 | 5.0 | 11.0 | 2500.0 | 22.7 | 110.8 |
| Example (5) | P-47 | 5.0 | 11.3 | 2500.0 | 22.2 | 107.4 |
| Example (6) | P-50 | 4.9 | 10.5 | 2500.0 | 23.9 | 115.8 |
| Example (7) | P-90 | 5.0 | 11.0 | 2500.0 | 22.8 | 109.2 |
| Example (8) | P-91 | 5.0 | 11.1 | 2500.0 | 22.5 | 107.7 |
| Example (9) | P-98 | 5.1 | 11.7 | 2500.0 | 21.4 | 105.5 |
| Example (10) | P-108 | 5.0 | 11.2 | 2500.0 | 22.4 | 112.0 |
| Example (11) | P-121 | 5.1 | 11.5 | 2500.0 | 21.7 | 106.4 |
| Example (12) | P-122 | 5.1 | 11.8 | 2500.0 | 21.1 | 106.1 |
| Example (13) | P-123 | 4.9 | 10.6 | 2500.0 | 23.6 | 113.5 |
| Example (14) | P-124 | 5.0 | 10.9 | 2500.0 | 22.9 | 108.1 |
| Example (15) | P-125 | 4.9 | 10.6 | 2500.0 | 23.6 | 117.5 |
| Example (16) | P-126 | 4.8 | 10.1 | 2500.0 | 24.8 | 120.1 |
| Example (17) | P-127 | 4.8 | 10.3 | 2500.0 | 24.2 | 114.3 |
| Example (18) | P-133 | 4.9 | 10.3 | 2500.0 | 24.2 | 116.6 |
| Example (19) | P-135 | 4.9 | 10.7 | 2500.0 | 23.3 | 113.2 |
| Example (20) | P-136 | 4.8 | 10.5 | 2500.0 | 23.9 | 117.6 |

As can be seen from the results in Table 4, when a red organic electroluminescence device is manufactured using a material for an organic electroluminescence device, it can be confirmed that the driving voltage, efficiency, and lifetime of the organic electroluminescence device are significantly improved in the examples using the compound of the present invention compared to the comparative examples using comparative compounds A to E as an emitting auxiliary layer.

Comparative compounds A to E are similar to the compound of the present invention in that they are tertiary amine compounds containing a substituted fluorene skeleton in the molecule. However, Comparative compounds A and B differ from the compound of the present invention in that the substituents corresponding to $R^a$ and $R^b$ of Formula 1 of the present invention form an aliphatic ring and a heterocyclic ring, respectively. Comparative compounds C and D are similar in that a substituent is introduced at position 4 of fluorene, but are different from the compound of the present invention in that the substituent does not include an alkyl group or an aliphatic ring group. In the case of comparative compound E, it is similar in that a substituent containing an alkyl group or an aliphatic ring group is substituted on the fluorene moiety, but the substitution position is different from that of the compound of the present invention.

To examine the influence of the compositional differences of these compounds, data measured using the DFT method (B3LYP/6-31g(D)) of the Gaussian program for comparative compounds and the compound of the present invention are as shown in Table 5.

TABLE 5

| compound | HOMO(eV) |
|---|---|
| Comparative compound A | 4.868 |
| Comparative compound B | 4.793 |
| Comparative compound C | 4.834 |
| Comparative compound D | 4.815 |
| Comparative compound E | 4.725 |
| P-3 | 4.647 |

As can be seen from the results in Table 5, it can be confirmed that the HOMO Energy Level (hereinafter, HOMO) value of the present invention is shallower than the HOMO values of comparative compounds A to E. As a result, when the compound of the present invention is applied to an element, it is thought that the driving voltage of the element is significantly reduced as hole injection and hole transfer from the hole transport layer to the emitting auxiliary layer becomes easier than with other comparative compounds.

For further verification, the Reorganization Energy (unit: eV, hereinafter REhole), Hole Small Polaron Stabilization Energy (unit: eV, hereinafter HSPSE), and Hole Neutral Stabilization Energy (unit: eV, HNSE) of the comparative compounds and the compound of the present invention were measured using molecular simulation (Schrodinger Materials Science Suite 4.9.128), and the data are shown in Table 6.

TABLE 6

| compound | $RE_{hole}$(eV) | HSPSE(eV) | HNSE(eV) |
|---|---|---|---|
| Comparative compound A | 0.2127 | 0.1093 | 0.1034 |
| Comparative compound B | 0.1454 | 0.0709 | 0.0744 |
| Comparative compound C | 0.1497 | 0.0732 | 0.0765 |
| Comparative compound D | 0.1243 | 0.0654 | 0.0588 |
| Comparative compound E | 0.1756 | 0.0941 | 0.0815 |
| P-3 | 0.1140 | 0.0591 | 0.0549 |

As can be seen from the results in Table 6, it can be confirmed that the REhole, HSPSE and HNSE values of compound P-3 of the present invention are significantly lower than those of comparative compounds A to E.

First, when comparing REhole, it can be confirmed that the REhole value of the compound of the present invention is significantly lower than that of other comparative compounds. As a result, when the compound of the present invention is applied to an element, it is thought that hole hopping occurs more quickly within the material than in comparative compounds, thereby improving hole mobility and allowing holes to be transferred to the emitting layer more quickly, thereby improving charge balance and significantly improving the operation and efficiency of the element.

Next, when comparing the HSPSE and HNSE values, it can be confirmed that the HSPSE and HNSE values of the compound of the present invention are significantly lower than those of the comparative compounds. This means that the compound of the present invention can reach a stable state more quickly and with less energy than comparative compounds after receiving holes from the hole transport layer within the element or transferring holes to the emitting layer, and as a result, it is thought that the lifetime of the element is significantly improved.

Stated differently, as can be seen from the results in Tables 4 to 6, it can be confirmed that the compound satisfying all the structural features and configurations disclosed in the present invention exhibits a remarkable effect in the organic electronic element, compared to the comparative compounds A to E having a structurally similar configuration to the compound of the present invention. This shows that the compound of the present invention satisfying all the specific configurations exhibits a remarkable effect, compared to other comparative compounds not described in the present specification.

These results show that even in compounds with similar molecular components, depending on the type and substitution position of the substituent, the properties of compounds such as the hole characteristics, light efficiency characteristics, energy level, hole injection and mobility characteristics, charge balance of holes and electrons, volume density, and intermolecular distance of the molecule may vary significantly enough to be difficult to predict, additionally, it suggests that rather than one configuration affecting the overall results of the element, the performance of the element may vary due to complex factors.

In the case of an emitting auxiliary layer, it is necessary to understand the relationship between the hole transport layer and the emitting layer (host). Therefore, even if a similar core is used, it would be very difficult for even a person skilled in the art to infer the characteristics exhibited by the emitting auxiliary layer using the compound of the present invention.

Rephrased, although the evaluation results of the aforementioned element fabrication explained the element characteristics in which the compound of the present invention was applied only to the emitting auxiliary layer, the compound of the present invention can be used by applying it to the hole transport layer or by applying it to both the hole transport layer and the emitting auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

INDUSTRIAL APPLICABILITY

According to the present invention, an organic element having excellent element characteristics of high brightness, high luminescence, and long lifetime can be manufactured, so it has industrial applicability.

The invention claimed is:

1. A compound represented by Formula 1:

<Formula 1>

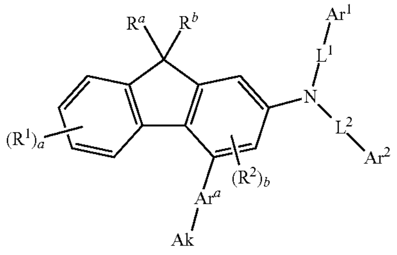

wherein:

$L^1$ and $L^2$ are independently selected from the group consisting of a single bond; a $C_6$-$C_{60}$ arylene group; a fluorenylene group; a $C_2$-$C_{60}$ heterocyclic group including at least one heteroatom of O, N, S, Si or P, $Ar^1$ and $Ar^2$ are independently selected from the group consisting of a $C_6$-$C_{60}$ aryl group; a fluorenyl group; a $C_2$-$C_{60}$ heterocyclic group including at least one heteroatom of O, N, S, Si or P, $R^a$ and $R^b$ are independently selected from the group consisting of a $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; a plurality of adjacent groups thereof may be bonded to each other to form a spirobifluorene group, $R^1$ and $R^2$ are the same or different from each other and are independently selected from the group consisting of hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; and a plurality of adjacent groups thereof may be bonded to each other to form a ring, a is an integer of 0 to 4, b is an integer of 0 to 2, $Ar^a$ is a $C_6$-$C_{60}$ arylene group, and Ak is a $C_1$-$C_{50}$ alkyl group; or a $C_3$-$C_{60}$ aliphatic ring, wherein the aryl group, arylene group, heterocyclic group, fluorenyl group, fluorenylene group, aliphatic ring group, fused ring group, alkyl group, alkenyl group, alkynyl group, alkoxy group and aryloxy group may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ aliphatic ring; a $C_7$-$C_{20}$ arylalkyl group; a $C_8$-$C_{20}$ arylalkenyl group; and a $C_7$-$C_{20}$ alkylaryl group, and the hydrogen of these substituents may be further substituted with one or more deuterium, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound according to claim 1, wherein any one of Art and $Ar^2$ is substituted with at least one of a $C_1$-$C_{20}$ alkyl group and a $C_3$-$C_{20}$ aliphatic ring group.

3. The compound according to claim 1, wherein Formula 1 is represented by Formula 1-1:

<Formula 1-1>

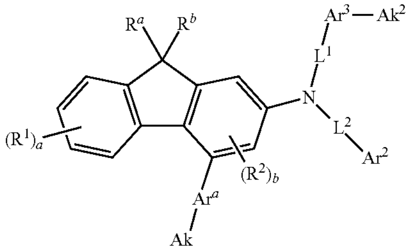

wherein:

$R^a$, $R^b$, $R^1$, $R^2$, a, b, $Ar^a$, Ak, $L^1$, $L^2$ and $Ar^2$ are the same as defined in claim 1, $Ar^3$ is a $C_6$-$C_{60}$ arylene group, or a $C_2$-$C_{60}$ heterocyclic group including at least one heteroatom of O, N, S, Si or P, and $Ak^2$ is a $C_1$-$C_{20}$ alkyl group or a $C_3$-$C_{20}$ aliphatic ring.

4. The compound according to claim 1, wherein Ak is represented by any one of Formulas Ak-1 to Ak-8:

Formula Ak-1

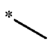

-continued

Formula Ak-2

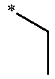

Formula Ak-3

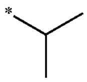

Formula Ak-4

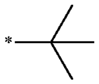

Formula Ak-5

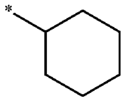

Formula Ak-6

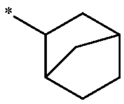

Formula Ak-7

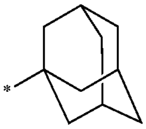

Formula Ak-8

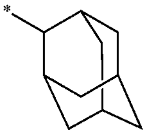

wherein:

* indicates the position to be bonded, and

Formulas Ak-1 to Ak-8 may each be further substituted with one or more deuterium.

5. The compound according to claim 1, wherein any one of $Ar^1$ or $Ar^2$ is represented by one of Formulas Ar-1 to Ar-11:

Formula Ar-1

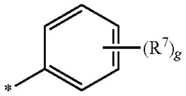

Formula Ar-2

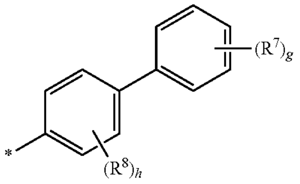

Formula Ar-3

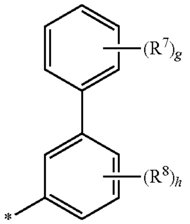

-continued

Formula Ar-4

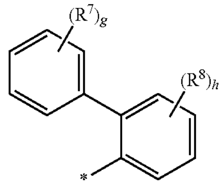

Formula Ar-5

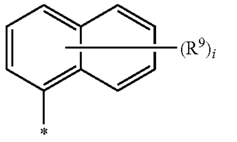

Formula Ar-6

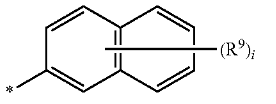

Formula Ar-7

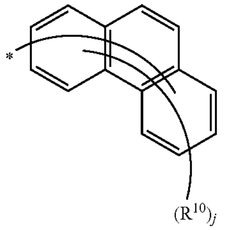

Formula Ar-8

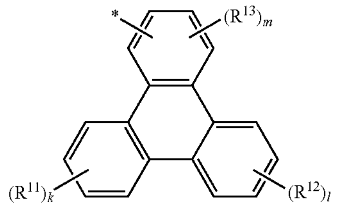

Formula Ar-9

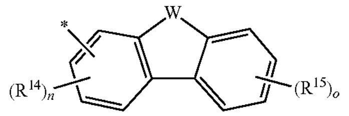

Formula Ar-10

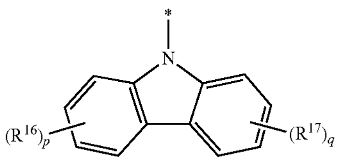

Formula Ar-11

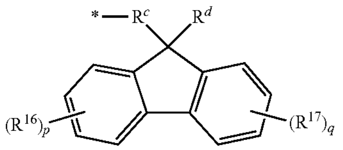

wherein:

$R^7$, $R^8$, $R^9$, $R^{10}$, $R^{11}$, $R^{12}$, $R^{13}$, $R^{14}$, $R^{15}$, $R^{16}$ and $R^{17}$ are the same or different from each other and are independently selected from the group consisting of hydrogen; deuterium; a $C_6$-$C_{20}$ aryl group; a fluorenyl group; a $C_2$-$C_{60}$-$C_{20}$ heterocyclic group including at least one heteroatom of O, N, S, Si or P; a $C_3$-$C_{20}$ aliphatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{20}$ aryloxy group, or a plurality of adjacent groups thereof may be bonded to each other to form a ring, $R^c$ is selected from the group consisting of a $C_6$-$C_{20}$ aryl group; and a $C_2$-$C_{20}$ heterocyclic group including at least one heteroatom of O, N, S, Si or P, $R^d$ is selected from the group consisting of hydrogen; deuterium; a $C_1$-$C_{20}$ alkyl group; a $C_2$-$C_{20}$ alkenyl group; a $C_6$-$C_{20}$ aryl group and a $C_2$-$C_{20}$ heterocyclic group including at least one heteroatom of O, N, S, Si or P, $R^c$ and $R^d$ may be bonded to each other to form a spiro ring, g is an integer of 0 to 5, h, k, l, o, p and q are independently an integer of 0 to 4, i is an integer of 0 to 7, j is an integer of 0 to 9, m and n are independently an integer of 0 to 3, W is O, S, $CR^{27}R^{28}$, $SiR^{27}R^{28}$ or $NR^{29}$, $R^{27}$, $R^{28}$ and $R^{29}$ are independently selected from the group consisting of a $C_6$-$C_{20}$ aryl group; a fluorenyl group; a $C_2$-$C_{20}$ heterocyclic group including at least one heteroatom of O, N, S, Si or P; a fused ring group of a $C_3$-$C_{20}$ aliphatic ring and a $C_6$-$C_{20}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{20}$ aryloxy group, and $R^{27}$ and $R^{28}$ may be bonded to each other to form a ring, and

* indicates the position to be bonded.

6. The compound according to claim 1, wherein $Ar^a$ is any one of Formulas L-1 to L-27, and $L^1$ and $L^2$ are each a single bond or any one of Formulas L-1 to L-27:

[Formula L-1]

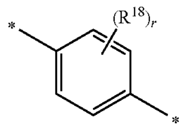

[Formula L-2]

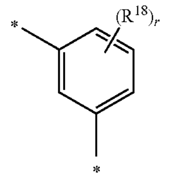

[Formula L-3]

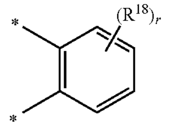

[Formula L-4]

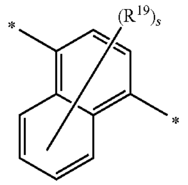

[Formula L-5]

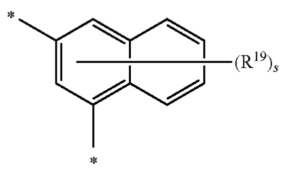

-continued
[Formula L-6]
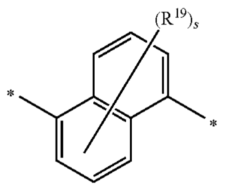
[Formula L-7]
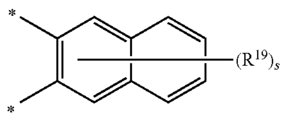
[Formula L-8]
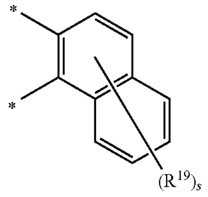
[Formula L-9]
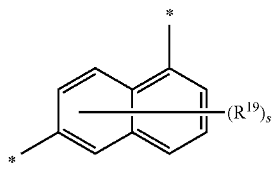
[Formula L-10]
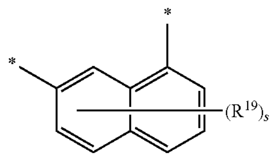
[Formula L-11]
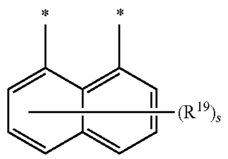
[Formula L-12]
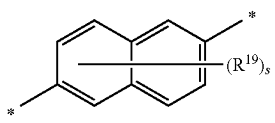
[Formula L-13]
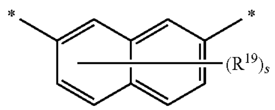
[Formula L-14]
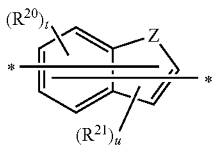
-continued
[Formula L-15]
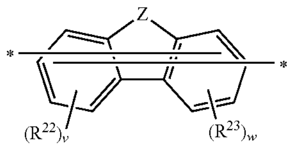
[Formula L-16]
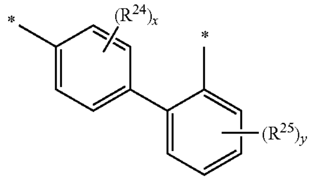
[Formula L-17]
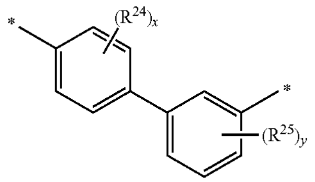
[Formula L-18]
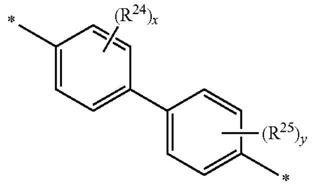
[Formula L-19]
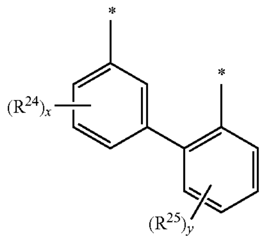
[Formula L-20]
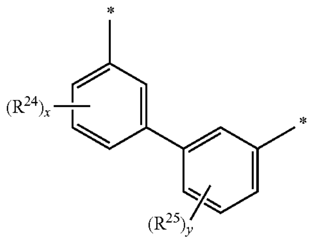
[Formula L-21]
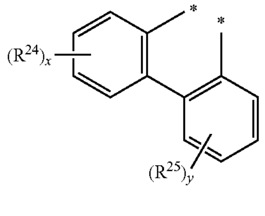

-continued

[Formula L-22]

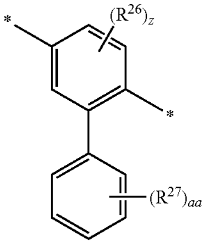

[Formula L-23]

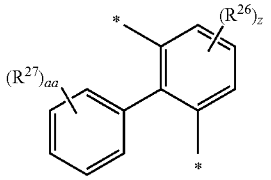

[Formula L-24]

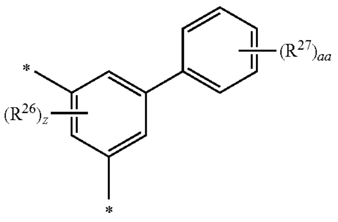

[Formula L-25]

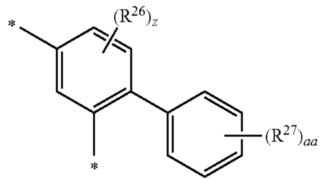

[Formula L-26]

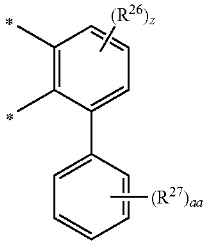

[Formula L-27]

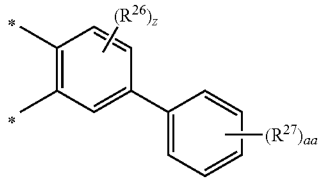

wherein:

Z is O, S, $CR^{30}R^{31}$ or N—$Ar^5$ $R^{18}$, $R^{19}$, $R^{20}$, $R^{21}$, $R^{22}$, $R^{23}$, $R^{24}$, $R^{25}$, $R^{26}$ and $R^{27}$ are the same or different from each other and are independently selected from the group consisting of hydrogen; deuterium; a $C_6$-$C_{20}$ aryl group; a fluorenyl group; a $C_2$-$C_{60}$ heterocyclic group including at least one heteroatom of O, N, S, Si or P; a $C_3$-$C_{20}$ aliphatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{20}$ aryloxy group, and a plurality of adjacent groups thereof may be bonded to each other to form a ring, or a plurality of adjacent groups may be bonded to each other to form a ring, $Ar^5$ is selected from the group consisting of a $C_1$-$C_{20}$ alkyl group; a $C_2$-$C_{20}$ alkenyl group; a $C_6$-$C_{20}$ aryl group; and a $C_2$-$C_{20}$ heterocyclic group including at least one heteroatom of O, N, S, Si or P, r, t, v, w, x and y are independently an integer of 0 to 4, s is an integer of 0 to 6, u is an integer of 0 to 2, z is an integer 0 to 3, aa is an integer of 0 to 5, and

* indicates the position to be bonded.

7. The compound according to claim 1, wherein at least one of $L^1$, $L^2$, $Ar^1$ and $Ar^2$ is a substituent comprising deuterium.

8. The compound according to claim 1, wherein the compound of Formula 1 is selected from the group consisting of compounds P-1 to P-136:

P-1

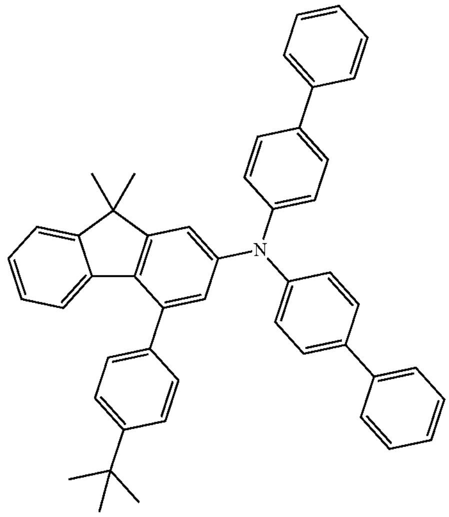

P-2

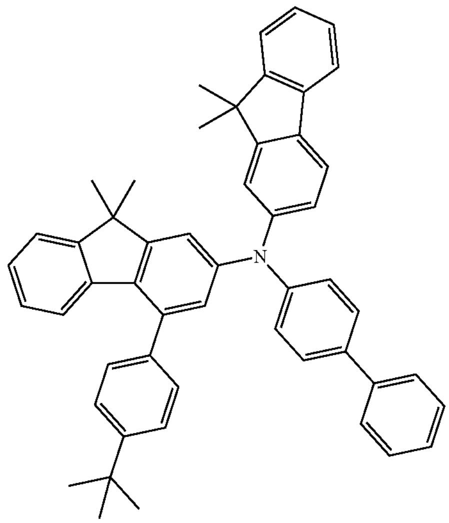

-continued
P-3
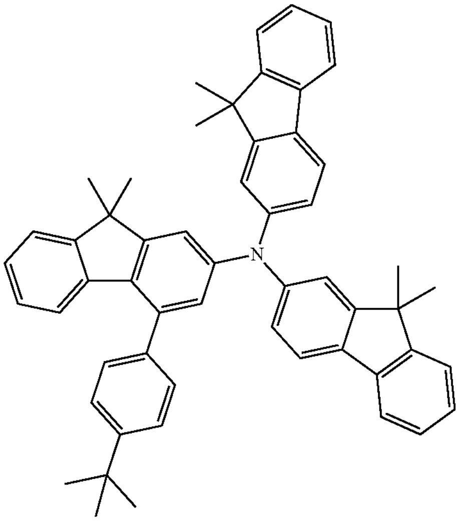
P-4
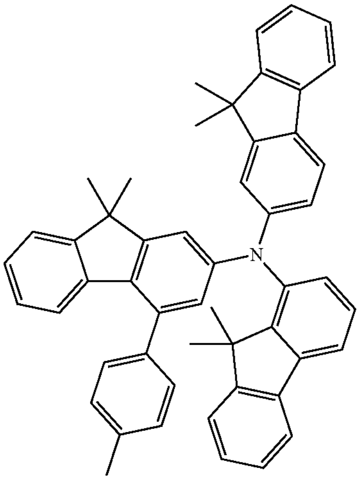
P-5
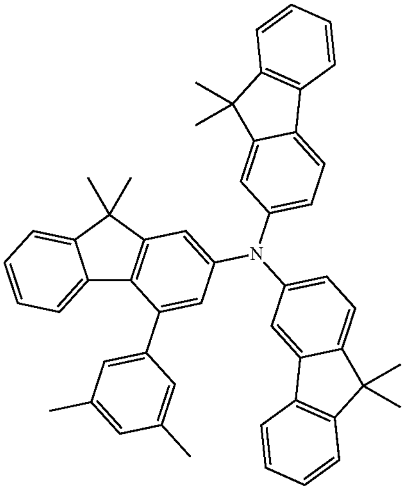
-continued
P-6
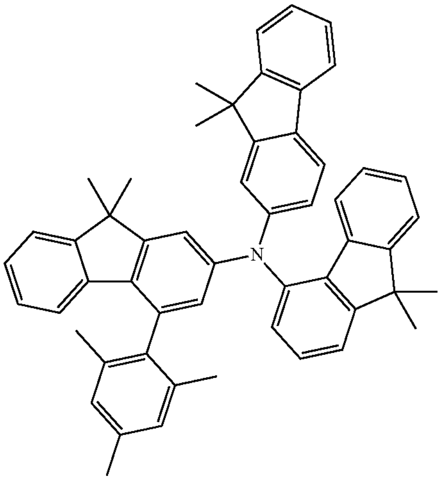
P-7
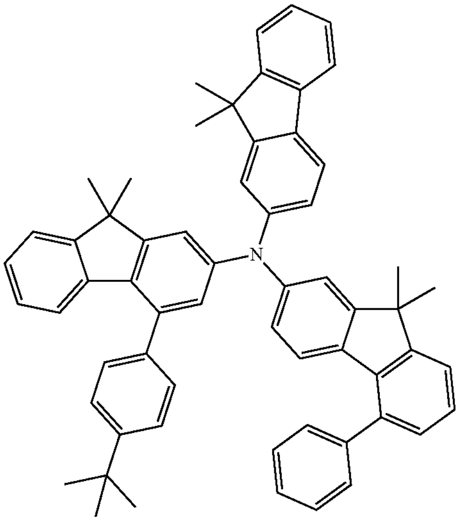
P-8
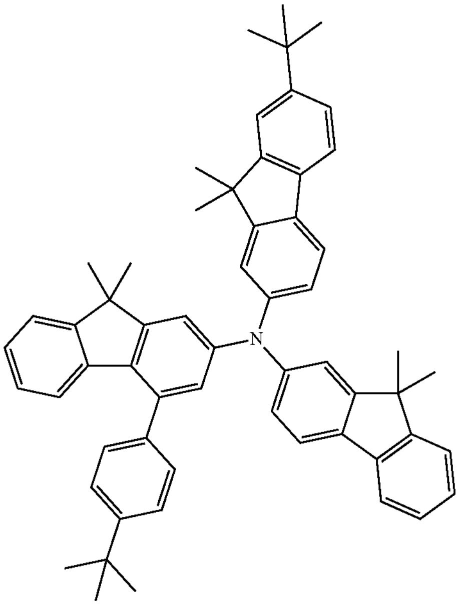

-continued
P-9
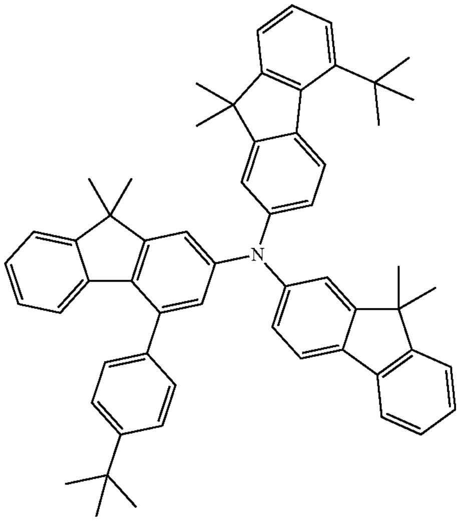
P-10
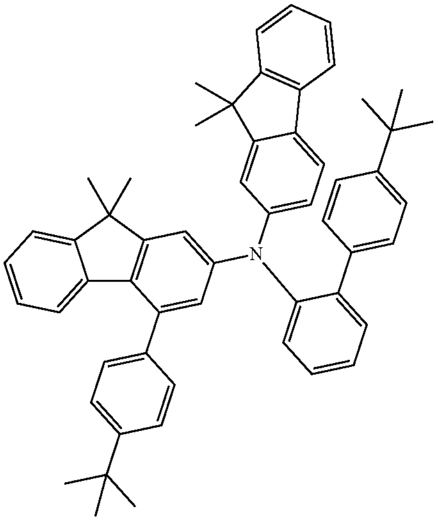
P-11
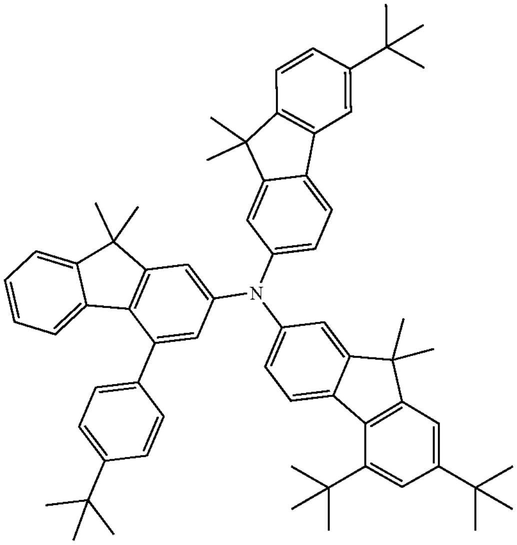
-continued
P-12
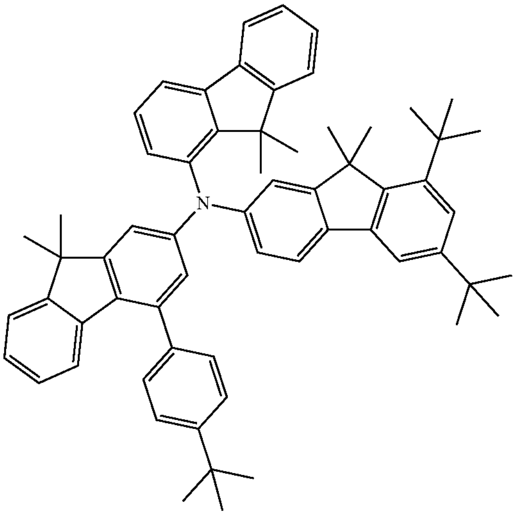
P-13
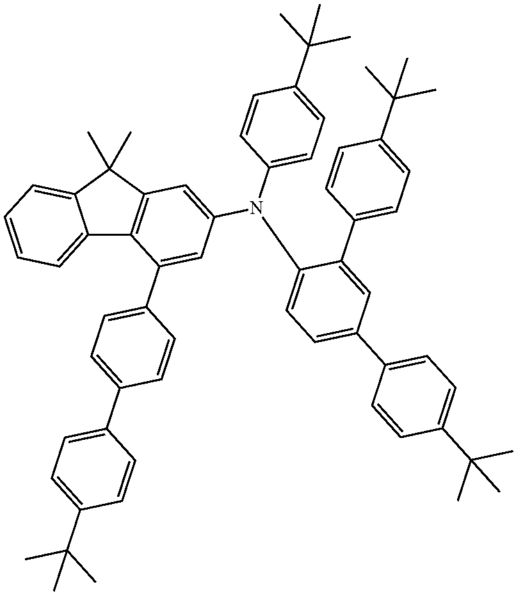

P-14
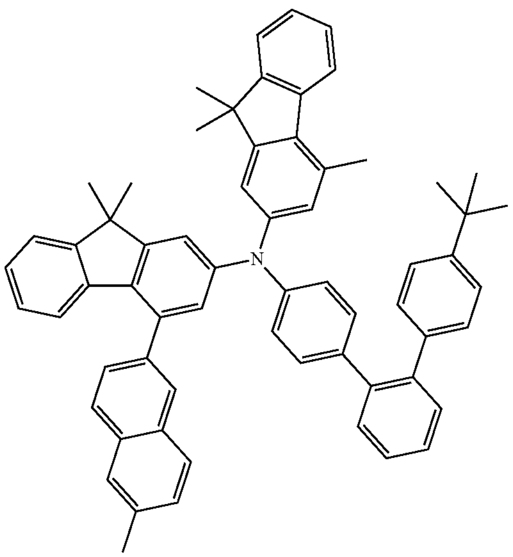
P-15
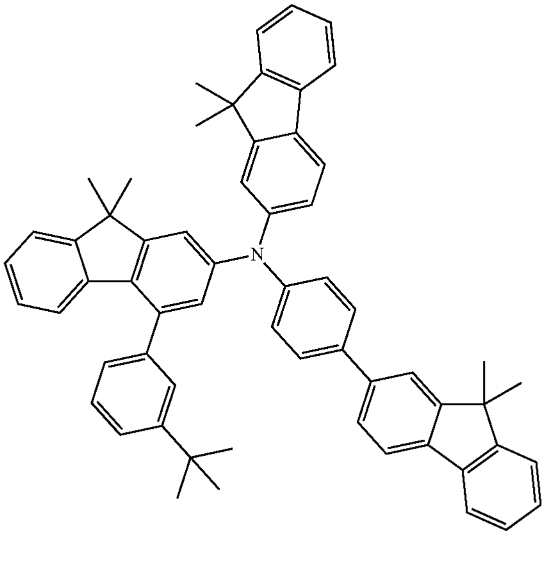
P-16
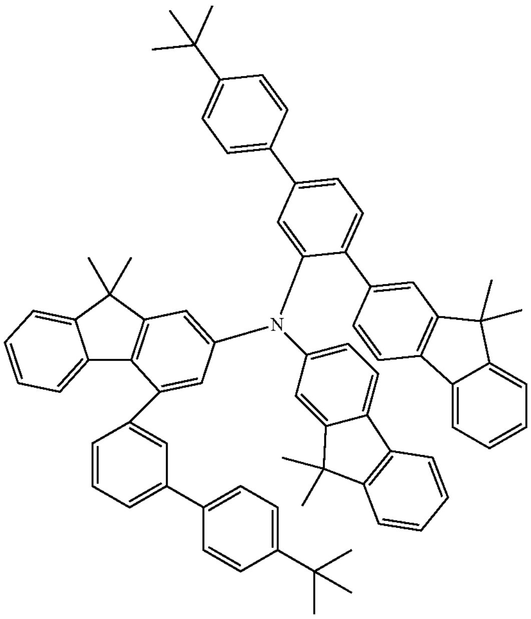
P-17
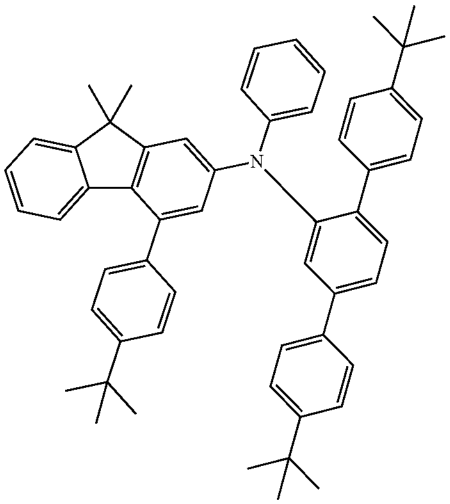
P-18
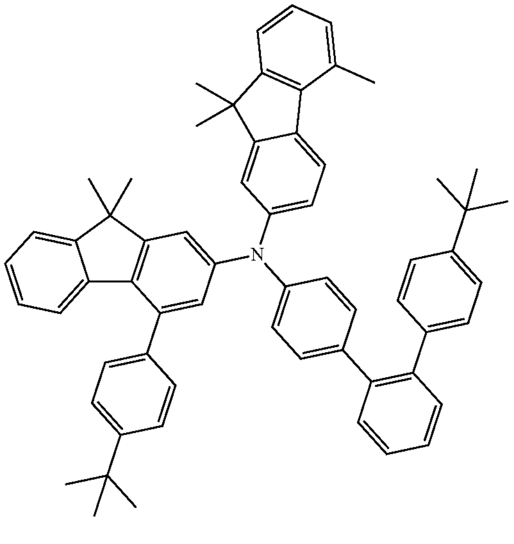

-continued
P-19
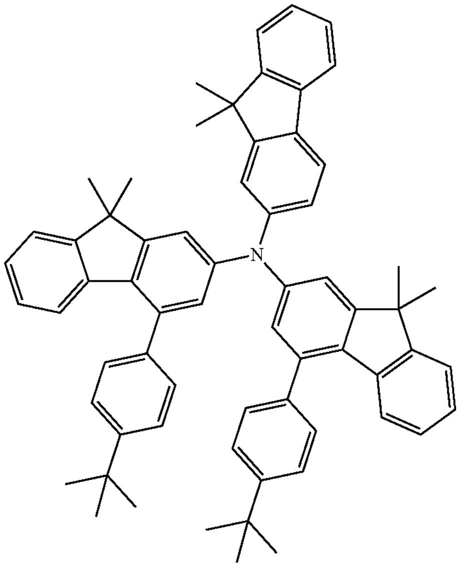
P-20
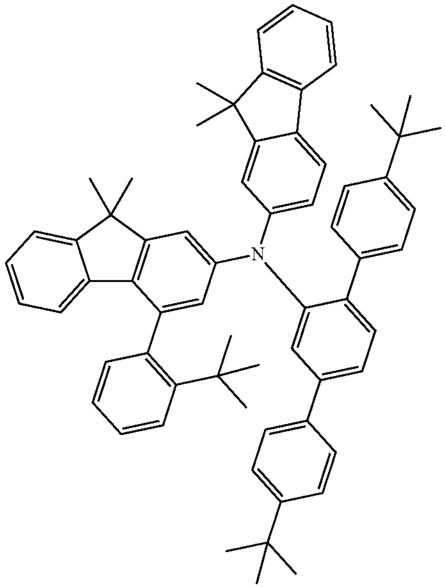
-continued
P-21
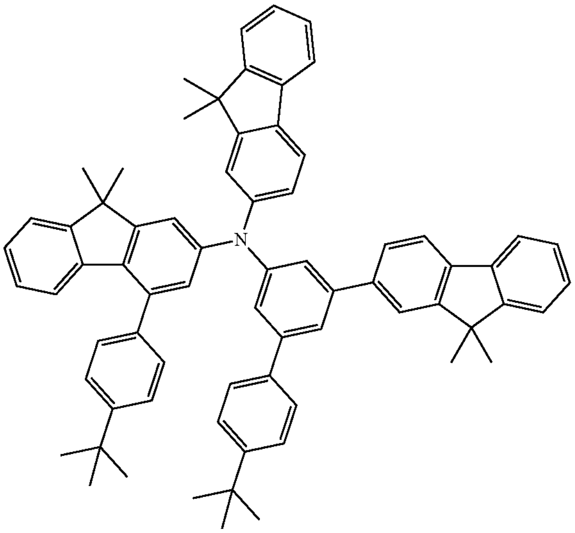
P-22
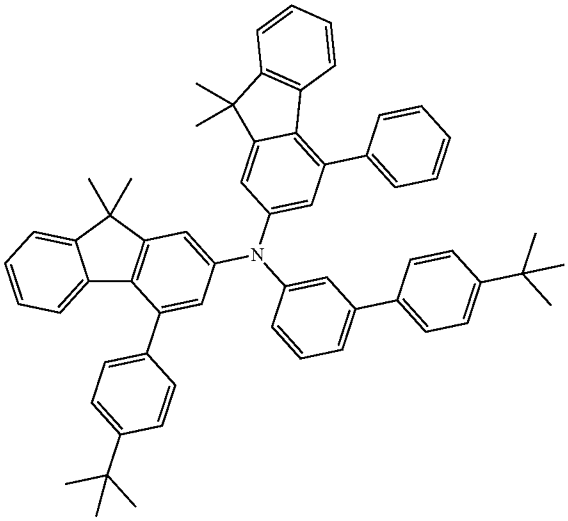
P-23
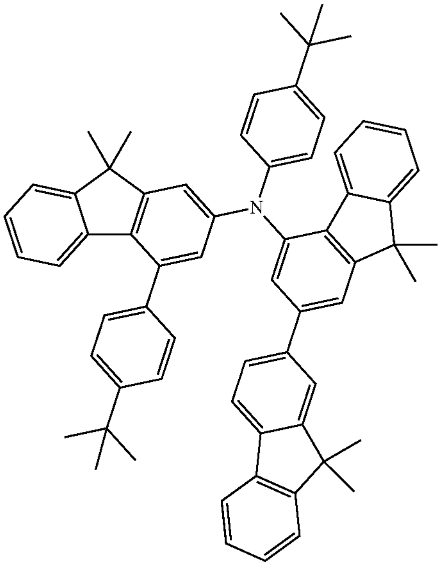

-continued
P-24
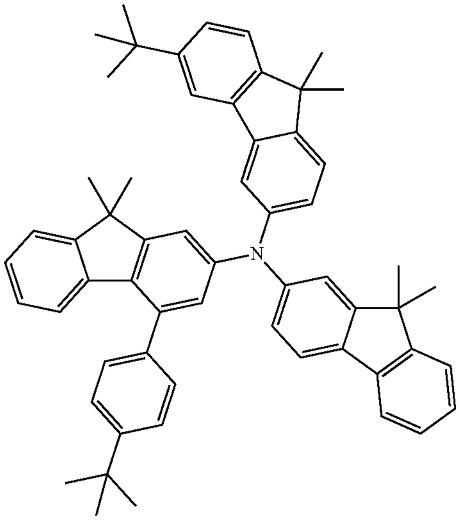
P-25
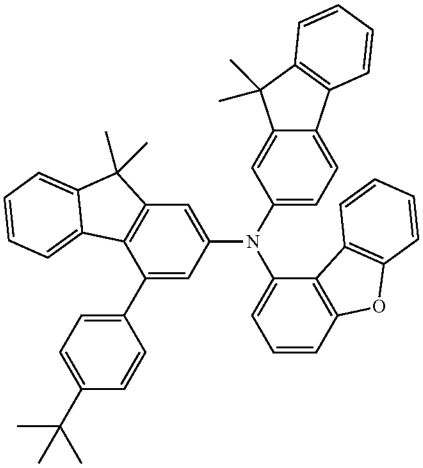
P-26
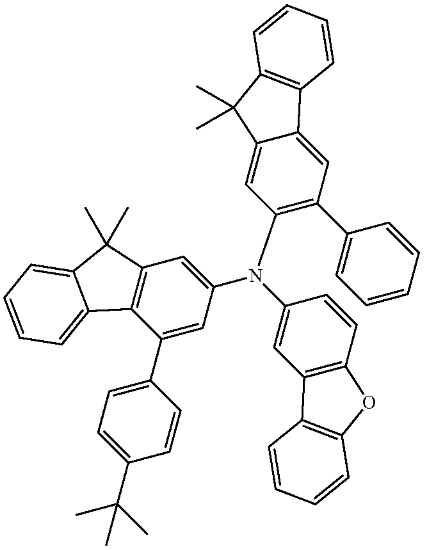
-continued
P-27
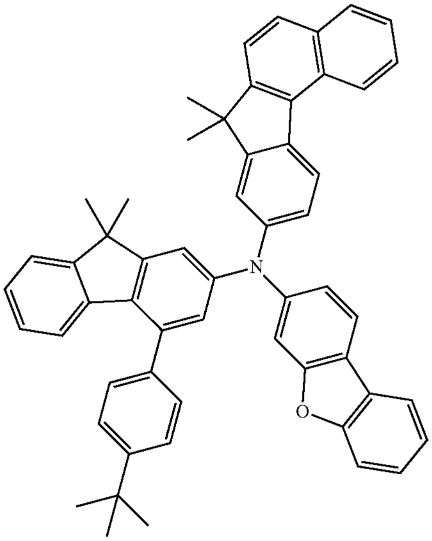
P-28
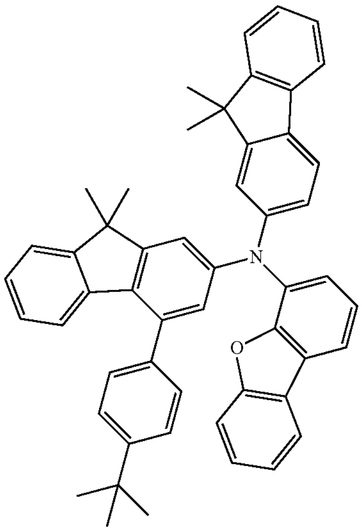
P-29
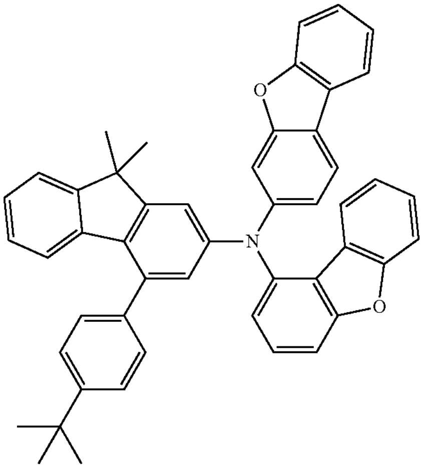

-continued
P-30
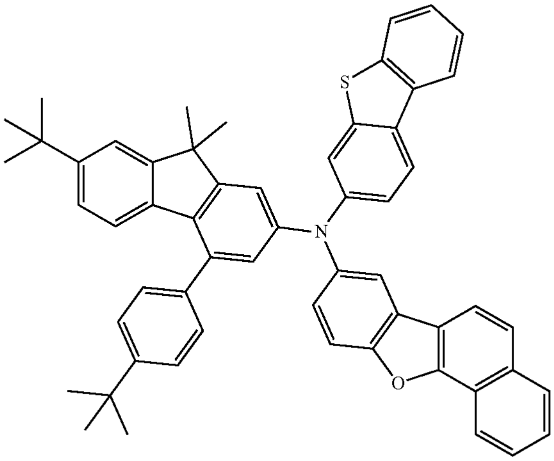
P-31
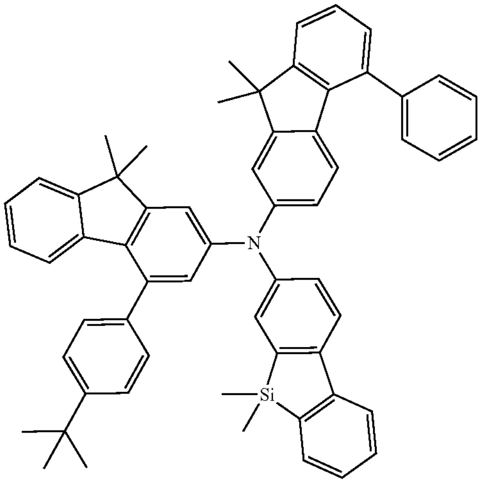
P-32
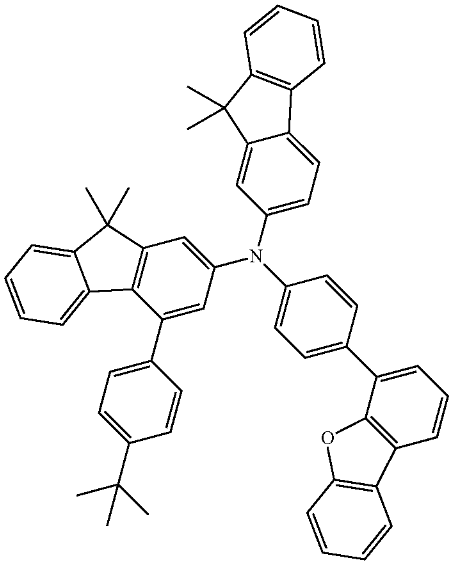
-continued
P-33
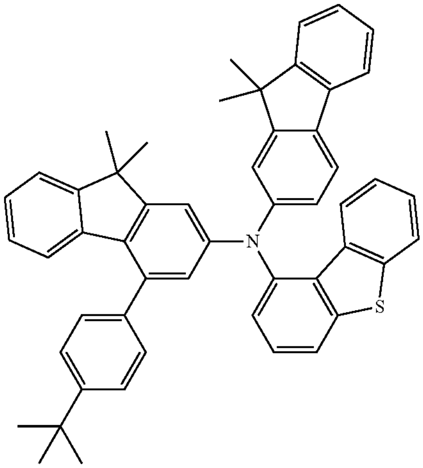
P-34
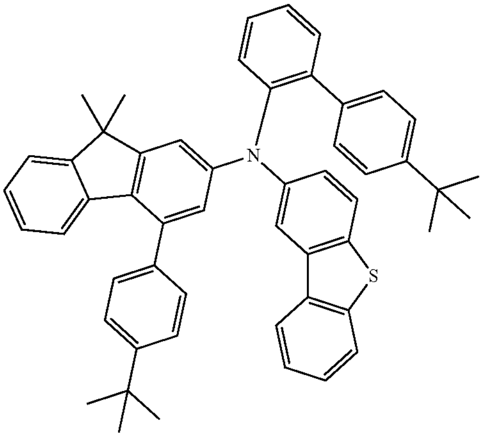
P-35
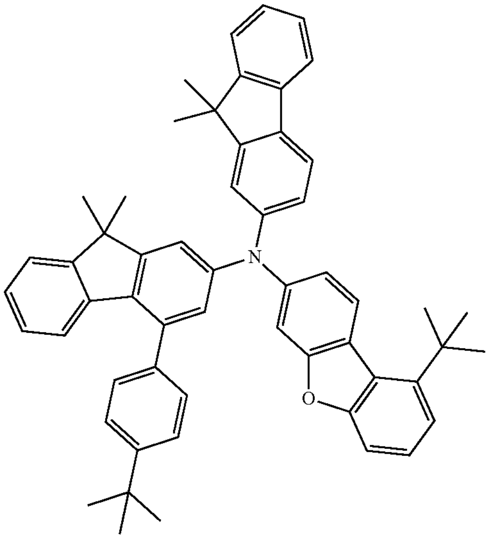

-continued
P-36
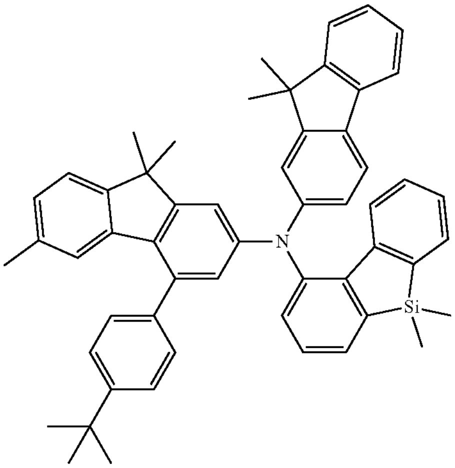
P-37
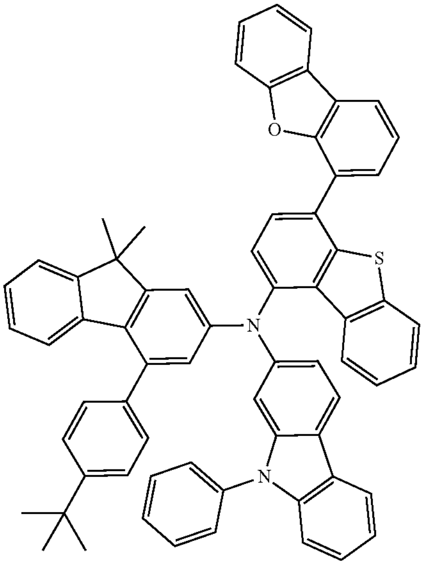
P-38
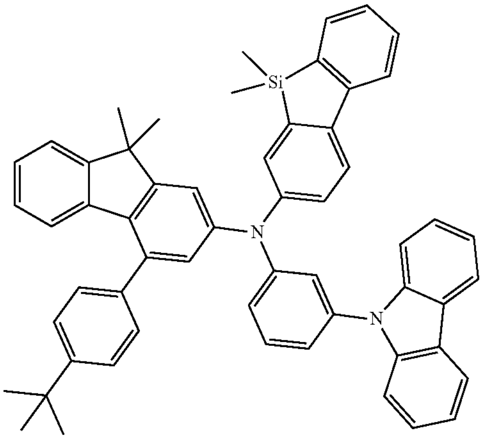
-continued
P-39
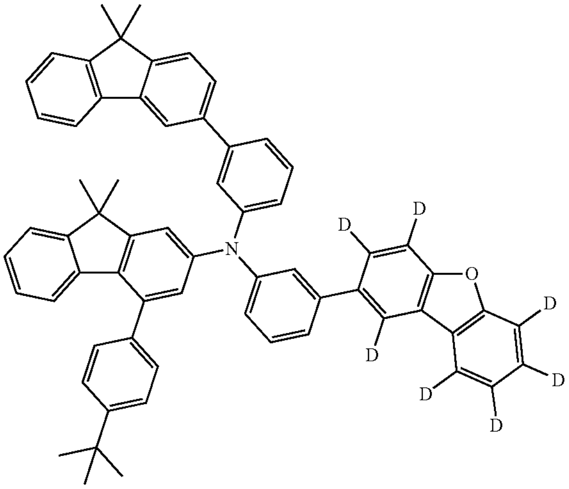
P-40
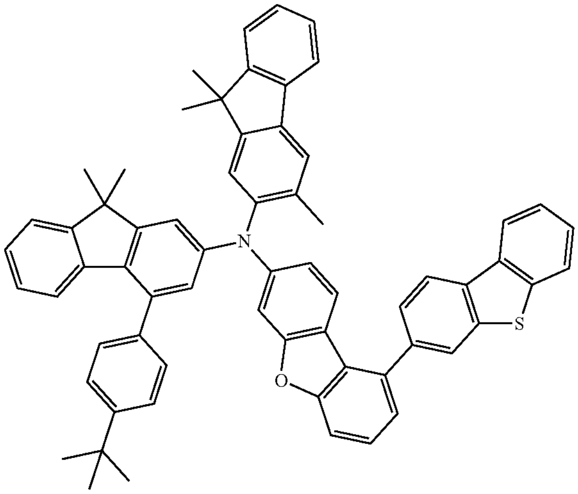
P-41
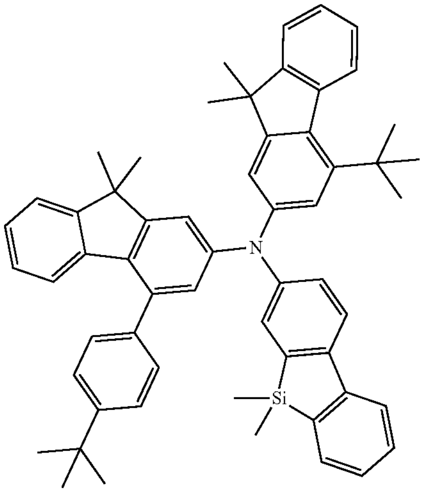

-continued
P-42
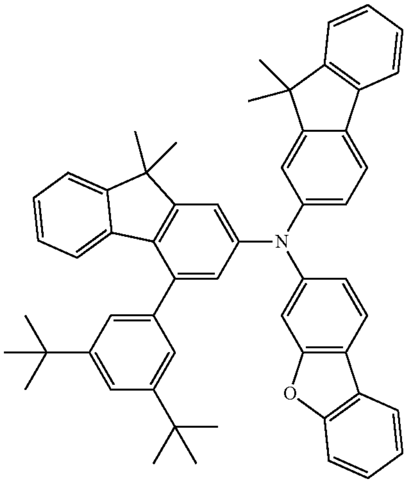
P-43
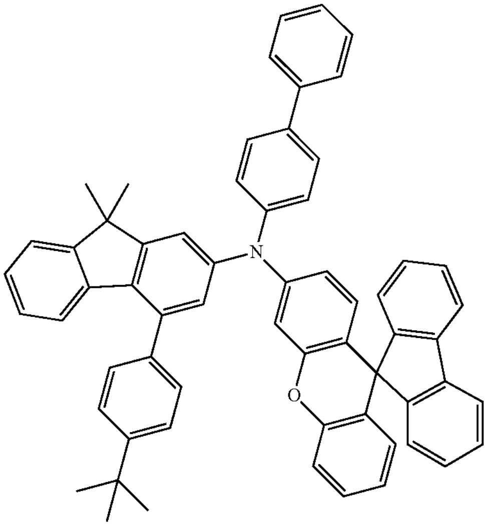
P-44
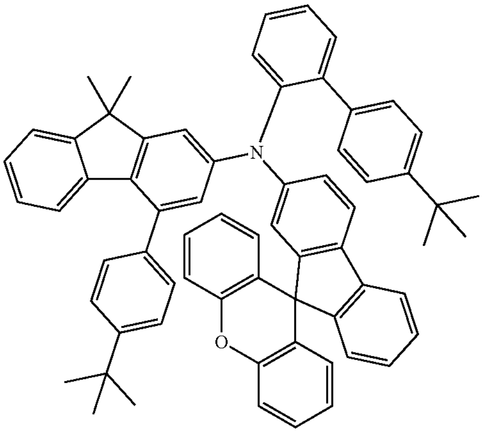
-continued
P-45
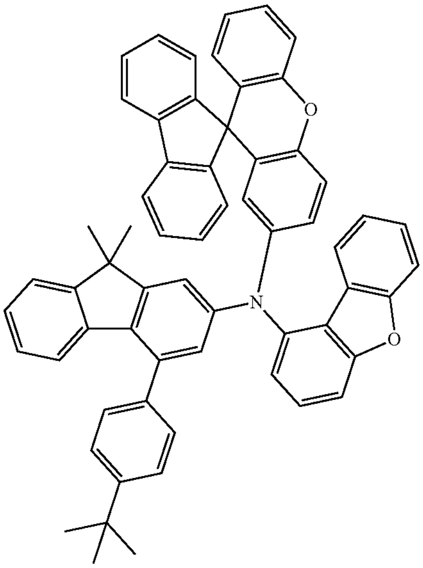
P-46
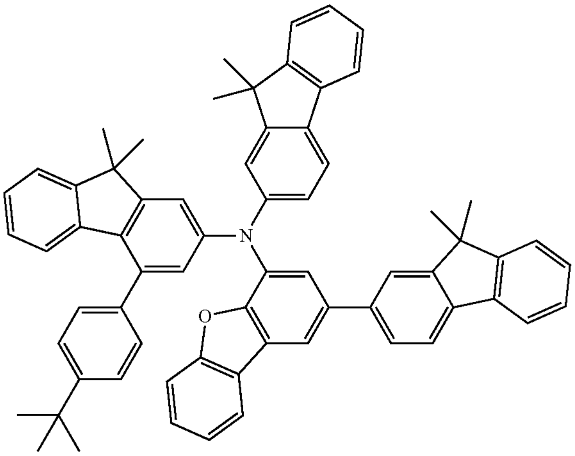
P-47
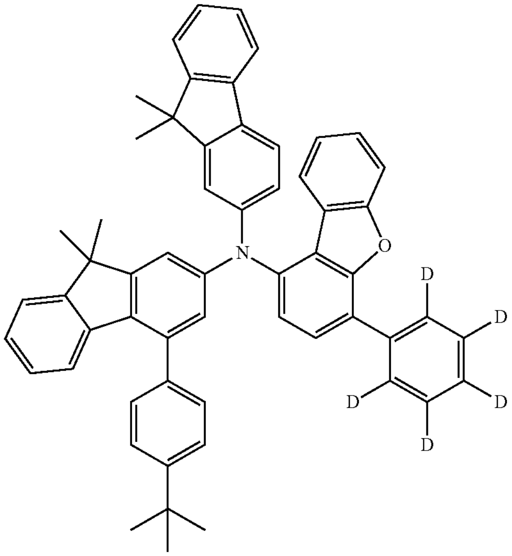

-continued
P-48
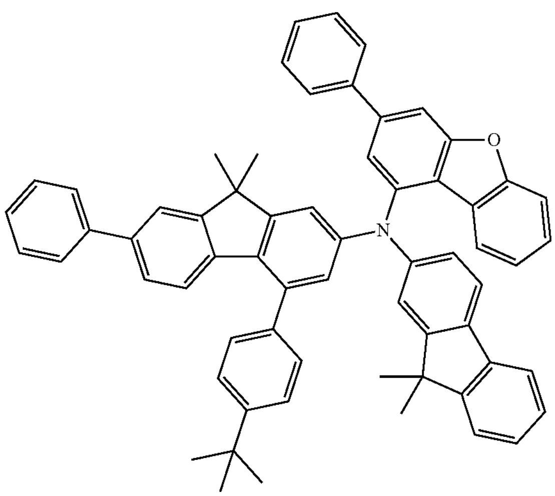
P-49
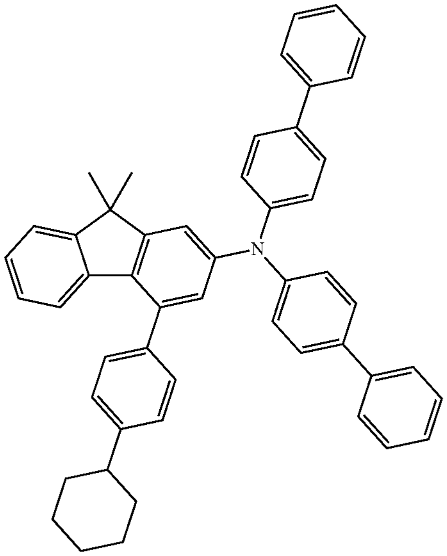
P-50
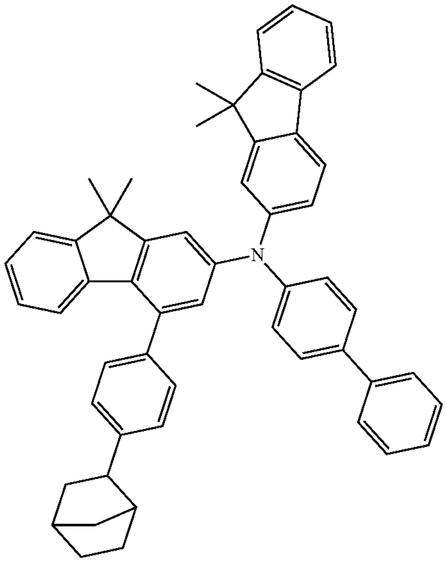
-continued
P-51
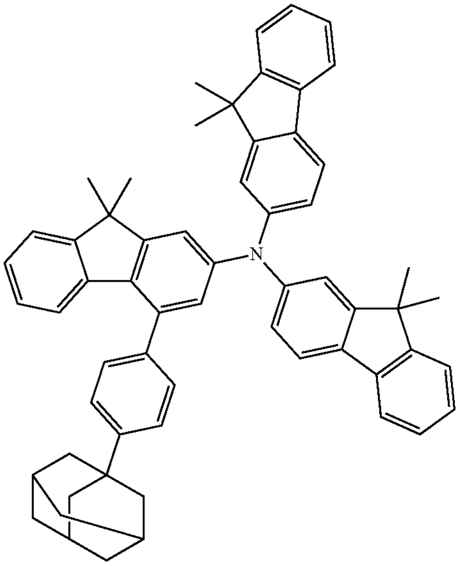
P-52
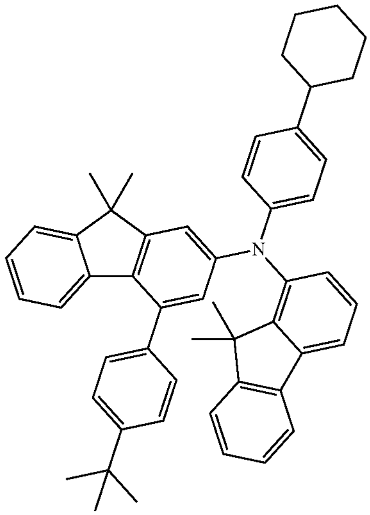
P-53
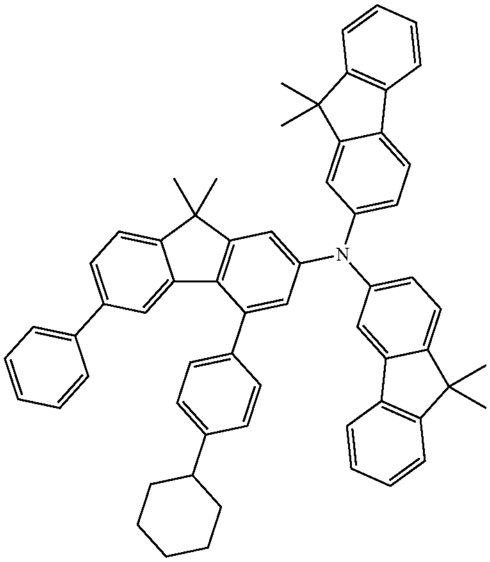

-continued
P-54
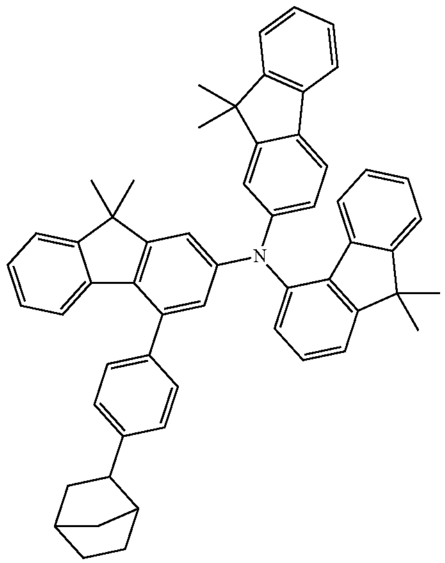
P-55
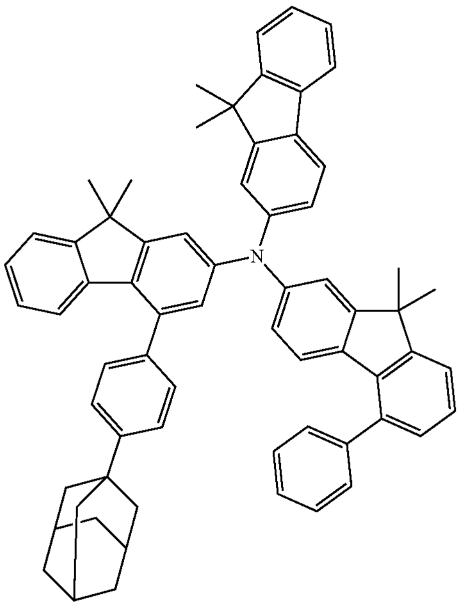
-continued
P-56
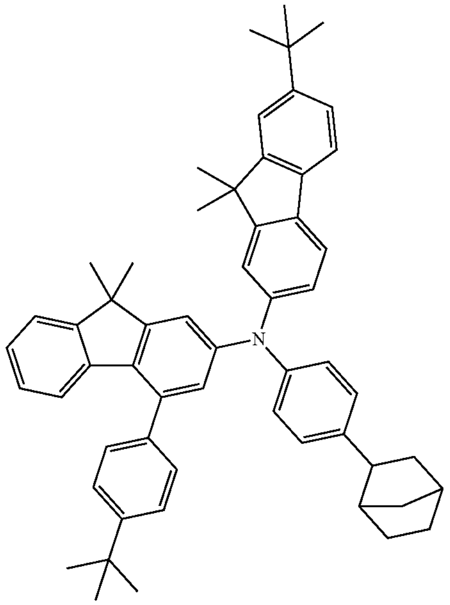
P-57
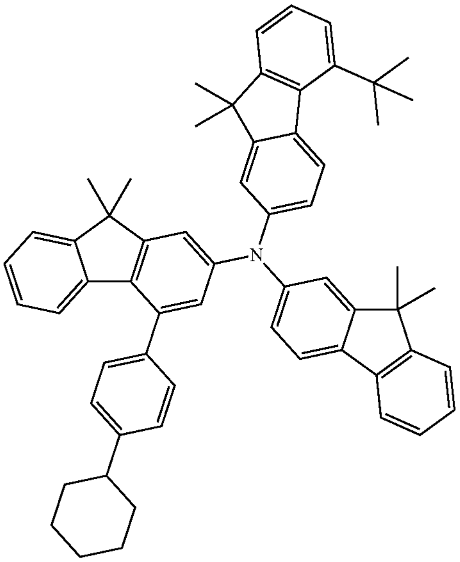

-continued
P-58
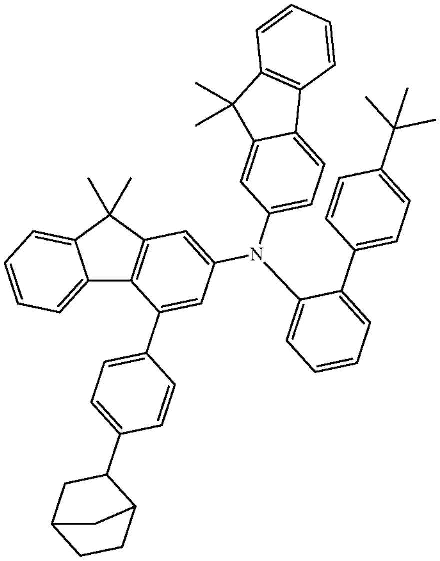
-continued
P-60
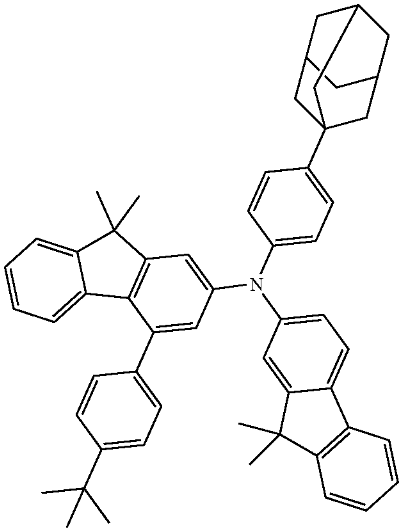
P-59
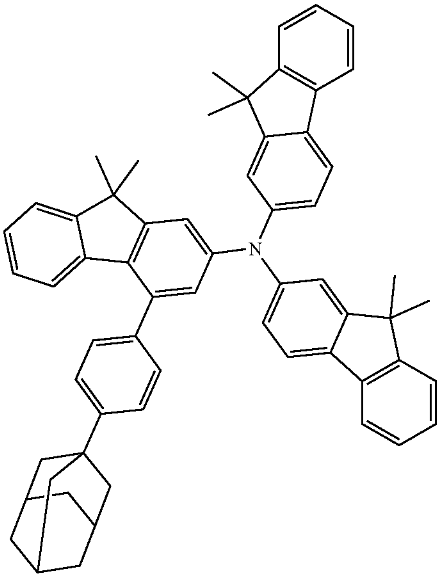
P-61
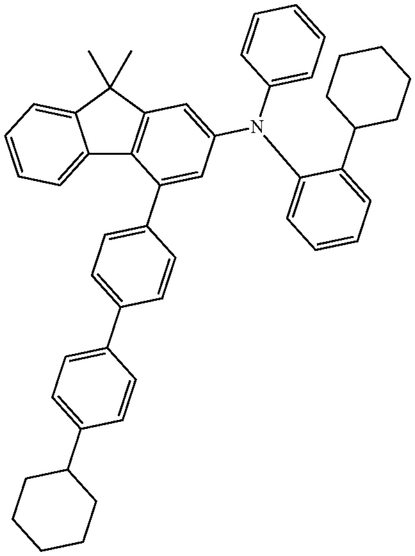

-continued
P-62
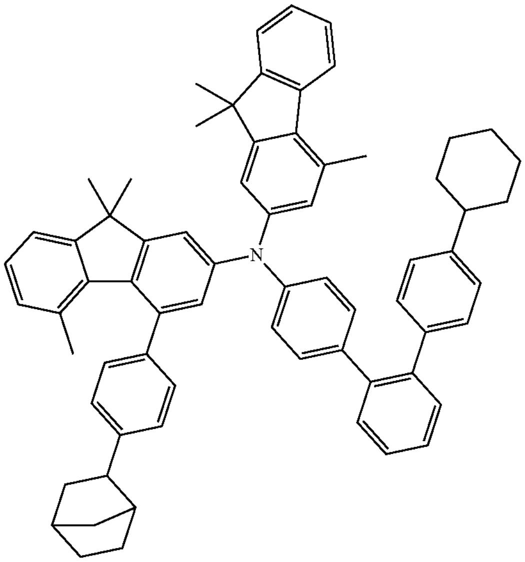
P-63
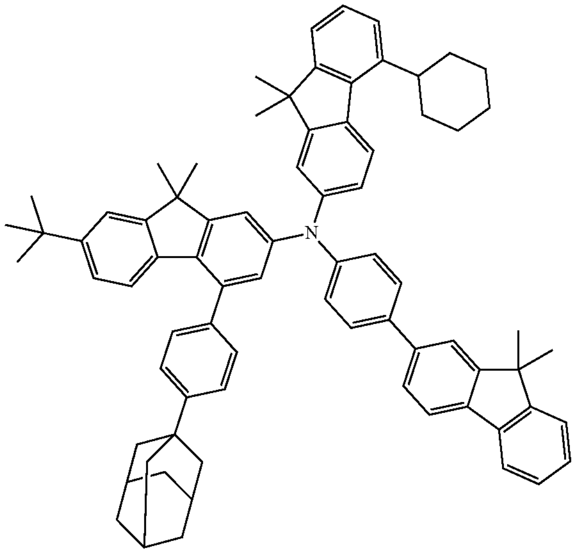
P-64
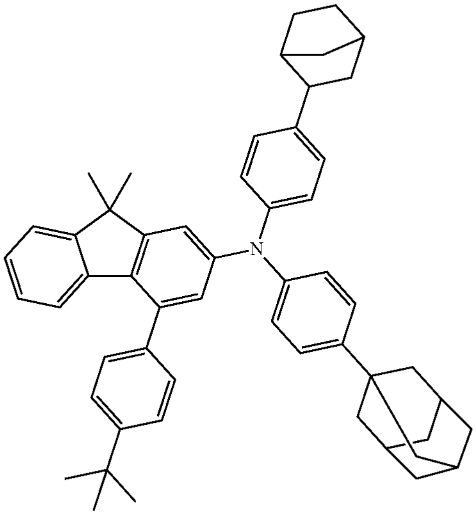
-continued
P-65
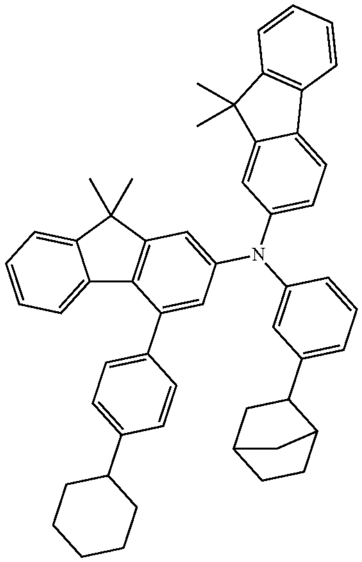
P-66
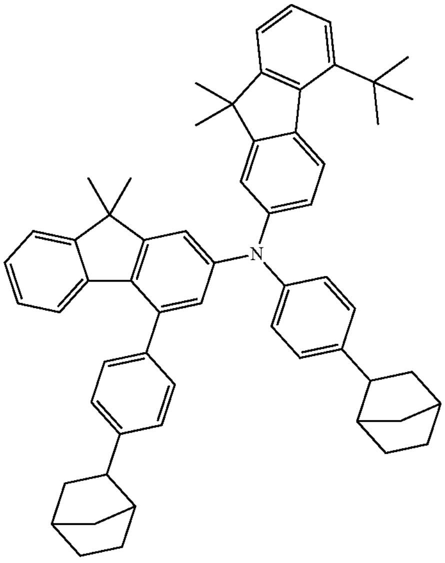

-continued
P-67
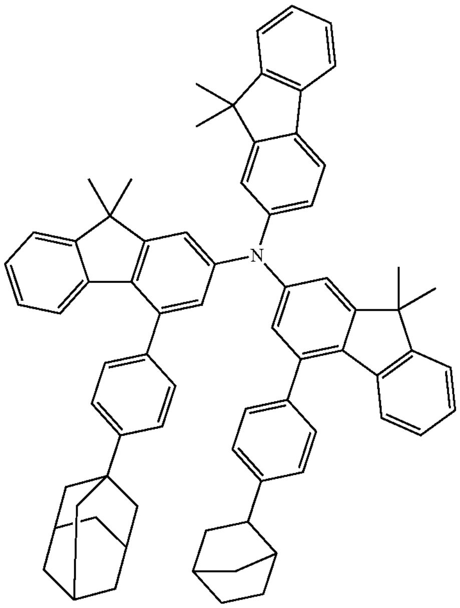
P-68
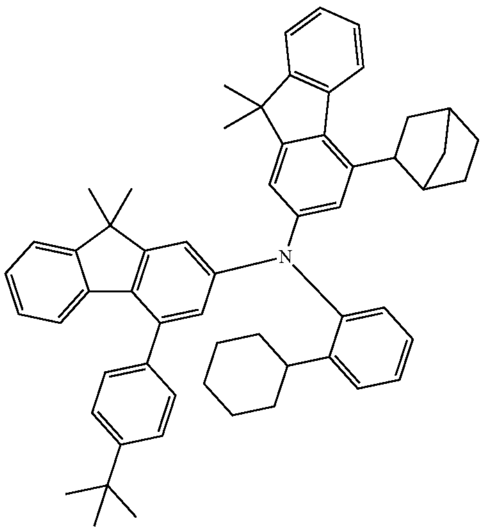
-continued
P-69
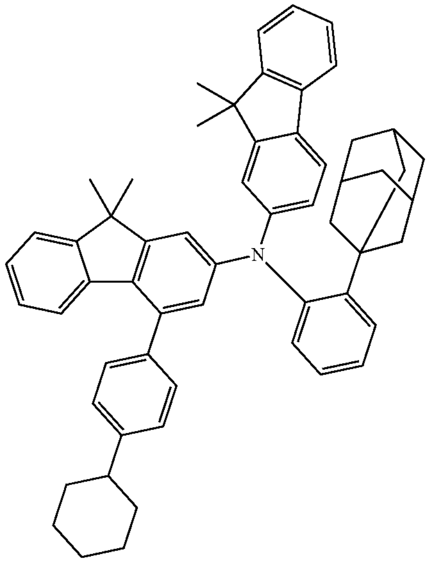
P-70
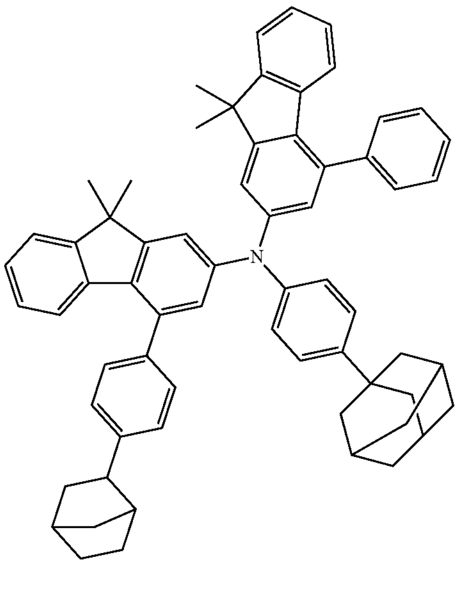

-continued
P-71
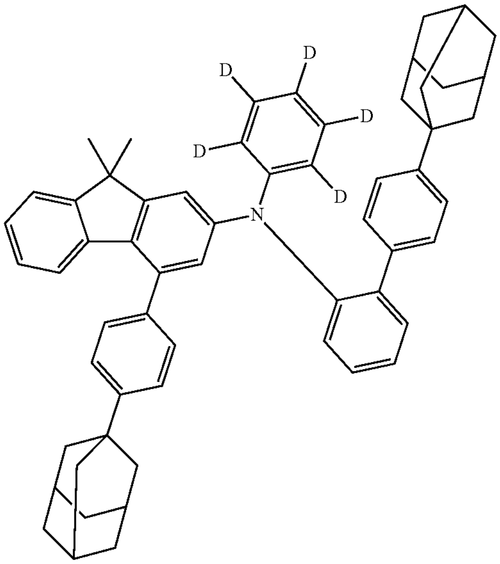
P-72
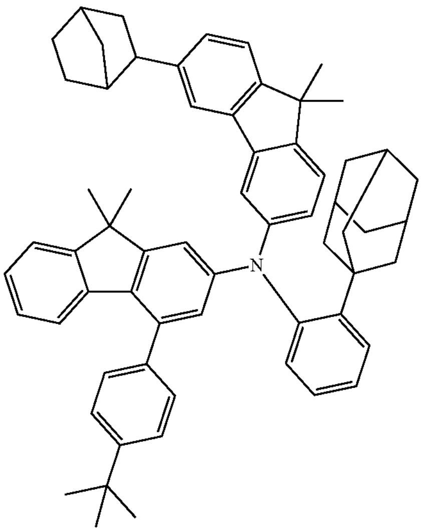
P-73
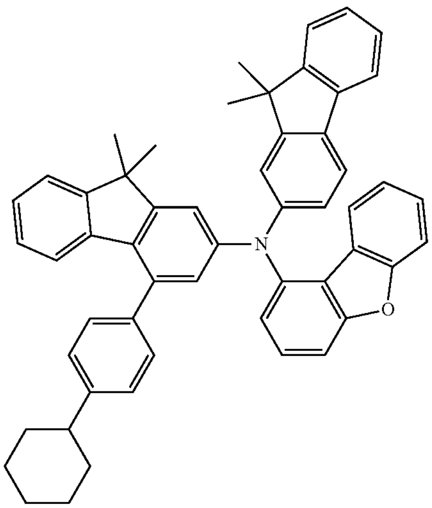
-continued
P-74
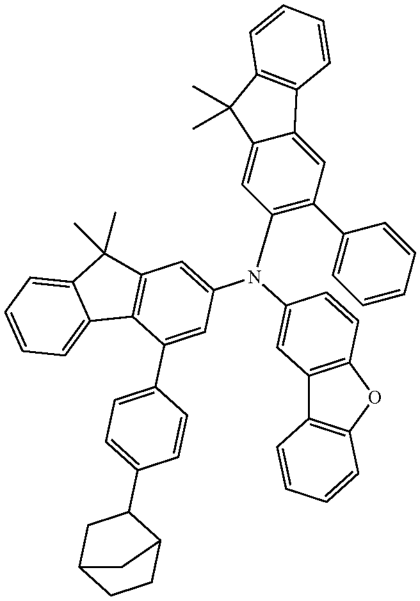
P-75
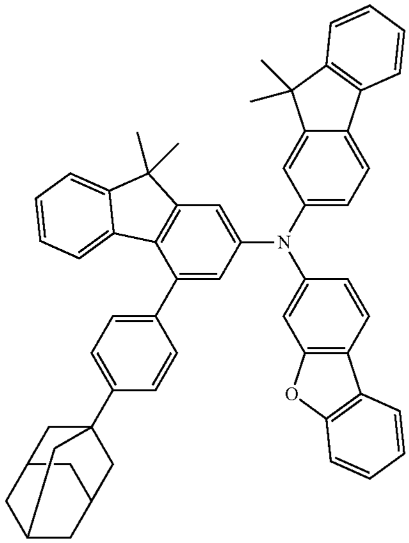

-continued
P-76
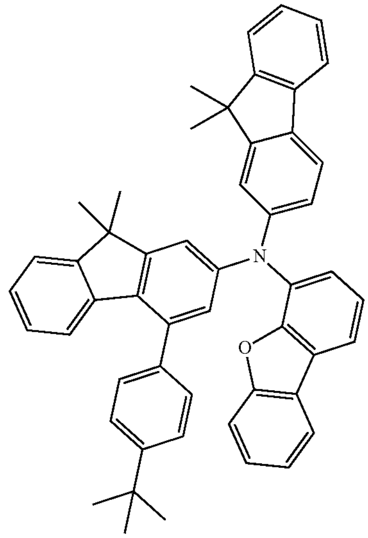
P-77
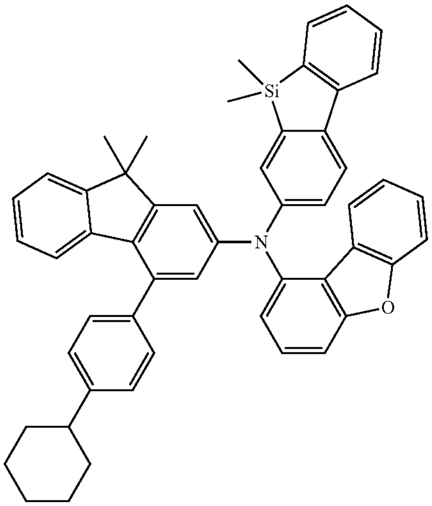
P-78
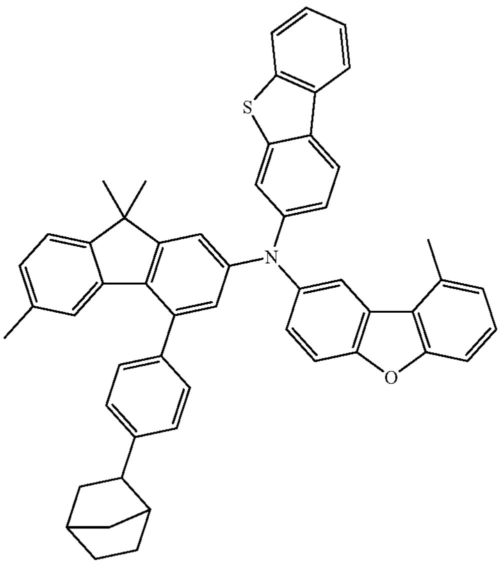
-continued
P-79
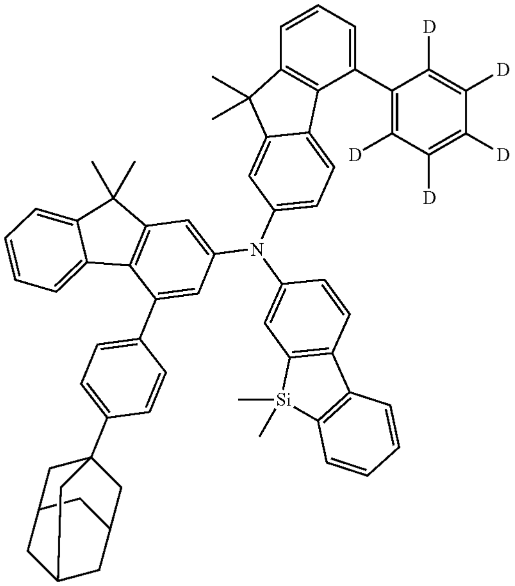
P-80
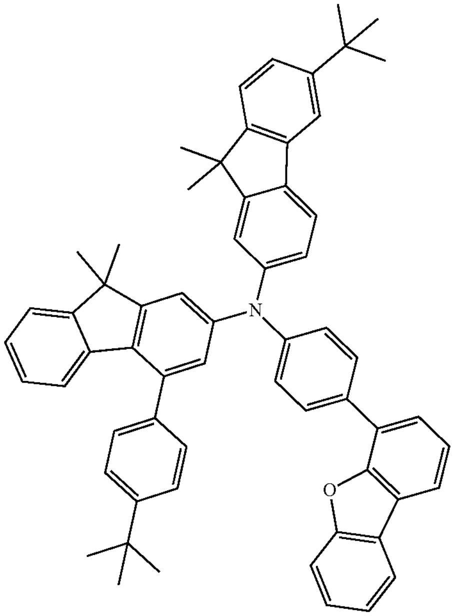

P-81
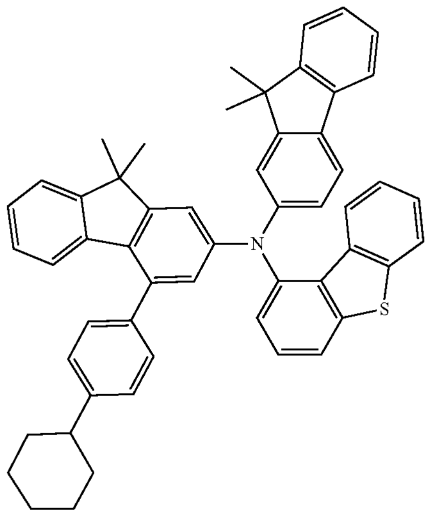
P-82
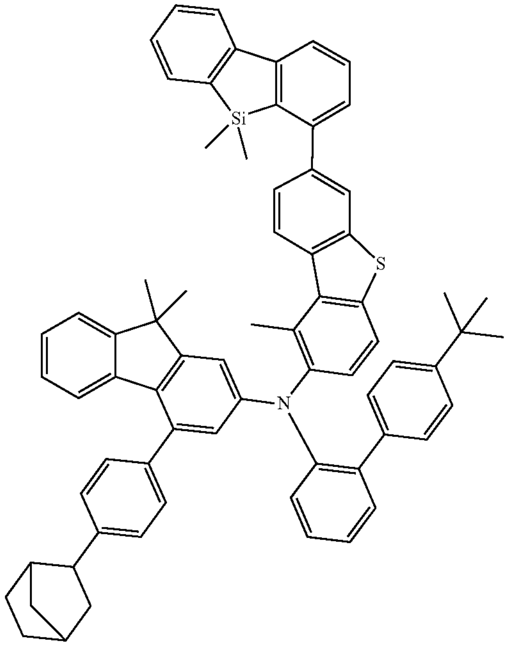
P-83
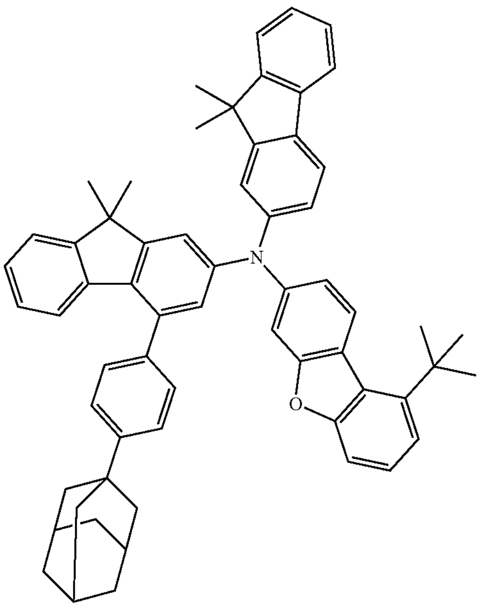
P-84
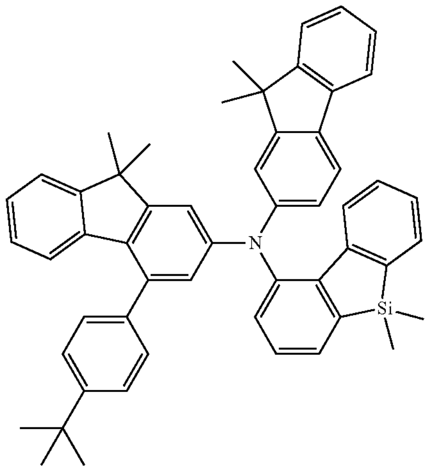
P-85
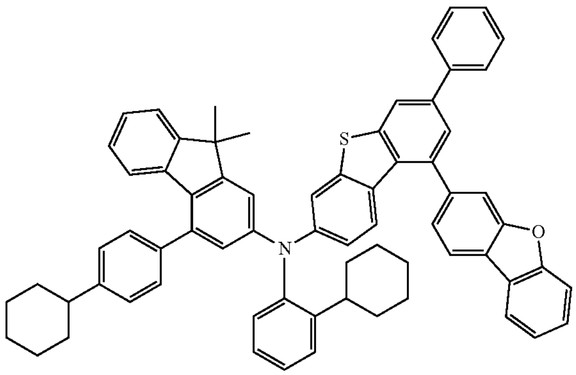

-continued
P-86
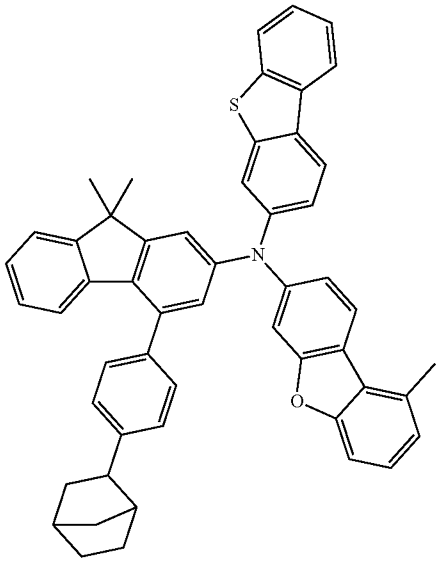
P-87
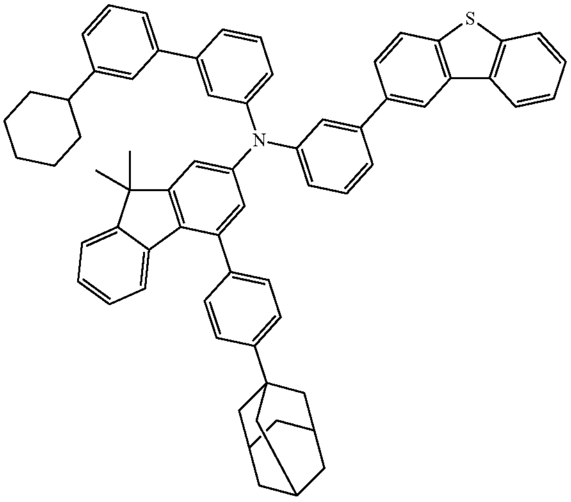
P-88
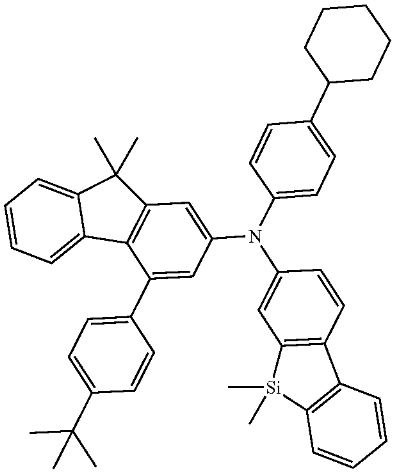
-continued
P-89
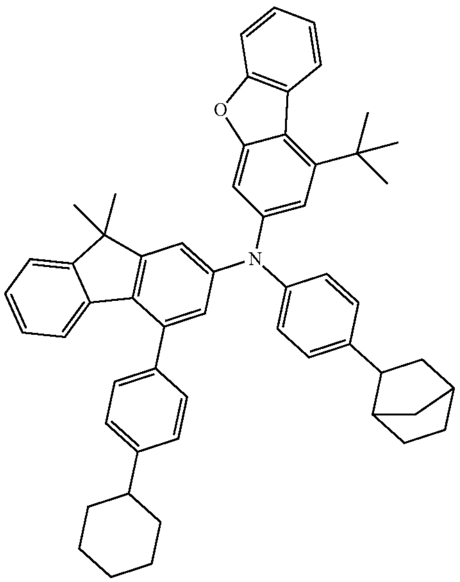
P-90
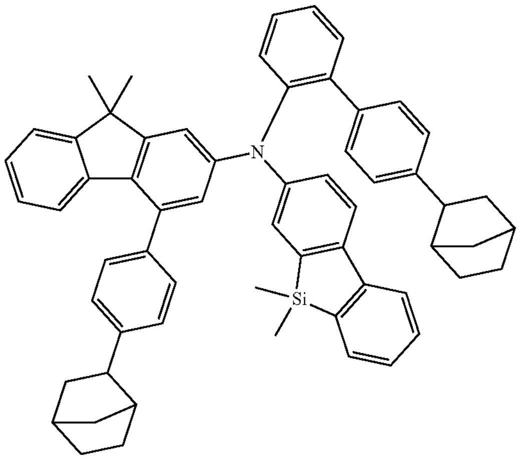
P-91
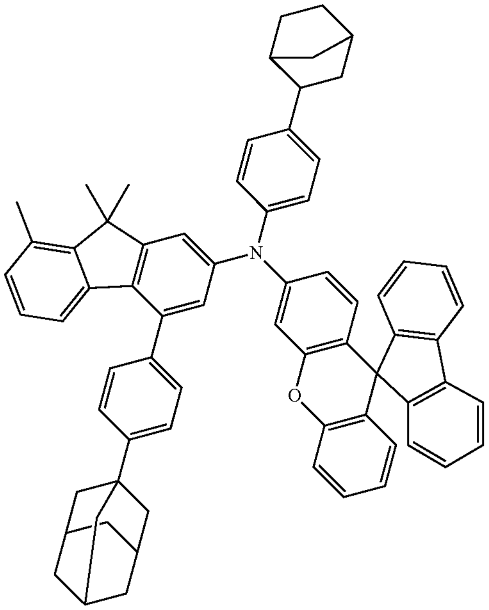

-continued
P-92
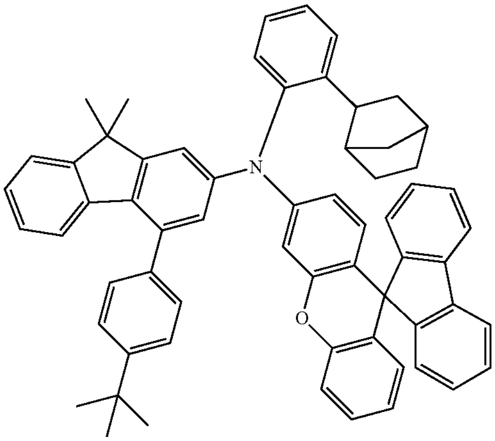
P-93
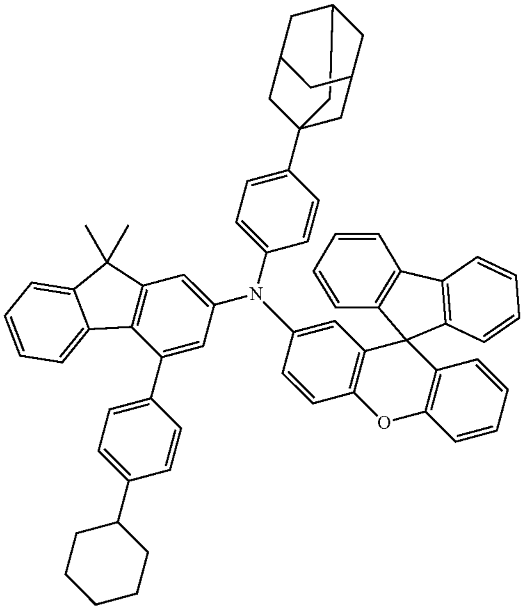
P-94
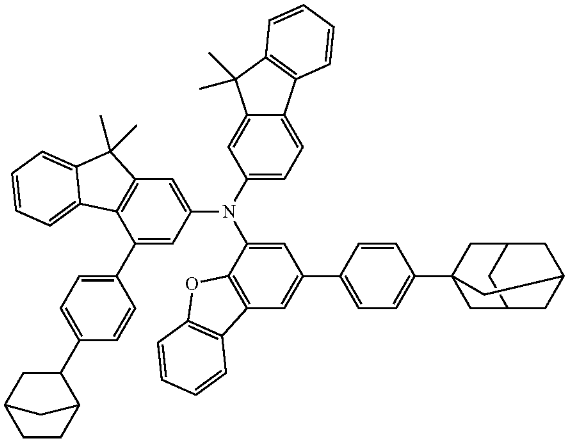
-continued
P-95
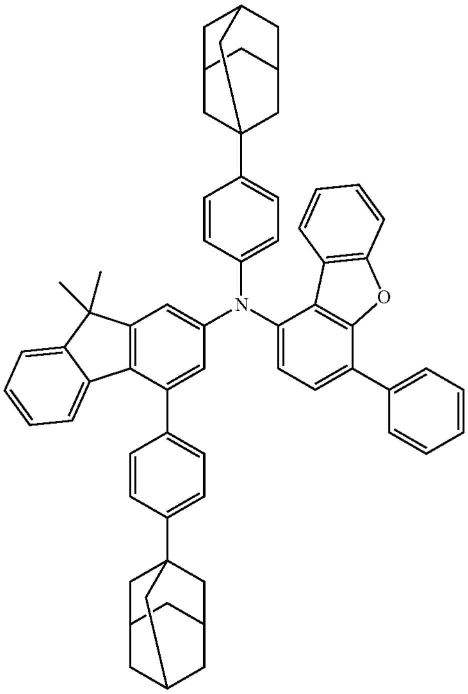
P-96
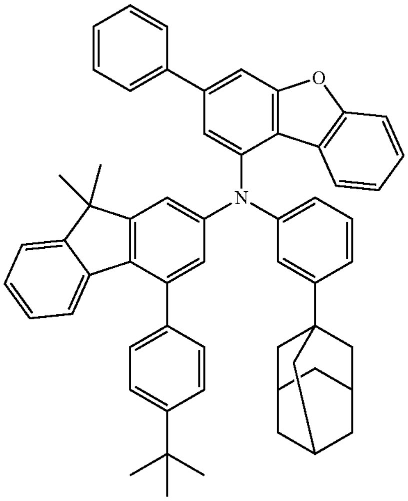
P-97
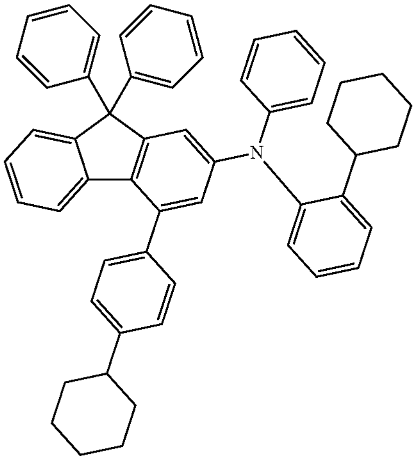

-continued
P-98
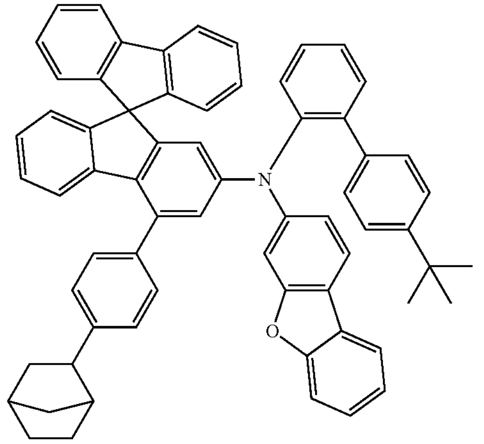
P-99
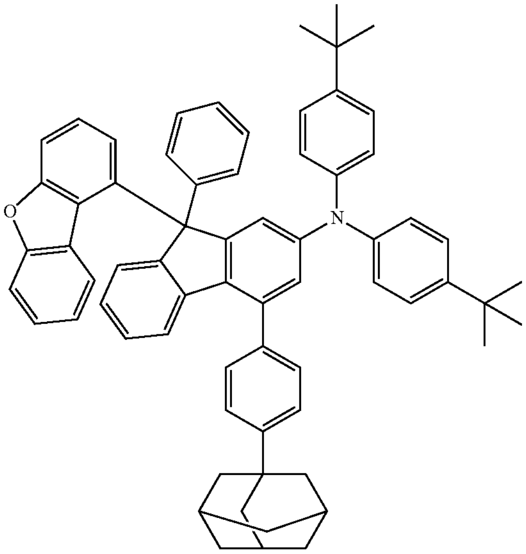
P-100
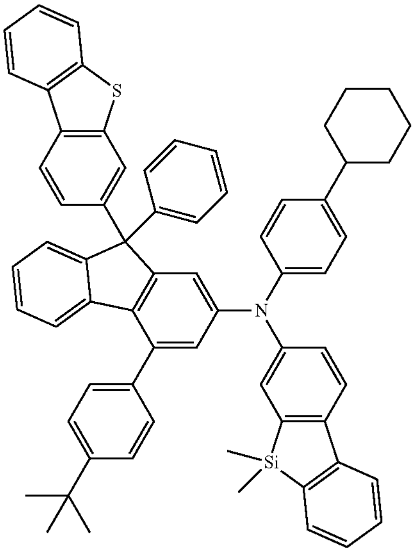
-continued
P-101
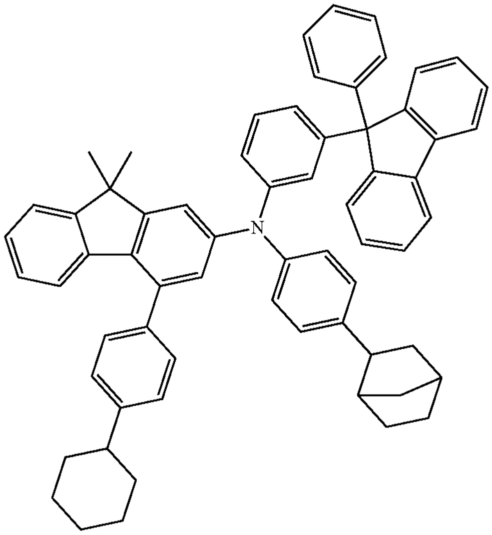
P-102
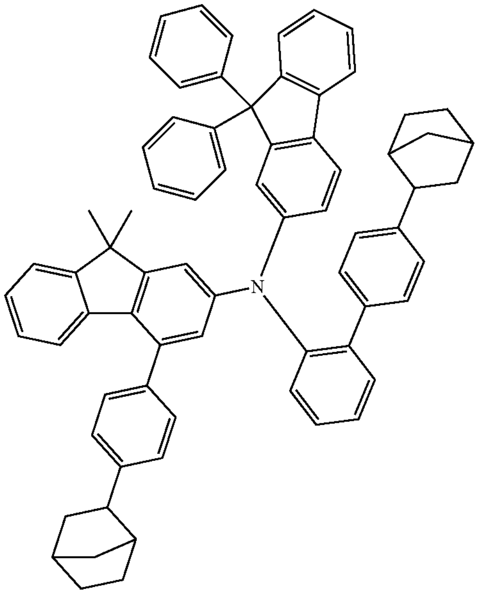

-continued
P-103
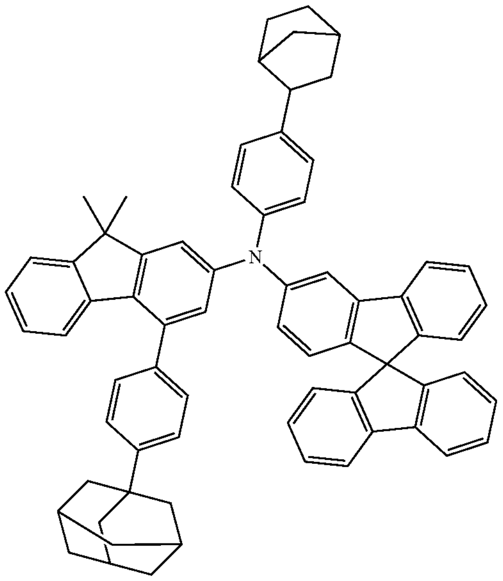
P-105
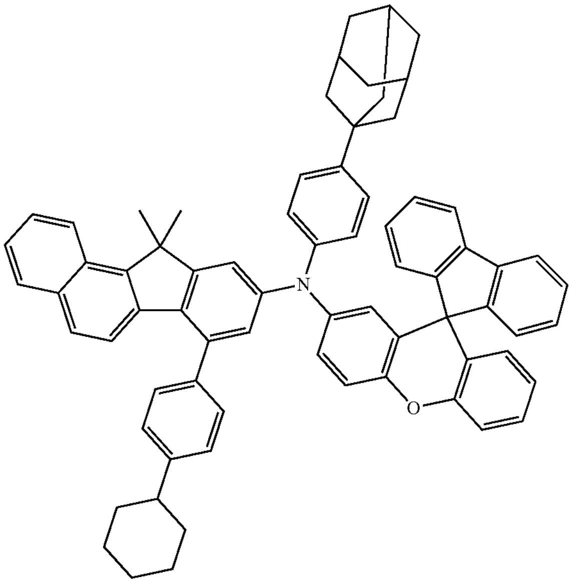
P-106
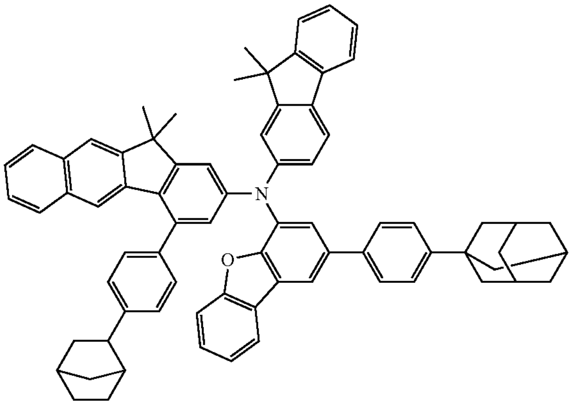
P-104
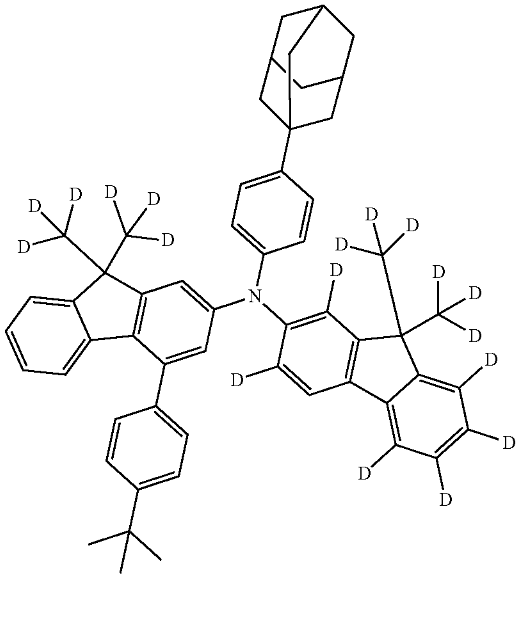
P-107
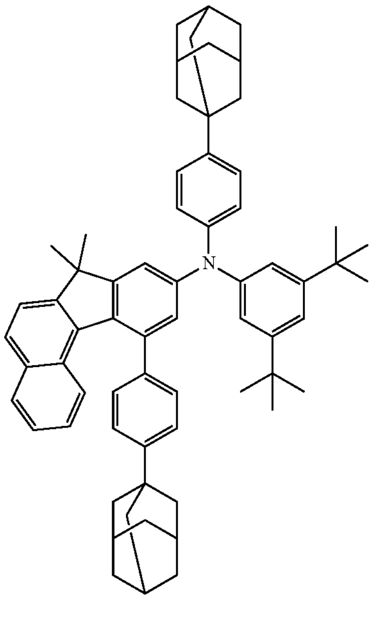

-continued
P-108
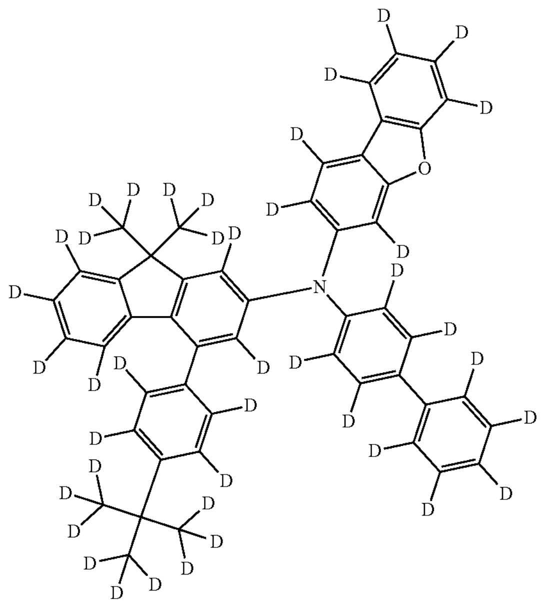
P-109
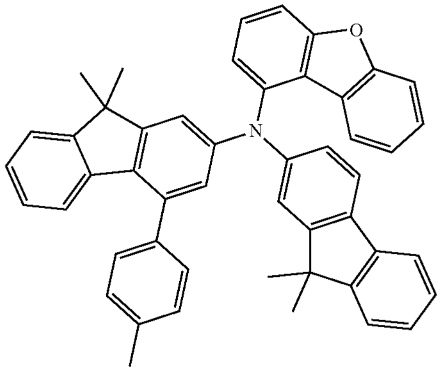
P-110
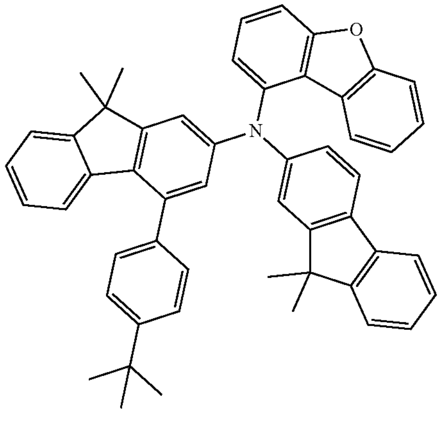
-continued
P-111
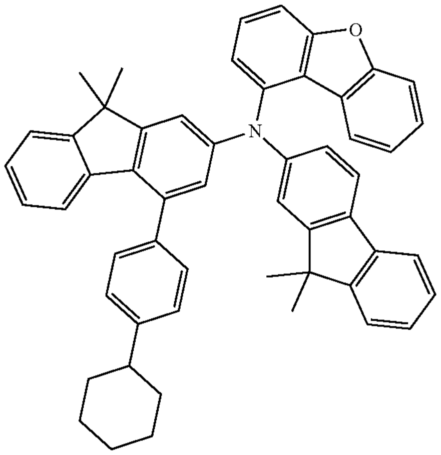
P-112
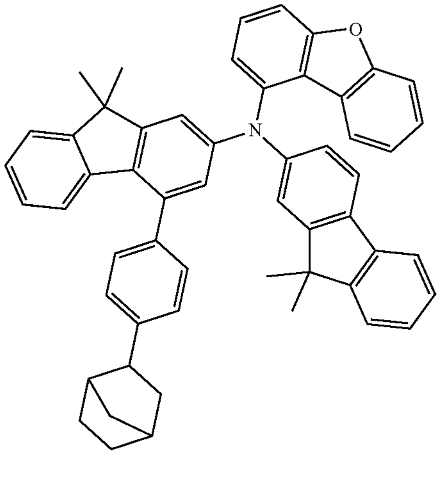
P-113
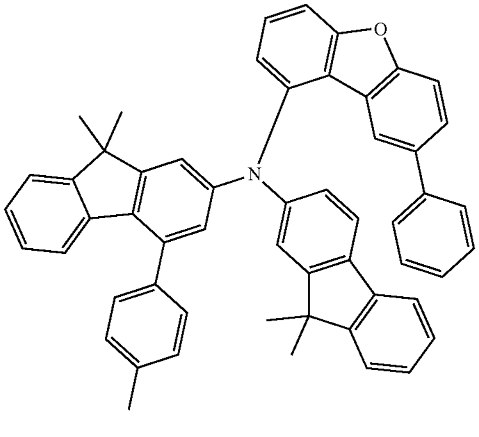

-continued
P-114
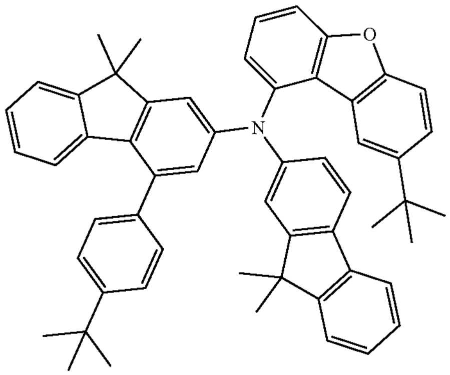
P-115
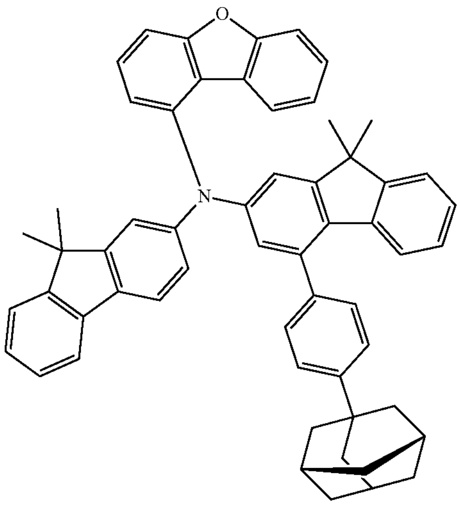
P-116
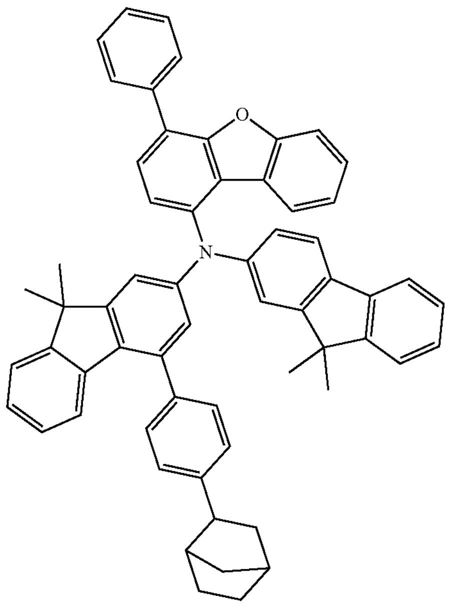
-continued
P-117
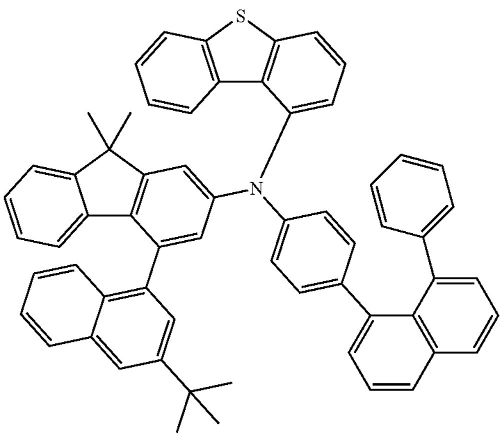
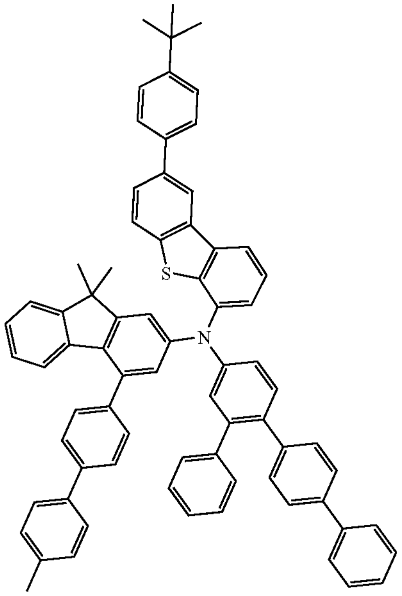
P-119
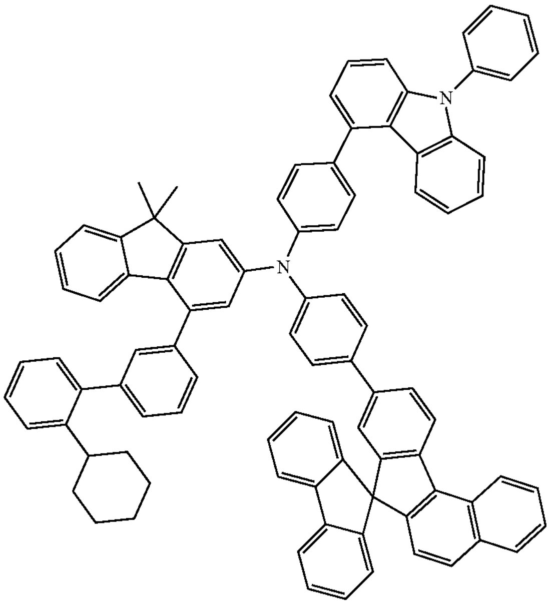

-continued
P-120
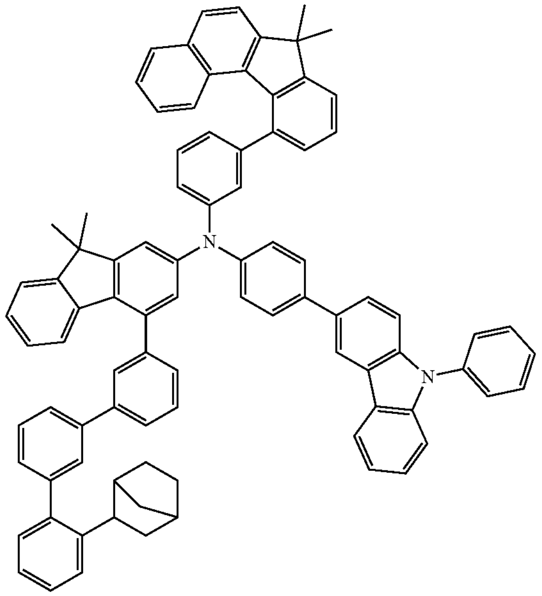
P-121
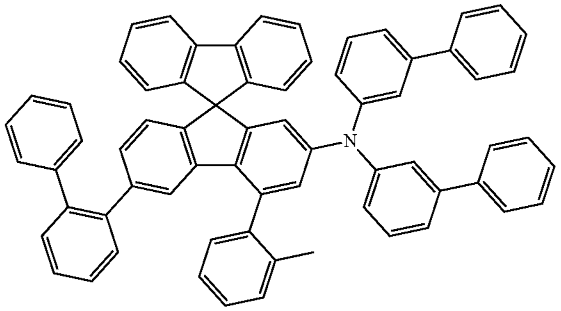
P-122
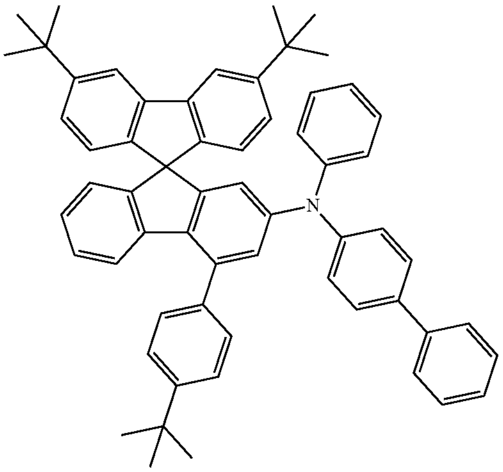
-continued
P-123
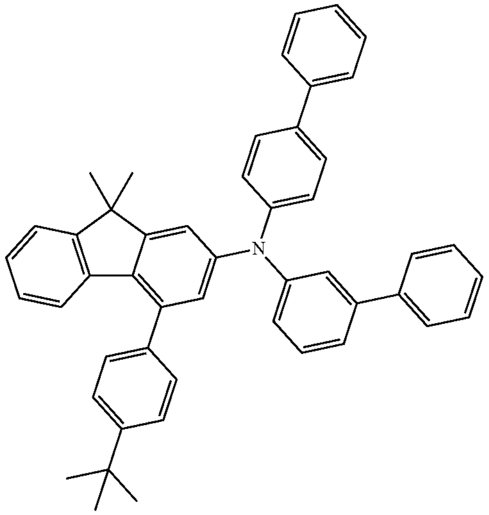
P-124
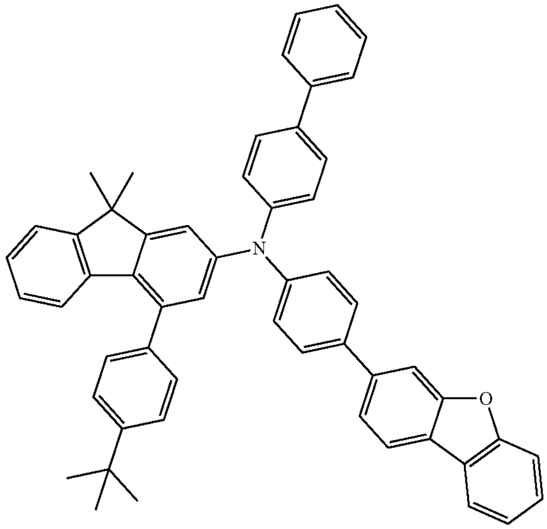
P-125
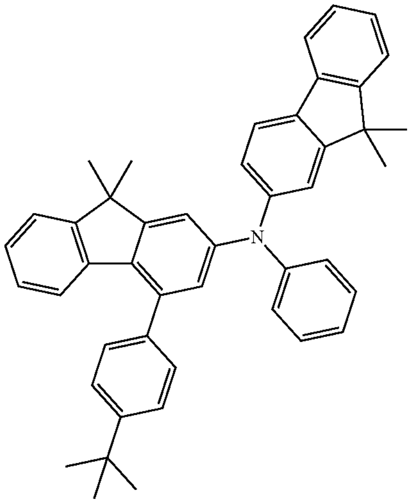

P-126
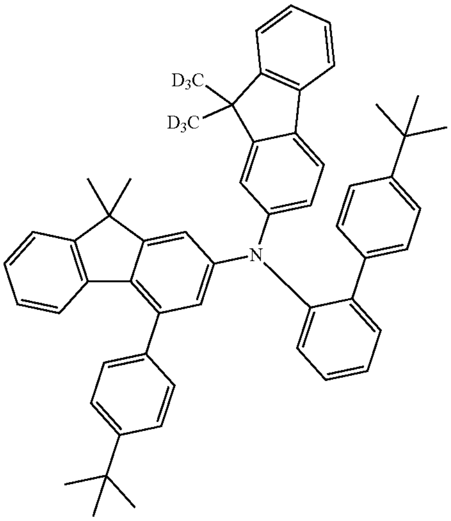
P-127
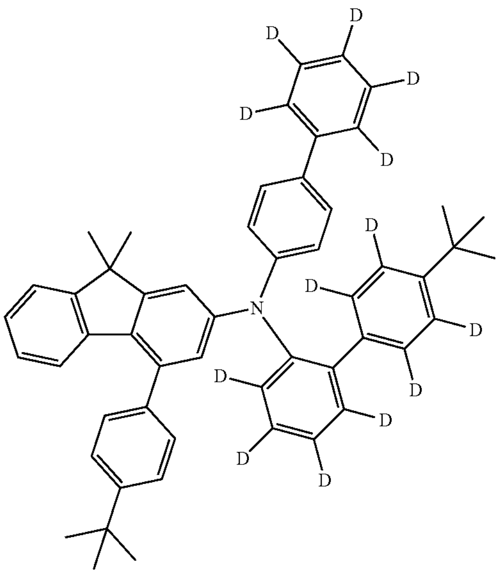
P-128
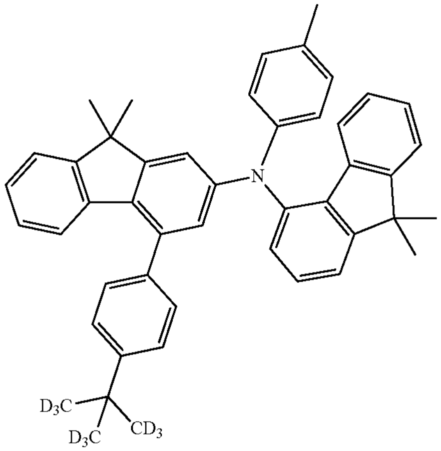
P-129
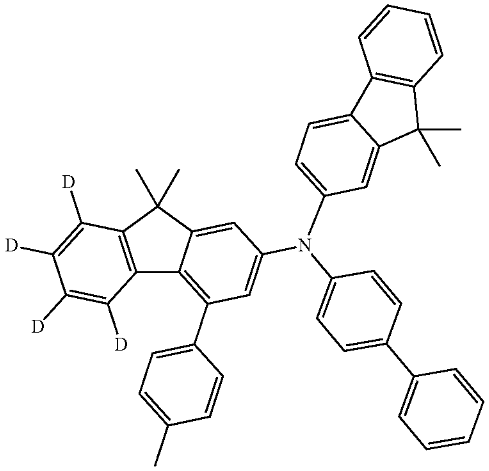
P-130
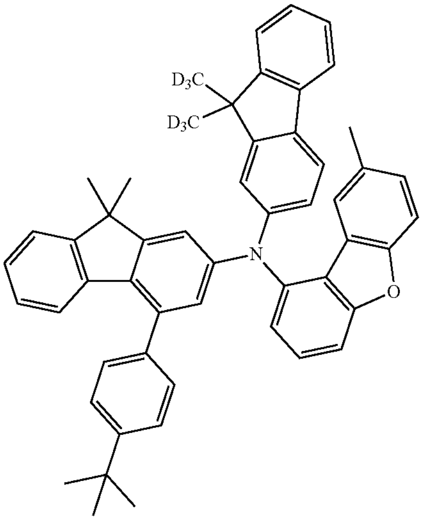
P-131
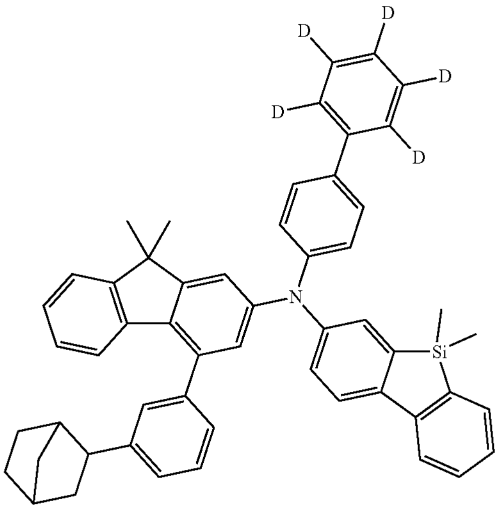

-continued

P-132

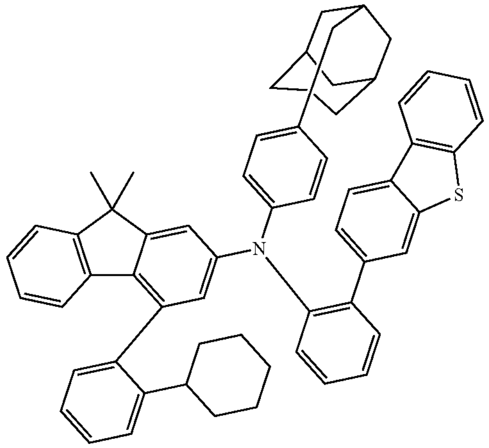

P-133

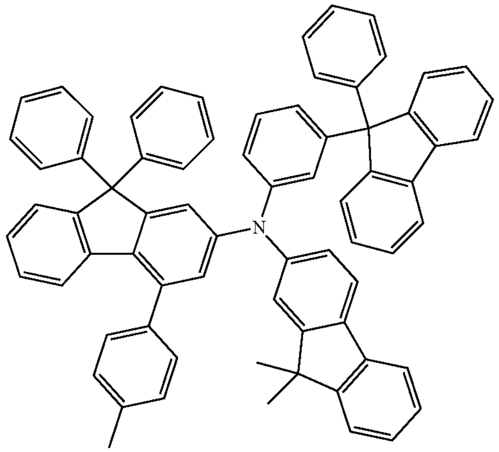

P-134

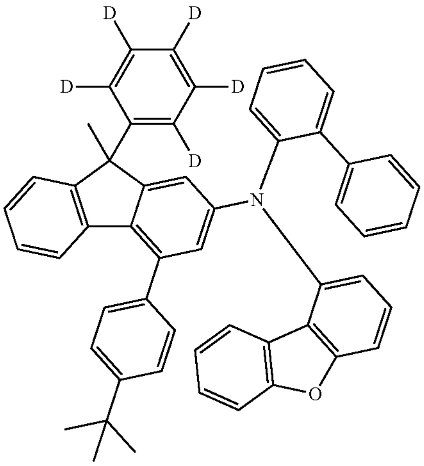

-continued

P-135

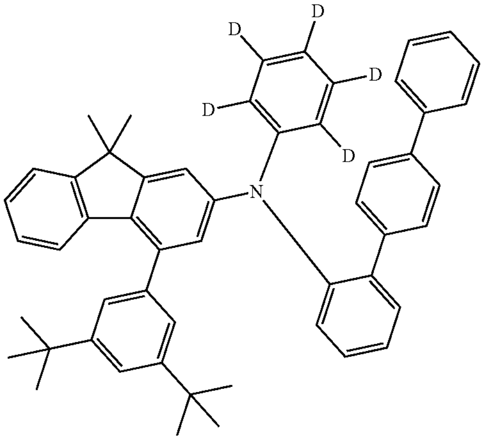

P-136

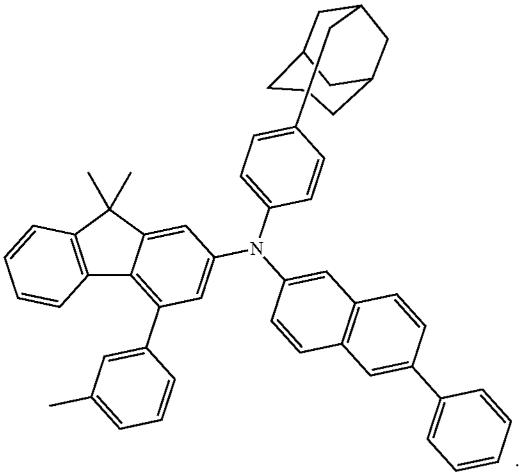

9. An organic electronic element comprising an anode, a cathode and an organic material layer formed between the anode and the cathode, wherein the organic material layer comprises a compound of Formula 1 of claim 1.

10. The organic electronic element according to claim 9, wherein the organic material layer comprises at least one of a hole injection layer, a hole transport layer, an emitting auxiliary layer, an emitting layer, an electron transport auxiliary layer, an electron transport layer, and an electron injection layer.

11. The organic electronic element according to claim 9, wherein the organic material layer comprises an emitting auxiliary layer.

12. The organic electronic element according to claim 9, further comprising a light efficiency enhancing layer formed on at least one surface of the anode and the cathode, the surface being opposite to the organic material layer.

13. The organic electronic element according to claim 9, wherein the organic material layer comprises 2 or more stacks, each stack comprising a hole transport layer, an emitting layer, and an electron transport layer, sequentially formed on the anode.

14. The organic electronic element according to claim 13, wherein the organic material layer further comprises a charge generation layer formed between the 2 or more stacks.

15. An electronic device comprising a display device comprising the organic electronic element of claim 9, and a control unit for driving the display device.

16. The electronic device according to claim 15, wherein the organic electronic element is at least one of an OLED, an organic solar cell, an organic photo conductor (OPC), organic transistor (organic TFT) and an element for monochromic or white illumination.

17. A method for reusing a compound of Formula 1 of claim 1 comprising:

depositing an organic light emitting material comprising the compound of Formula 1 to prepare an organic light emitting device;

removing impurities from the crude organic light emitting material;

recovering the removed impurities; and purifying the recovered impurities to have a purity of 99.9% or higher.

* * * * *